United States Patent
Pauza et al.

(10) Patent No.: US 11,911,458 B2
(45) Date of Patent: *Feb. 27, 2024

(54) HIV PRE-IMMUNIZATION AND IMMUNOTHERAPY

(71) Applicant: AMERICAN GENE TECHNOLOGIES INTERNATIONAL INC., Rockville, MD (US)

(72) Inventors: Charles David Pauza, Rockville, MD (US); Haishan Li, Rockville, MD (US); Tyler Lahusen, Rockville, MD (US); Gary Mansfield, Rockville, MD (US)

(73) Assignee: American Gene Technologies International Inc., Rockville, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/312,056

(22) PCT Filed: Jul. 7, 2017

(86) PCT No.: PCT/US2017/041168
§ 371 (c)(1),
(2) Date: Dec. 20, 2018

(87) PCT Pub. No.: WO2018/009847
PCT Pub. Date: Jan. 11, 2018

(65) Prior Publication Data
US 2019/0201523 A1    Jul. 4, 2019

Related U.S. Application Data

(63) Continuation-in-part of application No. PCT/US2017/013019, filed on Jan. 11, 2017.

(60) Provisional application No. 62/409,270, filed on Oct. 17, 2016, provisional application No. 62/385,864, filed on Sep. 9, 2016, provisional application No. 62/360,185, filed on Jul. 8, 2016.

(51) Int. Cl.
| | |
|---|---|
| A61K 39/12 | (2006.01) |
| A61K 31/7105 | (2006.01) |
| A61K 35/14 | (2015.01) |
| A61K 39/21 | (2006.01) |
| A61K 39/39 | (2006.01) |
| A61K 45/06 | (2006.01) |
| A61K 35/15 | (2015.01) |
| A61K 35/17 | (2015.01) |
| A61P 31/18 | (2006.01) |
| C12N 5/078 | (2010.01) |
| C12N 5/0783 | (2010.01) |
| C12N 7/00 | (2006.01) |
| C12N 15/11 | (2006.01) |
| C12N 15/86 | (2006.01) |
| C12N 15/113 | (2010.01) |
| C07K 14/715 | (2006.01) |
| A61K 39/00 | (2006.01) |
| A61K 35/12 | (2015.01) |

(52) U.S. Cl.
CPC .......... *A61K 39/21* (2013.01); *A61K 31/7105* (2013.01); *A61K 35/14* (2013.01); *A61K 39/12* (2013.01); *A61K 39/39* (2013.01); *A61K 45/06* (2013.01); *A61P 31/18* (2018.01); *C07K 14/7158* (2013.01); *C12N 5/0634* (2013.01); *C12N 5/0636* (2013.01); *C12N 7/00* (2013.01); *C12N 15/111* (2013.01); *C12N 15/1132* (2013.01); *C12N 15/1138* (2013.01); *C12N 15/86* (2013.01); *A61K 35/15* (2013.01); *A61K 35/17* (2013.01); *A61K 2035/124* (2013.01); *A61K 2039/5156* (2013.01); *A61K 2039/545* (2013.01); *A61K 2039/55561* (2013.01); *C12N 2310/122* (2013.01); *C12N 2310/14* (2013.01); *C12N 2310/141* (2013.01); *C12N 2320/32* (2013.01); *C12N 2330/51* (2013.01); *C12N 2510/00* (2013.01); *C12N 2710/24143* (2013.01); *C12N 2740/15021* (2013.01); *C12N 2740/15034* (2013.01); *C12N 2740/15043* (2013.01); *C12N 2740/15052* (2013.01); *C12N 2740/16022* (2013.01); *C12N 2740/16034* (2013.01); *C12N 2740/16043* (2013.01)

(58) Field of Classification Search
None
See application file for complete search history.

(56) References Cited

U.S. PATENT DOCUMENTS

| | | |
|---|---|---|
| 5,668,255 A | 9/1997 | Murphy |
| 5,674,703 A | 10/1997 | Woo et al. |
| 6,156,514 A | 12/2000 | Acevedo et al. |
| 6,399,383 B1 | 6/2002 | Apt et al. |

(Continued)

FOREIGN PATENT DOCUMENTS

| | | |
|---|---|---|
| BR | 2515 | 3/2019 |
| CN | 101160055 | 4/2008 |

(Continued)

OTHER PUBLICATIONS

Lee et al., Blood, 2005, 106:818-826. (Year: 2005).*

(Continued)

*Primary Examiner* — Nicole Kinsey White
(74) *Attorney, Agent, or Firm* — DLA Piper LLP (US)

(57) ABSTRACT

The present invention relates generally to immunization and immunotherapy for the treatment or prevention of HIV. In particular, the methods include in vivo and/or ex vivo enrichment of HIV-specific CD4+ T cells.

18 Claims, 36 Drawing Sheets
Specification includes a Sequence Listing.

(56) References Cited

U.S. PATENT DOCUMENTS

| | | |
|---|---|---|
| 6,635,472 B1 | 10/2003 | Lauermann |
| 7,371,542 B2 | 5/2008 | Ivanova et al. |
| 8,124,752 B2 | 2/2012 | Bumcrot et al. |
| 8,287,857 B2 | 10/2012 | Dudley et al. |
| 8,993,532 B2 | 3/2015 | Hannon et al. |
| 9,522,176 B2 | 12/2016 | DeRosa et al. |
| 9,527,904 B2 | 12/2016 | Balazs |
| 9,834,790 B1 | 12/2017 | Pauza et al. |
| 9,834,791 B2 | 12/2017 | Zhang |
| 9,914,938 B2 | 3/2018 | Pauza et al. |
| 10,023,880 B2 | 7/2018 | Pauza et al. |
| 10,036,038 B2 | 7/2018 | Pauza et al. |
| 10,036,040 B2 | 7/2018 | Pauza et al. |
| 10,137,144 B2 | 11/2018 | Pauza et al. |
| 10,208,295 B2 | 2/2019 | Derosa et al. |
| 10,233,464 B2 | 3/2019 | Pauza et al. |
| 10,494,647 B2 | 12/2019 | Pauza et al. |
| 10,888,613 B2 | 1/2021 | Pauza et al. |
| 11,090,379 B2 | 8/2021 | Pauza et al. |
| 2002/0168345 A1 | 11/2002 | Dong et al. |
| 2003/0013196 A1 | 1/2003 | Engleman et al. |
| 2003/0096787 A1 | 5/2003 | Perridcaudet et al. |
| 2003/0119770 A1 | 6/2003 | Lai |
| 2003/0138444 A1 | 7/2003 | Zavitz et al. |
| 2004/0142416 A1 | 7/2004 | Laipis et al. |
| 2004/0161412 A1 | 8/2004 | Penn et al. |
| 2004/0192629 A1 | 9/2004 | Xu et al. |
| 2004/0214158 A1 | 10/2004 | Sethi et al. |
| 2004/0248296 A1 | 12/2004 | Beresford et al. |
| 2004/0265306 A1 | 12/2004 | Arthos et al. |
| 2005/0019927 A1 | 1/2005 | Markus et al. |
| 2005/0138677 A1 | 6/2005 | Pfister et al. |
| 2006/0057553 A1 | 3/2006 | Aguilar-Cordova |
| 2006/0073576 A1 | 4/2006 | Barnett et al. |
| 2006/0183230 A1 | 8/2006 | Silla et al. |
| 2006/0246520 A1 | 11/2006 | Champagne et al. |
| 2007/0026521 A1 | 2/2007 | Colosi |
| 2007/0141679 A1 | 6/2007 | Sodroski |
| 2007/0203333 A1 | 8/2007 | McSwiggen et al. |
| 2008/0003225 A1 | 1/2008 | Vie et al. |
| 2008/0003682 A1 | 1/2008 | Lois-Caballe et al. |
| 2008/0039413 A1 | 2/2008 | Morris et al. |
| 2008/0131940 A1 | 6/2008 | Chiu |
| 2008/0153737 A1 | 6/2008 | Lieberman et al. |
| 2008/0199961 A1 | 8/2008 | Rasko et al. |
| 2008/0227736 A1 | 9/2008 | Chen et al. |
| 2008/0293142 A1 | 11/2008 | Liu et al. |
| 2009/0148936 A1 | 6/2009 | Stout et al. |
| 2009/0304688 A1 | 12/2009 | Fournie et al. |
| 2010/0017911 A1 | 1/2010 | Dawson et al. |
| 2010/0069372 A1 | 3/2010 | Kazantsev |
| 2010/0119511 A1 | 5/2010 | Wang et al. |
| 2010/0120155 A1 | 5/2010 | Brennan et al. |
| 2010/0286166 A1 | 11/2010 | Rodriguez et al. |
| 2010/0316676 A1 | 12/2010 | Sanders |
| 2011/0008417 A1 | 1/2011 | Peut et al. |
| 2011/0008803 A1 | 1/2011 | Stockwell et al. |
| 2011/0177155 A1* | 7/2011 | Peer ............ A61K 45/06 424/450 |
| 2011/0207226 A1 | 8/2011 | Ni et al. |
| 2012/0053223 A1 | 1/2012 | Benkirane et al. |
| 2012/0027725 A1 | 2/2012 | Galvin |
| 2012/0034197 A1* | 2/2012 | Young ............ A61P 31/12 424/93.21 |
| 2012/0076763 A1 | 3/2012 | Anderson et al. |
| 2012/0114607 A1 | 5/2012 | Lai et al. |
| 2012/0201794 A1 | 9/2012 | Chen et al. |
| 2013/0078276 A1* | 3/2013 | Robinson ............ A61K 39/21 424/208.1 |
| 2013/0090371 A1 | 4/2013 | Lu et al. |
| 2013/0122380 A1 | 5/2013 | Visco et al. |
| 2013/0142766 A1 | 6/2013 | Dodo et al. |
| 2013/0211380 A1 | 8/2013 | Aquino et al. |
| 2014/0155468 A1 | 6/2014 | Gregory et al. |
| 2014/0162894 A1 | 6/2014 | Hatchwell et al. |
| 2014/0178340 A1 | 6/2014 | Robbins et al. |
| 2014/0234958 A1 | 8/2014 | Kasahara et al. |
| 2014/0248277 A1 | 9/2014 | Hoffman et al. |
| 2014/0336245 A1 | 11/2014 | Mingozzi et al. |
| 2014/0348794 A1 | 11/2014 | Chiorini et al. |
| 2015/0010578 A1 | 1/2015 | Balazs et al. |
| 2015/0018539 A1 | 1/2015 | Fellmann |
| 2015/0126580 A1 | 5/2015 | DePinho et al. |
| 2015/0132255 A1 | 5/2015 | Sorensen et al. |
| 2015/0176006 A1 | 6/2015 | Krause et al. |
| 2016/0060707 A1 | 3/2016 | Goldenberg et al. |
| 2016/0243169 A1 | 8/2016 | Chen et al. |
| 2016/0289681 A1 | 10/2016 | Rossi |
| 2017/0015976 A1 | 1/2017 | Nelson |
| 2017/0028036 A1 | 2/2017 | Mingozzi et al. |
| 2017/0037369 A1 | 2/2017 | Ramsborg et al. |
| 2017/0240899 A1 | 8/2017 | Wu |
| 2017/0335344 A1 | 11/2017 | Pauza et al. |
| 2018/0010147 A1 | 1/2018 | Pauza |
| 2018/0142257 A1 | 5/2018 | Pauza |
| 2018/0142258 A1 | 5/2018 | Pauza |
| 2018/0161455 A1 | 6/2018 | Pauza |
| 2018/0177866 A1 | 6/2018 | Pauza |
| 2018/0195046 A1 | 7/2018 | Deng |
| 2018/0195050 A1 | 7/2018 | Szalay |
| 2018/0256624 A1 | 9/2018 | Pauza |
| 2018/0305716 A1 | 10/2018 | Pauza |
| 2018/0355032 A1 | 12/2018 | Roberts |
| 2019/0046633 A1 | 2/2019 | Pauza |
| 2019/0062786 A1 | 2/2019 | Pauza et al. |
| 2019/0078096 A1 | 3/2019 | Lahusen et al. |
| 2019/0083523 A1 | 3/2019 | Pauza |
| 2019/0218573 A1 | 7/2019 | Pauza et al. |
| 2019/0388456 A1 | 12/2019 | Pauza et al. |
| 2020/0063161 A1 | 2/2020 | Pauza |
| 2020/0087682 A1 | 3/2020 | Lahusen et al. |
| 2020/0109417 A1 | 4/2020 | Pauza et al. |
| 2020/0155590 A1 | 5/2020 | Zhennan |
| 2020/0181645 A1 | 6/2020 | Pauza |
| 2020/0318081 A1 | 10/2020 | Lahusen et al. |
| 2021/0047644 A1 | 2/2021 | Lahusen |
| 2021/0121561 A1 | 4/2021 | Pauza |
| 2023/0241200 A1 | 8/2023 | Pauza |

FOREIGN PATENT DOCUMENTS

| | | | |
|---|---|---|---|
| CN | 101516365 | 8/2009 | |
| CN | 101679466 | 3/2010 | |
| CN | 101805750 | 8/2010 | |
| CN | 103184224 | 7/2013 | |
| CN | 105112370 | 12/2015 | |
| CN | 108883100 | 11/2018 | |
| EP | 1647595 A1 * | 4/2006 | ......... C12N 15/1132 |
| EP | 3402483 | 11/2018 | |
| EP | 3413926 | 12/2018 | |
| EP | 3426777 | 1/2019 | |
| EP | 3468617 | 4/2019 | |
| EP | 3468618 | 4/2019 | |
| EP | 3481418 | 5/2019 | |
| EP | 3481435 | 5/2019 | |
| IN | 201947000153 | 2/2019 | |
| JP | 2002506652 | 3/2002 | |
| JP | 2007-527240 | 9/2007 | |
| JP | 2008518591 | 6/2008 | |
| JP | 2008-538174 | 10/2008 | |
| JP | 2010-520757 | 6/2010 | |
| JP | 2011036263 A | 2/2011 | |
| JP | 2011-517409 | 6/2011 | |
| JP | 2012508591 | 4/2012 | |
| JP | 2013-507107 | 3/2013 | |
| JP | 2013-5300152 | 7/2013 | |
| JP | 2014511704 A | 5/2014 | |
| JP | 2015-518838 | 7/2015 | |
| JP | 2016-502404 | 1/2016 | |
| JP | 2018-541270 | 4/2019 | |
| WO | 199947691 | 9/1999 | |
| WO | 2002020554 | 3/2002 | |
| WO | 2003093436 | 11/2003 | |
| WO | 2004053137 | 6/2004 | |

(56) References Cited

FOREIGN PATENT DOCUMENTS

| | | |
|---|---|---|
| WO | WO-2004104185 A1 | 12/2004 |
| WO | 2005028634 | 3/2005 |
| WO | 2005033282 | 4/2005 |
| WO | WO-2005051927 A1 | 6/2005 |
| WO | 2006039721 | 4/2006 |
| WO | 2006048215 | 5/2006 |
| WO | 2007000668 | 1/2007 |
| WO | 2007015122 | 2/2007 |
| WO | 2007132292 | 11/2007 |
| WO | 2007133674 | 11/2007 |
| WO | WO2008/025025 | 2/2008 |
| WO | WO-2008090185 A1 * | 7/2008 ............... C12N 7/00 |
| WO | WO 2008/109837 | 9/2008 |
| WO | 2009100928 | 8/2009 |
| WO | WO2009100955 | 8/2009 |
| WO | WO-2009120947 A1 | 10/2009 |
| WO | 2009147445 | 12/2009 |
| WO | 2010051521 | 5/2010 |
| WO | 2010117974 | 10/2010 |
| WO | 2010127166 | 11/2010 |
| WO | 2011008348 | 1/2011 |
| WO | WO-2011042180 A1 | 4/2011 |
| WO | 2011071476 | 6/2011 |
| WO | 2011119942 | 9/2011 |
| WO | 2012048303 | 4/2012 |
| WO | 2012061075 | 5/2012 |
| WO | WO-2012140127 A2 | 10/2012 |
| WO | WO2012145624 | 10/2012 |
| WO | 2013096455 | 6/2013 |
| WO | 2014016817 | 1/2014 |
| WO | 2014117050 | 7/2014 |
| WO | 2014187881 | 11/2014 |
| WO | 2015017755 | 2/2015 |
| WO | 2015042308 | 3/2015 |
| WO | 2015061491 | 4/2015 |
| WO | 2015078999 | 6/2015 |
| WO | 2015086854 | 6/2015 |
| WO | WO2015164759 | 10/2015 |
| WO | 2016046234 | 3/2016 |
| WO | 2016054654 | 4/2016 |
| WO | 2016061232 | 4/2016 |
| WO | WO2016061232 | 4/2016 |
| WO | WO-2016061232 A2 * | 4/2016 ......... C12N 15/1132 |
| WO | 2016069518 | 5/2016 |
| WO | 2016069716 | 5/2016 |
| WO | 2016200997 | 7/2016 |
| WO | WO 2016/186708 A1 | 11/2016 |
| WO | WO2016189159 | 12/2016 |
| WO | 2017007994 | 1/2017 |
| WO | 20170068077 | 4/2017 |
| WO | 2017100551 | 6/2017 |
| WO | 2017123918 | 7/2017 |
| WO | 2017139065 | 8/2017 |
| WO | WO2017139065 | 8/2017 |
| WO | 2017156311 | 9/2017 |
| WO | 20170173453 | 10/2017 |
| WO | 2017213697 | 12/2017 |
| WO | 2017214327 | 12/2017 |
| WO | 2018009246 | 1/2018 |
| WO | 2018009847 | 1/2018 |
| WO | 2018017882 | 1/2018 |
| WO | 2018126112 | 7/2018 |
| WO | 2018129540 | 7/2018 |
| WO | WO2018126112 | 7/2018 |
| WO | 20180148443 | 8/2018 |
| WO | WO 2018/025923 | 8/2018 |
| WO | 2018187231 | 10/2018 |
| WO | 2018232359 | 12/2018 |
| WO | WO2019070674 | 4/2019 |
| WO | WO-2020011247 A1 | 1/2020 |
| WO | 2020097049 | 5/2020 |
| WO | 2020243717 | 12/2020 |

OTHER PUBLICATIONS

Kaur et al., Virology, 2007, 369(1): 214-225. (Year: 2007).*
Venturini et al., Journal of Virology, 2002, 76(14):6987-6999. (Year: 2002).*
Chavez et al., PLoS Pathog, 2015, 11(6): e1004955 (Year: 2015).*
Curriu et al., PLoS ONE, 2012, 7(2): e30330. (Year: 2012).*
Rana et al., Journal of Virology, 1997, 71(4):3219-3227. (Year: 1997).*
Brites, C., M. Abrahao, P. Bozza, E. M. Netto, A. Lyra and F. Bahia (2018). "Infection by HTLV-1 Is Associated with High Levels of Proinflammatory Cytokines in HIV-HCV-Coinfected Patients." J Acquir Immune Defic Syndr 77(2): 230-234.
Douek, D. C., J. M. Brenchley, M. R. Betts, D. R. Ambrozak, B. J. Hill, et al. (2002). "HIV preferentially infects HIV-specific CD4+ T cells." Nature 417(6884): 95-98.
Eguchi, K., N. Matsuoka, H. Ida, M. Nakashima, M. Sakai, et al. (1992). "Primary Sjogren's syndrome with antibodies to HTLV-I: clinical and laboratory features." Ann Rheum Dis 51(6): 769-776.
Futsch, N., R. Mahieux and H. Dutartre (2017). "HTLV-1, the Other Pathogenic Yet Neglected Human Retrovirus: From Transmission to Therapeutic Treatment." Viruses, 10, 1; doi:10.3390/v10010001.
Gessain, A., F. Barin, J. C. Vernant, O. Gout, L. Maurs, A. Calender and G. de The (1985). "Antibodies to human T-lymphotropic virus type-I in patients with tropical spastic paraparesis." Lancet 2(8452): 407-410.
Gessain, A. and O. Cassar (2012). "Epidemiological Aspects and World Distribution of HTLV-1 Infection." Front Microbiol 3: 388.
Goncalves, D. U., F. A. Proietti, J. G. Ribas, M. G. Araujo, S. R. Pinheiro, A. C. Guedes and A. B. Carneiro-Proietti (2010). "Epidemiology, treatment, and prevention of human T-cell leukemia virus type 1-associated diseases." Clin Microbiol Rev 23(3): 577-589.
Kagdi, H., M. A. Demontis, J. C. Ramos and G. P. Taylor (2018). "Switching and loss of cellular cytokine producing capacity characterize in vivo viral infection and malignant transformation in human T- lymphotropic virus type 1 infection." PLoS Pathog 14(2): e1006861.
Kagdi, H. H., M. A. Demontis, P. A. Fields, J. C. Ramos, C. R. Bangham and G. P. Taylor (2017). "Risk stratification of adult T-cell leukemia/lymphoma using immunophenotyping." Cancer Med 6(1): 298-309.
Macnamara, A., A. Rowan, S. Hilburn, U. Kadolsky, H. Fujiwara, et al. (2010). "HLA class I binding of HBZ determines outcome in HTLV-1 infection." PLoS Pathog 6(9): e1001117.
Manel, N., F. J. Kim, S. Kinet, N. Taylor, M. Sitbon and J. L. Battini (2003). "The ubiquitous glucose transporter GLUT-1 is a receptor for HTLV." Cell 115(4): 449-459.
Martinez, M. P., J. Al-Saleem and P. L. Green (2019). "Comparative virology of HTLV-1 and HTLV-2." Retrovirology 16(1): 21.
Mochizuki, M., T. Watanabe, K. Yamaguchi, K. Takatsuki, K. Yoshimura, et al. (1992). "HTLV-I uveitis: a distinct clinical entity caused by HTLV-I." Jpn J Cancer Res 83(3): 236-239.
Mosley, A. J., B. Asquith and C. R. Bangham (2005). "Cell-mediated immune response to human T-lymphotropic virus type I." Viral Immunol 18(2): 293-305.
Nagai, M. and M. Osame (2003). "Human T-cell lymphotropic virus type I and neurological diseases." J Neurovirol 9(2): 228-235.
Yamano, Y. and T. Sato (2012). "Clinical pathophysiology of human T-lymphotropic virus-type 1-associated myelopathy/tropical spastic paraparesis." Front Microbiol 3: 389.
Nishioka, K., I. Maruyama, K. Sato, I. Kitajima, Y. Nakajima and M. Osame (1989). "Chronic inflammatory arthropathy associated with HTLV-I." Lancet 1(8635): 441.
Osame, M., K. Usuku, S. Izumo, N. Ijichi, H. Amitani, et al. (1986). "HTLV-I associated myelopathy, a new clinical entity." Lancet 1(8488): 1031-1032.
Poiesz, B. J., F. W. Ruscetti, A. F. Gazdar, P. A. Bunn, J. D. Minna and R. C. Gallo (1980). "Detection and isolation of type C retrovirus particles from fresh and cultured lymphocytes of a patient with cutaneous T-cell lymphoma." Proc Natl Acad Sci U S A 77(12): 7415-7419.
Poiesz, B. J., F. W. Ruscetti, J. W. Mier, A. M. Woods and R. C. Gallo (1980). "T-cell lines established from human T-lymphocytic

(56) References Cited

OTHER PUBLICATIONS neoplasias by direct response to T-cell growth factor." Proc Natl Acad Sci U S A 77(11): 6815-6819.

Roc, L., C. de Mendoza, M. Fernandez-Alonso, G. Reina, V. Soriano and H. N. Spanish (2019). "Rapid subacute myelopathy following kidney transplantation from HTLV-1 donors: role of immunosuppresors and failure of antiretrovirals." Ther Adv Infect Dis 6: 2049936119868028.

Soker, S., S. Takashima, H. Q. Miao, G. Neufeld and M. Klagsbrun (1998). "Neuropilin-1 is expressed by endothelial and tumor cells as an isoform-specific receptor for vascular endothelial growth factor." Cell 92(6): 735-745.

Uchiyama, T., J. Yodoi, K. Sagawa, K. Takatsuki and H. Uchino (1977). "Adult T-cell leukemia: clinical and hematologic features of 16 cases." Blood 50(3): 481-492.

Dickler, H. B., et al. (1973). "Lymphocyte binding of aggregated IgG and surface Ig staining in chronic lymphocytic leukaemia." Clin Exp Immunol 14(1): 97-106.

USPTO; Notice of Allowance dated May 18, 2020 in the U.S. Appl. No. 16/083,384.

USPTO; Final Office Action dated Jun. 2, 2020 in the U.S. Appl. No. 15/580,661.

USPTO; Non-Final Office Action dated Jun. 1, 2020 in the U.S. Appl. No. 16/530,908.

CN; 1st Office Action in the CN Application No. 201700177712.6 dated May 8, 2020.

EPO; Office Action in the EPO Application No. 16808223.8 dated May 11, 2020.

Pallikkuth et al., "Human Immunodeficiency Virus (HIV) gag Anti-Specific T-Helper and Granule-Dependent CD8 T-Cell Activities in Exposed but Uninfected Heterosexual Partners of HIV Type 1-Infected Individuals in North India," Clinical and Vaccine Immunology, vol. 14(9) pp. 1196-1202, (2007).

USPTO; Non-Final Office Action dated Feb. 21, 2020 in the U.S. Appl. No. 16/076,655.

EPO; Extended European Supplementary Search Report dated Feb. 6, 2020 in the Application No. 17825011.4.

EPO; Extended European Supplementary Search Report dated Feb. 6, 2020 in the Application No. 17824652.6.

Oh et al. "Lentiviral Vector Design Using Alternative RNA Export Elements," Retrovirology, vol. 4:38, pp. 1-10, (2007).

PCT; International Preliminary Report on Patentability dated Oct. 8, 2019 in the Application No. PCT/ US2018/025733.

PCT; International Search Report and Written Opinion of the International Search Report dated Jul. 22, 2019 in the Application No. PCT/US2019/024410.

USPTO; Notice of Allowance dated Nov. 27, 2019 in the U.S. Appl. No. 13/333,882.

Quan Jun-Jie et al., "Parp3 interacts with FoxMI to confer glioblastoma cell radioresistance", Tumor Biology, Karger, Basel, CH, vol. 36, No. 11, Jun. 4, 2015 (Jun. 4, 2015), pp. 8617-8624, XP036217799, ISSN: 1010-4283, DOI: 10.1007/S13277-015-3554-4 [retrieved on Jun. 4, 2015].

Jakobsson J. and Lundberg C.: "Lentiviral 1, 2, 4-10 vectors for use in the central nervous system", Molecular Therapy: The Journal of the American Society of Gene Therapy, Cell Press, US, vol. 13, No. 3, Mar. 1, 2006 (Mar. 1, 2006), pp. 484-493, XP005326761, ISSN: 1525-0016, DOI: 10.1016/ J.Ymthe.2005.11.012.

YunJong Lee et al., "Poly (ADP-ribose) in 1-15 the pathogenesis of Parkinson's disease", BMB Reports, vol. 47, No. 8, Aug. 31, 2014 (Aug. 31, 2014), pp. 424-432, XP55671927, KR, ISSN: 1976-6696, DOI: 10.5483/BMBRep.2014.47.8.119.

Lang Yoo et al., "Parp-1 regulates the expression of caspase-11", Biochemical and Biophysical Research Communications, vol. 408, No. 3, Apr. 22, 2011 (Apr. 22, 2011), pp. 489-493, XP028209824, ISSN: 0006-291X, DOI: 10.1016/ J. BBRC.2011.04.070 [retrieved on Apr. 22, 2011].

Tae-In Kam et al., "Poly (ADP-ribose) derived pathologic [alpha]-synuclein neurodegeneration in Parkinson's disease", Science, vol. 362, No. 6414, Nov. 1, 2018 (Nov. 1, 2018), p. eaat8407, XP55672116, US, ISSN: 00368075, DOI: 10.1126/science. aat8407.

Olsen A.L. and Feany M.B., "Parp Inhibitors and Parkinson's Disease", Jan. 1, 2019 (Jan. 1, 2019), XP55672111, retrieved from the Internet: URL: https://mfprac.com/web2019/07literature/literature/Neurology/ParkinsonPARPI_Olsen.pdf [retrieved on Feb. 27, 2020].

Richard Lu et al., "Siman Virus 40-Based Replication of Catalytically Inactive Human Immunodeficiency Virus Type 1 Integrase Mutants in Nonpermissive T Cells and Monocyte-Derived Macrophages", Journal of Virology, Jan. 2004, p. 658-668. DOI: 10.1128/JVI.78.2658-668.2004.

FM Sverdrup et al., "Development of human papillomavirus plasmids capable of episomal replication in human cell lines", Gene Therapy, Mar. 26, 1999, p. 1317-1321, Retrieved from the Internet: URL: http://www.stockton-pressco.uk/gt.

Kathleen Van Craenenbroeck et al., "Episomal vectors for gene expression in mammalian cells", Eur J. Biochem, vol. 267, p. 5665-5678, Jul. 14, 2000.

USPTO; Non-Final Office Action dated Mar. 16, 2020 in the U.S. Appl. No. 16/083,384.

EPO; Extended European Supplemental Search Report dated Mar. 11, 2020 in the Application No. 17831904.2.

JP; Japanese Office Action in the Application No. 2017-564550 dated Mar. 18, 2020.

USPTO; Final Office Action dated May 2, 2019 in U.S. Appl. No. 15/736,284.

USPTO; Final Office Action dated May 2, 2019 in U.S. Appl. No. 16/182,443.

USPTO; Non-Final Office Action dated May 7, 2019 in U.S. Appl. No. 16/008,991.

USPTO; Non-Final Office Action dated May 16, 2019 in U.S. Appl. No. 16/132,247.

PCT; International Search Report and Written Opinion in the PCT Application No. PCT/US2019/059828 dated Feb. 14, 2020.

Hee Yeon Kim., "Farnesyl diphosphate synthase is important for the maintenance of glioblastoma stemness," Experimental & Molecular Medicine, (2018).

Hong Wang., "Indirect Stimulation of Human V2V2 Cells Through Alterations in Isoprenoid Metabolism," The Journal of Immunology, (2011).

Z. Li, "Inhibition of farnesyl pyrophosphate synthase prevents angiotensin II-induced cardiac fibrosis in vitro," Clinical & Experimental Immunology, (2014).

Xiaofeng Jiang, "A novel EST-derived RNAi screen reveals a critical role for farnesyl diphosphate in B2-adrenerigic receptor internalization and down-regulation," The FASEB Journal, vol. 26, pp. 1-13(1995).

Jian Yang, "Lentiviral-Mediated Silencing of Farnesyl Pyrophosphate Synthase through RNA Interference in Mice," Biomed Research International, vol. 2015, Article ID 914026, 6 pages, (2015).

Yang Ye, "Knockdown of farnesyl pyrophosphate synthase prevents angiotensin II-medicated cardiac hypertrophy," The International Journal of Biochemistry & Cell Biology, vol. 42, pp. 2056-2064, (2010).

Jianqiang Li, "Reduced Expression of Mevalonate Pathway Enzyme Farnesyl Pyrophosphate Synthase Unveils Recognition of Tumor Cells by V9V2 Cells," The Journal of Immunology, pp. 8118-8124, (2019).

Daryl S. Schiller, "Parameters Influencing Measurement of the Gag Antigen-Specific T-Proliferative Response to HIV Type 1 Infection," AIDS Research and Human Retroviruses, vol. 16, No. 3, pp. 259-271, (2000).

PCT; International Search Report dated Jul. 22, 2019 in the Application No. PCT/US2019/24410.

PCT; Written Opinion of the International Search Report dated Jul. 22, 2019 in the Application No. PCT/US2019/24410.

PCT; International Preliminary Report on Patentability dated Jul. 9, 2019 in the Application No. PCT/US2018/012998.

USPTO; Notice of Allowance dated Jun. 18, 2019 in the U.S. Appl. No. 16/182,443.

USPTO; Notice of Allowance dated Jul. 3, 2019 in U.S. Appl. No. 16/182,443.

USPTO; Restriction Requirement dated Jul. 12, 2019 in the U.S. Appl. No. 15/736,284.

(56) References Cited

OTHER PUBLICATIONS

USPTO; Advisory Action dated Jul. 23, 2019 in the U.S. Appl. No. 15/736,284.
USPTO; Notice of Allowance dated Aug. 14, 2019 in the U.S. Appl. No. 16/008,991.
USPTO; Notice of Allowance dated Sep. 25, 2019 in the U.S. Appl. No. 16/218,010.
USPTO; Final Office Action dated Jul. 1, 2019 in the U.S. Appl. No. 16/132,247.
USPTO; Notice of Allowance dated Jul. 19, 2019 in the U.S. Appl. No. 16/132,247.
EPO; European Search Report dated Aug. 12, 2019 in the EP Application No. 17764128.9.
EPO; Supplementary European Search Report dated Sep. 6, 2019 in the Application No. 17750547.6.
EPO; Supplementary European Search Report dated Dec. 19, 2019 in the Application No. 16904834.5.
EPO; Supplementary European Search Report dated Dec. 19, 2019 in the Application No. 17810976.5.
Hassan et al., "Isolation of umbilical cord mesenchymal stem cells using human blood derivative accompanied with explant method," Stem Cell Investigation, pp. 1-8, (2019).
Huang et al., "An Efficient protocol to generate placental chorionic plate-derived mesenchymal stem cells with superior proliferative and immunomodulatory properties," Stem Cell Research & Therapy, pp. 1-15, (2019).
USPTO; Restriction Requirement dated Oct. 22, 2019 in the U.S. Appl. No. 15/580,661.
USPTO; Restriction Requirement dated Nov. 4, 2019 in the U.S. Appl. No. 16/076,655.
USPTO; Notice of Allowance dated Oct. 29, 2019 in the U.S. Appl. No. 13/333,882.
USPTO; Restriction Requirement dated Nov. 7, 2019 in the U.S. Appl. No. 16/083,384.
Vargas, J. Jr. et al., "Conditionally Replicating Lentiviral-Hybrid Episomal Vectors for Suicide Gene Therapy," Antiviral Research, vol. 80(3), pp. 288-294, (Dec. 2008).
Thompson et al., "Alkylamines Cause Vγ9Vδ2 T-Cell Activation and Proliferation by Inhibiting the Mevalonate Pathway," Blood, vol. 107, pp. 651-654, (Jan. 2006).
Gober et al., "Human T Cell Receptor γδ Cells Recognize Endogenous Mevalonate Metabolites in Tumor Cells," Journal of Experimental Medicine, vol. 197, pp. 163-168, (Jan. 2003).
Goepfert, et al., "Specificity and 6-Month Durability of Immune Responses Induced by DNA and Recombinant Modified Vaccinia Ankara Vaccines Expressing HIV-2 Virus-Like Particles," Journal of Infectious Diseases, vol. 210, pp. 99-110, (Jul. 2014).
Human papillomavirus type 16 (HPV16), complete genome; GenBank: K02718.1; Publication [online], Mar. 18, 1994, https://www.ncbi.nlm.nih.gov/nucleotide/333031?report=genbank&log$=nucltop&blast_rank=22&RID=H3E1THFU014; pp. 1-4.
{Long control region} [human papillomavirus, type 16, Genomic, 860 nt]; Accession S60559. Publication [online]. May 7, 1993, https://www.ncbi.nlm.nih.gov/nucleotide/237343?report=genbank&log$=nucltop&blast_rank=1&RID=H3FCKA00014; pp. 1.
Tebas, P. et al., "Antiviral Effects of Autologous CD4 T Cells Genetically Modified with a Conditionally Replicating Lentiviral Vector Expressing Long Antisense to HIV," Blood, vol. 121(9), pp. 1524-1533, (2003).
Tebas, P. et al., "Gene Editing of CCR5 in Autologous CD4 T Cells of Persons Infected with HIV," The New England Journal of Medicine, vol. 370(10), pp. 901-910, (Mar. 2014).
Li et al., "Reduced Expression of the Mevalonate Pathway Enzyme Farnesyl Pyrophosphate Synthase Unveils Recognition of Tumor Cells by Vγ2Vδ2 T Cells," Journal of Immunology, vol. 182, pp. 8118-8124, (2009).
Wang et al., "Indirect Stimulation of Human Vγ2Vδ2 T Cells through Alterations in Isoprenoid Metabolism," Journal of Immunology, vol. 187 pp. 5099-5113, (Nov. 2011).

Stunkel et al., "The Chromatin Structure of the Long Control Region of Human Papillomavirus Type 16 Repress Viral Oncoprotein Expression," Journal of Virology, vol. 73(3), pp. 1918-1930, (Mar. 1999).
Lu et al., "Anti-Sense-Mediated Inhibition of Human Immunodeficiency Virus (HIV) Replication by Use of an HIV Type 1-Based Vector Results in Severely Attenuated Mutants Incapable of Developing Resistance," Journal of Virology, vol. 79(13), pp. 7079-7088, (Jul. 2004).
Dieli et al., "Targeting Human γδ T Cells with Zoledronate and Interleukin-2 for Immunotherapy of Hormone-Refractory Prostate Cancer," Europe PMC Funders Group, Cancer Research, vol. 67(15), pp. 7450-1451, (Aug. 2007).
GenBank Accession No. S60559 "(long control region) [human papillomavirus, type 16, Genomic, 860 nt]" May 7, 1993 [located online Nov. 21, 2017 at https://ncbi.nlm.nih.gov/nuccore/S60559] entire DNA sequence.
GenBank Accession No. JG619773, MNESC1NG-T3-001_L15_Feb. 6, 2009_054 MNESC1NG cell culture from Mahonia nervosa Berberis nervosa cDNA, mRNA sequence, Feb. 13, 2014 (online). [Retrieved on Dec. 5, 2017]. Retrieved from the internet :<URL: https://www.ncbi.nlm.nih.gov/nucest/JG619773 > entire document.
Moser et al., "γδ T Cells: Novel Initiators of Adaptive Immunity," Immunological Reviews, vol. 215, pp. 89-102, (Feb. 2007).
Capietto, A. H. et al., "Stimulated γδ T Cells Increase the in Vivo Efficacy of Trastuzumab in HER-2+ Breast Cancer," Journal of Immunology, vol. 187(2), pp. 1031-1038, (2011).
Chen, Z. and M. S. Freedman, "CD16+ γδ T Cells Mediate Antibody Dependent Cellular Cytotoxicity: Potential Mechanism in the Pathogenesis of Multiple Sclerosis," Clinical Immunology, vol. 128(2), pp. 219-227, (2008).
Couzi, L. et al., "Antibody-Dependent Anti-Cytomegalovirus Activity of Human γδ T Cells Expressing CD16 (FcγRIIIa)," Blood, vol. 119(6), pp. 1418-1427, (2012).
Fisher, J. P. et al., "Effective Combination Treatment of GD2-Expressing Neuroblastoma and Ewing's Sarcoma Using Anti-GD2 ch14.18/CHO Antibody with Vγ9Vδ2+ γδT Cells," OncoImmunology, vol. 5(1), p. e1025194, (2016).
Gertner-Dardenne, J. et al., "Bromohydrin Pyrophosphate Enhances Antibody-Dependent Cell-Mediated Cytotoxicity Induced by Therapeutic Antibodies," Blood, vol. 113(20), pp. 4875-4884, (2009).
Poonia, B. and C. D. Pauza, "Gamma Delta T Cells from HIV+ Donors can be Expanded In Vitro by Zoledronate/Interleukin-2 to Become Cytotoxic Effectors for Antibody-Dependent Cellular Cytotoxicity," Cytotherapy, vol. 14(2), pp. 173-181, (2012).
Schiller, C. B. et al., "CD19-Specific Triplebody SPM-1 Engages NK and γδ T Cells for Rapid and Efficient Lysis of Malignant B-Lymphoid Cells," Oncotarget, vol. 7(50), pp. 83392-83408, (2016).
Tokuyama, H. et al., "Vγ9Vδ2 T Cell Cytotoxicity Against Tumor Cells is Enhanced by Monoclonal Antibody Drugs—Rituximab and Trastuzumab," International Journal of Cancer, vol. 122(11), pp. 2526-2534, (2008).
Zufferey et al., "Self-Inactivating Lentivirus Vector for Safe and Efficient In Vivo Gene Delivery," Journal of Virology, vol. 72(12), pp. 9873-9880, (1998).
Ostertag et al., "Brain Tumor Eradication and Prolonged Survival from Intratumoral Conversion of 5-Fluorocytosine to 5-fluorouracil Using a Nonlytic Retroviral Replicating Vector," Neuro-Oncology, vol. 14(2), pp. 145-159, (Feb. 2012).
Twitty et al., "Retroviral Replicating Vectors Deliver Cytosine Deaminase Leading to Targeted 5-Fluorouracil-Mediated Cytotoxicity in Multiple Human Cancer Types," Human Gene Therapy Methods, vol. 27(1), pp. 17-31, (Feb. 2016).
Charron et al., "Dominant-Negative Interference in the Pahenu2 Mouse Model of PKU: Effectiveness of Vectors Expressing Either Modified Forms of Phenylalanine Hydroxylase (PAH) or Ribozymes Plus a Hardened PAH mRNA," Molecular Therapy, vol. 11, pp. S163-S164, (2005).
Fusetti, et al., "Structure of Tetrameric Human Phenylalanine Hydroxylase and Its Implications for Phenylketonuria," Journal of Biological Chemistry, vol. 273(27), p. 16962-16967, (1998).

(56) References Cited

OTHER PUBLICATIONS

Hafid et al., "Phenylketonuria: A Review of Current and Future Treatments," Translational Pediatrics, vol. 4(4), pp. 304-317, (2015).
Blau et al., "Phenylketonuria," The Lancet, vol. 376(9750), pp. 1417-1427, (2010).
Chandler et al., "Vector Design Influences Hepatic Genotoxicity After Adeno-Associated Virus Gene Therapy," Journal of Clinical Investigation, vol. 125(2), pp. 870-880, (2015).
Christophersen et al., "A Technique of Transumbilical Portal Vein Catheterization in Adults," The Archives of Surgery, vol. 95(6), pp. 960-963, (1967). (Abstract Only).
Bartholome, "Genetics and Biochemistry of the Phenylketonuria-Present State," Human Genetics, vol. 51(3), pp. 241-245, (1979).
Donsante et al., "AAV Vector Integration Sites in Mouse Hepatocellular Carcinoma," Science, vol. 317(5837), p. 477, (2007).
Eisensmith et al., "Multiple Origins for Phenylketonuria in Europe," American Journal of Human Genetics, vol. 51(6), pp. 1355-1365, (1992).
Fisher et al., "The Inhibition of Phenylalanine and Tyrosine Hydroxylases by High Oxygen Levels," Journal of Neurochemistry, vol. 19(5), pp. 1359-1365, (1972). (Abstract Only).
Grisch-Chan et al., "Low-Dose Gene Therapy for Murine PKU Using Episomal Naked DNA Vectors Expressing PAH from Its Endogenous Liver Promoter," Molecular Therapy Nucleic Acids, vol. 7, pp. 339-349, (2017).
Guldberg et al., "Aberrant Phenylalanine Metabolism in Phenylketonuria Heterozygotes," Journal of Inherited Metabolic Disease, vol. 21(4), pp. 365-372, (1998).
Kaufman et al., "A Model of Human Phenylalanine Metabolism in Normal Subjects and in Phenylketonuric Patients," Proceedings of the National Academy of Sciences USA, vol. 96(6), pp. 3160-3164, (1999).
Kaufman et al., "Phenylalanine Hydroxylase Activity in Liver Biopsies from Hyperphenylalaninemia Heterozygotes: Deviation from Proportionality with Gene Dosage," Pediatric Research, vol. 9(8), pp. 632-634, (1975).
Longo et al., "Single-Dose, Subcutaneous Recombinant Phenylalanine Ammonia Lyase Conjugated with Polyethylene Glycol in Adult Patients with Phenylketonuria: An Open-Label, Multicentre, Phase 1 Dose-Escalation Trial," The Lancet, vol. 384(9937), pp. 37-44, (2014).
Mochizuki et al., "Long-Term Correction of Hyperphenylalaninemia by AAV-Mediated Gene Transfer Leads to Behavioral Recovery in Phenylketonuria Mice," Gene Therapy, vol. 11(13), pp. 1081-1086, (2004).
Nault et al., "Adeno-Associated Virus Type 2 as an Oncogenic Virus in Human Hepatocellular Carcinoma," Molecular & Cellular Oncology, vol. 3(2), p. e1095271, (2016).
Oh et al., "Reversal of Gene Expression Profile in the Phenylketonuria Mouse Model After Adeno-Associated Virus Vector-Mediated Gene Therapy," Molecular Genetics and Metabolism, vol. 86(Supp. 1), pp. S124-S132, (2005).
Oh et al., "Long-Term Enzymatic and Phenotypic Correction in the Phenylketonuria Mouse Model by Adeno-Associated Virus Vector-Mediated Gene Transfer," Pediatric Research, vol. 56(2), pp. 278-284, (2004).
Pan et al., "Biodistribution and Toxicity Studies of VSVG-Pseudotyped Lentiviral Vector After Intravenous Administration in Mice with the Observation of in Vivo Transduction of Bone Marrow," Molecular Therapy, vol. 6(1), pp. 19-29, (2002).
Shedlovsky et al., "Mouse Models of Human Phenylketonuria," Genetics, vol. 134(4), pp. 1205-1210, (1993).
Yagi et al., "Complete Restoration of Phenylalanine Oxidation in Phenylketonuria Mouse by a Self-Complementary Adeno-Associated Virus Vector," Journal of Gene Medicine, vol. 13(2), pp. 114-122, (2011).
Yano et al., "Evaluation of Tetrahydrobiopterin Therapy with Large Neutral Amino Acid Supplementation in Phenylketonuria: Effects on Potential Peripheral Biomarkers, Melatonin and Dopamine, for Brain Monoamine Neurotransmitters," PLoS One, vol. 11(8), p. e0160892, (2016).
Mason et al., "Inactivated Simian Immunodeficiency Virus-Pulsed Autologous Fresh Blood Cells as an Immunotherapy Strategy," Journal of Virology, vol. 83(3), pp. 1501-1510, (2009).
Blick et al., "Cyclophosphamide Enhances SB-728-T Engraftment to Levels Associated with HIV-RNA Control," CROI Conference on Retroviruses and Opportunistic Infections, Boston, Massachusetts, p. 141, (2014), (Abstract Only).
De Rose et al., "Safety, Immunogenicity and Efficacy of Peptide-Pulsed Cellular Immunotherapy in Macaques," Journal of Medical Primatology, vol. 27(2), pp. 69-78, (2008).
Smith et al., "Developments in HIV-1 Immunotherapy and therapeutic Vaccination," F1000Prime Reports, vol. 6, p. 42, (2014).
Charron, "Gene Therapy for Phenylketonuria: Dominant-Negative Interference in a Recessive Disease," Dissertation, University of Florida 2005, http://etd.fcla.edu/UF/UFE0011392/charron_c.pdf>, (retrieved Jul. 26, 2018) (2005).
Ding et al., "Administration-Route and Gender-Independent Long-Term Therapeutic Correction of Phenylketonuria (PKU) in a Mouse Model by Recombinant Adeno-Associated Virus 8 Pseudotyped Vector-Mediated Gene Transfer," Gene Therapy, vol. 13, pp. 583-587, (Dec. 2005).
Nowacki et al., "The PAH Mutation Analysis Consortium Database: Update 1996," Nucleic Acid Research, vol. 25(1), pp. 139-142, (Jan. 1997).
Condiotti et al., "Prolonged Liver-Specific Transgene Expression by a Non-Primate Lentiviral Vector," Biochemical and Biophysical Research Communications, vol. 320(3), pp. 998-1006, (Jul. 2004).
Wang et al., "Butyrophilin 3A1 Plays an Essential Role in Prenyl Pyrophosphate Stimulation of Human Vg2Vd2 T Cells," Journal of Immunology, vol. 191(3), pp. 1029-1042, (Jul. 2013).
Jiang et al., "A Novel EST-Derived RNAi Screen Reveals a Critical Role for Farnesyl Diphosphate Synthase in Beta2-Adrenergic Receptor Internalization and Down-Regulation," FASEB Journal, vol. 26(5), pp. 1-13, (Jan. 2012).
Miettinen et al., "Mevalonate Pathway Regulates Cell Size Homeostasis and Proteostasis Through Autophagy," Cell Reports, vol. 13(11), pp. 2610-2620, (Dec. 2015).
Tolmachov, "Designing Lentiviral Gene Vectors," Viral Gene Therapy, Chapter 13, pp. 263-284, (2011).
Tracey, "Human DNA Sequence from Clone RP1-288M22 on Chromosome 6q 12-13," Complete Sequence, National Center for Biotechnology. GenBank Entry. Retrieved from the internet: <https://www.ncbi.nlm.nih.gov/nucleotide/AL035467.23?report=genbank&log$=nucltop&blast_rank=1&RID=UUD4GX2D014>; pp. 1-34, (Jan. 2013).
Gorziglia et al., "Elimination of Both E1 and E2A from Adenovirus Vectors Further Improves Prospects for In Vivo Human gene Therapy," Journal of Virology, vol. 70(6), pp. 4173-4178, (1996).
Vargas et al., "Novel Integrase-Defective Lentiviral Episomal Vectors for Gene Transfer," Human Gene Therapy, vol. 15(4), pp. 361-372, (Apr. 2004).
Wendelburg et al., "An Enhanced EBNA1 Variant with reduced IR3 Domain for Long-Term Episomal Maintenance and Transgene Expression of ORIP-Based Plasmids in Human Cells," Gene Therapy, vol. 5, pp. 1389-1399, (Oct. 1998).
Westerhout et al., "A Conditionally Replicating HIV-Based Vector that Stably Expresses an Antiviral shRNA Against HIV-1 Replication," Molecular Therapy: The Journal of the American Society of Gene Therapy, vol. 14(2), pp. 268-275, (May 2006).
Lam et al., "T-Cell Therapies for HIV," Immunotherapy, Future Medicine, vol. 5(4), pp. 407-414, (Apr. 2013).
Munoz et al., "Ex Vivo Expansion and Lentiviral Transduction of *Macaca nemestrina* CD4 + T Cells," Journal of Medical Primatology, vol. 38(6), pp. 438-443, (Dec. 2009).
Porichis et al., "HIV-Specific CD4 T Cells and Immune Control of Viral Replication," Current Opinion in HIV and Aids, vol. 6(3), pp. 174-180, (May 2011).
Kavanagh et al., "Expansion of HIV-Specific CD4+ and CD8+ T Cells by Dendritic Cells Transfected with mRNA Encoding Cyto-

(56) References Cited

OTHER PUBLICATIONS plasm- or Lysosome-Targeted Nef," Blood, American Society of Hematology, vol. 107(5), pp. 1963-1969, (Mar. 2006).
Akinsheye et al., "Fetal Hemoglobin in Sickle Cell Anemia," Blood, vol. 118(1), pp. 19-27, (2011).
Lin et al., "Up-Regulation of Bcl-2 is Required for the Progression of Prostate Cancer Cells from an Androgen-Dependent to an Androgen-Independent Growth Stage," Cell Research, vol. 17, pp. 531-536, (2007).
GenBank Sequence M65141.1 Retrieved from the Internet <URL: https://www.ncbi.ntm.nih.gov/nuccore/M65141.1. Especially Sequence, nt 301-420, (Retrieved Mar. 31, 2019).
PCT: International Search Report dated Nov. 7, 2016 in Application No. PCT/US2016/036519.
PCT: Written Opinion dated Nov. 7, 2016 in Application No. PCT/US2016/036519.
PCT: International Search Report dated Oct. 19, 2016 in Application No. PCT/US2016/041456.
PCT: Written Opinion dated Oct. 19, 2016 in Application No. PCT/US2016/041456.
PCT: International Search Report dated Jul. 20, 2017 in Application No. PCT/US2017/043157.
PCT: Written Opinion dated Jul. 20, 2017 in application No. PCT/US2017/043157.
PCT: International Search Report dated Jun. 9, 2017 in Application No. PCT/US2016/066185.
PCT: Written Opinion dated Jun. 9, 2017 in Application No. PCT/US2016/066185.
PCT: International Search Report dated Jul. 17, 2017 in Application No. PCT/US2017/013019.
PCT: Written Opinion dated Jul. 17, 2017 in Application No. PCT/US2017/013019.
PCT: International Search Report dated May 26, 2017 in Application No. PCT/US2017/013399.
PCT: Written Opinion dated May 26, 2017 in Application No. PCT/US2017/013399.
PCT: International Search report dated Aug. 25, 2017 in Application No. PCT/US2017/021639.
PCT: Written Opinion dated Aug. 25, 2017 Application No. PCT/US2017/021639.
PCT: International Search Report dated Nov. 8, 2017 Application No. PCT/US2017/041168.
PCT: Written Opinion dated Nov. 8, 2017 in Application No. PCT/US2017/041168.
PCT: International Search Report dated Dec. 15, 2017 in Application No. PCT/US2017/36433.
PCT: Written Opinion dated Dec. 15, 2017 in Application No. PCT/US2017/36433.
PCT: International Search Report dated Jul. 14, 2017 in Application No. PCT/US2017/013024.
PCT: Written Opinion dated Jul. 14, 2017 in application No. PCT/US2017/013024.
PCT: International Search Report dated May 29, 2018 in Application No. PCT/US2018/012998.
PCT: Written Opinion dated May 29, 2018 in Application No. PCT/US2018/012998.
PCT; International Search Report dated Sep. 24, 2018 in Application No. PCT/US2018/025733.
PCT; Written Opinion dated Sep. 24, 2018 in Application No. PCT/US2018/025733.
PCT; International Search Report dated Nov. 9, 2018 in Application No. PCT/US2018/037924.
PCT; Written Opinion dated Nov. 9, 2018 in Application No. PCT/US2018/037924.
PCT; Invitation to Pay Additional Fees in Application No. PCT/US2018/053919 dated Feb. 22, 2019.
PCT; International Search Report dated Apr. 12, 2019 in Application No. PCT/ US2018/053919.
PCT; Written Opinion dated Apr. 12, 2019 in Application No. PCT/US2018/053919.
USPTO; Notice of Allowance dated Oct. 13, 2017 in U.S. Appl. No. 14/706,481.
USPTO; Requirement for Restriction dated Oct. 23, 2017 in U.S. Appl. No. 15/668,223.
USPTO; Notice of Allowance dated Nov. 2, 2017 in U.S. Appl. No. 15/652,080.
USPTO; Non-Final Office Action dated Feb. 22, 2018 in U.S. Appl. No. 15/850,937.
USPTO; Non-Final Office Action dated Feb. 22, 2018 in U.S. Appl. No. 15/849,062.
USPTO; Non-Final Office Action dated Feb. 22, 2018 in U.S. Appl. No. 13/333,882.
USPTO; Notice of Allowance dated Mar. 26, 2018 in U.S. Appl. No. 15/668,223.
USPTO; Notice of Allowance dated Apr. 23, 2018 in U.S. Appl. No. 15/850,937.
USPTO; Notice Allowance dated Apr. 26, 2018 in U.S. Appl. No. 15/849,062.
USPTO; Non-Final Office Action dated Jun. 15, 2018 in U.S. Appl. No. 15/904,131.
USPTO; Requirement for Restriction dated Jul. 12, 2018 in U.S. Appl. No. 15/736,284.
USPTO; Invitation to Pay Additional Fees And, Where Applicable, Protest Fee dated Jul. 17, 2018 in Application No. PCT/US2018/25733.
USPTO; Requirement for Restriction dated Aug. 3, 2018 in U.S. Appl. No. 16/011,550.
USPTO; Notice of Allowance dated Aug. 10, 2018 in U.S. Appl. No. 15/904,131.
USPTO; Final Office Action dated Aug. 27, 2018 in U.S. Appl. No. 13/333,882.
USPTO; Non-Final Office Action dated Sep. 19, 2018 in U.S. Appl. No. 16/011,550.
USPTO; Invitation to Pay Additional Fees And, Where Applicable, Protest Fee dated Sep. 11, 2018 in Application No. PCT/US2018/37924.
USPTO; Non-Final Office Action dated Oct. 19, 2018 in U.S. Appl. No. 15/736,284.
USPTO; Notice of Allowance dated Oct. 31, 2018 in U.S. Appl. No. 16/011,550.
USPTO; Advisory Action dated Nov. 16, 2018 in U.S. Appl. No. 13/333,882.
USPTO; Non-Final Office Action dated Dec. 31, 2018 in U.S. Appl. No. 16/182,443.
USPTO; Non-Final Office Action dated Apr. 18, 2019 in U.S. Appl. No. 13/333,882.
EPO; Extended Search Report dated Dec. 12, 2018 in EP Application No. 16808223.8.
EPO; Extended Search Report dated Dec. 11, 2018 in EP Application No. 16822021.8.
USPTO; Non-Final Office Action dated May 24, 2019 in U.S. Appl. No. 16/218,010.
EPO; Extended Search Report dated Jun. 6, 2019 in EP Application No. 17739028.3.
USPTO; Non-Final Office Action dated Jan. 13, 2020 in the U.S. Appl. No. 15/580,661.
Yang et al., "Construction of PARP-1 gene silencing cell lines by lentiviral-mediated RNA interference," School of Public Health, Guangdong Medical College, Abstract (2006).
Zhaobing Ding et al., "Liver-Directed, AAV- and Lentivirus-Mediated Gene Therapy in the Phenylketonuria Mouse Model Pah-enu2", Molecular Therapy, vol. 11, Supp. 1. (May 2005) XP055751452.
Ledley et al., "Retroviral-mediated gene transfer of human phenylalanine hydroxylase into NIH 3T3 and hepatoma cells", Proceedings of the National Academy of Sciences, vol. 83, No. 2. (Jan. 1, 1986), pp. 409-413, XP002583115.
Ledley et al., "Molecular biology of phenylalanine hydroxylase and penylketonurina", Trends in Genetics, Elsevier Science Publishers B.V. Amsterdam, NL, vol. 1. (Jan. 1, 1985), pp. 309-313, XP025943064.
USPTO; Notice of Allowance dated Jan. 13, 2021 in the U.S. Appl. No. 16/687,525.

(56) References Cited

OTHER PUBLICATIONS

EP; Supplementary Search Report in the EP Application No. 18781288.8 dated Dec. 8, 2020.
JP; Final Office Action in the JP Application No. 2018-536892 dated Nov. 16, 2020.
USPTO; Non-Final Office Action dated Oct. 29, 2020 in the U.S. Appl. No. 15/736,284.
JP; Japanese Office Action in the JP Application No. 2018-563892 dated Oct. 14, 2020.
Wang et al., "HIV Vaccine Research: The Challenge and the Way Forward," Journal of Immunology Research, vol. 2015, Article ID 503978, 5 pages.
Bourguigon et al., "Processing of blood samples influences PBMC viability and outcome of cell-mediated immune responses in antiretroviral therapy-naïve HIV-1-infected patients," Journal of Immunological Methods, vol. 414, p. 1-10 (2014).
Briz et al., "Validation of Generation 4 Phosphorus-Containing Polycationic Dendrimer for Gene Delivery Against HIV-1," Current Medical Chemistry, vol. 19, p. 5044-5051, (2012).
Anderson et al., "Preintegration HIV-1 Inhibition by a Combination Lentiviral Vector Containing a Chimeric TRIM5a Protein, a CCR5 shRNA, and TAR Decoy," Molecular Therapy, vol. 17, No. 12, p. 2103-2114, Dec. 2009.
JP; Japanese Office Action in the Application No. 2017-567175 dated Jun. 15, 2020.
EPO; Extended European Search Report in the Application No. 18736295.9 dated Aug. 20, 2020.
Cronin et al., "Altering the Tropism of Lentiviral Vectors through Pseudotyping", Curr Gene Ther, Aug. 2005, vol. 5(4), pp. 687-398.
Cannon et al., "Pseudotype-Dependent Lentiviral Transduction of Astrocytes or Neurons in the Rat Substantia Nigra", Experimental Neurology, vol. 228, (Year: 2011), pp. 41-52, doi:10.1016/J.expneurol.2010.10.016.
USPTO; Non-Final Office Action dated Nov. 18, 2020 in the U.S. Appl. No. 16/318,345.
USPTO; Restriction Requirement dated Nov. 19, 2020 in the U.S. Appl. No. 16/593,882.
USPTO; Non-Final Office Action dated Nov. 25, 2020 in the U.S. Appl. No. 16/943,800.
USPTO; Notice of Allowance dated Dec. 2, 2020 in the U.S. Appl. No. 16/076,655.
USPTO; Restriction Requirement dated Dec. 8, 2020 in the U.S. Appl. No. 16/563,738.
Bergvall et al. "The E1 proteins", Virology 445; p. 35-56, (Year:2013).
McBride, A., "The Papillomavirus E2 proteins", Virology 445: p. 57-79, (Year: 2013).
Chiang C-m et al., "Viral E1 and E2 proteins support replication of homologous and heterologous papillomaviral origins." PNAS 89: p. 5799-5803, (Year: 1992).
Krajinovic et al., "Sequencing data on the long control region of human papillomavirus type 16." Journal of General Virology 72:2573-2576, (Year: 1991).
Seedorg et al., "Human Papillomavirus type 16 DNA sequence." Virology 145: p. 181-185, (Year: 1985).
Jaalouk, et al. "A Self-inactivating retrovector incorporating the IL-2 promoter for activation-induced transgene expression engineered t-cells," Virology Journal: p. 1-12, (Year: 2006).
USPTO; Non-Final Office Action dated Sep. 22, 2020 in the U.S. Appl. No. 16/308,373.
USPTO; Notice of Allowance dated Jul. 10, 2020 in the U.S. Appl. No. 16/530,908.
USPTO; Final Office Action dated Jul. 27, 2020 in the U.S. Appl. No. 16/076,655.
JP; Japanese Office Action in the Application No. 2018-536892 dated Jun. 26, 2020.
EPO; Examination Report dated Oct. 7, 2021 in App. No. 16822021.8.
Nada et al, "Enhancing adoptive cancer immunotherapy with Vγ2Vδ2 T cells through pulse zoledronate stimulation", Journal for Immunotherapy of Cancer, vol. 5, No. 1, (Feb. 21, 2017), pp. 1-23, (2017) DOI 10.1186/s40425-017-0209-6.
Benyamine et al., "BTN3A molecules considerably improve V γ9Vδ2T cells-based immunotherapy in acute myeloid leukemia," OncoImmunology, vol. 5, No. 10, 10 pages, (Oct. 2, 2016), E1146843.
Harly et al., "Key implication of CD277/butyrophilin-3 (BTN3A) in cellular stress sensing by a major human γδ T-cell subset," American Society of Hematology, vol. 120, No. 11, (Sep. 13, 2012), pp. 2269-2279, XP055081172, ISSN: 0006-4971, DOI: 10.1182/blood-2012-05-430470.
Wang et al., "Intravenous Delivery of SiRNA Targeting CD47 Effectively Inhibits Melanoma Tumor Growth and Lung Metastasis", Molecular Therapy, pp. 1919-1929, vol. 21, No. 10, Oct. 2013.
USPTO; Notice of Allowance dated Feb. 10, 2021 in the U.S. Appl. No. 16/943,800.
USPTO; Non-Final Office Action dated Feb. 19, 2021 in the U.S. Appl. No. 15/580,661.
USPTO; Corrected Notice of Allowance dated Mar. 3, 2021 in the U.S. Appl. No. 16/687,525.
USPTO; Non-Final Office Action dated Mar. 12, 2021 in the U.S. Appl. No. 16/563,738.
CN; 1st Office Action in the CN Application No. 202010396594.8 dated Jan. 15, 2021.
EP; Supplementary Search Report in the EP Application No. 18817253 dated Feb. 10, 2021.
JP; Office Action in the JP Application No. 2018-547354 dated Feb. 16, 2021.
JP; Office Action in the JP Application No. 2018-541270 dated Jan. 8, 2021.
USPTO; Final Office Action dated May 27, 2021 in the U.S. Appl. No. 15/736,384.
JP; Office Action in the JP Application No. 2019-500475 dated Mar. 4, 2021.
JP; Office Action in the JP Application No. 2019-500423 dated Jun. 2, 2021.
USPTO; Notice of Allowance dated Jan. 26, 2021 in the U.S. Appl. No. 16/593,882.
Wolstein et al., "Preclinical Safety and Efficacy of an Anti-HIV-1 Lentiviral Vector Containing a Short Hairpin RNA to CCR5 and the C46 Fusion Inhibitor," Molecular Therapy—Methods & Clinical Development (2014).
Anderson et al., "HIV-1 Resistance Conferred by siRNA Cosuppression of CXCR4 and CCR5 Coreceptors by a Bispecific Lentiviral Vector," Aids Research and Therapy, 2:1, pp. 1-12, 2005.
USPTO; Non-Final Office Action dated Jun. 27, 2022 in U.S. Appl. No. 15/736,284.
EP Office Action in European Application No. 17750547.6, dated Apr. 29, 2022, 4 pages.
JP Office Action in Japanese Application No. 2019-500423, dated Apr. 27, 2022, 9 pages (with English translation).
JP Office Action in Application No. 2021-84813, dated Jun. 23, 2022, 6 pages.
Anderson et al., Specific Transduction of HIV-Susceptible Cells for CCR5 Knockdown and Resistance to HIV Infection: A Novel Method for Targeted Gene Therapy and Intracellular Immuniczation, J. Acquir, Immune. Defic. Syndr., vol. 52, No. 2 Oct. 1, 2009.
Zhang et al. "Uracils at Nucleotide Position 9-11 are Required for the Rapid Turnover of miR-29 Family," Nucleic Acids Research, vol. 39, No. 10, pp. 4387-4398, 2011.
IL Office Action in App. No. 284348, dated Jun. 12, 2022, 3 pages.
BR Office Action in App. No. BR112019014082-4, dated Jul. 26, 2022, 3 pages.
JP Office Action in Japanese Application No. 2019-536901, dated Jul. 27, 2022, 12 pages.
JP Office Action in Japanese Application No. 2021-174409, dated Nov. 7, 2022, 4 pages (with English translation).
CN Office Action in Chinese Application No. 201880016715, dated Nov. 15, 2022, 13 pages (with English translation).
EP Office Action in European Application No. 18736295, dated Dec. 20, 2022, 10 pages.
IL Office Action in Application No. 266188.3, dated Nov. 21, 2022, 6 pages.

(56) References Cited

OTHER PUBLICATIONS

U.S. Non-Final Action in U.S. Appl. No. 16/476,529, dated Dec. 23, 2022, 65 pages.
IL Notice of Allowance in Israeli Application No. 284348, dated Oct. 23, 2022, 3 pages.
IN Office Action in Indian Application No. 201947000153, dated Oct. 28, 2022, 8 pages.
U.S. Final Office Action in U.S. Appl. No. 17/089,468, dated Nov. 1, 2022, 19 pages.
U.S. Notice of Allowance in U.S. Appl. No. 17/175,278, dated Nov. 9, 2022, 16 pages.
JP Notice of Allowance in Japanese Application No. 2018-541270, dated Aug. 31, 2022, 6 pages (with English translation).
CN; Office Action issued in Application No. 201880016715.2 dated Sep. 21, 2023.
KR; Office Action issued in Application No. 10-2023-7020872 dated Sep. 26, 2023.
U.S. Office Action issued in U.S. Appl. No. 16/476,529 dated Sep. 29, 2023.
KR; Office Action issued in Application No. 10-2019-7023287 dated Oct. 11, 2023.
Hill et al., "Functional and Evolutionary Significance of Human MicroRNA Seed Region Mutations," PLoS ONE 9(12), e115241, pp. 1-13, Dec. 2014.
Japan Office Action dated Apr. 4, 2023 issued in Application No. 2022-071538.
Canada; Office Action dated May 17, 2023 issued in Application No. 3028982.
Korea; Office Action dated Apr. 21, 2023 issued in Application No. 10-2019-7023287.
[Online], "CD4+ T Cell Isolation Kit Human," Miltenyi Biotec, published online in 2015, 3 pages.
AU Office Action in Australian Application No. 2018205388, dated Mar. 3, 2023, 5 pages.
JP Office Action in Japanese Application No. 2020-551499, dated Mar. 10, 2023, 10 pages (with English translation).
Choi J-G., et al., "Multiplexing Seven miRNA-Based shRNAs to Suppress HIV Replication," Molecular Therapy : The Journal of the American Society of Gene Therapy, Feb. 2015, vol. 23, No. 02, pp. 310-320, DOI: 10.1038/mt.2014.205, ISSN 1525-0016, XP055432740.
Davis-Gardner M.E., et al., "eCD4-Ig promotes ADCC activity of sera from HIV-1-infected patients", Department of Immunology and Microbiology, The Scripps Research Institute, PLOS Pathogen, Dec. 18, 2017, 19 Pages, Retrieved from URL: https://doi.org/10.1371/journal.ppat.1006786.
Office Action for Japanese Patent Application No. 2019-500475, dated Jun. 12, 2020, 11 Pages.
Office Action for Japanese Patent Application No. 2021174409, dated May 2, 2023, 13 pages.
Office Action for Japanese Patent Application No. 2022133225, dated Jun. 26, 2023, 10 Pages.
Spartevello F., et al., "Development of Lentiviral Vectors Simultaneously Expressing Multiple siRNAs Against CCR5, vif and tat/rev Genes for an HIV-1 Gene Therapy Approach," Molecular TherapyNucleic Acids, Apr. 19, 2016, vol. 5, pp. 1-12.
EP Office Action in European Application No. 18736295, dated Jan. 25, 2023, 10 pages.
Anderson et al., Safety and Efficacy of a Lentiviral Vector Containing Three Anti-HIV Genes-CCR5 Ribozyme, Tat-Rev siRNA, and TAR Decoy-in SCID-hu Mouse-Derived T Cells, Mol. Ther., vol. 15, pp. 1182-1188, 2007.
JP Notice of Allowance in Japanese Application No. 2019-536901, dated Mar. 3, 2023, 6 pages (with English translation).
JP Office Action in Japanese Application No. 2021-084813, dated Feb. 10, 2023, 10 pages (with English translation).
Kretova et al., Generation of Genetic Constructs that Simultaneously Express Several shRNAs, Biotechniques, vol. 52, 3 pages, 2012.
Spanevello et al., "Combinatorial RNA Interference as a Gene Therapy Strategy for HIV-1 Infection," Retrovirology, vol. 10, 2013.
U.S. Final Office Action in U.S. Appl. No. 16/312,056, dated Jan. 31, 2023, 36 pages.
EP Office Action in European Application No. 16822021, dated Oct. 7, 2021, 4 pages.
JP Office Action in Japanese Application No. 2018-541270, dated Dec. 23, 2021, 19 pages (with English translation).
Yokota, "Gene therapy of virus replication with RNAi", Virus, vol. 55, No. 1, pp. 1-8.
Prebensen et al., "Regulation of Gag- and Env-Specific CD8* T Cell Responses in ART-Naïve HIV- Infected Patients: Potential Implications for Individualized Immunotherapy," PloS ONE 9(12), e115241, pp. 1-13, Dec. 2014.
Lam et al., "Broadly-Specific Cytotoxic T Cells Targeting Multiple HIV Antigens Are Expanded From HIV+ Patients: Implications for Immunotherapy," Molecular Therapy, vol. 23, No. 2, pp. 387-295, Feb. 2015.
U.S.; Office Action issued in U.S. Appl. No. 17/042,043 dated Dec. 6, 2023.
JP; Office Action issued in Application No. 2021-84813 dated Oct. 31, 2023.
JP; Office Action issued in Application No. 2020-551499 dated Nov. 22, 2023.
JP; Office Action issued in Application No. 2022-189475 dated Oct. 10, 2023.

* cited by examiner

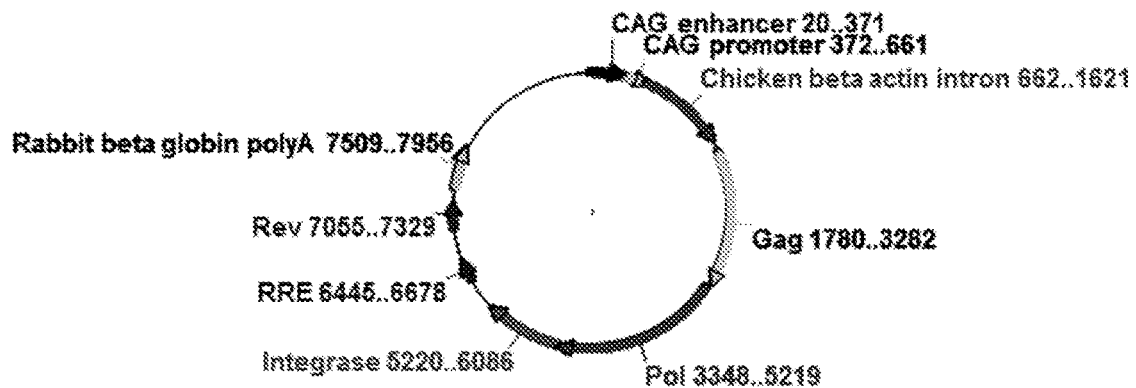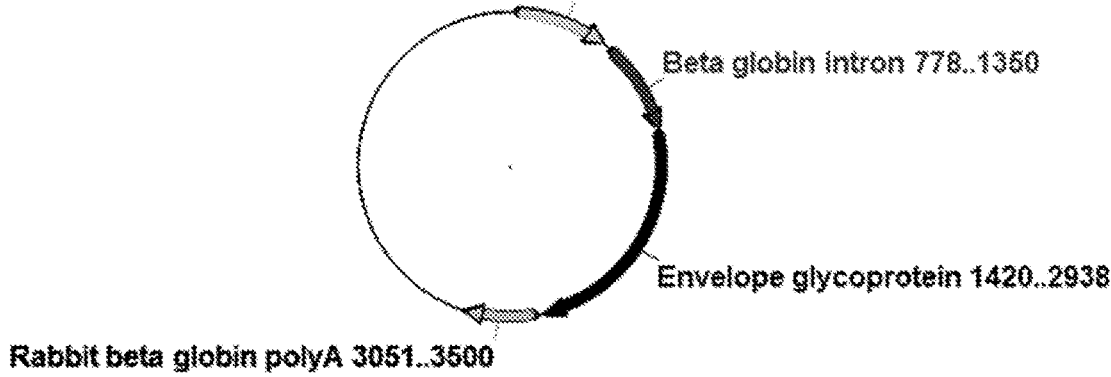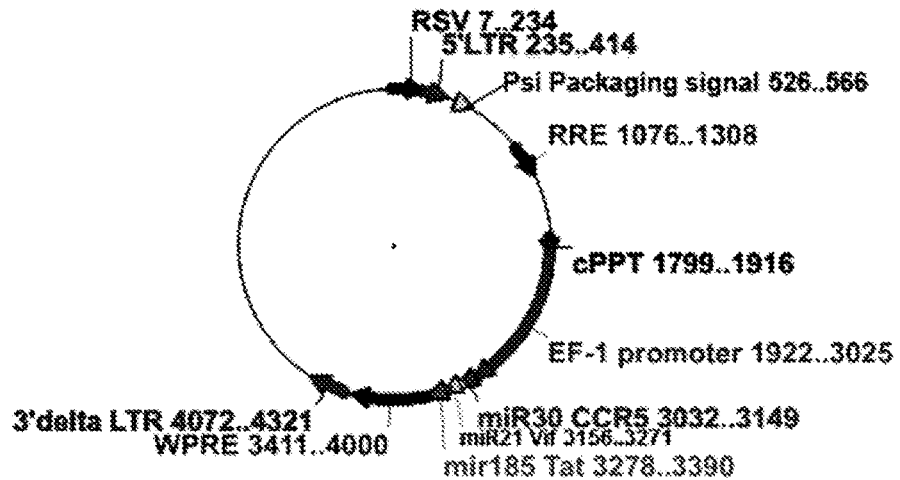
Figure 4

Elongation Factor-1 alpha (EF1-alpha) promoter (SEQ ID NO: 108)

*CCGGTGCCTAGAGAAGGTGGCGCGGGGTAAACTGGGAAAGTGATGTCGTGTACTGGCTCCGCCTT
TTTCCCGAGGGTGGGGGAGAACCGTATATAAGTGCAGTAGTCGCCGTGAACGTTCTTTTTCGCAA
CGGGTTTGCCGCCAGAACACAGGTAAGTGCCGTGTGTGGTTCCCGCGGGCCTGGCCTCTTTACGG
GTTATGGCCCTTGCGTGCCTTGAATTACTTCCACGCCCCTGGCTGCAGTACGTGATTCTTGATCC
CGAGCTTCGGGTTGGAAGTGGGTGGGAGAGTTCGAGGCCTTGCGCTTAAGGAGCCCCTTCGCCTC
GTGCTTGAGTTGAGGCCTGGCCTGGGCGCTGGGGCCGCCGCGTGCGAATCTGGTGGCACCTTCGC
GCCTGTCTCGCTGCTTTCGATAAGTCTCTAGCCATTTAAAATTTTTGATGACCTGCTGCGACGCT
TTTTTTCTGGCAAGATAGTCTTGTAAATGCGGGCCAAGATCTGCACACTGGTATTTCGGTTTTTG
GGGCCGCGGGCGGCGACGGGCCCGTGCGTCCCAGCGCACATGTTCGGCGAGGCGGGGCCTGCGA
GCGCGGCCACCGAGAATCGGACGGGGGTAGTCTCAAGCTGGCCGGCCTGCTCTGGTGCCTGGCCT
CGCGCCGCCGTGTATCGCCCCGCCCTGGGCGGCAAGGCTGGCCCGGTCGGCACCAGTTGCGTGAG
CGGAAAGATGGCCGCTTCCCGGCCCTGCTGCAGGGAGCTCAAAATGGAGGACGCGGCGCTCGGGA
GAGCGGGCGGGTGAGTCACCCACACAAAGGAAAAGGGCCTTTCCGTCCTCAGCCGTCGCTTCATG
TGACTCCACGGAGTACCGGGCGCCGTCCAGGCACCTCGATTAGTTCTCGAGCTTTTGGAGTACGT
CGTCTTTAGGTTGGGGGAGGGGTTTTATGCGATGGAGTTTCCCCACACTGAGTGGGTGGAGACT
GAAGTTAGGCCAGCTTGGCACTTGATGTAATTCTCCTTGGAATTTGCCCTTTTTGAGTTTGGATC
TTGGTTCATTCTCAAGCCTCAGACAGTGGTTCAAAGTTTTTTCTTCCATTTCAGGTGTCGTGAT
GTACA* miR30 CCR5 (SEQ ID NO: 1)
<u>AGGTATATTGCTGTTGACAGTGAGCGACTGTAAACTGAGCTTGCTCTACTGTGAAGCCACAGATG
GGTAGAGCAAGCACAGTTTACCGCTGCCTACTGCCTCGGACTTCAAGGGGCTT</u> miR21 Vif (SEQ ID NO: 109)
CCCGGG*<u>CATCTCCATGGCTGTACCACCTTGTCGGGGATGTGTACTTCTGAACTTGTGTTGAATC
TCATGGAGTTCAGAAGAACACATCCGCACTGACATTTTGGTATCTTTCATCTGACCA</u>* miR185 Tat (SEQ ID NO: 110; SEQ ID NO: 111 (underlined portion))
GCTAGC<u>**GGGCCTGGCTCGAGCAGGGGGCGAGGGATTCCGCTTCTTCCTGCCATAGCGTGGTCCCC
TCCCCTATGGCAGGCAGAAGCGGCACCTTCCCTCCAATGACCGCGTCTTCGTC**</u>

FIG. 7

Vector 1
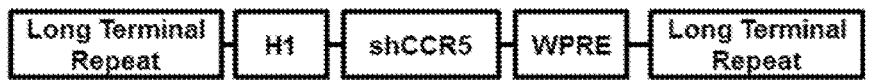
Vector 2
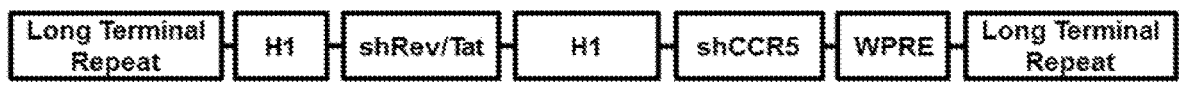
Vector 3
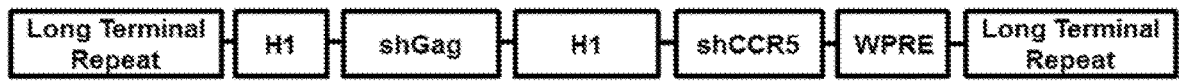
Vector 4
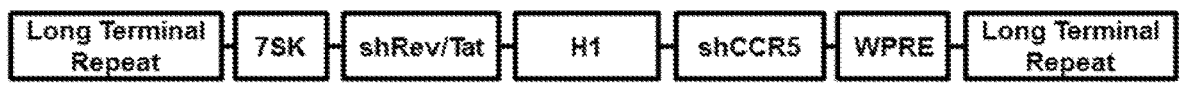
Vector 5
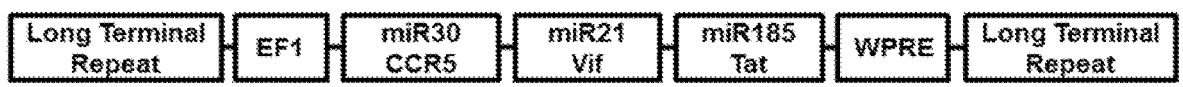
Vector 6
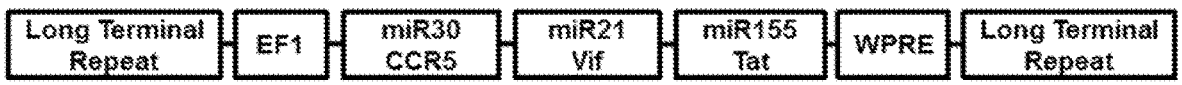
Vector 7
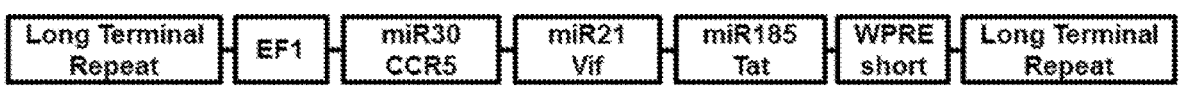
Vector 8
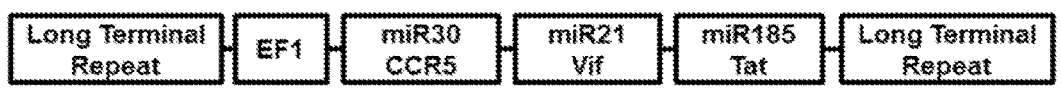
Vector 9
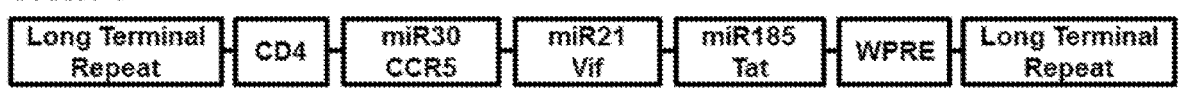
FIG. 8

HIV PRE-IMMUNIZATION AND IMMUNOTHERAPY

CROSS-REFERENCE TO RELATED APPLICATIONS

This application claims priority to: U.S. Provisional Patent Application No. 62/360,185 filed on Jul. 8, 2016 entitled "HIV PRE-IMMUNIZATION AND IMMUNOTHERAPY", U.S. Provisional Patent Application No. 62/385,864 filed on Sep. 9, 2016 entitled "HIV PRE-IMMUNIZATION AND IMMUNOTHERAPY", U.S. Provisional Patent Application No. 62/409,270 filed on Oct. 17, 2016 entitled "HIV PRE-IMMUNIZATION AND IMMUNOTHERAPY," and PCT/US17/13019 filed on Jan. 11, 2017 entitled "HIV PRE-IMMUNIZATION AND IMMUNOTHERAPY", the disclosures of which are incorporated herein by reference.

FIELD OF THE INVENTION

The present invention relates generally to the field of immunization and immunotherapy for the treatment and prevention of HIV. In particular, the disclosed methods relate to obtaining and processing leukocytes from HIV+ individuals seeking a functional cure to prepare a cell product suitable for infusion to such HIV+ individuals.

BACKGROUND OF THE INVENTION

Combination antiretroviral therapy (cART) (also known as Highly Active Antiretroviral Therapy or HAART) limits HIV-1 replication and slows disease progression, but drug toxicities and the emergence of drug-resistant viruses are challenges for long-term control in HIV-infected persons. Additionally, traditional antiretroviral therapy, while successful at delaying the onset of AIDS or death, has yet to provide a functional cure. Alternative treatment strategies are needed.

Intense interest in immunotherapy for HIV infection has been precipitated by emerging data indicating that the immune system has a major, albeit usually insufficient, role in limiting HIV replication. Virus-specific T-helper cells, which are critical to maintenance of cytolytic T cell (CTL) function, likely play a role. Viremia is also influenced by neutralizing antibodies, but they are generally low in magnitude in HIV infection and do not keep up with evolving viral variants in vivo.

Together these data indicate that increasing the strength and breadth of HIV-specific cellular immune responses may have a clinical benefit through so-called HIV immunotherapy. Some studies have tested vaccines against HIV, but success has been limited to date. Additionally, there has been interest in augmenting HIV immunotherapy by utilizing gene therapy techniques, but as with other immunotherapy approaches, success has been limited.

Viral vectors can be used to transduce genes into target cells owing to specific virus-host cell interactions and mechanisms for expressing therapeutic gene constructs. As a result, viral vectors have been used as vehicles for the transfer of genes into many different cell types including whole T cells or other immune cells as well as embryos, fertilized eggs, isolated tissue samples, tissue targets in situ and cultured cells. The ability to introduce and express foreign or altered genes in a cell is useful for therapeutic interventions such as gene therapy, somatic cell reprogramming of induced pluripotent stem cells, and various types of immunotherapy.

Gene therapy is one of the ripest areas of biomedical research with the potential to create new therapeutics that may involve the use of viral vectors. In view of the wide variety of potential genes available for therapy, an efficient means of delivering these genes is needed to fulfill the promise of gene therapy as a means of treating infectious and non-infectious diseases. Several viral systems including murine retrovirus, adenovirus, parvovirus (adeno-associated virus), coxsackie virus, vaccinia virus, and herpes virus have been proposed as therapeutic gene transfer vectors.

There are many factors that must be considered when developing viral vectors including tissue tropism, stability of virus preparations, stability and control of expression, genome packaging capacity, construct-dependent vector stability, and whether or not the desired outcome is to have stable gene integration into the host genome. In addition, in vivo application of viral vectors is often limited by host immune responses against viral structural proteins and/or transduced gene products.

Thus, toxicity and safety are key hurdles that must be overcome for viral vectors to be used in vivo for the treatment of subjects. There are numerous historical examples of gene therapy applications in humans that have met with problems associated with the host immune responses against the gene delivery vehicles or the therapeutic gene products. Viral vectors (e.g., adenovirus) which co-transduce several viral genes together with one or more therapeutic gene(s) are particularly problematic.

Although lentiviral vectors do not generally induce cytotoxicity and do not elicit strong host immune responses, some lentiviral vectors such as HIV-1, which encode several immunostimulatory gene products, have the potential to cause cytotoxicity and induce strong immune responses in vivo. However, this may not be a concern for lentivirus-derived transducing vectors that do not encode viral genes after transduction. Of course, this may not always be the case, as sometimes the purpose of the vector is to encode a protein that will provoke a clinically useful immune response.

Another important issue related to the use of lentiviral vectors is that of possible cytopathogenicity upon exposure to some cytotoxic viral proteins. Exposure to certain HIV-1 proteins may induce cell death or functional unresponsiveness in T cells. Likewise, the possibility of generating replication-competent, virulent virus by recombination is often a concern. Accordingly, there remains a need for improved treatments of HIV.

SUMMARY OF THE INVENTION

In one aspect, a method of treating cells infected with HIV is provided. The method variously includes contacting peripheral blood mononuclear cells (PBMC) isolated from a subject infected with HIV with a therapeutically effective amount of a stimulatory agent, wherein the contacting is carried out ex vivo; transducing the PBMC ex vivo with a viral delivery system encoding at least one genetic element; and culturing the transduced PBMC for a sufficient period of time to ensure adequate transduction. In embodiments, the transduced PBMC are cultured from about 1 to about 35 days. In embodiments, the method further includes infusing the transduced PBMC into a subject. In embodiments, the method further includes positively selecting HIV-specific CD4+ T cells from the PBMC. In further embodiments, the HIV-specific CD4+ T cells are positively selected using at least one physical method of selection. In embodiments, the subject is a human. In embodiments, the stimulatory agent includes any agent suitable for stimulating a T cell response in a subject. In embodiments, the stimulatory agent is a peptide or mixture of peptides, and in embodiments includes a gag peptide. In further embodiments, the stimulatory agent is a vaccine. In embodiments, the vaccine is a HIV vaccine, and in embodiments, the HIV vaccine is a MVA/HIV62B vaccine or a variant thereof. In embodiments, the viral delivery system includes a lentiviral particle. In embodiments, the at least one genetic element includes a small RNA capable of inhibiting production of chemokine receptor CCR5. In further embodiments, the at least one genetic element includes at least one small RNA capable of targeting a HIV RNA sequence. In further embodiments, the at least one genetic element includes a small RNA capable of inhibiting production of chemokine receptor CCR5 and at least one small RNA capable of targeting an HIV RNA sequence. The HIV RNA sequence includes any HIV sequence suitable for targeting by a viral delivery system. In embodiments, the HIV RNA sequence includes one or more of a HIV Vif sequence, a HIV Tat sequence, or a variant thereof. The at least one genetic element includes any genetic element capable of being expressed by a viral delivery system. In embodiments, the at least one genetic element includes a microRNA or a shRNA. In further embodiments, the at least one genetic element comprises a microRNA cluster.

In another aspect, a method is disclosed that includes obtaining peripheral blood from HIV+ individuals; fractionating the blood to obtain a PBMC population; contacting the PBMC population with purified antigen-presenting cells or peptides or proteins representing components of HIV; culturing the contacted PBMC population for about 1 to about 35 days to increase the number of antigen-specific T cells; positively selecting cells that respond to peptide stimulation to produce an enriched cell fraction; transducing the enriched cell fraction ex vivo with a viral delivery system as detailed herein, and culturing the transduced cell fraction for a period of time sufficient to ensure adequate transduction. The order of the method steps disclosed herein can be changed. As a non-limiting example, the steps of positively selecting cells and transducing cells may be reversed and polyclonal stimulation may also be added to improve transduction efficiency.

In embodiments, the PBMC population is further purified to produce a purified fraction of PBMC. In embodiments, further purified fractions of PBMC are contacted with peptides or proteins representing components of HIV.

In another aspect, the at least one genetic element includes a microRNA having at least 80%, or at least 85%, or at least 90%, or at least 95% percent identity with AGGTATATTGCTGTTGACAGTGAGCGACTGTAAACTGAGCTTGCTCTACTGTGAAG CCACAGATGGGTAGAGCAAGCACAGTTTACCGCTGCCTACTGCCTCGGACTTCAA GGGGCTT (SEQ ID NO: 1). In embodiments, the at least one genetic element comprises SEQ ID NO: 1.

In another aspect, the at least one genetic element includes a microRNA having at least 80%, or at least 85%, or at least 90%, or at least 95% percent identity with CATCTCCATGGCTGTACCACCTTGTCGGGG-GATGTGTACTTCTGAACTTGTGTTGA ATCTCATG-GAGTTCAGAAGAACACATCCGCACTGACATTTTGG-TATCTTTCATCTG ACCA (SEQ ID NO: 2); or at least 80%, or at least 85%, or at least 90%, or at least 95% percent identity with GGGCCTGGCTCGAGCAGGGGGCGAGG-GATTCCGCTTCTTCCTGCCATAGCGTGG TCCCCTCCCC-TATGGCAGGCAGAAGCGGCACCTTCCCTCC-CAATGACCGCGTCTTC GTCG (SEQ ID NO: 3). In embodiments, the at least one genetic element includes SEQ ID NO: 2; or SEQ ID NO: 3.

In another aspect, the microRNA cluster includes a sequence having at least 80%, or at least 85%, or at least 90%, or at least 95% percent identity with AGGTATATTGCTGTTGACAGTGAGCGACTGTAAACTGAGCTTGCTCTACTGTGAAG CCACAGATGGGTAGAGCAAGCACAGTTTACCGCTGCCTACTGCCTCGGACTTCAA GGGGCTTCCCGGGCATCTCCATGGCTGTACCACCTTGTCGGGG-GATGTGTACTTCT GAACTTGTGTTGAATCTCATGGAGTTCAGAAGAACACATCCGCACTGACATTTTGG TATCTTT-CATCTGACCAGCTAGCGGGCCTGGCTCGAGCAGG-GGGCGAGGGATTCC GCTTCTTCCTGCCATAGCGTGGTCCCCTCCCC-TATGGCAGGCAGAAGCGGCACCTT CCCTCC-CAATGACCGCGTCTTCGTC (SEQ ID NO: 31). In embodiments, the microRNA cluster includes SEQ ID NO: 31.

In another aspect, a method of treating HIV infection in a subject is disclosed. The method variously includes immunizing the subject with an effective amount of a first stimulatory agent; removing leukocytes from the subject and obtaining peripheral blood mononuclear cells (PBMC). The method further includes contacting the PBMC ex vivo with a therapeutically effective amount of a second stimulatory agent; transducing the PBMC ex vivo with a viral delivery system encoding at least one genetic element; and culturing the transduced PBMC for a sufficient period of time to ensure adequate transduction. In embodiments, the transduced PBMC may be cultured from about 1 to about 35 days. In embodiments, the method further includes positively selecting HIV-specific CD4+ T cells from the PBMC. In further embodiments, the HIV-specific CD4+ T cells are positively selected using at least one physical method of selection. In embodiments, the method further involves infusing the transduced PBMC into a subject. The subject may be a human. The first and second stimulatory agents may be the same or different. The first and second stimulatory agents may include one or more of a peptide or mixture of peptides. In embodiments, at least one of the first and second stimulatory agents includes a gag peptide. In embodiments, at least one of the first and second stimulatory agents includes a mixture of gag peptides that are recognized by immune cells resident in the PBMC or in the purified fractions of PBMC. The at least one of the first and second stimulatory agents may include a vaccine. In embodiments, the vaccine is a HIV vaccine; in further embodiments, the HIV vaccine is a MVA/HIV62B vaccine or a variant thereof. In embodiments, the viral delivery system includes a lentiviral particle. In embodiments, the at least one genetic element includes a small RNA capable of inhibiting production of chemokine receptor CCR5. In embodiments, the at least one genetic element includes at least one small RNA capable of targeting an HIV RNA sequence. In embodiments, the at least one genetic element includes a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one genetic element may include a microRNA or a shRNA. In embodiments, the at least one genetic element comprises a synthetic microRNA cluster designed for simultaneous expression of all elements in the cluster under control of a single transcriptional promoter. In embodiments, the PBMC population is further purified to produce a purified fraction of PBMC.

In another aspect, the at least one genetic element includes a microRNA having at least 80%, or at least 85%, or at least 90%, or at least 95% percent identity with AGGTATAT-TGCTGTTGACAGTGAGCGACTGTAAACT-GAGCTTGCTCTACTGTGAAG CCACA-GATGGGTAGAGCAAGCACAGTTTACCGCTGCCTAC-TGCCTCGGACTTCAA GGGGCTT (SEQ ID NO: 1). In embodiments, the at least one genetic element comprises SEQ ID NO: 1.

In another aspect, the at least one genetic element includes a microRNA having at least 80%, or at least 85%, or at least 90%, or at least 95% percent identity with CATCTC-CATGGCTGTACCACCTTGTCGGGG-GATGTGTACTTCTGAACTTGTGTTGA ATCTCATG-GAGTTCAGAAGAACACATCCGCACTGACATTTTGG-TATCTTTCATCTG ACCA (SEQ ID NO: 2); or at least 80%, or at least 85%, or at least 90%, or at least 95% percent identity with GGGCCTGGCTCGAGCAGGGGGCGAGG-GATTCCGCTTCTTCCTGCCATAGCGTGG TCCCCTCCCC-TATGGCAGGCAGAAGCGGCACCTTCCCTCC-CAATGACCGCGTCTTC GTCG (SEQ ID NO: 3). In embodiments, the at least one genetic element includes SEQ ID NO: 2 or SEQ ID NO: 3.

In another aspect, the microRNA cluster includes a sequence having at least 80%, or at least 85%, or at least 90%, or at least 95% percent identity with AGGTATAT-TGCTGTTGACAGTGAGCGACTGTAAACT-GAGCTTGCTCTACTGTGAAG CCACA-GATGGGTAGAGCAAGCACAGTTTACCGCTGCCTAC-TGCCTCGGACTTCAA GGGGCTTCCCGGGCATCTC-CATGGCTGTACCACCTTGTCGGGG-GATGTGTACTTCT GAACTTGTGTTGAATCTCATG-GAGTTCAGAAGAACACATCCGCACTGACATTTTGG TATCTTT-CATCTGACCAGCTAGCGGGCCTGGCTCGAGCAGG-GGGCGAGGGATTCC GCTTCTTCCTGCCAT-AGCGTGGTCCCCTCCCC-TATGGCAGGCAGAAGCGGCACCTT CCCTCC-CAATGACCGCGTCTTCGTC (SEQ ID NO: 31). In embodiments, the microRNA cluster includes SEQ ID NO: 31.

In another aspect, a lentiviral vector is disclosed. The lentiviral vector includes at least one encoded genetic element, wherein the at least one encoded genetic element comprises a small RNA capable of inhibiting production of chemokine receptor CCR5. The at least one encoded genetic element may also comprise at least one small RNA capable of targeting an HIV RNA sequence. In another aspect, the at least one encoded genetic element comprises a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one encoded genetic element may include a microRNA or a shRNA. The at least one encoded genetic element may include a synthetic microRNA cluster designed for simultaneous expression of all elements in the cluster under control of a single transcriptional promoter.

In another aspect, the at least one genetic element includes a microRNA having at least 80%, or at least 85%, or at least 90%, or at least 95% percent identity with AGGTATAT-TGCTGTTGACAGTGAGCGACTGTAAACT-GAGCTTGCTCTACTGTGAAG CCACA-GATGGGTAGAGCAAGCACAGTTTACCGCTGCCTA-CTGCCTCGGACTTCAA GGGGCTT (SEQ ID NO: 1). In embodiments, the at least one genetic element comprises SEQ ID NO: 1.

In another aspect, the at least one genetic element includes a microRNA having at least 80%, or at least 85%, or at least 90%, or at least 95% percent identity with CATCTC-CATGGCTGTACCACCTTGTCGGGG-GATGTGTACTTCTGAACTTGTGTTGA ATCTCATG-GAGTTCAGAAGAACACATCCGCACTGACATTTTGG-TATCTTTCATCTG ACCA (SEQ ID NO: 2); or at least 80%, or at least 85%, or at least 90%, or at least 95% percent identity with GGGCCTGGCTCGAGCAGGGGGCGAGG-GATTCCGCTTCTTCCTGCCATAGCGTGG TCCCCTCCCC-TATGGCAGGCAGAAGCGGCACCTTCCCTCC-CAATGACCGCGTCTTC GTCG (SEQ ID NO: 3). In embodiments, the at least one genetic element includes SEQ ID NO: 2; or SEQ ID NO: 3.

In another aspect, the microRNA cluster includes a sequence having at least 80%, or at least 85%, or at least 90%, or at least 95% percent identity with AGGTATAT-TGCTGTTGACAGTGAGCGACTGTAAACT-GAGCTTGCTCTACTGTGAAG CCACA-GATGGGTAGAGCAAGCACAGTTTACCGCTGCCTAC-TGCCTCGGACTTCAA GGGGCTTCCCGGGCATCTC-CATGGCTGTACCACCTTGTCGGGG-GATGTGTACTTCT GAACTTGTGTTGAATCTCATG-GAGTTCAGAAGAACACATCCGCACTGACATTTTGG TATCTTT-CATCTGACCAGCTAGCGGGCCTGGCTCGAGCAGG-GGGCGAGGGATTCC GCTTCTTCCTGCCAT-AGCGTGGTCCCCTCCCC-TATGGCAGGCAGAAGCGGCACCTT CCCTCC-CAATGACCGCGTCTTCGTC (SEQ ID NO: 31). In embodiments, the microRNA cluster includes SEQ ID NO: 31.

In another aspect, a lentiviral vector system for expressing a lentiviral particle is disclosed. The system includes a lentiviral vector as described herein; an envelope plasmid for expressing an envelope protein preferably optimized for infecting a cell; and at least one helper plasmid for expressing genes of interest. In embodiments, the genes of interest include one or more of gag, pol, and rev genes. In embodiments, the lentiviral vector, the envelope plasmid, and the at least one helper plasmid are transfected into a packaging cell line. In further embodiments, a lentiviral particle is produced by the packaging cell line. In embodiments, the lentiviral particle is capable of modulating production of a target of interest. In embodiments, the target of interest is any of chemokine receptor CCR5 or an HIV RNA sequence. The system may further include a first helper plasmid and a second helper plasmid. In embodiments, a first helper plasmid expresses the gag and pol genes, and a second helper plasmid expresses the rev gene.

In another aspect, a lentiviral particle capable of infecting a cell is provided. The lentiviral particle includes an envelope protein preferably optimized for infecting a cell, and a lentiviral vector as described herein. In embodiments, the envelope protein may be optimized for infecting a T cell. In embodiments, the envelope protein is optimized for infecting a CD4+ T cell.

In another aspect, a modified cell is provided. The modified cell includes any cell capable of being infected with a lentiviral vector system for use in accordance with present aspects and embodiments. In embodiments, the cell is a CD4+ T cell that is infected with a lentiviral particle. In embodiments, the CD4+ T cell also has been selected to recognize an HIV antigen. In embodiments, the HIV antigen includes a gag antigen. In embodiments, the CD4+ T cell expresses a decreased level of CCR5 following infection with the lentiviral particle.

In another aspect, a method of selecting a subject for a therapeutic treatment regimen is provided. The method variously includes immunizing the subject with an effective amount of a first stimulatory agent; removing leukocytes from the subject and purifying peripheral blood mononuclear cells (PBMC) and determining a first quantifiable measurement associated with at least one factor associated with the PBMC; contacting the PBMC ex vivo with a therapeutically effective amount of a second stimulatory agent, and determining a second measurement associated with the at least one factor associated with the PBMC, whereby when the second quantifiable measurement is higher than the first quantifiable measurement, the subject is selected for the treatment regimen. The at least one factor may include any factor associated with T cell proliferation or IFN gamma production.

The foregoing general description and following brief description of the drawings and detailed description are exemplary and explanatory and are intended to provide further explanation of the invention as claimed. Other objects, advantages, and novel features will be readily apparent to those skilled in the art from the following brief description of the drawings and detailed description of the invention.

BRIEF DESCRIPTION OF THE DRAWINGS

FIG. 4 depicts an exemplary 3-vector lentiviral vector system in a circularized form.

FIG. 7 depicts exemplary vector sequences. Positive (i.e., genomic) strand sequences of the promoter and miR cluster were developed for inhibiting the spread of CCR5-tropic HIV strains. Sequences that are not underlined comprise the EF-1 alpha promoter of transcription that was selected as being a preferable promoter for this miR cluster. Sequences that are underlined show the miR cluster consisting of miR30 CCR5, miR21 Vif, and miR185 Tat (as shown collectively in SEQ ID NO: 33).

FIG. 8 depicts exemplary lentiviral vector constructs according to various aspects of this disclosure.

DETAILED DESCRIPTION

Overview Disclosed herein are methods and compositions for treating and/or preventing human immunodeficiency virus (HIV) disease to achieve a functional cure. The methods and compositions include integrating lentivirus, non-integrating lentivirus, and related viral vector technology as described below.

Figure 1:
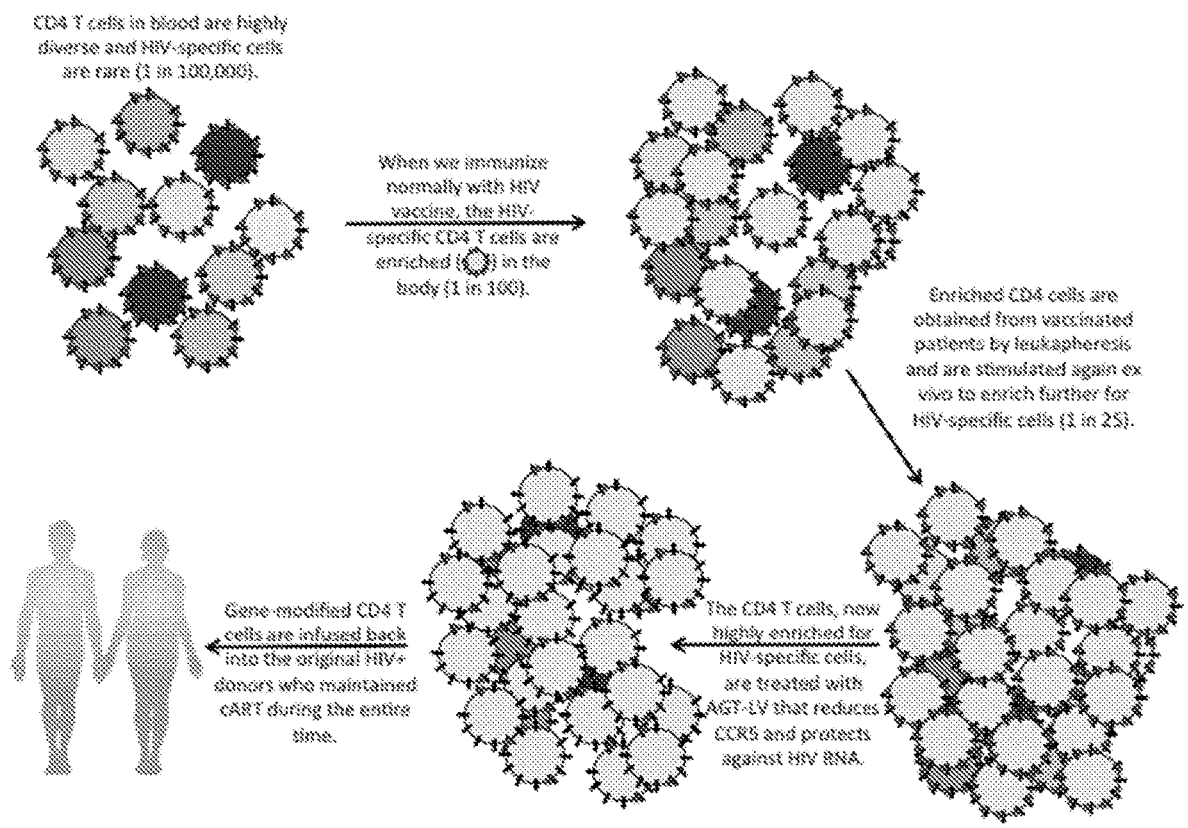
FIG. 1 depicts a flow diagram of an ex vivo treatment method of the present disclosure.

Disclosed herein are therapeutic viral vectors (e.g., lentiviral vectors), immunotherapies, and methods for their use for treating HIV infection. In embodiments, methods and compositions for achieving a functional cure for HIV infection are provided. As depicted in FIG. 1 herein, the various aspects and embodiments include a first stimulation event, for example a first therapeutic immunization with vaccines intended to produce strong immune responses against HIV in HIV-infected patients, for example with stable suppression of viremia due to daily administration of HAART. In embodiments, the first stimulation event enriches the fraction of HIV-specific CD4 T cells. This is followed by (1) isolating peripheral leukocytes by leukapheresis or purifying PBMC or purifying fractions of PBMC from venous blood, (2) a second stimulating event, for example stimulating CD4 T cells ex vivo with a suitable stimulatory agent, such as any vaccine or protein, for example, HIV or HIV-related peptides, (3) selecting an enriched cell population based on a biological response to peptide stimulation, (4) performing therapeutic lentivirus transduction, ex vivo T cell culture, and (5) re-infusion back into the original patient.

Figure 2:
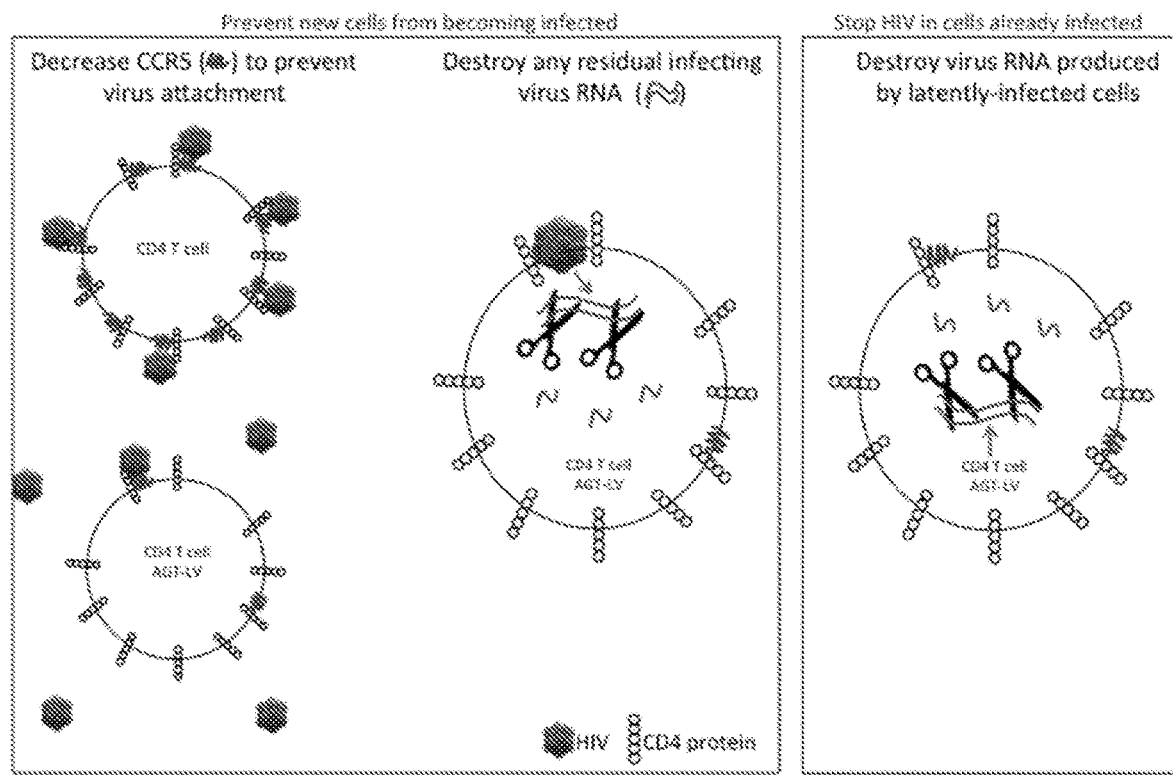
FIG. 2 depicts CD4+ T cell alteration and prevention of new infection in accordance with the present disclosure.

The various methods and compositions can be used to prevent new cells, such as CD4+ T cells, from becoming infected with HIV. For example as illustrated in FIG. 2, to prevent new cells from becoming infected, CCR5 expression can be targeted to prevent virus attachment. Further, destruction of any residual infecting viral RNA can also be targeted. In respect of the foregoing, and in reference to FIG. 2 herein, compositions and methods are provided to stop the HIV viral cycle in cells that have already become infected with HIV. To stop the HIV viral cycle, viral RNA produced by latently-infected cells, such as latently-infected CD4+ T cells, is targeted.

Previous efforts to achieve a cure for HIV have fallen short due to, among others, the failure to obtain sufficient numbers of HIV-specific CD4 T cells with protective genetic modifications. When this number is below a critical threshold, a functional cure as described herein is not achieved. For example, upon termination of antiretroviral therapy HIV re-emergence generally follows. Thereafter, patients often experience rapid destruction of HIV-specific CD4 T cells, followed by return to progression of disease despite prior genetic therapy. By employing selective enrichment for HIV-specific T cells in accordance with the compositions and methods described herein, a new HIV treatment regimen has been developed including, in various embodiments, a functional cure.

Definitions and Interpretation

Unless otherwise defined herein, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art. The methods and techniques of the present disclosure are generally performed according to conventional methods well-known in the art and as described in various general and more specific references that are cited and discussed throughout the present specification unless otherwise indicated. See, e.g.: Sambrook J. & Russell D. Molecular Cloning: A Laboratory Manual, 3rd ed., Cold Spring Harbor Laboratory Press, Cold Spring Harbor, N.Y. (2000); Ausubel et al., Short Protocols in Molecular Biology: A Compendium of Methods from Current Protocols in Molecular Biology, Wiley, John & Sons, Inc. (2002); Harlow and Lane, Using Antibodies: A Laboratory Manual; Cold Spring Harbor Laboratory Press, Cold Spring Harbor, N.Y. (1998); and Coligan et al., Short Protocols in Protein Science, Wiley, John & Sons, Inc. (2003). Any enzymatic reactions or purification techniques are performed according to manufacturer's specifications, as commonly accomplished in the art or as described herein. The nomenclature used in connection with, and the laboratory procedures and techniques of, analytical chemistry, synthetic organic chemistry, and medicinal and pharmaceutical chemistry described herein are those well-known and commonly used in the art.

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

As used herein, the terms "administration of" or "administering" an active agent means providing an active agent of the invention to the subject in need of treatment in a form that can be introduced into that individual's body in a therapeutically useful form and therapeutically effective amount.

As used herein, the term "AGT103" refers to a particular embodiment of a lentiviral vector that contains a miR30-CCR5/miR21-Vif/miR185-Tat microRNA cluster sequence, as detailed herein.

As used herein, the term "AGT103T" refers to a cell that has been transduced with a lentivirus that contains the AGT103 lentiviral vector.

As used herein, the term "CCR5" refers to C-C chemokine receptor 5. Reference herein to "CCR5delta32" is reference to a mutant genotype in the CCR5 gene.

As used herein, the term "CD" refers to a particular cluster of differentiation protein. A non-limiting example of this terminology as used herein is CD4 protein expression. Examples of such proteins include, but are not limited to CD4.

As used herein, the term "cART" refers to combination antiretroviral therapy. The term "cART" may be used synonymously with HAART (Highly Active Antiretroviral Therapy).

Throughout this specification and claims, the word "comprise," or variations such as "comprises" or "comprising," will be understood to imply the inclusion of a stated integer or group of integers but not the exclusion of any other integer or group of integers. Further, as used herein, the term "includes" means includes without limitation.

As used herein, the term "engraftment" refers to the ability for one skilled in the art to determine a quantitative level of sustained engraftment in a subject following infusion of a cellular source (see for e.g.: Rosenberg et al., *N. Engl. J Med.* 323:570-578 (1990); Dudley el al., *J Immunother.* 24:363-373 (2001); Yee et al., *Curr. Opin. Immunol.* 13:141-146 (2001); Rooney et al., *Blood* 92:1549-1555 (1998)).

The terms, "expression," "expressed," or "encodes" refer to the process by which polynucleotides are transcribed into mRNA and/or the process by which the transcribed mRNA is subsequently being translated into peptides, polypeptides, or proteins. Expression may include splicing of the mRNA in a eukaryotic cell or other forms of post-transcriptional modification or post-translational modification.

The term "functional cure", as referenced above, and further defined herein, refers to a state or condition wherein HIV+ individuals who previously required ongoing HIV therapies such as cART or HAART, may survive with low or undetectable virus replication using lower doses, intermittent doses, alternate drug combinations or single agents, or discontinued dosing of such HIV therapies. An individual may be said to have been "functionally cured" while still requiring adjunct therapy to maintain low level virus replication and slow or eliminate disease progression. A possible outcome of a functional cure is the eventual eradication of all or virtually all HIV such that no recurrence is detected within a specified time frame, for example, 1 month, 3 months, 6 months, 1 year, 3 years, and 5 years, and all other time frames as may be defined.

The term "HIV vaccine" encompasses immunogens plus vehicle plus adjuvant intended to elicit HIV-specific immune responses. The term "HIV vaccine" is within the meaning of the term "stimulatory agent" as described herein. A "HIV vaccine" may include purified or whole inactivated virus particles that may be HIV or recombinant virus vectors capable of expressing HIV proteins, protein fragments or peptides, glycoprotein fragments or glycopeptides, in addition to recombinant bacterial vectors, plasmid DNA or RNA capable of directing cells to producing HIV proteins, glycoproteins or protein fragments able to elicit specific immunity. Alternately, specific methods for immune stimulation including anti-CD3/CD28 beads, T cell receptor-specific antibodies, mitogens, superantigens, cytokines and other chemical or biological stimuli may be used to activate dendritic, T or B cells for the purposes of enriching HIV-specific CD4 T cells prior to transduction or for in vitro assay of lentivirus-transduced CD4 T cells.

Activating substances may be soluble, polymeric assemblies, liposome or endosome-based or linked to beads. Cytokines including interleukin-2, 6, 7, 12, 15, 23 or others may be added to improve cellular responses to stimuli and/or improve the survival of CD4 T cells throughout the culture and transduction intervals. Alternately, and without limiting any of the foregoing, the term "HIV vaccine" encompasses the MVA/HIV62B vaccine and variants thereof. The MVA/HIV62B vaccine is a known highly attenuated double recombinant MVA vaccine. The MVA/HIV62B vaccine was constructed through the insertion of HIV-1 gag-pol and env sequences into the known MVA vector (see: for e.g.: Goepfert et al. (2014) *J Infect. Dis.* 210(1): 99-110, and see WO2006026667, both of which are incorporated herein by reference). The term "HIV vaccine" also includes any one or more vaccines provided in Table 1, below and in any similar tables contained in the priority documents (all of which are incorporated herein in their entirety).

TABLE 1

| IAVI Clinical Trial ID* | Prime** |
| --- | --- |
| HVTN 704 AMP | VRC-HIVMAB060-00-AB |
| VAC89220HPX2004 | Ad26.Mos.HIV Trivalent |
| 01-I-0079 | VRC4302 |
| 04/400-003-04 | APL 400-003 GENEVAX-HIV |
| 10-1074 | 10-1074 |
| 87 I-114 | gp160 Vaccine (Immuno-AG) |
| ACTG 326; PACTG 326 | ALVAC vCP1452 |
| Ad26.ENVA.01 | Ad26.EnvA-01 |
| Ad5HVR48.ENVA.01 | Ad5HVR48.ENVA.01 |
| ANRS VAC 02 | rgp 160 + peptide V3 ANRS VAC 02 |
| ANRS VAC 04 | LIPO-6 |
| ANRS VAC 05 | ALVAC vCP125 |
| ANRS VAC 07 | ALVAC vCP300 |
| ANRS VAC 08 | ALVAC-HIV MN120TMG strain (vCP205) |
| ANRS VAC 09 bis | LIPO-6 |
| ANRS VAC 12 | LPHIV1 |
| ANRS VAC 14 | gp160 MN/LAI |
| ANRS VAC 16 | LPHIV1 |
| ANRS VAC 18 | LIPO-5 |
| APL 400-003RX101 | APL 400-003 GENEVAX-HIV |
| AVEG 002 | HIVAC-1e |
| AVEG 003 | VaxSyn gp160 Vaccine (MicroGeneSys) |
| AVEG 004 | gp160 Vaccine (Immuno-AG) |
| AVEG 005A/B | Env 2-3 |
| AVEG 006X; VEU 006 | MN rgp120 |
| AVEG 007A/B | rgp120/HIV-1 SF-2 |
| AVEG 011 | UBI HIV-1 Peptide Immunogen, Multivalent |
| AVEG 013A | gp160 Vaccine (Immuno-AG) |
| AVEG 014A/B | TBC-3B |
| AVEG 017 | UBI HIV-1 Peptide Vaccine, Microparticulate Monovalent |
| AVEG 019 | p17/p24:Ty-VLP |
| AVEG 020 | gp120 C4-V3 |
| AVEG 021 | P3C541b Lipopeptide |
| AVEG 022 | ALVAC-HIV MN120TMG strain (vCP205) |
| AVEG 028 | Salmonella typhi CVD 908-HIV-1 LAI gp 120 |
| AVEG 031 | APL 400-047 |
| AVEG 034/034A | ALVAC vCP1433 |
| C060301 | GTU-MultiHIV |
| C86P1 | HIV gp140 ZM96 |
| Cervico-vaginal CN54gp 140-hsp70 Conjugate Vaccine (TL01) | CN54gp140 |
| CM235 and SF2gp120 | CM235 (ThaiE) gp120 plus SF2(B) gp120 |
| CombiHIVvac (KombiVIChvak) | CombiHIVvac |
| CRC282 | P2G12 |
| CUTHIVAC002 | DNA-C CN54ENV |
| DCVax-001 | DCVax-001 |
| DNA-4 | DNA-4 |
| DP6?001 | DP6?001 DNA |
| DVP-1 | EnvDNA |
| EN41-UGR7C | EN41-UGR7C |
| EnvPro | EnvPro |
| EuroNeut41 | EN41-FPA2 |
| EV01 | NYVAC-C |
| EV02 (EuroVacc 02) | DNA-C |
| Extention HVTN 073E/SAAVI 102 | Sub C gp140 |
| F4/AS01 | F4/AS01 |
| FIT Biotech | GTU-Nef |
| Guangxi CDC DNA vaccine | Chinese DNA |
| HGP-30 memory responses | HGP-30 |
| HIV-CORE002 | ChAdV63.HIVconsv |
| HIV-POL-001 | MVA-mBN32 |
| HIVIS 01 | HIVIS-DNA |
| HIVIS 02 | MVA-CMDR |
| HVRF-380-131004 | Vichrepol |
| HVTN 040 | AVX101 |
| HVTN 041 | rgp120w61d |
| HVTN 044 | VRC-HIVDNA009-00-VP |
| HVTN 045 | pGA2/JS7 DNA |
| HVTN 048 | EP HIV-1090 |
| HVTN 049 | Gag and Env DNA/PLG microparticles |
| HVTN 050/Merck 018 | MRKAd5 HIV-1 gag |
| HVTN 052 | VRC-HIVDNA009-00-VP |

TABLE 1-continued

| IAVI Clinical Trial ID* | Prime** |
|---|---|
| HVTN 054 | VRC-HIVADV014-00-VP |
| HVTN 055 | TBC-M335 |
| HVTN 056 | MEP |
| HVTN 059 | AVX101 |
| HVTN 060 | HIV-1 gag DNA |
| HVTN 064 | EP HIV-1043 |
| HVTN 065 | pGA2/JS7 DNA |
| HVTN 067 | EP-1233 |
| HVTN 070 | PENNVAX-B |
| HVTN 072 | VRC-HIVDNA044-00-VP |
| HVTN 073 | SAAVI DNA-C2 |
| HVTN 076 | VRC-HIVDNA016-00-VP |
| HVTN 077 | VRC-HIVADV027-00-VP |
| HVTN 078 | NYVAC-B |
| HVTN 082 | VRC-HIVDNA016-00-VP |
| HVTN 084 | VRC-HIVADV054-00-VP |
| HVTN 086, SAAVI 103 | SAAVI MVA-C |
| HVTN 087 | HIV-MAG |
| HVTN 088 | Oligomeric gp140/MF59 |
| HVTN 090 | VSV-Indiana HIV gag vaccine |
| HVTN 092 | DNA-HIV-PT123 |
| HVTN 094 | GEO-D03 |
| HVTN 096 | DNA-HIV-PT123 |
| HVTN 097 | ALVAC-HIV vCP1521 |
| HVTN 100 | ALVAC-HIV-C (vCP2438) |
| HVTN 101 | DNA-HIV-PT123 |
| HVTN 104 | VRC-HIVMAB060-00-AB |
| HVTN 105 | AIDSVAX B/E |
| HVTN 106 | DNA Nat-B env |
| HVTN 110 | Ad4-mgag |
| HVTN 112 | HIV-1 nef/tat/vif, env pDNA vaccine |
| HVTN 116 | VRC-HIVMAB060-00-AB |
| HVTN 205 | pGA2/JS7 DNA |
| HVTN 702 | ALVAC-HIV-C (vCP2438) |
| HVTN 703 AMP | VRC-HIVMAB060-00-AB |
| HVTN 908 | pGA2/JS7 DNA |
| IAVI 001 | DNA.HIVA |
| IAVI 016 | MVA.HIVA |
| IAVI A001 | tgAAC09 |
| IAVI A003 | AAV1-PG9 |
| IAVI B001 | Ad35-GRIN/ENV |
| IAVI B002 | Adjuvanted GSK investigational HIV vaccine formulation 1 |
| IAVI B003 | Ad26.EnvA-01 |
| IAVI B004 | HIV-MAG |
| IAVI C001 | ADVAX |
| IAVI C002 | ADMVA |
| IAVI D001 | TBC-M4 |
| IAVI N004 HIV-CORE 004 | Ad35-GRIN |
| IAVI R001 | rcAd26.MOS1.HIVEnv |
| IAVI S001 | SeV-G |
| IDEA EV06 | DNA-HIV-PT123 |
| IHV01 | Full-Length Single Chain (FLSC) |
| IMPAACT P1112 | VRC-HIVMAB060-00-AB |
| IPCAVD006 | MVA mosaic |
| IPCAVD008 | Trimeric gp140 |
| IPCAVD009 | Ad26.Mos.HIV Trivalent |
| ISS P-001 | Tat vaccine |
| LFn-p24 vaccine | LFn-p24 |
| MCA-0835 | 3BNC117 |
| Mucovac2 | CN54gp140 |
| MV1-F4 | Measles Vector - GSK |
| MYM-V101 | Virosome-Gp41 |
| NCHECR-AE1 | pHIS-HIV-AE |
| PEACHI-04 | ChAdV63.HIVconsv |
| PedVacc001 & PedVacc002 | MVA.HIVA |
| PolyEnv1 | PolyEnv1 |
| PXVX-HIV-100-001 | Ad4-mgag |
| RISVAC02 | MVA-B |
| RV 151/WRAIR 984 | LFn-p24 |
| RV 158 | MVA-CMDR |
| SG06RS02 | HIV gp140 ZM96 |
| TAB9 | TAB9 |
| TaMoVac II | HIVIS-DNA |
| UBI V106 | UBI HIV-1 Peptide Vaccine, Microparticulate Monovalent |
| UCLA MIG-001 | TBC-3B |
| UKHVCSpoke003 | DNA - CN54ENV and ZM96GPN |
| V3-MAPS | V3-MAPS |
| VAX 002 | AIDSVAX B/B |
| VAX 003 | AIDSVAX B/E |
| VRC 602 | VRC-HIVMAB060-00-AB |
| VRC 607 | VRCHIVMAB080-00-AB |

*IAVI is the International AIDS Vaccine Initiative, whose clinical trials database is publicly available at http://www.iavi.org/trials-database/trials.
**As used herein, the term "Prime" refers to the composition initially used as an immunological inoculant in a given clinical trial as referenced in Table 1 herein.

The term "in vivo" refers to processes that occur in a living organism. The term "ex vivo" refers to processes that occur outside of a living organism. For example, in vivo treatment refers to treatment that occurs within a patient's body, while ex vivo treatment is one that occurs outside of a patient's body, but still uses or accesses or interacts with tissues from that patient. Thereafter, an ex vivo treatment step may include a subsequent in vivo treatment step.

The term "miRNA" refers to a microRNA, and also may be referred to herein as "miR". The term "microRNA cluster" refers to at least two microRNAs that are situate on a vector in close proximity to each other and are co-expressed.

The term "packaging cell line" refers to any cell line that can be used to express a lentiviral particle.

The term "PBMC" refers to peripheral blood mononuclear cells.

The term "percent identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of ordinary skill in the art) or by visual inspection. Depending on the application, the "percent identity" can exist over a region of the sequence being compared, e.g., over a functional domain, or, alternatively, exist over the full length of the two sequences to be compared. For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information website.

The percent identity between two nucleotide sequences can be determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (*CABIOS*, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J Mol. Biol.* (48):444-453 (1970)) algorithm which has been incorporated into the GAP program in the GCG software package (available at http://www.gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences of the present disclosure can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, word length=12 to obtain nucleotide sequences homologous to the nucleic acid molecules of the invention. BLAST protein searches can be performed with the XBLAST program, score=50, wordlength=3 to obtain amino acid sequences homologous to the protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

As used herein, "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

As used herein, a "pharmaceutically acceptable carrier" refers to, and includes, any and all solvents, dispersion media, coatings, antibacterial and antifungal agents, isotonic and absorption delaying agents, and the like that are physiologically compatible. The compositions can include a pharmaceutically acceptable salt, e.g., an acid addition salt or a base addition salt (see, e.g., Berge et al. (1977) *J Pharm Sci* 66:1-19).

As used herein, the term "physical method of selection" refers to any physical method that can be used to positively select for a cell type within a larger mixture of cells (e.g., PBMC). A non-limiting example of a physical method of selection is magnetic bead sorting.

As used herein, the term "SEQ ID NO" is synonymous with the term "Sequence ID No."

As used herein, "small RNA" refers to non-coding RNA that are generally less than about 200 nucleotides or less in length and possess a silencing or interference function. In other embodiments, the small RNA is about 175 nucleotides or less, about 150 nucleotides or less, about 125 nucleotides or less, about 100 nucleotides or less, or about 75 nucleotides or less in length. Such RNAs include microRNA (miRNA), small interfering RNA (siRNA), double stranded RNA (dsRNA), and short hairpin RNA (shRNA). "Small RNA" of the disclosure should be capable of inhibiting or knocking-down gene expression of a target gene, for example through pathways that result in the destruction of the target gene mRNA.

As used herein, the term "stimulatory agent" refers to any exogenous agent that can stimulate an immune response, and includes, without limitation, a vaccine, a HIV vaccine, and HIV or HIV-related peptides. A stimulatory agent can preferably stimulate a T cell response.

As used herein, the term "subject" includes a human patient but also includes other mammals. The terms "subject," "individual," "host," and "patient" may be used interchangeably herein.

The term "Tat" refers to the HIV tat gene and its gene product, and variants thereof.

The term "therapeutically effective amount" refers to a sufficient quantity of the active agents of the present invention, in a suitable composition, and in a suitable dosage form to treat or prevent the symptoms, progression, or onset of the complications seen in patients suffering from a given ailment, injury, disease, or condition. The therapeutically effective amount will vary depending on the state of the patient's condition or its severity, and the age, weight, etc., of the subject to be treated. A therapeutically effective amount can vary, depending on any of a number of factors, including, e.g., the route of administration, the condition of the subject, as well as other factors understood by those in the art.

As used herein, the term "therapeutic vector" is synonymous with a lentiviral vector such as the AGT103 vector.

The term "treatment" or "treating" generally refers to an intervention in an attempt to alter the natural course of the subject being treated, and can be performed either for prophylaxis or during the course of clinical pathology. Desirable effects include, but are not limited to, preventing occurrence or recurrence of disease, alleviating symptoms, suppressing, diminishing or inhibiting any direct or indirect pathological consequences of the disease, ameliorating or palliating the disease state, and causing remission or improved prognosis.

The term "vaccine", which is used interchangeably with the term "therapeutic vaccine" refers to an exogenous agent that can elicit an immune response in an individual and includes, without limitation, purified proteins, inactivated viruses, virally vectored proteins, bacterially vectored proteins, peptides or peptide fragments, or virus-like particles (VLPs).

The term "Vif" refers to the HIV vif gene and its gene product, and variants thereof.

Description of Aspects of the Disclosure

As detailed herein, in one aspect, a method of treating cells infected with HIV is provided. The method generally includes contacting peripheral blood mononuclear cells (PBMC) isolated from a subject infected with HIV with a therapeutically effective amount of a stimulatory agent, wherein the contacting step is carried out ex vivo; transducing the PBMC ex vivo with a viral delivery system encoding at least one genetic element; and culturing the transduced PBMC for a period of time sufficient to achieve such transduction. In embodiments, the transduced PBMC are cultured from about 1 to about 35 days. In embodiments, the method further includes infusing the transduced PBMC into a subject. In embodiments, the subject is a human. In embodiments, the stimulatory agent is a peptide or mixture of peptides, and in embodiments includes a gag peptide. In further embodiments, the stimulatory includes a vaccine. In embodiments, the vaccine is a HIV vaccine, and in further embodiments, the HIV vaccine is a MVA/HIV62B vaccine or a variant thereof. In embodiments, the viral delivery system includes a lentiviral particle. In embodiments, the at least one genetic element includes a small RNA capable of inhibiting production of chemokine receptor CCR5. In embodiments, the at least one genetic element includes at least one small RNA capable of targeting an HIV RNA sequence. In other embodiments, the at least one genetic element includes a small RNA capable of inhibiting production of chemokine receptor CCR5 and at least one small RNA capable of targeting an HIV RNA sequence. In embodiments, the HIV RNA sequence includes a HIV Vif sequence, a HIV Tat sequence, or variants thereof. In embodiments, the at least one genetic element includes at least one of a microRNA or a shRNA. In further embodiments, the at least one genetic element comprises a microRNA cluster.

In another aspect, a method is disclosed which includes obtaining peripheral blood from HIV+ individuals; fractionating the blood to obtain a PBMC population; contacting the PBMC population with purified antigen-presenting cells or peptides or proteins representing components of HIV; culturing the contacted PBMC population for about 1 to about 12 days to expand an antigen-specific population; positively selecting cells that respond to peptide stimulation to produce an enriched cell fraction; transducing the enriched cell fraction ex vivo with a viral delivery system as detailed herein, and culturing the transduced cell fraction for a period of time sufficient to ensure adequate transduction.

In embodiments, the PBMC population is further purified to produce a purified fraction of PBMC. In embodiments, further purified fractions of PBMC are contacted with peptides or proteins representing components of HIV.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1. In embodiments, the at least one genetic element comprises SEQ ID NO: 1.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 2; or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 3. In embodiments, the at least one genetic element includes SEQ ID NO: 2 or SEQ ID NO: 3.

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 31. In embodiments, the microRNA cluster includes SEQ ID NO: 31.

In another aspect, a method of manufacturing a cell product for treating HIV infection in a subject is disclosed. The method generally includes obtaining blood leukocytes; removing leukocytes from the subject and purifying peripheral blood mononuclear cells (PBMC) or defined fractions of PBMC. The method further includes contacting the PBMC or purified fraction of PBMC ex vivo with a therapeutically effective amount of a stimulatory agent; positive selection based on response to stimulatory agent to enrich the proportion of antigen-specific T cells; transducing the PBMC or purified fraction of PBMC ex vivo with a viral delivery system encoding at least one genetic element; and culturing the transduced PBMC or a purified fraction of PBMC for a period of time sufficient to achieve transduction and growth of the modified cell population. The method may further include further enrichment of the PBMC, for example, by preferably enriching the PBMC for CD4+ T cells or selecting for antigen-specific cells based on cytokine expression or combinations of selection methods to enrich for the therapeutic fraction of cells. In embodiments, the transduced PBMC or purified fraction of PBMC are cultured from about 1 to about 35 days. The method may further involve infusing the transduced PBMC or purified fraction of PBMC into a subject. The subject may be a human. The at least one of the first stimulatory agents may include a peptide or mixture of peptides and may represent one, two, three or more of proteins encoded by the HIV genome. In embodiments, at least one of the first stimulatory agents includes a gag peptide. The at least one of the first stimulatory agents may include a vaccine. In embodiments, the vaccine is a HIV vaccine, and in further embodiments, the HIV vaccine is a MVA/HIV62B vaccine or a variant thereof. In embodiments, the first stimulatory agent is a mixture of gag peptides.

In embodiments, the viral delivery system includes a lentiviral particle. In embodiments, the at least one genetic element includes a small RNA capable of inhibiting production of chemokine receptor CCR5. In embodiments, the at least one genetic element includes at least one small RNA capable of targeting an HIV RNA sequence. In embodiments, the at least one genetic element includes a small RNA capable of inhibiting production of chemokine receptor CCR5 and at least one small RNA capable of targeting an HIV RNA sequence. The HIV RNA sequence may include a HIV Vif sequence, a HIV Tat sequence, or variants thereof. The at least one genetic element may include a microRNA or a shRNA, or a cluster thereof. In embodiments, the at least one genetic element comprises a synthetic microRNA cluster.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1. In embodiments, the at least one genetic element comprises SEQ ID NO: 1.

In another aspect, the at least one genetic element includes a microRNA having at least 80%, or at least 85%, or at least 90%, or at least 95% percent identity with SEQ ID NO: 2; or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 3. In embodiments, the at least one genetic element includes SEQ ID NO: 2 or SEQ ID NO: 3.

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 31. In embodiments, the microRNA cluster includes SEQ ID NO: 31.

In another aspect, a lentiviral vector is disclosed. The lentiviral vector includes at least one encoded genetic element, wherein the at least one encoded genetic element comprises a small RNA capable of inhibiting production of chemokine receptor CCR5 or at least one small RNA capable of targeting an HIV RNA sequence. In another aspect a lentiviral vector is disclosed in the at least one encoded genetic element comprises a small RNA capable of inhibiting production of chemokine receptor CCR5 and at least one small RNA capable of targeting an HIV RNA sequence. The HIV RNA sequence may include a HIV Vif sequence, a HIV Tat sequence, or a variant thereof. The at least one encoded genetic element may include a microRNA or a shRNA. The at least one encoded genetic element may include a microRNA cluster.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 1. In embodiments, the at least one genetic element comprises SEQ ID NO: 1.

In another aspect, the at least one genetic element includes a microRNA having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 2; or at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 3. In embodiments, the at least one genetic element includes SEQ ID NO: 2; or SEQ ID NO: 3.

In another aspect, the microRNA cluster includes a sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95% or more percent identity with SEQ ID NO: 31. In embodiments, the microRNA cluster includes SEQ ID NO: 31.

In another aspect, a lentiviral vector system for expressing a lentiviral particle is provided. The system includes a lentiviral vector as described herein; at least one envelope plasmid for expressing an envelope protein preferably optimized for infecting a cell; and at least one helper plasmid for expressing a gene of interest, for example any of gag, pol, and rev genes, wherein when the lentiviral vector, the at least one envelope plasmid, and the at least one helper plasmid are transfected into a packaging cell, wherein a lentiviral particle is produced by the packaging cell, wherein the lentiviral particle is capable of modulating a target sequence of interest, for example inhibiting production of chemokine receptor CCR5 or targeting an HIV RNA sequence.

In another aspect, a lentiviral particle capable of infecting a cell is disclosed. The lentiviral particle includes at least one envelope protein preferably optimized for infecting a cell, and a lentiviral vector as described herein. The envelope protein may be optimized for infecting a T cell. In embodiments, the envelope protein is optimized for infecting a CD4+ T cell.

In another aspect, a modified cell is disclosed. In embodiments, the modified cell is a CD4+ T cell. In embodiments, the CD4+ T cell is infected with a lentiviral particle as described herein. In embodiments, the CD4+ T cell also has been selected to recognize an HIV antigen based on the prior immunization with a stimulatory agent. In a further embodiment, the HIV antigen that is recognized by the CD4+ T cell includes a gag antigen. In a further embodiment, the CD4+ T cell expresses a decreased level of CCR5 following infection with the lentiviral particle.

In another aspect, a method of selecting a subject for a therapeutic treatment regimen is disclosed. The method generally includes immunizing the subject with an effective amount of a first stimulatory agent; removing leukocytes from the subject and purifying peripheral blood mononuclear cells (PBMC) and determining a first quantifiable measurement associated with at least one factor associated with the PBMC; contacting the PBMC ex vivo with a therapeutically effective amount of a second stimulatory agent, and determining a second measurement associated with the at least one factor associated with the PBMC, whereby when the second quantifiable measurement is different (e.g., higher) than the first quantifiable measurement, the subject is selected for the treatment regimen. The at least one factor may be T cell proliferation or IFN gamma production.

Human Immunodeficiency Virus (HIV)

Human Immunodeficiency Virus, which is also commonly referred to as "HIV", is a retrovirus that causes acquired immunodeficiency syndrome (AIDS) in humans. AIDS is a condition in which progressive failure of the immune system allows life-threatening opportunistic infections and cancers to thrive. Without treatment, average survival time after infection with HIV is estimated to be 9 to 11 years, depending upon the HIV subtype and genetics of the host population. Infection with HIV occurs by the transfer of bodily fluids, including but not limited to blood, semen, vaginal fluid, pre-ejaculate, saliva, tears, lymph or cerebro-spinal fluid, or breast milk, or use of contaminated blood or tissue products. HIV may be present in an infected individual as both free virus particles and within infected immune cells.

HIV infects vital cells in the human immune system such as helper T cells, although tropism can vary among HIV subtypes. Immune cells that may be specifically susceptible to HIV infection include but are not limited to CD4+ T cells, macrophages, and dendritic cells. HIV infection leads to low levels of CD4+ T cells through a number of mechanisms, including but not limited to apoptosis of uninfected bystander cells, direct viral killing of infected cells, and killing of infected CD4+ T cells by CD8 cytotoxic lymphocytes that recognize infected cells. When CD4+ T cell numbers decline below a critical level, cell-mediated immunity is lost, and the body becomes progressively more susceptible to opportunistic infections and cancer.

Structurally, HIV is distinct from many other retroviruses. The RNA genome consists of at least seven structural landmarks (LTR, TAR, RRE, PE, SLIP, CRS, and INS), and at least nine genes (gag, pol, env, tat, rev, nef, vif, vpr, vpu, and sometimes a tenth tev, which is a fusion of tat, env and rev), encoding 19 proteins. Three of these genes, gag, pol, and env, contain information needed to make the structural proteins for new virus particles.

HIV replicates primarily in CD4 T cells, and causes cellular destruction or dysregulation to reduce host immunity. Because HIV establishes infection as an integrated provirus and may enter a state of latency wherein virus expression in a particular cell decreases below the level for cytopathology affecting that cell or detection by the host immune system, HIV is difficult to treat and has not been eradicated even after prolonged intervals of combination antiretroviral therapy (cART). In most cases, HIV infection causes fatal disease although survival may be prolonged by cART.

A major goal in the fight against HIV is to develop strategies for curing disease. Prolonged cART has not accomplished this goal, so investigators have turned to alternative procedures. Early efforts to improve host immunity by therapeutic immunization (using a vaccine after infection has occurred) had marginal or no impact. Likewise, treatment intensification had moderate or no impact.

Some progress has been made using genetic therapy, but positive results are sporadic and found only among rare human beings carrying defects in one or both alleles of the gene encoding CCR5, which plays a critical role in viral penetration of host cells. However, many investigators are optimistic that genetic therapy holds the best promise for eventually achieving an HIV cure.

As disclosed herein, the methods and compositions of the invention are able to achieve a functional cure that may or may not include complete eradication of all HIV from the body. As mentioned above, a functional cure is defined as a state or condition wherein HIV+ individuals who previously required cART, may survive with low or undetectable virus replication and using lower or intermittent doses of cART, or are potentially able to discontinue cART altogether. As used herein, a functional cure may still possibly require adjunct therapy to maintain low level virus replication and slow or eliminate disease progression. A possible outcome of a functional cure is the eventual eradication of HIV to prevent all possibility of recurrence.

The primary obstacles to achieving a functional cure lie in the basic biology of HIV itself. Virus infection deletes CD4 T cells that are critical for nearly all immune functions. Most importantly, HIV infection and depletion of CD4 T cells requires activation of individual cells. Activation is a specific mechanism for individual CD4 T cell clones that recognize pathogens or other molecules, using a rearranged T cell receptor.

In the case of HIV, infection activates a population of HIV-specific T cells that become infected and are consequently depleted before other T cells that are less specific for the virus, which effectively cripples the immune system's defense against the virus. The capacity for HIV-specific T cell responses is rebuilt during prolonged cART; however, when cART is interrupted the rebounding virus infection repeats the process and again deletes the virus-specific cells, resetting the clock on disease progression.

Clearly, a functional cure is only possible if enough HIV-specific CD4 T cells are protected to allow for a host's native immunity to confront and control HIV once cART is interrupted. In one embodiment, the present invention provides methods and compositions for improving the effectiveness of genetic therapy to provide a functional cure of HIV disease. In another embodiment, the present invention provides methods and compositions for enhancing host immunity against HIV to provide a functional cure. In yet another embodiment, the present invention provides methods and compositions for enriching HIV-specific CD4 T cells in a patient to achieve a functional cure.

In one embodiment of the invention, treatment results in enriching a subject's HIV-specific CD4 T cells by about 100%, about 200%, about 300%, about 400%, about 500%, about 600%, about 700%, about 800%, about 900%, or about 1000%.

Gene Therapy

Viral vectors are used to deliver genetic constructs to host cells for the purposes of disease therapy or prevention. Genetic constructs can include, but are not limited to, functional genes or portions of genes to correct or complement existing defects, DNA sequences encoding regulatory proteins, DNA sequences encoding regulatory RNA molecules including antisense, short homology RNA, long non-coding RNA, small interfering RNA or others, and decoy sequences encoding either RNA or proteins designed to compete for critical cellular factors to alter a disease state. Gene therapy involves delivering these therapeutic genetic constructs to target cells to provide treatment or alleviation of a particular disease.

There are multiple ongoing efforts to utilize genetic therapy in the treatment of HIV disease, but thus far, the results have been poor. A small number of treatment successes were obtained in rare HIV patients carrying a spontaneous deletion of the CCR5 gene (an allele known as CCR5delta32).

Lentivirus-delivered nucleases or other mechanisms for gene deletion/modification may be used to lower the overall expression of CCR5 and/or help to lower HIV replication. At least one study has reported having success in treating the disease when lentivirus was administered in patients with a genetic background of CCR5delta32. However, this was only one example of success, and many other patients without the CCR5delta32 genotype have not been treated as successfully. Consequently, there is a substantial need to improve the performance of viral genetic therapy against HIV, both in terms of performance for the individual viral vector construct and for improved use of the vector through a strategy for achieving functional HIV cure.

For example, some existing therapies rely on zinc finger nucleases to delete a portion of CCR5 in an attempt to render cells resistant to HIV infection. However, even after optimal treatment, only 30% of T cells had been modified by the nuclease at all, and of those that were modified, only 10% of the total CD4 T cell population had been modified in a way that would prevent HIV infection. In contrast, the disclosed methods result in virtually every cell carrying a lentivirus transgene having a reduction in CCR5 expression below the level needed to allow HIV infection.

For the purposes of the disclosed methods, gene therapy can include, but is not limited to, affinity-enhanced T cell receptors, chimeric antigen receptors on CD4 T cells (or alternatively on CD8 T cells), modification of signal transduction pathways to avoid cell death cause by viral proteins, increased expression of HIV restriction elements including TREX, SAMHD1, MxA or MxB proteins, APOBEC complexes, TRIM5-alpha complexes, tetherin (BST2), and similar proteins identified as being capable of reducing HIV replication in mammalian cells.

Immunotherapy

Historically, vaccines have been a go-to weapon against deadly infectious diseases, including smallpox, polio, measles, and yellow fever. Unfortunately, there is no currently approved vaccine for HIV. The HIV virus has unique ways of evading the immune system, and the human body seems incapable of mounting an effective immune response against it. As a result, scientists do not have a clear picture of what is needed to provide protection against HIV.

However, immunotherapy may provide a solution that was previously unaddressed by conventional vaccine approaches. Immunotherapy, also called biologic therapy, is a type of treatment designed to boost the body's natural defenses to fight infections or cancer. It uses materials either made by the body or in a laboratory to improve, target, or restore immune system function.

In some embodiments of the disclosed invention, immunotherapeutic approaches may be used to enrich a population of HIV-specific CD4 T cells for the purpose of increasing the host's anti-HIV immunity. In some embodiments of the disclosed invention, integrating or non-integrating lentivirus vectors may be used to transduce a host's immune cells for the purposes of increasing the host's anti-HIV immunity. In yet another embodiment of the invention, a vaccine comprising HIV proteins including but not limited to a killed particle, a virus-like particle, HIV peptides or peptide fragments, a recombinant viral vector, a recombinant bacterial vector, a purified subunit or plasmid DNA combined with a suitable vehicle and/or biological or chemical adjuvants to increase a host's immune responses may be used to enrich the population of virus-specific T cells or antibodies, and these methods may be further enhanced through the use of HIV-targeted genetic therapy using lentivirus or other viral vector.

Methods

In one aspect, the disclosure provides methods for using viral vectors to achieve a functional cure for HIV disease. The methods generally include immunotherapy to enrich the proportion of HIV-specific CD4 T cells, followed by lentivirus transduction to deliver inhibitors of HIV and CCR5 and CXCR4 as required.

In one embodiment, the methods include a first stimulation event to enrich a proportion of HIV-specific CD4 T cells. The first stimulation can include administration of one or more of any agent suitable for enriching a patient's HIV-specific CD4+ T cells including but not limited to a vaccine.

Therapeutic vaccines can include one or more HIV protein with protein sequences representing the predominant viral types of the geographic region where treatment is occurring. Therapeutic vaccines will include purified proteins, inactivated viruses, virally vectored proteins, bacterially vectored proteins, peptides or peptide fragments, virus-like particles (VLPs), biological or chemical adjuvants including cytokines and/or chemokines, vehicles, and methods for immunization. Vaccinations may be administered according to standard methods known in the art and HIV patients may continue antiretroviral therapy during the interval of immunization and subsequent ex vivo lymphocyte culture including lentivirus transduction.

In some embodiments, HIV+ patients are immunized with an HIV vaccine, increasing the frequency of HIV-specific CD4 T cells by about 2, about 25, about 250, about 500, about 750, about 1000, about 1250, or about 1500-fold (or any amount in between these values). The vaccine may be any clinically utilized or experimental HIV vaccine, including the disclosed lentiviral, other viral vectors or other bacterial vectors used as vaccine delivery systems. In another embodiment, the vectors encode virus-like particles (VLPs) to induce higher titers of neutralizing antibodies. In another embodiment, the vectors encode peptides or peptide fragments associated with HIV including but not limited to gag, pol, and env, tat, rev, nef, vif, vpr, vpu, and tev, as well as LTR, TAR, RRE, PE, SLIP, CRS, and INS. Alternatively, the HIV vaccine used in the disclosed methods may comprise purified proteins, inactivated viruses, virally vectored proteins, bacterially vectored proteins, peptides or peptide fragments, virus-like particles (VLPs), or biological or chemical adjuvants including cytokines and/or chemokines.

In one embodiment, the methods include ex vivo re-stimulation of CD4 T cells from persons or patients previously immunized by therapeutic vaccination, using purified proteins, inactivated viruses, virally vectored proteins, bacterially vectored proteins, biological or chemical adjuvants including cytokines and/or chemokines, vehicles, and methods for re-stimulation. Ex vivo re-stimulation may be performed using the same vaccine or immune stimulating compound used for in vivo immunization, or it may be performed using a different vaccine or immune stimulating compound than those used for in vivo immunization. Moreover, in some embodiments, the patient does not require prior therapeutic vaccination or re-stimulation of CD4 T cells if the individual has sufficiently high antigen-specific CD4 T cell responses to HIV proteins. In these embodiments, such a patient may only require ex vivo stimulation of CD4 T cells with viral antigens, vaccines or peptides followed by selection for HIV-specific T cells based on the response to stimulation. Enriched cell preparations may include 1%, 5%, 10%, 20%, 30%, 40%, 50% or more of the HIV-specific CD4+ T cells and are used for lentivirus transduction of genes able to protection from HIV-mediated depletion. Stimulation with polyclonal mitogen plus cytokines increases the number of enriched and transduced T cells until appropriate levels are reached for infusion back into the original patient.

In embodiments, peripheral blood mononuclear cells (PBMCs) are obtained by leukapheresis and treated ex vivo to obtain about $1 \times 10^9$ CD4 T cells of which about 0.1%, about 1%, about 5% or about 10% or about 30% or about 40% or about 50% are both HIV-specific in terms of antigen responses, and HIV-resistant by virtue of carrying the therapeutic transgene delivered by the disclosed lentivirus vector. Alternatively, about $1 \times 10^7$, about $1 \times 10^8$, about $1 \times 10^9$, about $1 \times 10^{10}$, about $1 \times 10^{11}$, or about $1 \times 10^{12}$ CD4 T cells may be isolated for re-stimulation. Any suitable amount of CD4 T cells are isolated for ex vivo re-stimulation.

The isolated CD4 T cells can be cultured in appropriate medium throughout re-stimulation with HIV vaccine antigens, which may include antigens present in the prior therapeutic vaccination. Antiretroviral therapeutic drugs including inhibitors of reverse transcriptase, protease or integrase may be added to prevent virus re-emergence during prolonged ex vivo culture. CD4 T cell re-stimulation is used to enrich the proportion of HIV-specific CD4 T cells in culture. The same procedure may also be used for analytical objectives wherein smaller blood volumes with peripheral blood mononuclear cells obtained by purification, are used to identify HIV-specific T cells and measure the frequency of this subpopulation.

The PBMC fraction may be enriched for HIV-specific CD4 T cells by contacting the cells with HIV proteins matching or complementary to the components of the vaccine previously used for in vivo immunization. Ex vivo re-stimulation can increase the relative frequency of HIV-specific CD4 T cells by about 2, about 5, about 10, about 25, about 50, about 75, about 100, about 125, about 150, about 175, or about 200-fold. Further enrichment is obtained by positive selection for cells responding to HIV antigens, vaccines or peptides. Positive selection is accomplished, for example, with the CliniMACS Cytokine Capture System (Miltenyi Biotec Product number 130-028-701, San Diego, CA 92121) or similar manual or automated system including the Miltenyi Prodigy System (Miltenyi Biotec Product number 200-075-301, San Diego, CA 92121) that is compatible with selecting viable cells based on expression of a cytokine (including but not limited to interferon gamma or tumor necrosis factor alpha) that is captured by a bi-specific reagent and labeled with a magnetic bead antibody to enable positive selection on a magnetic column. Enrichment may also be accomplished by labeling stimulated cells with antibodies capable of detecting cell surface markers expressed preferentially on activated T cells including CD45RO, MHC Class II and others known in the art. Purification of labeled cells may be by fluorescence activated cell sorting, magnetic bead sorting or other physical methods capable of purifying viable cells based on phenotypic characteristics.

The methods additionally include combining in vivo therapeutic immunization and ex vivo re-stimulation of CD4 T cells with ex vivo lentiviral transduction and culturing.

Thus, in one embodiment, the re-stimulated PBMC or fraction of PBMC that has been enriched for HIV-specific CD4 T cells can be positively selected as described above, cultured for 1, 2, 3, 4, 5 or up to 12, 20 or 30 days before activating again with a polyclonal mitogen such as Miltenyi GMP TransAct T cell reagent (Miltenyi Biotec Product number 170-076-156, San Diego, CA 92121) or other plant- or fungal based agglutinins or other reagents capable of recognizing cell surface CD3 and CD28 to cross link these molecules and cause polyclonal T cell activation. After polyclonal stimulation cells are transduced with therapeutic anti-HIV lentivirus or other vectors and maintained in culture for a sufficient period of time for such transduction, for example from about 1 to about 21 days, including up to about 35 days. Alternatively, the cells may be cultured for about 1-about 18 days, about 1-about 15 days, about 1-about 12 days, about 1-about 9 days, or about 3-about 7 days. Thus, the transduced cells may be cultured for about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, or about 35 days. Activation with a polyclonal mitogen may or may not be included in the cell product manufacturing process.

In further embodiments, once the transduced cells have been cultured for a sufficient period of time, transduced CD4 T cells are infused back into the original patient. Infusion can be performed using various devices and methods known in the art. In some embodiments, infusion may be accompanied by pre-treatment with cyclophosphamide or similar compounds to increase the efficiency of re-engraftment.

In some embodiments, a CCR5-targeted therapy may be added to a subject's antiretroviral therapy regimen, which was continued throughout the treatment process. Examples of CCR5-targeted therapies include but are not limited to Maraviroc (a CCR5 antagonist) or Rapamycin (immunosuppressive agent that lowers CCR5). In some embodiments, the antiretroviral therapy may be ceased and the subject can be tested for virus rebound. If no rebound occurs, adjuvant therapy can also be removed and the subject can be tested again for virus rebound.

In various embodiments, continued virus suppression with reduced or no antiretroviral therapy including cART or HAART, and reduced or no adjuvant therapy for about 26 weeks can be considered a functional cure for HIV. Other definitions of a functional cure are described herein.

The lentiviral and other vectors used in the disclosed methods may encode at least one, at least two, at least three, at least four, or at least five genes, or at least six genes, or at least seven genes, or at least eight genes, or at least nine genes, or at least ten genes, or at least eleven genes, or at least twelve genes of interest. Given the versatility and therapeutic potential of HIV-targeted gene therapy, a viral vector of the invention may encode genes or nucleic acid sequences that include but are not limited to (i) an antibody directed to an antigen associated with an infectious disease or a toxin produced by the infectious pathogen, (ii) cytokines including interleukins that are required for immune cell growth or function and may be therapeutic for immune dysregulation encountered in HIV and other chronic or acute human viral or bacterial pathogens, (iii) factors that suppress the growth of HIV in vivo including CD8 suppressor factors, (iv) mutations or deletions of chemokine receptor CCR5, mutations or deletions of chemokine receptor CXCR4, or mutations or deletions of chemokine receptor CXCR5, (v) antisense DNA or RNA against specific receptors or peptides associated with HIV or host protein associated with HIV, (vi) small interfering RNA against specific receptors or peptides associated with HIV or host protein associated with HIV, or (vii) a variety of other therapeutically useful sequences that may be used to treat HIV or AIDS.

Additional examples of HIV-targeted gene therapy that can be used in the disclosed methods include, but are not limited to, affinity-enhanced T cell receptors, chimeric antigen receptors on CD4 T cells (or alternatively on CD8 T cells), modification of signal transduction pathways to avoid cell death cause by viral proteins, increased expression of HIV restriction elements including TREX, SAMHD1, M×A or M×B proteins, APOBEC complexes, TRIM5-alpha complexes, tetherin (BST2), and similar proteins identified as being capable of reducing HIV replication in mammalian cells.

In some embodiments, a patient may be undergoing cART or HAART concurrently while being treated according to the methods of the invention. In other embodiments, a patient may undergo cART or HAART before or after being treated according to the methods of the invention. In some embodiments, cART or HAART is maintained throughout treatment according to the methods of the invention and the patient may be monitored for HIV viral burden in blood and frequency of lentivirus-transduced CD4 T cells in blood. Preferably, a patient receiving cART or HAART prior to being treated according to the methods of the invention is able to discontinue or reduce cART or HAART following treatment according to the methods of the invention.

For efficacy purposes, the frequency of transduced, HIV-specific CD4 T cells, which is a novel surrogate marker for gene therapy effects, may be determined, as discussed in more detail herein.

Compositions

In various aspects, the disclosure provides lentiviral vectors capable of delivering genetic constructs to inhibit HIV penetration of susceptible cells. For instance, one mechanism of action in accordance herein is to reduce mRNA levels for CCR5 and/or CXCR4 chemokine receptors for reducing the rates for viral entry into susceptible cells.

Alternatively, the disclosed lentiviral vectors are capable of inhibiting the formation of HIV-infected cells by reducing the stability of incoming HIV genomic RNA. And in yet another embodiment, the disclosed lentivirus vectors are capable of preventing HIV production from a latently infected cell, wherein the mechanism of action is to cause instability of viral RNA sequences through the action of inhibitory RNA including short-homology, small-interfering or other regulatory RNA species.

The therapeutic lentiviruses disclosed generally comprise at least one of two types of genetic cargo. First, the lentiviruses may encode genetic elements that direct expression of small RNA capable of inhibiting the production of chemokine receptors CCR5 and/or CXCR4 that are important for HIV penetration of susceptible cells. The second type of genetic cargo includes constructs capable of expressing small RNA molecules targeting HIV RNA sequences for the purpose of preventing reverse transcription, RNA splicing, RNA translation to produce proteins, or packaging of viral genomic RNA for particle production and spreading infection. An exemplary structure is diagrammed in FIG. 3.

Figure 3:
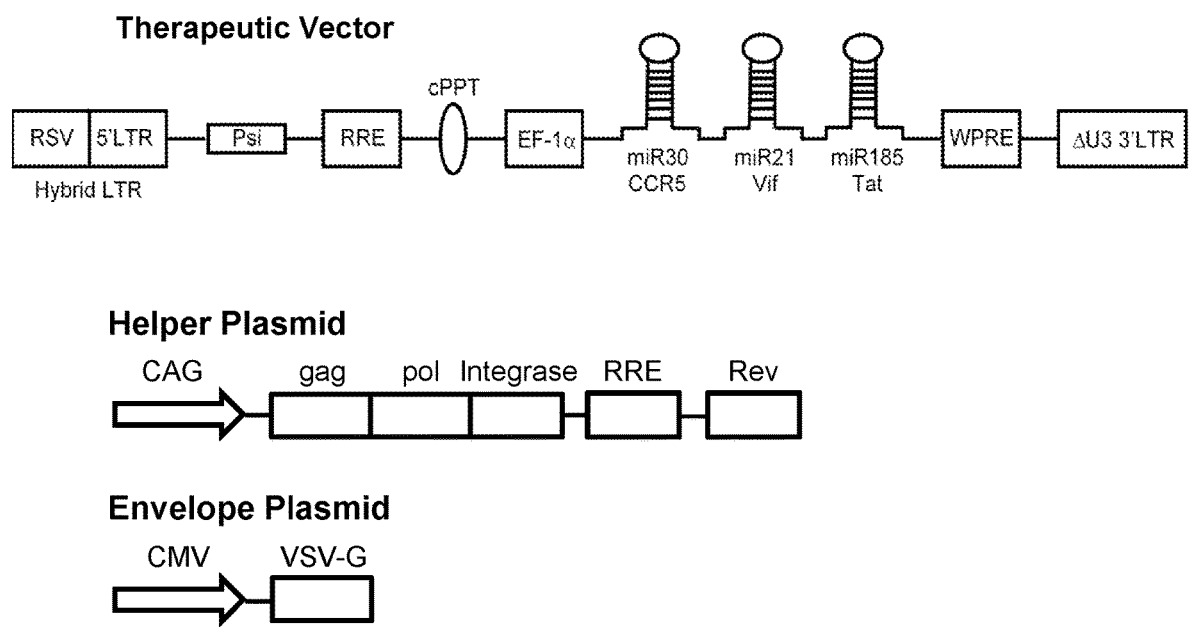
FIG. 3 depicts an exemplary lentiviral vector system comprised of a therapeutic vector, a helper plasmid, and an envelope plasmid. The therapeutic vector shown here is a preferred therapeutic vector, which is also referred to herein as AGT103, and contains miR30CCR5-miR21Vif-miR185-Tat.

As shown in FIG. 3 (top panel), an exemplary construct may comprise numerous sections or components. For example, in one embodiment, an exemplary LV construct may comprise the following sections or components:

RSV—a Rous Sarcoma virus long terminal repeat;
5'LTR—a portion of an HIV long terminal repeat that can be truncated to prevent replication of the vector after chromosomal integration;
Psi—a packaging signal that allows for incorporation of the vector RNA genome into viral particles during packaging;
RRE—a Rev Responsive element can be added to improve expression from the transgene by mobilizing RNA out of the nucleus and into the cytoplasm of cells;
cPPT—a Poly purine tract that facilitates second strand DNA synthesis prior to integration of the transgene into the host cell chromosome;
Promoter—a promoter initiates RNA transcription from the integrated transgene to express micro-RNA clusters (or other genetic elements of the construct), and in some embodiments, the vectors may use an EF-1 promoter;
Anti-CCR5—a micro RNA targeting messenger RNA for the host cell factor CCR5 to reduce its expression on the cell surface;
Anti-Rev/Tat—a micro RNA targeting HIV genomic or messenger RNA at the junction between HIV Rev and Tat coding regions, which is sometimes designated miRNA Tat or given a similar description in this application;
Anti-Vif—a micro RNA targeting HIV genomic or messenger RNA within the Vif coding region;
WPRE—a woodchuck hepatitis virus post-transcriptional regulatory element is an additional vector component that can be used to facilitate RNA transport of the nucleus; and
deltaU3 3'LTR—a modified version of a HIV 3' long terminal repeat where a portion of the U3 region has been deleted to improve safety of the vector.

One of ordinary skill in the art will recognize that the above components are merely examples, and that such components may be reorganized, substituted with other elements, or otherwise changed, so long as the construct is able to prevent expression of HIV genes and decrease the spread of infection.

Vectors of the invention may include either or both of the types of genetic cargo discussed above (i.e., genetic elements that direct expression of a gene or small RNAs, such as siRNA, shRNA, or miRNA that can prevent translation or transcription), and the vectors of the invention may also encode additionally useful products for the purpose of treatment or diagnosis of HIV. For instance, in some embodiments, these vectors may also encode green fluorescent protein (GFP) for the purpose of tracking the vectors or antibiotic resistance genes for the purposes of selectively maintaining genetically-modified cells in vivo.

The combination of genetic elements incorporated into the disclosed vectors is not particularly limited. For example, a vector herein may encode a single small RNA, two small RNAs, three small RNA, four small RNAs, five small RNAs, six small RNAs, seven small RNAs, eight small RNAs, nine small RNAs, or ten small RNAs, or eleven small RNAs, or twelve small RNAs. Such vectors may additionally encode other genetic elements to function in concert with the small RNAs to prevent expression and infection of HIV.

Those of ordinary skill in the art will understand that the therapeutic lentivirus may substitute alternate sequences for the promoter region, targeting of regulatory RNA, and types of regulatory RNA. Further, the therapeutic lentivirus of the disclosure may comprise changes in the plasmids used for packaging the lentivirus particles; these changes are required to increase levels of production in vitro.

Lentiviral Vector System

A lentiviral virion (particle) in accordance with various aspects and embodiments herein is expressed by a vector system encoding the necessary viral proteins to produce a virion (viral particle). In various embodiments, one vector containing a nucleic acid sequence encoding the lentiviral pol proteins is provided for reverse transcription and integration, operably linked to a promoter. In another embodiment, the pol proteins are expressed by multiple vectors. In other embodiments, vectors containing a nucleic acid sequence encoding the lentiviral Gag proteins for forming a viral capsid, operably linked to a promoter, are provided. In embodiments, this gag nucleic acid sequence is on a separate vector than at least some of the pol nucleic acid sequence. In other embodiments, the gag nucleic acid is on a separate vector from all the pol nucleic acid sequences that encode pol proteins.

Numerous modifications can be made to the vectors herein, which are used to create the particles to further minimize the chance of obtaining wild type revertants. These include, but are not limited to deletions of the U3 region of the LTR, tat deletions and matrix (MA) deletions. In embodiments, the gag, pol and env vector(s) do not contain nucleotides from the lentiviral genome that package lentiviral RNA, referred to as the lentiviral packaging sequence.

The vector(s) forming the particle preferably do not contain a nucleic acid sequence from the lentiviral genome that expresses an envelope protein. Preferably, a separate vector that contains a nucleic acid sequence encoding an envelope protein operably linked to a promoter is used. This env vector also does not contain a lentiviral packaging sequence. In one embodiment the env nucleic acid sequence encodes a lentiviral envelope protein.

In another embodiment the envelope protein is not from the lentivirus, but from a different virus. The resultant particle is referred to as a pseudotyped particle. By appropriate selection of envelopes one can "infect" virtually any cell. For example, one can use an env gene that encodes an envelope protein that targets an endocytic compartment such as that of the influenza virus, VSV-G, alpha viruses (Semliki forest virus, Sindbis virus), arenaviruses (lymphocytic choriomeningitis virus), flaviviruses (tick-borne encephalitis virus, Dengue virus, hepatitis C virus, GB virus), rhabdoviruses (vesicular stomatitis virus, rabies virus), paramyxoviruses (mumps or measles) and orthomyxoviruses (influenza virus). Other envelopes that can preferably be used include those from Moloney Leukemia Virus such as MLV-E, MLV-A and GALV. These latter envelopes are particularly preferred where the host cell is a primary cell. Other envelope proteins can be selected depending upon the desired host cell. For example, targeting specific receptors such as a dopamine receptor can be used for brain delivery. Another target can be vascular endothelium. These cells can be targeted using a filovirus envelope. For example, the GP of Ebola, which by post-transcriptional modification become the GP, and GP2 glycoproteins. In another embodiment, one can use different lentiviral capsids with a pseudotyped envelope (for example, FIV or SHIV [U.S. Pat. No. 5,654, 195]). A SHIV pseudotyped vector can readily be used in animal models such as monkeys.

Lentiviral vector systems as provided herein typically include at least one helper plasmid comprising at least one of a gag, pol, or rev gene. Each of the gag, pol and rev genes may be provided on individual plasmids, or one or more genes may be provided together on the same plasmid. In one embodiment, the gag, pol, and rev genes are provided on the same plasmid (e.g., FIG. 4). In another embodiment, the gag and pol genes are provided on a first plasmid and the rev gene is provided on a second plasmid (e.g., FIG. 5). Accordingly, both 3-vector (e.g., FIGS. 4 and 6) and 4-vector (e.g., FIG. 5) systems can be used to produce a lentivirus as described herein. In embodiments, the therapeutic vector, at least one envelope plasmid and at least one helper plasmid are transfected into a packaging cell, for example a packaging cell line. A non-limiting example of a packaging cell line is the 293T/17 HEK cell line. When the therapeutic vector, the envelope plasmid, and at least one helper plasmid are transfected into the packaging cell line, a lentiviral particle is ultimately produced.

In another aspect, a lentiviral vector system for expressing a lentiviral particle is disclosed. The system includes a lentiviral vector as described herein; an envelope plasmid for expressing an envelope protein optimized for infecting a cell; and at least one helper plasmid for expressing gag, pol, and rev genes, wherein when the lentiviral vector, the envelope plasmid, and the at least one helper plasmid are transfected into a packaging cell line, a lentiviral particle is produced by the packaging cell line, wherein the lentiviral particle is capable of inhibiting production of chemokine receptor CCR5 or targeting an HIV RNA sequence.

In another aspect, the lentiviral vector, which is also referred to herein as a therapeutic vector, includes the following elements: hybrid 5' long terminal repeat (RSV/5' LTR) (SEQ ID NOS: 34-35), Psi sequence (RNA packaging site) (SEQ ID NO: 36), RRE (Rev-response element) (SEQ ID NO: 37), cPPT (polypurine tract) (SEQ ID NO: 38), EF-1α promoter (SEQ ID NO: 4), miR30CCR5 (SEQ ID NO: 1), miR21Vif (SEQ ID NO: 2), miR185Tat (SEQ ID NO: 3), Woodchuck Post-Transcriptional Regulatory Element (WPRE) (SEQ ID NOS: 32 or 80), and ΔU3 3' LTR (SEQ ID NO: 39). In another aspect, sequence variation, by way of substitution, deletion, addition, or mutation can be used to modify the sequences references herein.

In another aspect, a helper plasmid includes the following elements: CAG promoter (SEQ ID NO: 41); HIV component gag (SEQ ID NO: 43); HIV component pol (SEQ ID NO: 44); HIV Int (SEQ ID NO: 45); HIV RRE (SEQ ID NO: 46); and HIV Rev (SEQ ID NO: 47). In another aspect, the helper plasmid may be modified to include a first helper plasmid for expressing the gag and pol genes, and a second and separate plasmid for expressing the rev gene. In another aspect, sequence variation, by way of substitution, deletion, addition, or mutation can be used to modify the sequences references herein.

In another aspect, an envelope plasmid includes the following elements: RNA polymerase II promoter (CMV) (SEQ ID NO: 60) and vesicular stomatitis virus G glycoprotein (VSV-G) (SEQ ID NO: 62). In another aspect, sequence variation, by way of substitution, deletion, addition, or mutation can be used to modify the sequences references herein.

In various aspects, the plasmids used for lentiviral packaging are modified by substitution, addition, subtraction or mutation of various elements without loss of vector function. For example, and without limitation, the following elements can replace similar elements in the plasmids that comprise the packaging system: Elongation Factor-1 (EF-1), phosphoglycerate kinase (PGK), and ubiquitin C (UbC) promoters can replace the CMV or CAG promoter. SV40 poly A and bGH poly A can replace the rabbit beta globin poly A. The HIV sequences in the helper plasmid can be constructed from different HIV strains or clades. The VSV-G glycoprotein can be substituted with membrane glycoproteins from feline endogenous virus (RD114), gibbon ape leukemia virus (GALV), Rabies (FUG), lymphocytic choriomeningitis virus (LCMV), influenza A fowl plague virus (FPV), Ross River alphavirus (RRV), murine leukemia virus 10A1 (MLV), or Ebola virus (EboV).

Various lentiviral packaging systems can be acquired commercially (e.g., *Lenti*-vpak packaging kit from OnGene Technologies, Inc., Rockville, MD), and can also be designed as described herein. Moreover, it is within the skill of a person ordinarily skilled in the art to substitute or modify aspects of a lentiviral packaging system to improve any number of relevant factors, including the production efficiency of a lentiviral particle.

Bioassays

In various aspects, the present invention includes bioassays for determining the success of HIV treatment for achieving a functional cure. These assays provide a method for measuring the efficacy of the disclosed methods of immunization and treatment by measuring the frequency of transduced, HIV specific CD4 T cells in a patient. HIV-specific CD4 T cells are recognizable because, among others, they proliferate, change the composition of cell surface markers, induce signaling pathways including phosphorylation, and/or express specific marker proteins that may be cytokines, chemokines, caspases, phosphorylated signaling molecules or other cytoplasmic and/or nuclear components. Specific responding CD4 T cells are recognized for example, using labeled monoclonal antibodies or specific in situ amplification of mRNA sequences, that allow sorting of HIV-specific cells using flow cytometry sorting, magnetic bead separation or other recognized methods for antigen-specific CD4 T cell isolation. The isolated CD4 T cells are tested to determine the frequency of cells carrying integrated therapeutic lentivirus. Single cell testing methods may also be used including microfluidic separation of individual cells that are coupled with mass spectrometry, PCR, ELISA or antibody staining to confirm responsiveness to HIV and presence of integrated therapeutic lentivirus.

Thus, in various embodiments, following application of a treatment according to the invention (e.g., (a) immunization, (b) ex vivo leukocyte/lymphocyte culture; (c) re-stimulation with purified proteins, inactivated viruses, virally vectored proteins, bacterially vectored proteins, biological or chemical adjuvants including cytokines and/or chemokines, vehicles; and (d) infusion of the enriched, transduced T cells), a patient may be subsequently assayed to determine the efficacy of the treatment. A threshold value of target T cells in the body may be established to measure a functional cure at a determined value, for example, at about $1 \times 10^8$ HIV-specific CD4 T cells bearing genetic modification from therapeutic lentivirus. Alternatively, the threshold value may be about $1 \times 10^5$, about $1 \times 10^6$, about $1 \times 10^7$, about $1 \times 10^8$, about $1 \times 10^9$, or about $1 \times 10^{10}$ CD4 T cells in the body of the patient.

HIV-specific CD4 T cells bearing genetic modification from therapeutic lentivirus can be determined using any suitable method, such as but not limited to flow cytometry, cell sorting, FACS analysis, DNA cloning, PCR, RT-PCR or Q-PCR, ELISA, FISH, western blotting, southern blotting, high throughput sequencing, RNA sequencing, oligonucleotide primer extension, or other methods known in the art.

While methods for defining antigen specific T cells with genetic modifications are known in the art, utilizing such methods to combine identifying HIV-specific T cells with integrated or non-integrated gene therapy constructs as a standard measure for efficacy is a novel concept in the field of HIV treatment, as described variously herein.

Doses and Dosage Forms

The disclosed methods and compositions can be used for treating HIV+ patients during various stages of their disease. Accordingly, dosing regimens may vary based upon the condition of the patient and the method of administration.

In various embodiments, HIV-specific vaccines for the initial in vivo immunization are administered to a subject in need in varying doses. In general, vaccines delivered by intramuscular injection include about 10 pg to about 300 pg, about 25 pg to about 275 pg, about 50 pg to about 250 pg, about 75 pg to about 225, or about 100 pg to about 200 pg of HIV protein, either total virus protein prepared from inactivated virus particles, virus-like particles or purified virus protein from recombinant systems or purified from virus preparations. Recombinant viral or bacterial vectors may be administered by any and all of the routes described. Intramuscular vaccines will include about 1 pg to about 100 pg, about 10 pg to about 90 pg, about 20 pg to about 80 pg, about 30 pg to about 70 pg, about 40 pg to about 60 pg, or about 50 pg of suitable adjuvant molecules and be suspended in oil, saline, buffer or water in volumes of 0.1 to 5 ml per injection dose, and may be soluble or emulsion preparations. Vaccines delivered orally, rectally, bucally, at genital mucosal or intranasally, including some virally-vectored or bacterially-vectored vaccines, fusion proteins, liposome formulations or similar preparations, may contain higher amounts of virus protein and adjuvant. Dermal, sub-dermal or subcutaneous vaccines utilize protein and adjuvant amounts more similar to oral, rectal or intranasal-delivered vaccines. Depending on responses to the initial immunization, vaccination may be repeated 1-5 times using the same or alternate routes for delivery. Intervals may be of 2-24 weeks between immunizations. Immune responses to vaccination are measured by testing HIV-specific antibodies in serum, plasma, vaginal secretions, rectal secretions, saliva or bronchoalveolar lavage fluids, using ELISA or similar methodology. Cellular immune responses are tested by in vitro stimulation with vaccine antigens followed by staining for intracellular cytokine accumulation followed by flow cytometry or similar methods including lymphoproliferation, expression of phosphorylated signaling proteins or changes in cell surface activation markers. Upper limits of dosing may be determined based on the individual patient and will depend on toxicity/safety profiles for each individual product or product lot.

Immunization may occur once, twice, three times, or repeatedly. For instance, an agent for HIV immunization may be administered to a subject in need once a week, once every other week, once every three weeks, once a month, every other month, every three months, every six months, every nine months, once a year, every eighteen months, every two years, every 36 months, or every three years.

Immunization will generally occur at least once before ex vivo expansion and enrichment of CD4 T cells, and immunization may occur once, twice, three times, or more after ex vivo leukocyte/lymphocyte culture/re-stimulation and infusion.

In one embodiment, HIV vaccines for immunization are administered as a pharmaceutical composition. In one embodiment, the pharmaceutical composition comprising an HIV vaccine is formulated in a wide variety of nasal, pulmonary, oral, topical, or parenteral dosage forms for clinical application. Each of the dosage forms can comprise various disintegrating agents, surfactants, fillers, thickeners, binders, diluents such as wetting agents or other pharmaceutically acceptable excipients. The pharmaceutical composition comprising an HIV vaccine can also be formulated for injection.

HIV vaccine compositions for the purpose of immunization can be administered using any pharmaceutically acceptable method, such as intranasal, buccal, sublingual, oral, rectal, ocular, parenteral (intravenously, intradermally, intramuscularly, subcutaneously, intracisternally, intraperitoneally), pulmonary, intravaginal, locally administered, topically administered, topically administered after scarification, mucosally administered, via an aerosol, or via a buccal or nasal spray formulation.

Further, the HIV vaccine compositions can be formulated into any pharmaceutically acceptable dosage form, such as a solid dosage form, tablet, pill, lozenge, capsule, liquid dispersion, gel, aerosol, pulmonary aerosol, nasal aerosol, ointment, cream, semi-solid dosage form, and a suspension. Further, the composition may be a controlled release formulation, sustained release formulation, immediate release formulation, or any combination thereof. Further, the composition may be a transdermal delivery system.

In another embodiment, the pharmaceutical composition comprising an HIV vaccine is formulated in a solid dosage form for oral administration, and the solid dosage form can be powders, granules, capsules, tablets or pills. In yet another embodiment, the solid dosage form includes one or more excipients such as calcium carbonate, starch, sucrose, lactose, microcrystalline cellulose or gelatin. In addition, the solid dosage form can include, in addition to the excipients, a lubricant such as talc or magnesium stearate. In some embodiments, the oral dosage form is in immediate release or a modified release form. Modified release dosage forms include controlled or extended release, enteric release, and the like. The excipients used in the modified release dosage forms are commonly known to a person of ordinary skill in the art.

In a further embodiment, the pharmaceutical composition comprising a HIV vaccine is formulated as a sublingual or buccal dosage form. Such dosage forms comprise sublingual tablets or solution compositions that are administered under the tongue and buccal tablets that are placed between the cheek and gum.

In yet a further embodiment, the pharmaceutical composition comprising an HIV vaccine is formulated as a nasal dosage form. Such dosage forms of the present invention comprise solution, suspension, and gel compositions for nasal delivery.

In one embodiment, the pharmaceutical composition is formulated in a liquid dosage form for oral administration, such as suspensions, emulsions or syrups. In other embodiments, the liquid dosage form can include, in addition to commonly used simple diluents such as water and liquid paraffin, various excipients such as humectants, sweeteners, aromatics or preservatives. In particular embodiments, the composition comprising HIV vaccine or a pharmaceutically acceptable salt thereof is formulated to be suitable for administration to a pediatric patient.

In one embodiment, the pharmaceutical composition is formulated in a dosage form for parenteral administration, such as sterile aqueous solutions, suspensions, emulsions, non-aqueous solutions or suppositories. In other embodiments, the non-aqueous solutions or suspensions includes propyleneglycol, polyethyleneglycol, vegetable oils such as olive oil or injectable esters such as ethyl oleate. As a base for suppositories, witepsol, macrogol, tween 61, cacao oil, laurin oil or glycerinated gelatin can be used.

The dosage of the pharmaceutical composition can vary depending on the patient's weight, age, gender, administration time and mode, excretion rate, and the severity of disease.

For the purposes of re-stimulation, lymphocytes, PBMCs, and/or CD4 T cells are generally removed from a patient and isolated for re-stimulation and culturing. The isolated cells may be contacted with the same HIV vaccine or activating agent used for immunization or a different HIV vaccine or activating agent. In one embodiment, the isolated cells are contacted with about 10 ng to 5 pg of an HIV vaccine or activating agent per about $10^6$ cells in culture (or any other suitable amount). More specifically, the isolated cells may be contacted with about 50 ng, about 100 ng, about 200 ng, about 300 ng, about 400 ng, about 500 ng, about 600 ng, about 700 ng, about 800 ng, about 900 ng, about 1 pg, about 1.5 pg, about 2 pg, about 2.5 pg, about 3 pg, about 3.5 pg, about 4 pg, about 4.5 pg, or about 5 pg of an HIV vaccine or activating agent per about $10^6$ cells in culture.

Activating agents or vaccines are generally used once for each in vitro cell culture but may be repeated after intervals of about 15 to about 35 days. For example, a repeat dosing could occur at about 15, about 16, about 17, about 18, about 19, about 20, about 21, about 22, about 23, about 24, about 25, about 26, about 27, about 28, about 29, about 30, about 31, about 32, about 33, about 34, or about 35 days.

Figure 6:
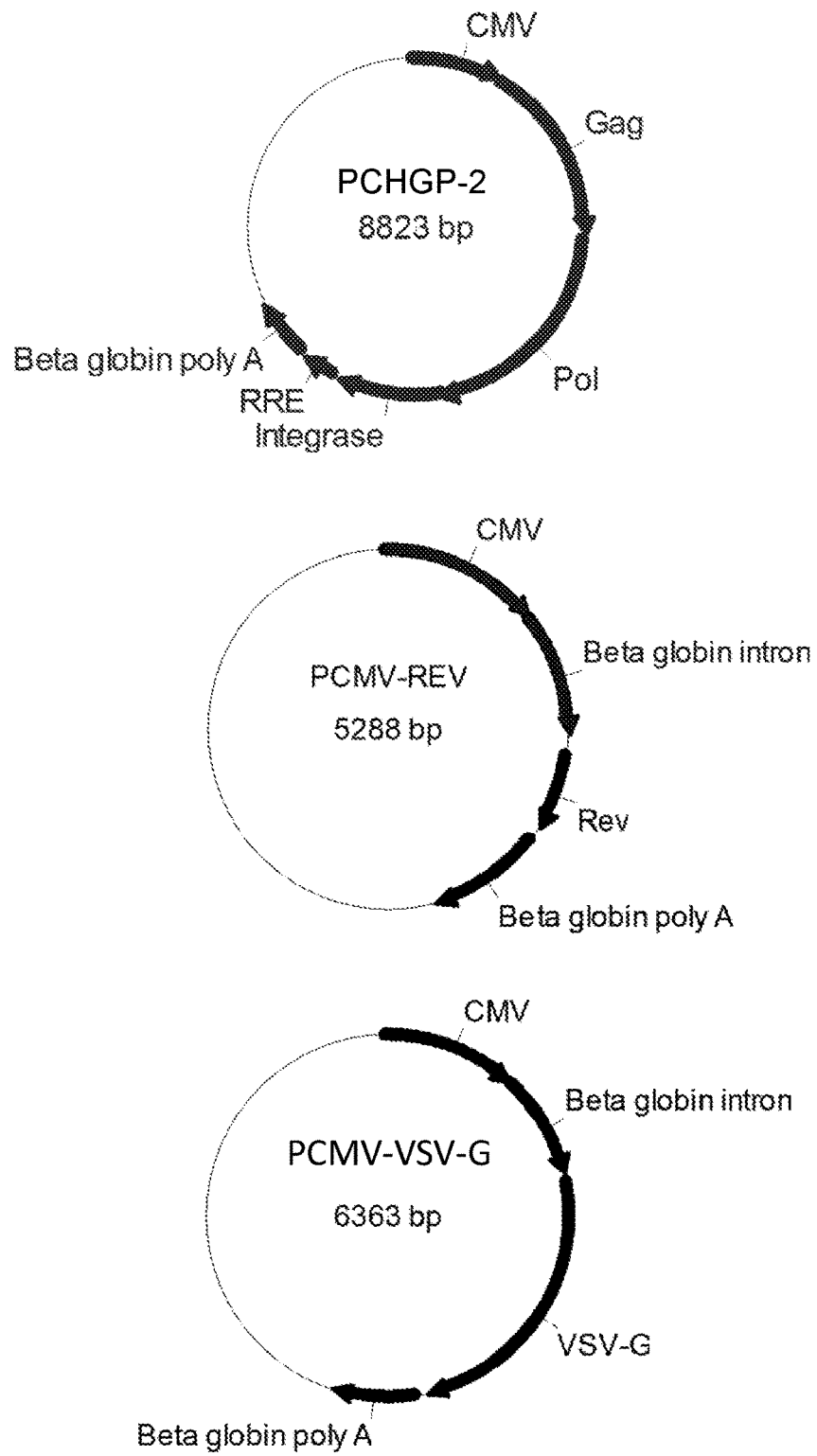
FIG. 6 depicts a further exemplary 3-vector lentiviral vector system in a circularized form.

For transduction of the enriched, re-stimulated cells, the cells may be transduced with lentiviral vectors or with other known vector systems as disclosed, for example, in FIG. 4 or FIG. 6. The cells being transduced may be contacted with about 1-1,000 viral genomes (measured by RT-PCR assay of culture fluids containing lentivirus vector) per target cell in culture (or any other suitable amount). Lentivirus transduction may be repeated 1-5 times using the same range of 1-1,000 viral genomes per target cell in culture.

Cellular Enrichment

In various embodiments, cells such as T cells are obtained from an HIV infected patient and cultured. Culturing can occur in multiwell plates in a culture medium comprising conditioned media ("CM"). The levels of supernatant $p24^{gag}$ ("p24") and viral RNA levels may be assessed by standard means. Those patients whose CM-cultured cells have peak p24 supernatant levels of less than 1 ng/ml may be suitable patients for large-scale T-cell expansion in CM with or without the use of additional anti-viral agents. Additionally, different drugs or drug combinations of interest may be added to different wells and the impact on virus levels in the sample may be assessed by standard means. Those drug combinations providing adequate viral suppression are therapeutically useful combinations. It is within the capacity of a competent technician to determine what constitutes adequate viral suppression in relation to a particular subject. In order to test the effectiveness of drugs of interest in limiting viral expansion, additional factors such as anti-CD3 antibodies may be added to the culture to stimulate viral production. Unlike culture methods for HIV infected cell samples known in the art, CM allows the culture of T cells for periods of over two months, thereby providing an effective system in which to assay long term drug effectiveness.

This approach allows the inhibition of gene expression driven by the HIV LTR promoter region in a cell population by the culture of cells in a medium comprising the CM. Culture in CM4 likely inhibits HIV LTR driven gene expression by altering one or more interactions between transcription mediating proteins and HIV gene expression regulatory elements. Transcription-mediating proteins of interest include host cell encoded proteins such as AP-1, NFkappaB, NF-AT, IRF, LEF-1 and Sp1, and the HIV encoded protein Tat. HIV gene expression regulatory elements of interest include binding sites for AP-1, NFkappaB, NF-AT, IRF, LEF-1 and Sp1, as well as the transacting responsive element ("TAR") which interacts with Tat.

In a preferred embodiment, the HIV infected cells are obtained from a subject with susceptible transcription mediating protein sequences and susceptible HIV regulatory element sequences. In a more preferred embodiment, the HIV infected cells are obtained from a subject having wild-type transcription-mediating protein sequences and wild-type HIV regulatory sequences.

Another method of enriching T Cells utilizes immunoaffinity-based selection. This method includes the simultaneous enrichment or selection of a first and second population of cells, such as a CD4+ and CD8+ cell population. Cells containing primary human T cells are contacted with a first immunoaffinity reagent that specifically binds to CD4 and a second immunoaffinity reagent that specifically binds to CD8 in an incubation composition, under conditions whereby the immunoaffinity reagents specifically bind to CD4 and CD8 molecules, respectively, on the surface of cells in the sample. Cells bound to the first and/or the second immunoaffinity reagent are recovered, thereby generating an enriched composition comprising CD4+ cells and CD8+ cells. This approach may include incubation of the composition with a concentration of the first and/or second immunoaffinity reagent that is at a sub-optimal yield concentration. Notably, in some embodiments, transduced cells are a mixed T cell population, and in other embodiments transduced cells are not a mixed T cell population.

In some embodiments, immunoaffinity-based selection is used where the solid support is a sphere, such as a bead, such as a microbead or nanobead. In other embodiments, the bead can be a magnetic bead. In another embodiment, the antibody contains one or more binding partners capable of forming a reversible bond with a binding reagent immobilized on the solid surface, such as a sphere or chromatography matrix, wherein the antibody is reversibly mobilized to the solid surface. In some embodiments, cells expressing a cell surface marker bound by the antibody on said solid surface are capable of being recovered from the matrix by disruption of the reversible binding between the binding reagent and binding partner. In some embodiments, the binding reagent is streptavidin or is a streptavidin analog or mutant. In some embodiments, immunoaffinity-based selection is used to capture cells specifically responding to HIV proteins, vaccines or peptides based on expression of cytokines in these cells. A bi-specific capture reagent binds to T cells and also captures cytokine released from that cell. The cytokine is preferably interferon gamma but may include tumor necrosis factor alpha or other cytokines known to be produced by T cells. The immobilized cytokine is recognized by a second immune-affinity reagent that is modified by a magnetic bead. Cells with the first capture reagentcytokine-second immune-affinity reagent and magnetic bead are retained on a magnetic column and are thus purified away from cells that did not express cytokine after HIV protein, vaccine or peptide stimulation and are maintained in a viable state. Removing the matrix from a magnetic field allows release of the labeled cells and capture as a highly enriched population. In some cases, the enriched cells may be cultured for 1-30 days to increase in number before being stimulated with a polyclonal mitogen such as anti-CD3/anti-CD28 microbeads or similar stimulation reagents that are compatible with lentivirus transduction.

Stable transduction of primary cells of the hematopoietic system and/or hematopoietic stem cells may be obtained by contacting, in vitro or ex vivo, the surface of the cells with both a lentiviral vector and at least one molecule which binds the cell surface. The cells may be cultured in a ventilated vessel comprising two or more layers under conditions conducive to growth and/or proliferation. In some embodiments, this approach may be used in conjunction with non-CD4+ T cell depletion and/or broad polyclonal expansion.

In another approach to T cell enrichment, PBMCs are stimulated with a peptide and enriched for cells secreting a cytokine, such as interferon-gamma. This approach generally involves stimulating a mixture of cells containing T cells with antigen, and effecting a separation of antigen-stimulated cells according to the degree to which they are labeled with the product. Antigen stimulation is achieved by exposing the cells to at least one antigen under conditions effective to elicit antigen-specific stimulation of at least one T cell. Labeling with the product is achieved by modifying the surface of the cells to contain at least one capture moiety, culturing the cells under conditions in which the product is secreted, released and specifically bound ("captured" or "entrapped") to said capture moiety; and labeling the captured product with a label moiety, where the labeled cells are not lysed as part of the labeling procedure or as part of the separation procedure. The capture moiety may incorporate detection of cell surface glycoproteins CD3 or CD4 to refine the enrichment step and increase the proportion of antigen-specific T cells in general, of CD4+ T cells in specific.

The following examples are given to illustrate aspects of the present invention. It should be understood, however, that the invention is not to be limited to the specific conditions or details described in these examples. All printed publications referenced herein are specifically incorporated by reference.

Examples

Example 1: Development of a Lentiviral Vector System

A lentiviral vector system was developed as summarized in FIG. 3 (linear form) and FIG. 4 (circularized form). Referring first to the top portion of FIG. 3, a representative therapeutic vector has been designed and produced with the following elements being from left to right: hybrid 5' long terminal repeat (RSV/5' LTR) (SEQ ID NOS: 34-35), Psi sequence (RNA packaging site) (SEQ ID NO: 36), RRE (Rev-response element) (SEQ ID NO: 37), cPPT (polypurine tract) (SEQ ID NO: 38), EF-lu promoter (SEQ ID NO: 4), miR30CCR5 (SEQ ID NO: 1), miR21Vif (SEQ ID NO: 2), miR185Tat (SEQ ID NO: 3), Woodchuck Post-Transcriptional Regulatory Element (WPRE) (SEQ ID NOS: 32 or 80), and AU3 3' LTR (SEQ ID NO: 39). The therapeutic vector detailed in FIG. 3 is also referred to herein as AGT103.

Referring next to the middle portion of FIG. 3, a helper plasmid has been designed and produced with the following elements being from left to right: CAG promoter (SEQ ID NO: 41); HIV component gag (SEQ ID NO: 43); HIV component pol (SEQ ID NO: 44); HIV Int (SEQ ID NO: 45); HIV RRE (SEQ ID NO: 46); and HIV Rev (SEQ ID NO: 47).

Referring next to the lower portion of FIG. 3, an envelope plasmid has been designed and produced with the following elements being from left to right: RNA polymerase II promoter (CMV) (SEQ ID NO: 60) and vesicular stomatitis virus G glycoprotein (VSV-G) (SEQ ID NO: 62).

Lentiviral particles were produced in 293T/17 HEK cells (purchased from American Type Culture Collection, Manassas, VA) following transfection with the therapeutic vector, the envelope plasmid, and the helper plasmid (as shown in FIG. 3). The transfection of 293T/17 HEK cells, which produced functional viral particles, employed the reagent Poly(ethylenimine) (PEI) to increase the efficiency of plasmid DNA uptake. The plasmids and DNA were initially added separately in culture medium without serum in a ratio of 3:1 (mass ratio of PEI to DNA). After 2-3 days, cell medium was collected and lentiviral particles were purified by high-speed centrifugation and/or filtration followed by anion-exchange chromatography. The concentration of lentiviral particles can be expressed in terms of transducing units/ml (TU/ml). The determination of TU was accomplished by measuring HIV p24 levels in culture fluids (p24 protein is incorporated into lentiviral particles), measuring the number of viral DNA copies per cell by quantitative PCR, or by infecting cells and using light (if the vectors encode luciferase or fluorescent protein markers).

As mentioned above, a 3-vector system (i.e., a 2-vector lentiviral packaging system) was designed for the production of lentiviral particles. A schematic of the 3-vector system is shown in FIG. 4. The schematic of FIG. 4 is a circularized version of the linear system previously described in FIG. 3. Briefly, and with reference to FIG. 4, the top-most vector is a helper plasmid, which, in this case, includes Rev. The vector appearing in the middle of FIG. 4 is the envelope plasmid. The bottom-most vector is the previously described therapeutic vector.

Referring more specifically to FIG. 4, the Helper plus Rev plasmid includes a CAG enhancer (SEQ ID NO: 40); a CAG promoter (SEQ ID NO: 41); a chicken beta actin intron (SEQ ID NO: 42); a HIV gag (SEQ ID NO: 43); a HIV Pol (SEQ ID NO: 44); a HIV Int (SEQ ID NO: 45); a HIV RRE (SEQ ID NO: 46); a HIV Rev (SEQ ID NO: 47); and a rabbit beta globin poly A (SEQ ID NO: 48).

The Envelope plasmid includes a CMV promoter (SEQ ID NO: 60); a beta globin intron (SEQ ID NO: 61); a VSV-G (SEQ ID NO: 62); and a rabbit beta globin poly A (SEQ ID NO: 63).

In an alternate vector system, and with respect to FIG. 6, the vector sequences are provided herein as SEQ ID NOs: 105-107.

Synthesis of a 2-vector lentiviral packaging system including Helper (plus Rev) and Envelope plasmids.

Materials and Methods:

Construction of the helper plasmid: The helper plasmid was constructed by initial PCR amplification of a DNA fragment from the pNL4-3 HIV plasmid (NIH Aids Reagent Program) containing Gag, Pol, and Integrase genes. Primers were designed to amplify the fragment with EcoRI and NotI restriction sites which could be used to insert at the same sites in the pCDNA3 plasmid (Invitrogen). The forward primer was (5'-TAAGCAGAATTC ATGAATTTGCCAG-GAAGAT-3') (SEQ ID NO: 81) and reverse primer was (5'-CCATACAAT-GAATGGACACTAGGCGGCCGCACGAAT-3') (SEQ ID NO: 82). The sequence for the Gag, Pol, Integrase fragment was as follows:

(SEQ ID NO: 83)
GAATTCATGAATTTGCCAGGAAGATGGAAACCAAAAATGATAGGGGGAAT

TGGAGGTTTTATCAAAGTAAGACAGTATGATCAGATACTCATAGAAATCT

GCGGACATAAAGCTATAGGTACAGTATTAGTAGGACCTACACCTGTCAAC

ATAATTGGAAGAAATCTGTTGACTCAGATTGGCTGCACTTTAAATTTTCC

CATTAGTCCTATTGAGACTGTACCAGTAAAATTAAAGCCAGGAATGGATG

GCCCAAAAGTTAAACAATGGCCATTGACAGAAGAAAAAATAAAAGCATTA

GTAGAAATTTGTACAGAAATGGAAAAGGAAGGAAAAATTTCAAAAATTGG

GCCTGAAAATCCATACAATACTCCAGTATTTGCCATAAAGAAAAAAGACA

GTACTAAATGGAGAAAATTAGTAGATTTCAGAGAACTTAATAAGAGAACT

CAAGATTTCTGGGAAGTTCAATTAGGAATACCACATCCTGCAGGGTTAAA

ACAGAAAAAATCAGTAACAGTACTGGATGTGGGCGATGCATATTTTCAG

TTCCCTTAGATAAAGACTTCAGGAAGTATACTGCATTTACCATACCTAGT

ATAAACAATGAGACACCAGGGATTAGATATCAGTACAATGTGCTTCCACA

GGGATGGAAAGGATCACCAGCAATATTCCAGTGTAGCATGACAAAAATCT

TAGAGCCTTTTAGAAAACAAAATCCAGACATAGTTCATCTATCAATACATG

GATGATTTGTATGTAGGATCTGACTTAGAAATAGGGCAGCATAGAACAAA

AATAGAGGAACTGAGACAACATCTGTTGAGGTGGGGATTTACCACACCAG

ACAAAAAACATCAGAAAGAACCTCCATTCCTTTGGATGGGTTATGAACTC

CATCCTGATAAATGGACAGTACAGCCTATAGTGCTGCCAGAAAAGGACAG

CTGGACTGTCAATGACATACAGAAATTAGTGGGAAAATTGAATTGGGCAA

GTCAGATTTATGCAGGGATTAAAGTAAGGCAATTATGTAAACTTCTTAGG

GGAACCAAAGCACTAACAGAAGTAGTACCACTAACAGAAGAAGCAGAGCT

AGAACTGGCAGAAAACAGGGAGATTCTAAAAGAACCGGTACATGGAGTGT

ATTATGACCCATCAAAAGACTTAATAGCAGAAATACAGAAGCAGGGCAA

GGCCAATGGACATATCAAATTTATCAAGAGCCATTTAAAAATCTGAAAAC

AGGAAAGTATGCAAGAATGAAGGGTGCCCACACTAATGATGTGAAACAAT

TAACAGAGGCAGTACAAAAAATAGCCACAGAAAGCATAGTAATATGGGGA

AAGACTCCTAAATTTAAATTACCCATACAAAAGGAAACATGGGAAGCATG

GTGGACAGAGTATTGGCAAGCCACCTGGATTCCTGAGTGGGAGTTTGTCA

ATACCCCTCCCTTAGTGAAGTTATGGTACCAGTTAGAGAAAGAACCCATA

ATAGGAGCAGAAACTTTCTATGTAGATGGGGCAGCCAATAGGGAAACTAA

ATTAGGAAAAGCAGGATATGTAACTGACAGAGGAAGACAAAAAGTTGTCC

CCCTAACGGACACAACAAATCAGAAGACTGAGTTACAAGCAATTCATCTA

GCTTTGCAGGATTCGGGATTAGAAGTAAACATAGTGACAGACTCACAATA

TGCATTGGGAATCATTCAAGCACAACCAGATAAGAGTGAATCAGAGTTAG

TCAGTCAAATAATAGAGCAGTTAATAAAAAAGGAAAAAGTCTACCTGGCA

TGGGTACCAGCACACAAAGGAATTGGAGGAAATGAACAAGTAGATAAATT

GGTCAGTGCTGGAATCAGGAAAGTACTATTTTTAGATGGAATAGATAAGG

CCCAAGAAGAACATGAGAAATATCACAGTAATTGGAGAGCAATGGCTAGT

GATTTTAACCTACCACCTGTAGTAGCAAAAGAAATAGTAGCCAGCTGTGA

TAAATGTCAGCTAAAAGGGGAAGCCATGCATGGACAAGTAGACTGTAGCC

CAGGAATATGGCAGCTAGATTGTACACATTTAGAAGGAAAAGTTATCTTG

GTAGCAGTTCATGTAGCCAGTGGATATATAGAAGCAGAAGTAATTCCAGC

AGAGACAGGGCAAGAAACAGCATACTTCCTCTTAAAATTAGCAGGAAGAT

GGCCAGTAAAAACAGTACATACAGACAATGGCAGCAATTTCACCAGTACT

ACAGTTAAGGCCGCCTGTTGGTGGGCGGGGATCAAGCAGGAATTTGGCAT

TCCCTACAATCCCCAAAGTCAAGGAGTAATAGAATCTATGAATAAAGAAT

TAAAGAAAATTATAGGACAGGTAAGAGATCAGGCTGAACATCTTAAGACA

GCAGTACAAATGGCAGTATTCATCCACAATTTTAAAAGAAAAGGGGGGAT

TGGGGGGTACAGTGCAGGGGAAAGAATAGTAGACATAATAGCAACAGACA

TACAAACTAAAGAATTACAAAAACAAATTACAAAAATTCAAAATTTTCGG

GTTTATTACAGGGACAGCAGAGATCCAGTTTGGAAAGGACCAGCAAAGCT

CCTCTGGAAAGGTGAAGGGGCAGTAGTAATACAAGATAATAGTGACATAA

AAGTAGTGCCAAGAAGAAAAGCAAAGATCATCAGGGATTATGGAAAACAG

ATGGCAGGTGATGATTGTGTGGCAAGTAGACAGGATGAGGATTAA

Next, a DNA fragment containing the Rev, RRE, and rabbit beta globin poly A sequence with XbaI and XmaI flanking restriction sites was synthesized by MWG Operon. The DNA fragment was then inserted into the plasmid at the XbaI and XmaI restriction sites The DNA sequence was as follows:

(SEQ ID NO: 84)
TCTAGAATGGCAGGAAGAAGCGGAGACAGCGACGAAGAGCTCATCAGAAC

AGTCAGACTCATCAAGCTTCTCTATCAAAGCAACCCACCTCCCAATCCCG

AGGGGACCCGACAGGCCCGAAGGAATAGAAGAAGAAGGTGGAGAGAGAGA

CAGAGACAGATCCATTCGATTAGTGAACGGATCCTTGGCACTTATCTGGG

ACGATCTGCGGAGCCTGTGCCTCTTCAGCTACCACCGCTTGAGAGACTTA

CTCTTGATTGTAACGAGGATTGTGGAACTTCTGGGACGCAGGGGTGGGA

AGCCCTCAAATATTGGTGGAATCTCCTACAATATTGGAGTCAGGAGCTAA

AGAATAGAGGCTTTGTTCCTTGGGTTCTTGGGAGCAGCAGGAAGCACT

ATGGGCGCAGCGTCAATGACGCTGACGGTACAGGCCAGACAATTATTGTC

TGGTATAGTGCAGCAGCAGAACAATTTGCTGAGGGCTATTGAGGCGCAAC

AGCATCTGTTGCAACTCACAGTCTGGGGCATCAAGCAGCTCCAGGCAAGA

ATCCTGGCTGTGGAAAGATACCTAAAGGATCAACAGCTCCTAGATCTTTT

TCCCTCTGCCAAAAATTATGGGGACATCATGAAGCCCCTTGAGCATCTGA

CTTCTGGCTAATAAAGGAAATTTATTTTCATTGCAATAGTGTGTTGGAAT

TTTTTGTGTCTCTCACTCGGAAGGACATATGGGAGGGCAAATCATTTAAA

ACATCAGAATGAGTATTTGGTTTAGAGTTTGGCAACATATGCCATATGCT

GGCTGCCATGAACAAAGGTGGCTATAAAGAGGTCATCAGTATATGAAACA

GCCCCCTGCTGTCCATTCCTTATTCCATAGAAAAGCCTTGACTTGAGGTT

AGATTTTTTTTATATTTTGTTTTGTGTTATTTTTTTCTTTAACATCCCTA

AAATTTTCCTTACATGTTTTACTAGCCAGATTTTTCCTCCTCTCCTGACT

ACTCCCAGTCATAGCTGTCCCTCTTCTCTTATGAAGATCCCTCGACCTGC

AGCCCAAGCTTGGCGTAATCATGGTCATAGCTGTTTCCTGTGTGAAATTG

TTATCCGCTCACAATTCCACACAACATACGAGCCGGAAGCATAAAGTGTA

AAGCCTGGGGTGCCTAATGAGTGAGCTAACTCACATTAATTGCGTTGCGC

TCACTGCCCGCTTTCCAGTCGGGAAACCTGTCGTGCCAGCGGATCCGCAT

CTCAATTAGTCAGCAACCATAGTCCCGCCCCTAACTCCGCCCATCCCGCC

CCTAACTCCGCCCAGTTCCGCCCATTCTCCGCCCCATGGCTGACTAATTT

TTTTTATTTATGCAGAGGCCGAGGCCGCCTCGGCCTCTGAGCTATTCCAG

AAGTAGTGAGGAGGCTTTTTTGGAGGCCTAGGCTTTTGCAAAAAGCTAAC

TTGTTTATTGCAGCTTATAATGGTTACAAATAAAGCAATAGCATCACAAA

TTTCACAAATAAAGCATTTTTTTCACTGCATTCTAGTTGTGGTTTGTCCA

AACTCATCAATGTATCTTATCAGCGGCCGCCCCGGG

Finally, the CMV promoter of pCDNA3.1 was replaced with the CAG enhancer/promoter plus a chicken beta actin intron sequence. A DNA fragment containing the CAG enhancer/promoter/intron sequence with MluI and EcoRI flanking restriction sites was synthesized by MWG Operon. The DNA fragment was then inserted into the plasmid at the MluI and EcoRI restriction sites. The DNA sequence was as follows:

(SEQ ID NO: 85)
ACGCGTTAGTTATTAATAGTAATCAATTACGGGGTCATTAGTTCATAGCC

CATATATGGAGTTCCGCGTTACATAACTTACGGTAAATGGCCCGCCTGGC

TGACCGCCCAACGACCCCCGCCCATTGACGTCAATAATGACGTATGTTCC

CATAGTAACGCCAATAGGGACTTTCCATTGACGTCAATGGGTGGACTATT

TACGGTAAACTGCCCACTTGGCAGTACATCAAGTGTATCATATGCCAAGT

ACGCCCCCTATTGACGTCAATGACGGTAAATGGCCCGCCTGGCATTATGC

CCAGTACATGACCTTATGGGACTTTCCTACTTGGCAGTACATCTACGTAT

TAGTCATCGCTATTACCATGGGTCGAGGTGAGCCCCACGTTCTGCTTCAC

TCTCCCCATCTCCCCCCCCTCCCCACCCCCAATTTTGTATTTATTTATTT

TTTAATTATTTTGTGCAGCGATGGGGGCGGGGGGGGGGGGGCGCGCGCC

AGGCGGGGCGGGGCGGGGCGAGGGGCGGGGCGGGGCGAGGCGGAGAGGTG

CGGCGGCAGCCAATCAGAGCGGCGCGCTCCGAAAGTTTCCTTTTATGGCG

AGGCGGCGGCGGCGGCGGCCCTATAAAAAGCGAAGCGCGCGGCGGGCGGG

AGTCGCTGCGTTGCCTTCGCCCCGTGCCCCGCTCCGCGCCGCCTCGCGCC

GCCCGCCCCGGCTCTGACTGACCGCGTTACTCCCACAGGTGAGCGGGCGG

GACGGCCCTTCTCCTCCGGGCTGTAATTAGCGCTTGGTTTAATGACGGCT

CGTTTCTTTTCTGTGGCTGCGTGAAAGCCTTAAAGGGCTCCGGGAGGGCC

CTTTGTGCGGGGGGGAGCGGCTCGGGGGGTGCGTGCGTGTGTGTGTGCGT

GGGGAGCGCCGCGTGCGGCCCGCGCTGCCCGGCGGCTGTGAGCGCTGCGG

GCGCGGCGCGGGGCTTTGTGCGCTCCGCGTGTGCGCGAGGGGAGCGCGGC

CGGGGGCGGTGCCCCGCGGTGCGGGGGGGCTGCGAGGGGAACAAAGGCTG

CGTGCGGGGTGTGTGCGTGGGGGGGTGAGCAGGGGGTGTGGGCGCGGCGG

TCGGGCTGTAACCCCCCCCTGCACCCCCCTCCCCGAGTTGCTGAGCACGG

CCCGGCTTCGGGTGCGGGGCTCCGTGCGGGGCGTGGCGCGGGGCTCGCCG

TGCCGGGCGGGGGGTGGCGGCAGGTGGGGGTGCCGGGCGGGGCGGGGCCG

CCTCGGGCCGGGGAGGGCTCGGGGGAGGGGCGCGGCGGCCCCGGAGCGCC

GGCGGCTGTCGAGGCGCGGCGAGCCGCAGCCATTGCCTTTTATGGTAATC

GTGCGAGAGGGCGCAGGGACTTCCTTTGTCCCAAATCTGGCGGAGCCGAA

ATCTGGGAGGCGCCGCCGCACCCCCTCTAGCGGGCGCGGGCGAAGCGGTG

CGGCGCCGGCAGGAAGGAAATGGGCGGGGAGGGCCTTCGTGCGTCGCCGC

GCCGCCGTCCCCTTCTCCATCTCCAGCCTCGGGGCTGCCGCAGGGGGACG

GCTGCCTTCGGGGGGGACGGGGCAGGGCGGGGTTCGGCTTCTGGCGTGTG

ACCGGCGGGAATTC

Construction of the VSV-G Envelope Plasmid:

The vesicular stomatitis Indiana virus glycoprotein (VSV-G) sequence was synthesized by MWG Operon with flanking EcoRI restriction sites. The DNA fragment was then inserted into the pCDNA3. 1 plasmid (Invitrogen) at the EcoRI restriction site and the correct orientation was determined by sequencing using a CMV specific primer. The DNA sequence was as follows:

(SEQ ID NO: 86)
GAATTCATGAAGTGCCTTTTGTACTTAGCCTTTTTATTCATTGGGGTGAA

TTGCAAGTTCACCATAGTTTTTCCACACAACCAAAAAGGAAACTGGAAAA

ATGTTCCTTCTAATTACCATTATTGCCCGTCAAGCTCAGATTTAAATTGG

CATAATGACTTAATAGGCACAGCCTTACAAGTCAAAATGCCCAAGAGTCA

CAAGGCTATTCAAGCAGACGGTTGGATGTGTCATGCTTCCAAATGGGTCA

CTACTTGTGATTTCCGCTGGTATGGACCGAAGTATATAACACATTCCATC

CGATCCTTCACTCCATCTGTAGAACAATGCAAGGAAAGCATTGAACAAAC

GAAACAAGGAACTTGGCTGAATCCAGGCTTCCCTCCTCAAAGTTGTGGAT

ATGCAACTGTGACGGATGCCGAAGCAGTGATTGTCCAGGTGACTCCTCAC

CATGTGCTGGTTGATGAATACACAGGAGAATGGGTTGATTCACAGTTCAT

CAACGGAAAATGCAGCAATTACATATGCCCCACTGTCCATAACTCTACAA

CCTGGCATTCTGACTATAAGGTCAAAGGGCTATGTGATTCTAACCTCATT

TCCATGGACATCACCTTCTTCTCAGAGGACGGAGAGCTATCATCCCTGGG

AAAGGAGGGCACAGGGTTCAGAAGTAACTACTTTGCTTATGAAACTGGAG

GCAAGGCCTGCAAAATGCAATACTGCAAGCATTGGGGAGTCAGACTCCCA

TCAGGTGTCTGGTTCGAGATGGCTGATAAGGATCTCTTTGCTGCAGCCAG

ATTCCCTGAATGCCCAGAAGGGTCAAGTATCTCTGCTCCATCTCAGACCT

CAGTGGATGTAAGTCTAATTCAGGACGTTGAGAGGATCTTGGATTATTCC

CTCTGCCAAGAAACCTGGAGCAAAATCAGAGCGGGTCTTCCAATCTCTCC

AGTGGATCTCAGCTATCTTGCTCCTAAAAACCCAGGAACCGGTCCTGCTT

TCACCATAATCAATGGTACCCTAAAATACTTTGAGACCAGATACATCAGA

GTCGATATTGCTGCTCCAATCCTCTCAAGAATGGTCGGAATGATCAGTGG

AACTACCACAGAAAGGGAACTGTGGGATGACTGGGCACCATATGAAGACG

TGGAAATTGGACCCAATGGAGTTCTGAGGACCAGTTCAGGATATAAGTTT

CCTTTATACATGATTGGACATGGTATGTTGGACTCCGATCTTCATCTTAG

CTCAAAGGCTCAGGTGTTCGAACATCCTCACATTCAAGACGCTGCTTCGC

AACTTCCTGATGATGAGAGTTTATTTTTTGGTGATACTGGGCTATCCAAA

AATCCAATCGAGCTTGTAGAAGGTTGGTTCAGTAGTTGGAAAAGCTCTAT

TGCCTCTTTTTTCTTTATCATAGGGTTAATCATTGGACTATTCTTGGTTC

TCCGAGTTGGTATCCATCTTTGCATTAAATTAAAGCACACCAAGAAAAGA

CAGATTTATACAGACATAGAGATGAGAATTC

Figure 5:
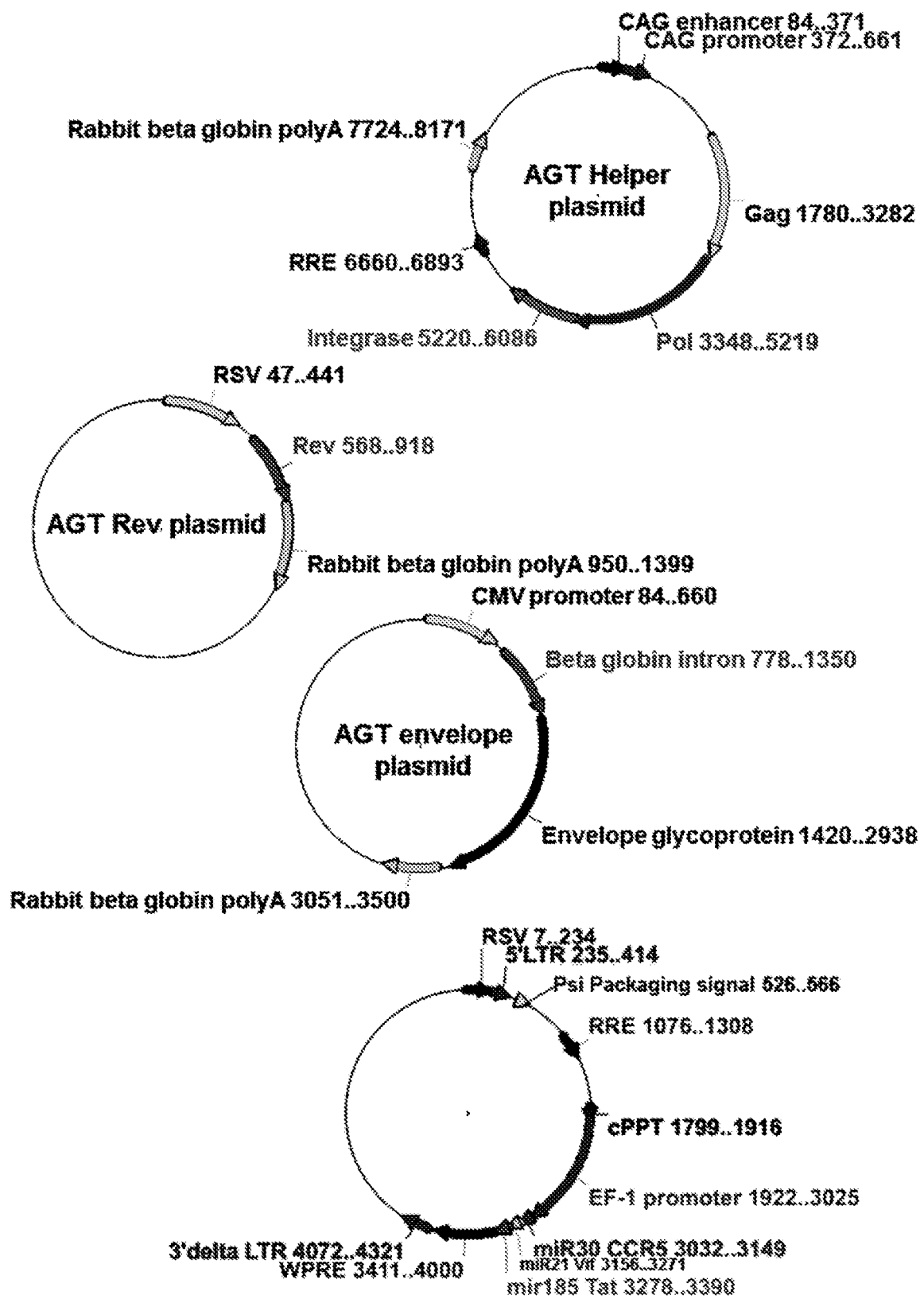
FIG. 5 depicts an exemplary 4-vector lentiviral vector system in a circularized form.

A 4-vector system (i.e., a 3-vector lentiviral packaging system) has also been designed and produced using the methods and materials described herein. A schematic of the 4-vector system is shown in FIG. 5. Briefly, and with reference to FIG. 5, the top-most vector is a helper plasmid, which, in this case, does not include Rev. The vector second from the top is a separate Rev plasmid. The vector second from the bottom is the envelope plasmid. The bottom-most vector is the previously described therapeutic vector.

Referring, in part, to FIG. 5, the Helper plasmid includes a CAG enhancer (SEQ ID NO: 49); a CAG promoter (SEQ ID NO: 50); a chicken beta actin intron (SEQ ID NO: 51); a HIV gag (SEQ ID NO: 52); a HIV Pol (SEQ ID NO: 53); a HIV Int (SEQ ID NO: 54); a HIV RRE (SEQ ID NO: 55); and a rabbit beta globin poly A (SEQ ID NO: 56).

The Rev plasmid includes a RSV promoter (SEQ ID NO: 57); a HIV Rev (SEQ ID NO: 58); and a rabbit beta globin poly A (SEQ ID NO: 59).

The Envelope plasmid includes a CMV promoter (SEQ ID NO: 60); a beta globin intron (SEQ ID NO: 61); a VSV-G (SEQ ID NO: 62); and a rabbit beta globin poly A (SEQ ID NO: 63).

Synthesis of a 3-vector lentiviral packaging system including Helper, Rev, and Envelope plasmids.
  Materials and Methods:
  Construction of the Helper Plasmid without Rev:

The Helper plasmid without Rev was constructed by inserting a DNA fragment containing the RRE and rabbit beta globin poly A sequence. This sequence was synthesized by MWG Operon with flanking XbaI and XmaI restriction sites. The RRE/rabbit poly A beta globin sequence was then inserted into the Helper plasmid at the XbaI and XmaI restriction sites. The DNA sequence is as follows:

(SEQ ID NO: 87)
TCTAGAAGGAGCTTTGTTCCTTGGGTTCTTGGGAGCAGCAGGAAGCACTA

TGGGCGCAGCGTCAATGACGCTGACGGTACAGGCCAGACAATTATTGTCT

GGTATAGTGCAGCAGCAGAACAATTTGCTGAGGGCTATTGAGGCGCAACA

GCATCTGTTGCAACTCACAGTCTGGGGCATCAAGCAGCTCCAGGCAAGAA

TCCTGGCTGTGGAAAGATACCTAAAGGATCAACAGCTCCTAGATCTTTTT

CCCTCTGCCAAAAATTATGGGGACATCATGAAGCCCCTTGAGCATCTGAC

TTCTGGCTAATAAAGGAAATTTATTTTTCATTGCAATAGTGTGTTGGAATT

TTTTGTGTCTCTCACTCGGAAGGACATATGGGAGGGCAAATCATTTAAAA

CATCAGAATGAGTATTTGGTTTAGAGTTTGGCAACATATGCCATATGCTG

GCTGCCATGAACAAAGGTGGCTATAAAGAGGTCATCAGTATATGAAACAG

CCCCCTGCTGTCCATTCCTTATTCCATAGAAAAGCCTTGACTTGAGGTTA

GATTTTTTTATATTTTGTTTTGTGTTATTTTTTCTTTAACATCCCTAA

AATTTTCCTTACATGTTTTACTAGCCAGATTTTTCCTCCTCTCCTGACTA

CTCCCAGTCATAGCTGTCCCTCTTCTCTTATGAAGATCCCTCGACCTGCA

GCCCAAGCTTGGCGTAATCATGGTCATAGCTGTTTCCTGTGTGAAATTGT

TATCCGCTCACAATTCCACACAACATACGAGCCGGAAGCATAAAGTGTAA

AGCCTGGGGTGCCTAATGAGTGAGCTAACTCACATTAATTGCGTTGCGCT

CACTGCCCGCTTTCCAGTCGGGAAACCTGTCGTGCCAGCGGATCCGCATC

TCAATTAGTCAGCAACCATAGTCCCGCCCCTAACTCCGCCCATCCCGCCC

CTAACTCCGCCCAGTTCCGCCCATTCTCCGCCCCATGGCTGACTAATTTT

TTTTATTTATGCAGAGGCCGAGGCCGCCTCGGCCTCTGAGCTATTCCAGA

AGTAGTGAGGAGGCTTTTTTGGAGGCCTAGGCTTTTGCAAAAAGCTAACT

TGTTTATTGCAGCTTATAATGGTTACAAATAAAGCAATAGCATCACAAAT

TTCACAAATAAAGCATTTTTTTCACTGCATTCTAGTTGTGGTTTGTCCAA

ACTCATCAATGTATCTTATCACCCGGG

Construction of the Rev Plasmid:

The RSV promoter and HIV Rev sequence was synthesized as a single DNA fragment by MWG Operon with flanking MfeI and XbaI restriction sites. The DNA fragment was then inserted into the pCDNA3.1 plasmid (Invitrogen) at the MfeI and XbaI restriction sites in which the CMV promoter is replaced with the RSV promoter. The DNA sequence was as follows:

(SEQ ID NO: 88)
CAATTGCGATGTACGGGCCAGATATACGCGTATCTGAGGGGACTAGGGTG

TGTTTAGGCGAAAAGCGGGGCTTCGGTTGTACGCGGTTAGGAGTCCCCTC

AGGATATAGTAGTTTCGCTTTTGCATAGGGAGGGGGAAATGTAGTCTTAT

GCAATACACTTGTAGTCTTGCAACATGGTAACGATGAGTTAGCAACATGC

CTTACAAGGAGAGAAAAGCACCGTGCATGCCGATTGGTGGAAGTAAGGT

GGTACGATCGTGCCTTATTAGGAAGGCAACAGACAGGTCTGACATGGATT

GGACGAACCACTGAATTCCGCATTGCAGAGATAATTGTATTTAAGTGCCT

AGCTCGATACAATAAACGCCATTTGACCATTCACCACATTGGTGTGCACC

TCCAAGCTCGAGCTCGTTTAGTGAACCGTCAGATCGCCTGGAGACGCCAT

CCACGCTGTTTTGACCTCCATAGAAGACACCGGGACCGATCCAGCCTCCC

CTCGAAGCTAGCGATTAGGCATCTCCTATGGCAGGAAGAAGCGGAGACAG

CGACGAAGAACTCCTCAAGGCAGTCAGACTCATCAAGTTTCTCTATCAAA

-continued

GCAACCCACCTCCCAATCCCGAGGGGACCCGACAGGCCCGAAGGAATAGA

AGAAGAAGGTGGAGAGAGAGACAGAGACAGATCCATTCGATTAGTGAACG

GATCCTTAGCACTTATCTGGGACGATCTGCGGAGCCTGTGCCTCTTCAGC

TACCACCGCTTGAGAGACTTACTCTTGATTGTAACGAGGATTGTGGAACT

TCTGGGACGCAGGGGGTGGGAAGCCCTCAAATATTGGTGGAATCTCCTAC

AATATTGGAGTCAGGAGCTAAAGAATAGTCTAGA

The plasmids for the 2-vector and 3-vector packaging systems could be modified with similar elements and the intron sequences could potentially be removed without loss of vector function. For example, the following elements could replace similar elements in the 2-vector and 3-vector packaging system:

Promoters: Elongation Factor-1 (EF-1) (SEQ ID NO: 64), phosphoglycerate kinase (PGK) (SEQ ID NO: 65), and ubiquitin C (UbC) (SEQ ID NO: 66) can replace the CMV (SEQ ID NO: 60) or CAG promoter (SEQ ID NO: 100). These sequences can also be further varied by addition, substitution, deletion or mutation.

Poly A sequences: SV40 poly A (SEQ ID NO: 67) and bGH poly A (SEQ ID NO: 68) can replace the rabbit beta globin poly A (SEQ ID NO: 48). These sequences can also be further varied by addition, substitution, deletion or mutation.

HIV Gag, Pol, and Integrase sequences: The HIV sequences in the Helper plasmid can be constructed from different HIV strains or clades. For example, HIV Gag (SEQ ID NO: 69); HIV Pol (SEQ ID NO: 70); and HIV Int (SEQ ID NO: 71) from the Bal strain can be interchanged with the gag, pol, and int sequences contained in the helper/helper plus Rev plasmids as outlined herein. These sequences can also be further varied by addition, substitution, deletion or mutation.

Envelope: The VSV-G glycoprotein can be substituted with membrane glycoproteins from feline endogenous virus (RD114) (SEQ ID NO: 72), gibbon ape leukemia virus (GALV) (SEQ ID NO: 73), Rabies (FUG) (SEQ ID NO: 74), lymphocytic choriomeningitis virus (LCMV) (SEQ ID NO: 75), influenza A fowl plague virus (FPV) (SEQ ID NO: 76), Ross River alphavirus (RRV) (SEQ ID NO: 77), murine leukemia virus 10A1 (MLV) (SEQ ID NO: 78), or Ebola virus (EboV) (SEQ ID NO: 79). Sequences for these envelopes are identified in the sequence portion herein. Further, these sequences can also be further varied by addition, substitution, deletion or mutation.

In summary, the 3-vector versus 4-vector systems can be compared and contrasted, in part, as follows. The 3-vector lentiviral vector system contains: 1. Helper plasmid: HIV Gag, Pol, Integrase, and Rev/Tat; 2. Envelope plasmid: VSV-G/FUG envelope; and 3. Therapeutic vector: RSV 5'LTR, Psi Packaging Signal, Gag fragment, RRE, Env fragment, cPPT, WPRE, and 3'delta LTR. The 4-vector lentiviral vector system contains: 1. Helper plasmid: HIV Gag, Pol, and Integrase; 2. Rev plasmid: Rev; 3. Envelope plasmid: VSV-G/FUG envelope; and 4. Therapeutic vector: RSV 5'LTR, Psi Packaging Signal, Gag fragment, RRE, Env fragment, cPPT, WPRE, and 3'delta LTR. Sequences corresponding with the above elements are identified in the sequence listings portion herein.

Example 2: Development of an Anti-HIV Lentivirus Vector

The purpose of this example was to develop an anti-HIV lentivirus vector.

Inhibitory RNA Designs. The sequence of *Homo sapiens* chemokine C-C motif receptor 5 (CCR5) (GC03P046377) mRNA was used to search for potential siRNA or shRNA candidates to knockdown CCR5 levels in human cells. Potential RNA interference sequences were chosen from candidates selected by siRNA or shRNA design programs such as from the Broad Institute or the BLOCK-iT RNAi Designer from Thermo Scientific. Individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters. The microRNA backbone was selected from mirbase.org. RNA sequences were also synthesized as synthetic siRNA oligonucleotides and introduced directly into cells without using a lentiviral vector.

The genomic sequence of Bal strain of human immunodeficiency virus type 1 (HIV-1 85US_BaL, accession number AY713409) was used to search for potential siRNA or shRNA candidates to knockdown HIV replication levels in human cells. Based on sequence homology and experience, the search focused on regions of the Tat and Vif genes of HIV although an individual of skill in the art will understand that use of these regions is non-limiting and other potential targets might be selected. Importantly, highly conserved regions of gag or pol genes could not be targeted by shRNA because these same sequences were present in the packaging system complementation plasmids needed for vector manufacturing. As with the CCR5 (NM 000579.3, NM 001100168.1-specific) RNAs, potential HIV-specific RNA interference sequences were chosen from candidates selected by siRNA or shRNA design programs such as from the Gene-E Software Suite hosted by the Broad Institute (broadinstitute.org/mai/public) or the BLOCK-iT RNAi Designer from Thermo Scientific (madesigner.thermofisher.com/maiexpress/setOption.do?designOption=shma&pid=67126273 60706061801). Individual selected shRNA sequences were inserted into lentiviral vectors immediately 3' to a RNA polymerase III promoter such as H1, U6, or 7SK to regulate shRNA expression. These lentivirus-shRNA constructs were used to transduce cells and measure the change in specific mRNA levels. The shRNA most potent for reducing mRNA levels were embedded individually within a microRNA backbone to allow for expression by either the CMV or EF-1alpha RNA polymerase II promoters.

Vector Constructions. For CCR5, Tat or Vif shRNA, oligonucleotide sequences containing BamHI and EcoRI restriction sites were synthesized by Eurofins MWG Operon, LLC. Overlapping sense and antisense oligonucleotide sequences were mixed and annealed during cooling from 70 degrees Celsius to room temperature. The lentiviral vector was digested with the restriction enzymes BamHI and EcoRI for one hour at 37 degrees Celsius. The digested lentiviral vector was purified by agarose gel electrophoresis and extracted from the gel using a DNA gel extraction kit from Invitrogen. The DNA concentrations were determined and vector to oligo (3:1 ratio) were mixed, allowed to anneal, and ligated. The ligation reaction was performed with T4 DNA ligase for 30 minutes at room temperature. 2.5 microliters of the ligation mix were added to 25 microliters of STBL3 competent bacterial cells. Transformation was achieved after heat-shock at 42 degrees Celsius. Bacterial cells were spread on agar plates containing ampicillin and drug-resistant colonies (indicating the presence of ampicillin-resistance plasmids) were recovered, purified and expanded in LB broth. To check for insertion of the oligo sequences, plasmid DNA were extracted from harvested bacteria cultures with the Invitrogen DNA mini prep kit. Insertion of the shRNA sequence in the lentiviral vector was verified by DNA sequencing using a specific primer for the promoter used to regulate shRNA expression. Exemplary vector sequences that were determined to restrict HIV replication can be found in FIG. 7. For example, the shRNA sequences with the highest activity against CCR5, Tat or Vif gene expression were then assembled into a microRNA (miR) cluster under control of the EF-1alpha promoter. The promoter and miR sequences are depicted in FIG. 7.

Further, and using standard molecular biology techniques (e.g., Sambrook; *Molecular Cloning: A Laboratory Manual*, 4$^{th}$ Ed.) as well as the techniques described herein, a series of lentiviral vectors have been developed as depicted in FIG. 8 herein.

Vector 1 was developed and contains, from left to right: a long terminal repeat (LTR) portion (SEQ ID NO: 35); a H1 element (SEQ ID NO: 101); a shCCR5 (SEQ ID NOS: 16, 18, 20, 22, or 24-Y); a posttranscriptional regulatory element of woodchuck hepatitis virus (WPRE) (SEQ ID NOS: 32, 80); and a long terminal repeat portion (SEQ ID NO: 102).

Vector 2 was developed and contains, from left to right: a long terminal repeat (LTR) portion (SEQ ID NO: 35); a H1 element (SEQ ID NO: 101); a shRev/Tat (SEQ ID NO: 10); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 3 was developed and contains, from left to right: a long terminal repeat (LTR) portion (SEQ ID NO: 35); a H1 element (SEQ ID NO: 101); a shGag (SEQ ID NO: 12); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 4 was developed and contains, from left to right: a long terminal repeat (LTR) portion (SEQ ID NO: 35); a 7SK element (SEQ ID NO: 103); a shRev/Tat (SEQ ID NO: 10); a H1 element (SEQ ID NO: 101); a shCCR5 (SEQ ID NOS: 16, 18, 20, 22, or 24); a posttranscriptional regulatory element of woodchuck hepatitis virus (WPRE) (SEQ ID NOS: 32, 80); and a long terminal repeat portion (SEQ ID NO: 102).

Vector 5 was developed and contains, from left to right: a long terminal repeat (LTR) portion (SEQ ID NO: 35); a EF1 element (SEQ ID NO: 4); miR30CCR5 (SEQ ID NO: 1); MiR21Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Vector 6 was developed and contains, from left to right: a long terminal repeat (LTR) portion (SEQ ID NO: 35); a EF1 element (SEQ ID NO: 4); miR30CCR5 (SEQ ID NO: 1); MiR21Vif (SEQ ID NO: 2); miR155Tat (SEQ ID NO: 104); a posttranscriptional regulatory element of woodchuck hepatitis virus (WPRE) (SEQ ID NOS: 32, 80); and a long terminal repeat portion (SEQ ID NO: 102).

Vector 7 was developed and contains, from left to right: a long terminal repeat (LTR) portion (SEQ ID NO: 35); a EF1 element (SEQ ID NO: 4); miR30CCR5 (SEQ ID NO: 1); MiR21Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Vector 8 was developed and contains, from left to right: a long terminal repeat (LTR) portion (SEQ ID NO: 35); a EF1 element (SEQ ID NO: 4); miR30CCR5 (SEQ ID NO: 1); MiR21Vif (SEQ ID NO: 2); miR185Tat (SEQ ID NO: 3); and a long terminal repeat portion (SEQ ID NO: 102).

Vector 9 was developed and contains, from left to right: a long terminal repeat (LTR) portion (SEQ ID NO: 35); a CD4 element (SEQ ID NO: 30); miR30CCR5 (SEQ ID NO: 1); miR21Vif (SEQ ID NO: 2); miR185Tat (SEQ ID NO: 3); a posttranscriptional regulatory element of woodchuck hepatitis virus (WPRE) (SEQ ID NOS: 32, 80); and a long terminal repeat portion (SEQ ID NO: 102).

Development of Vectors

It should be noted that not all vectors developed for these experiments necessarily worked as might be predicted. More specifically, a lentivirus vector against HIV might include three main components: 1) inhibitory RNA to reduce the level of HIV binding proteins (receptors) on the target cell surface to block initial virus attachment and penetration; 2) overexpression of the HIV TAR sequence that will sequester viral Tat protein and decrease its ability to transactivate viral gene expression; and 3) inhibitory RNA that attack important and conserved sequences within the HIV genome.

With respect to the first point above, a key cell surface HIV binding protein is the chemokine receptor CCR5. HIV particles attach to susceptible T cells by binding to the CD4 and CCR5 cell surface proteins. Because CD4 is an essential glycoprotein on the cell surface that is important for the immunological function of T cells, this was not chosen as a target to manipulate its expression levels. However, people born homozygous for null mutations in the CCR5 gene and completely lacking receptor expression, live normal lives save for enhanced susceptibility to a few infectious diseases and the possibility of developing rare autoimmunity. Thus, modulating CCR5 was determined to be a relatively safe approach and was a primary target in the development of anti-HIV lentivirus vectors.

With respect to the second point above, the viral TAR sequence is a highly structured region of HIV genomic RNA that binds tightly to viral Tat protein. The Tat:TAR complex is important for efficient generation of viral RNA. Overexpression of the TAR region was envisioned as a decoy molecule that would sequester Tat protein and decrease the levels of viral RNA. However, TAR proved toxic to most mammalian cells including cells used for manufacturing lentivirus particles. Further, TAR was inefficient for inhibiting viral gene expression in other laboratories and has been discarded as a viable component in HIV gene therapy.

In various embodiments, viral gene sequences have been identified that meet 3 criteria: i) Sequences that are reasonably conserved across a range of HIV isolates representative of the epidemic in a geographic region of interest; ii) reduction in RNA levels due to the activity of an inhibitory RNA in a viral vector will reduce the corresponding protein levels by an amount sufficient to meaningfully reduce HIV replication; and iii) the viral gene sequence(s) targeted by inhibitory RNA are not present in the genes required for packaging and assembling viral vector particles during manufacturing. In various embodiments, a sequence at the junction of HIV Tat and Rev genes and a second sequence within the HIV Vif gene have been targeted by inhibitory RNA. The Tat/Rev targeting has an additional benefit of reducing HIV envelope glycoprotein expression because this region overlaps with the envelope gene in the HIV genome.

Various methods for vector development and testing relies first on identifying suitable targets (as described herein) followed by constructing plasmid DNAs expressing individual or multiple inhibitory RNA species for testing in cell models, and finally constructing lentivirus vectors containing inhibitory RNA with proven anti-HIV function. The lentivirus vectors are tested for toxicity, yield during in vitro production, and effectiveness against HIV in terms of reducing CCR5 expression levels or lowering viral gene products to inhibit virus replication.

Table 2 below demonstrates progression through multiple versions of inhibitory constructs until arriving at a clinical candidate. Initially, shRNA (short homology RNA) molecules were designed and expressed from plasmid DNA constructs.

Plasmids 1-4, as detailed in Table 2 below, tested shRNA sequences against Gag, Pol and RT genes of HIV. While each shRNA was active for suppressing viral protein expression in a cell model, there were two important problems that prevented further development. First, the sequences were targeted to a laboratory isolate of HIV that was not representative of Clade B HIV strains currently circulating in North America and Europe. Second, these shRNA targeted critical components in the lentivirus vector packaging system and would severely reduce vector yield during manufacturing. Plasmid 5, as detailed in Table 2, was selected to target CCR5 and provided a lead candidate sequence. Plasmids 6, 7, 8, 9, 10, and 11, as detailed in Table 2, incorporated the TAR sequence and it was found they produced unacceptable toxicity for mammalian cells including cells used for lentivirus vector manufacturing. Plasmid 2, as detailed in Table 2, identified a lead shRNA sequence capable of reducing Tat RNA expression. Plasmid 12, as detailed in Table 2, demonstrated the effectiveness of shCCR5 expressed as a microRNA (miR) in a lentiviral vector and confirmed it should be in the final product. Plasmid 13, as detailed in Table 2, demonstrated the effectiveness of a shVif expressed as a microRNA (miR) in a lentiviral vector and confirmed it should be in the final product. Plasmid 14, as detailed in Table 2, demonstrated the effectiveness of shTat expressed as a microRNA (miR) in a lentiviral vector and confirmed it should be in the final product. Plasmid 15, as detailed in Table 2, contained the miR CCR5, miR Tat and miR Vif in the form of a miR cluster expressed from a single promoter. These miR do not target critical components in the lentivirus vector packaging system and proved to have negligible toxicity for mammalian cells. The miRs within the cluster were equally effective to individual miR that were tested previously, and the overall impact was a substantial reduction in replication of a CCR5-tropic HIV BaL strain.

TABLE 2

Development of HIV Vectors

| | Internal Code | Material | Description | Remarks | Decision |
|---|---|---|---|---|---|
| 1 | SIH-H1-shRT-1,3 | Lentiviral vector | shRNA construct for RT of LAI strain | Wrong target, lab virus, no virus test | Abandon |
| 2 | SIH-H1-shRT43 (Tat/Rev NL4-3) | Lentiviral vector | H1 promoter shRNA Tat/Rev overlap | Tat protein knock-down >90% | Lead |

Vector Construction: For Rev/Tat (RT) shRNA, oligonucleotide sequences containing BamHI and EcoRI restriction sites were synthesized by MWG Operon. Two different Rev/Tat target sequences were tested for their ability to decrease Tat mRNA expression. The RT1,3 target sequence is (5'-ATGGCAGGAAGAAGCGGAG-3')(SEQ ID NO: 89) and shRNA sequence is (5'-ATGGCAGGAAGAAGCGGAGTTCAAGAGACTCCGCTTCTTCCTGCCATTTTTT-3')(SEQ ID NO: 90). The RT43 sequence is (5'-GCGGAGACAGCGACGAAGAGC-3') (SEQ ID NO: 9) and shRNA sequence is (5'-GCGGAGACAGCGACGAAGAGCTTCAAGAGAGCTCTTCGTCGCTGTCTCCGCTTTTT-3')(SEQ ID NO: 10). Oligonucleotide sequences were inserted into the pSIH lentiviral vector (System Biosciences).

Functional test for shRNA against Rev/Tat: The ability of the vector to reduce Tat expression was tested using a luciferase reporter plasmid which contained the Rev/Tat target sequences inserted into the 3'-UTR (untranslated region of the mRNA). Either the shRT1,3 or shRT43 plasmid was co-transfected with the plasmid containing luciferase and the Rev/Tar target sequence. There was a 90% reduction in light emission indicating strong function of the shRT43 shRNA sequence but less than 10% with the shRT1,3 plasmid.

Conclusion: The SIH-H1-shRT43 was superior to SIH-H1-shRT-1,3 in terms of reducing mRNA levels in the Luciferase assay system. This indicates potent inhibitory activity of the shRT43 sequence and it was selected as a lead candidate for further development.

| | Internal Code | Material | Description | Remarks | Decision |
|---|---|---|---|---|---|
| 3 | SIH-H1-shGag-1 | Lentiviral vector | shRNA construct for LAI | Inhibits Gag expression but will Gag | Abandon inhibit packaging |

Vector Construction: For Gag shRNA, oligonucleotide sequences containing BamHI and EcoRI restriction sites were synthesized by MWG Operon. A Gag target sequence was tested

TABLE 2-continued

Development of HIV Vectors

| Internal Code | Material | Description | Remarks | Decision |
|---|---|---|---|---| for their ability to decrease Gag mRNA expression. The Gag target sequence is (5'-GAAGAAATGATGACAGCAT-3')(SEQ ID NO: 11) and shRNA sequence is (5'-GAAGAAATGATGACAGCATTTCAAGAGAATGCTGTCATCATTTCTTCTTTTT-3') (SEQ ID NO: 12). Oligonucleotide sequences were inserted into the pSIH lentiviral vector (System Biosciences).

Functional test for shRNA against Gag: The ability of the vector to reduce Gag expression was tested using a luciferase reporter plasmid which contained the Gag target sequences inserted into the 3'-UTR (untranslated region of the mRNA). The Gag plasmid was co-transfected with the plasmid containing luciferase and the Gag target sequence. There was nearly a 90% reduction in light emission indicating a strong effect of the shGag shRNA sequence.

Conclusion: This shRNA sequence is potent against HIV Gag expression but was abandoned. The lentivirus packaging system requires production of Gag from the helper plasmid and shRNA inhibition of Gag will reduce lentivirus vector yield. This shRNA sequence could be used as an oligonucleotide inhibitor of HIV or incorporated into an alternate viral vector packaging system that uses a different vector genome or is modified to resist inhibition by this shRNA.

| Internal Code | Material | Description | Remarks | Decision |
|---|---|---|---|---|
| 4 SIH-H1-shPol-1 | Lentiviral vector | shRNA construct for Pol | Inhibits Pol expression but will inhibit packaging | Abandon |

Vector Construction: A Pol shRNA was constructed with oligonucleotide sequences containing BamHI and EcoRI restriction sites that were synthesized by MWG Operon. A Pol target sequence was tested for its ability to decrease Pol mRNA expression. The Pol target sequence is (5'-CAGGAGCAGATGATACAG-3')(SEQ ID NO: 13) and shRNA sequence is (5'-CAGGAGATGATACAGTTCAAGAGACTGTATCATCTGCTCCTGTTTTT-3')(SEQ ID NO: 14). Oligonucleotide sequences were inserted into the pSIH lentiviral vector (System Biosciences).

Functional tests for shRNA against HIV Pot: The ability of the vector to reduce Pol expression was tested using a luciferase reporter plasmid which contained the Pol target sequences inserted into the 3'-UTR (untranslated region of the mRNA). The Pol plasmid was co-transfected with the plasmid containing luciferase and the Pol target sequence. There was a 60% reduction in light emission indicating a strong effect of the shPol shRNA sequence.

Conclusion: This shRNA sequence is potent against HIV Pol expression but was abandoned. The lentivirus packaging system requires production of Pol from the helper plasmid and shRNA inhibition of Pol will reduce lentivirus vector yield. This shRNA sequence could be used as an oligonucleotide inhibitor of HIV or incorporated into an alternate viral vector packaging system that uses a different vector genome or is modified to resist inhibition by this shRNA.

| Internal Code | Material | Description | Remarks | Decision |
|---|---|---|---|---|
| 5 SIH-H1-shCCR5-1 | Lentiviral vector | shRNA construct for CCR5 | Best of 5 candidates, Extracellular CCR5 protein reduction >90% | Lead |

Vector Construction: A CCR5 shRNA was constructed with oligonucleotide sequences containing BamHI and EcoRI restriction sites that were synthesized by MWG Operon. Oligonucleotide sequences were inserted into the pSIH lentiviral vector (System Biosciences). The CCR5 target sequence #1, which focuses on CCR5 gene sequence 1 (SEQ ID NO: 25), is (5'-GTGTCAAGTCCAATCTATG-3')(SEQ ID NO: 15) and the shRNA sequence is (5'-GTGTCAAGTCCAATCTATGTTCAAGAGACATAGATTGGACTTGACACTTTTT-3') (SEQ ID NO: 16). The CCR5 target sequence #2, which focuses on CCR5 gene sequence 2 (SEQ ID NO: 26), is (5'-GAGCATGACTGACATCTAC-3')(SEQ ID NO: 17) and the shRNA sequence is (5'-GAGCATGACTGACATCTACTTCAAGAGAGTAGATGTCAGTCATGCTCTTTTT-3') (SEQ ID NO: 18). The CCR5 target sequence #3, which focuses on CCR5 gene sequence 3 (SEQ ID NO: 27), is (5'-GTAGCTCTAACAGGTTGGA-3')(SEQ ID NO: 19) and the shRNA sequence is (5'-GTAGCTCTAACAGGTTGGATTCAAGAGATCCAACCTGTTAGAGCTACTTTTT-3') (SEQ ID NO: 20). The CCR5 target sequence #4, which focuses on CCR5 gene sequence 4 (SEQ ID NO: 28, is (5'-GTTCAGAAACTACCTCTTA-3')(SEQ ID NO: 21) and the shRNA sequence is (5'-GTTCAGAAACTACCTCTTATTCAAGAGATAAGAGGTAGTTTCTGAACTTTTT-3') (SEQ ID NO: 22). The CCR5 target sequence #5, which focuses on CCR5 gene sequence 5 (SEQ ID NO: 29), is (5'-GAGCAAGCTCAGTTTACACC-3')(SEQ ID NO: 23) and the shRNA sequence is (5'-GAGCAAGCTCAGTTTACACCTTCAAGAGAGGTGTAAACTGAGCTTGCTCTTTTT-3') (SEQ ID NO: 24).

TABLE 2-continued

Development of HIV Vectors

| Internal Code | Material | Description | Remarks | Decision |
|---|---|---|---|---|

Functional test for shRNA against CCR5: The ability of a CCR5 shRNA sequence to knock-down CCR5 RNA expression was initially tested by co-transfecting each of the lentiviral plasmids, in separate experiments for each plasmid, containing one of the five CCR5 target sequences with a plasmid expressing the human CCR5 gene. CCR5 mRNA expression was then assessed by qPCR analysis using CCR5-specific primers.

Conclusion: Based on the reduction in CCR5 mRNA levels the shRNACCR5-1 was most potent for reducing CCR5 gene expression. This shRNA was selected as a lead candidate.

| Internal Code | Material | Description | Remarks | Decision |
|---|---|---|---|---|
| 6 SIH-U6-TAR | Lentiviral vector | U6 promoter-TAR | Toxic to cells | Abandon |
| 7 SIH-U6-TAR-H1-shCCR5 | Lentiviral vector | U6 promoter-TAR-H1-shCCR5 | Toxic to cells | Abandon |
| 8 U6-TAR-H1-shRT | Lentiviral vector | U6 promoter-TAR-H1-RT | Suppress HIV, toxic to cells, poor packaging | Abandon |
| 9 U6-TAR-7SK-shRT | Lentiviral vector | Change shRNA promoter to 7SK | Toxic, poor packaging | Abandon |
| 10 U6-TAR-H1-shRT-H1-shCCR5 | Lentiviral vector | U6 promoter-TAR-H1-RT-H1-shCCR5 | Toxic, poor packaging, H1 repeats | Abandon |
| 11 U6-TAR-7SK-shRT-H1-CCR5 | Lentiviral vector | Change shRNA promoter to 7SK | Toxic, poor packaging | Abandon |

Vector Construction: A TAR decoy sequence containing flanking KpnI restriction sites was synthesized by MWG operon and inserted into the pSIH lentiviral vector (System Biosciences) at the KpnI site. In this vector, TAR expression is regulated by the U6 promoter. The TAR decoy sequence is (5'-
CTTGCAATGATGTCGTAATTTGCGTCTTACCTCGTTCTCGACAGCGACCAGATCTG
AGCCTGGGAGCTCTCTGGCTGTCAGTAAGCTGGTACAGAAGGTTGACGAAAATTC
TTACTGAGCAAGAAA-3')(SEQ ID NO: 8). Expression of the TAR decoy sequence was determined by qPCR analysis using specific primers for the TAR sequence. Additional vectors were constructed also containing the TAR sequence. The H1 promoter and shRT sequence was inserted in this vector in the XhoI site. The H1 shRT sequence is (5'-
GAACGCTGACGTCATCAACCCGCTCCAAGGAATCGCGGGCCCAGTGTCACTAGGC
GGGAACACCCAGCGCGCGTGCGCCCTGGCAGGAAGATGGCTGTGAGGGACAGGG
GAGTGGCGCCCTGCAATATTTGCATGTCGCTATGTGTTCTGGGAAATCACCATAAA
CGTGAAATGTCTTTGGATTTGGGAATCTTATAAGTTCTGTATGAGACCACTTGGAT
CCGCGGAGACAGCGACGAAGAGCTTCAAGAGAGCTCTTCGTCGCTGTCTCCGCTTT
TT-3')(SEQ ID NO: 91). This vector could express TAR and knockdown RT. The 7SK promoter was also substituted for the H1 promoter to regulate shRT expression. Another vector was constructed containing U6 TAR, H1 shRT, and H1 shCCR5. The H1 shCCR5 sequence was inserted into the SpeI site of the plasmid containing U6 TAR and H1 shRT. The H1 CCR5 sequence is (5'-
GAACGCTGACGTCATCAACCCGCTCCAAGGAATCGCGGGCCCAGTGTCACTAGGC
GGGAACACCCAGCGCGCGTGCGCCCTGGCAGGAAGATGGCTGTGAGGGACAGGG
GAGTGGCGCCCTGCAATATTTGCATGTCGCTATGTGTTCTGGGAAATCACCATAAA
CGTGAAATGTCTTTGGATTTGGGAATCTTATAAGTTCTGTATGAGACCACTTGGAT
CCGTGTCAAGTCCAATCTATGTTCAAGAGACATAGATTGGACTTGACACTTTTT-3')
(SEQ ID NO: 92). The 7SK promoter was also substituted for the H1 promoter to regulate shRT expression.

Functional test for TAR decoy activity: We tested the effect of SIH-U6-TAR on packaging efficiency. When TAR sequence was included, the yield of vector in the SIH packaging system was reduced substantially.

Conclusion: Lentivirus vectors expressing the TAR decoy sequence are unsuitable for commercial development due to low vector yields. These constructs were abandoned.

| Internal Code | Material | Description | Remarks | Decision |
|---|---|---|---|---|
| 12 shCCR5 | Lentiviral vector | microRNA sequence | Extracellular CCR5 protein reduction >90% | Lead |

Vector Construction: A CCR5 microRNA was constructed with oligonucleotide sequences containing BsrGI and NotI restriction sites that were synthesized by MWG Operon. Oligonucleotide sequences were inserted into the pCDH lentiviral vector (System

TABLE 2-continued

Development of HIV Vectors

| Internal Code | Material | Description | Remarks | Decision |
|---|---|---|---|---|

Biosciences). The EF-1 promoter was substituted for a CMV promoter that was used in the plasmid construct Test Material 5. The EF-1 promoter was synthesized by MWG Operon containing flanking ClaI and BsrGI restriction sites and inserted into the pCDH vector containing shCCR5-1. The EF-1 promoter sequence is (5'-
CCGGTGCCTAGAGAAGGTGGCGCGGGGTAAACTGGGAAAGTGATGTCGTGTACTG
GCTCCGCCTTTTTCCCGAGGGTGGGGGAGAACCGTATATAAGTGCAGTAGTCGCC
GTGAACGTTCTTTTTCGCAACGGGTTTGCCGCCAGAACACAGGTAAGTGCCGTGTG
TGGTTCCCGCGGGCCTGGCCTCTTTACGGGTTATGGCCCTTGCGTGCCTTGAATTA
CTTCCACGCCCCTGGCTGCAGTACGTGATTCTTGATCCCGAGCTTCGGGTTGGAAG
TGGGTGGGAGAGTTCGAGGCCTTGCGCTTAAGGAGCCCCTTCGCCTCGTGCTTGAG
TTGAGGCCTGGCCTGGGCGCTGGGGCCGCCGCGTGCGAATCTGGTGGCACCTTCG
CGCCTGTCTCGCTGCTTTCGATAAGTCTCTAGCCATTTAAAATTTTTGATGACCTGC
TGCGACGCTTTTTTTCTGGCAAGATAGTCTTGTAAATGCGGGCCAAGATCTGCACA
CTGGTATTTCGTTTTTGGGGCCGCGGGCGGCGACGGGGCCCGTGCGTCCCAGCGC
ACATGTTCGGCGAGGCGGGGCCTGCGAGCGCGGCCACCGAGAATCGGACGGGGG
TAGTCTCAAGCTGGCCGGCCTGCTCTGGTGCCTGGCCTCGCGCCGCCGTGTATCGC
CCCGCCCTGGGCGGCAAGGCTGGCCCGGTCGGCACCAGTTGCGTGAGCGGAAAGA
TGGCCGCTTCCCGGCCCTGCTGCAGGGAGCTCAAAATGGAGGACGCGGCGCTCGG
GAGAGCGGGCGGGTGAGTCACCCACACAAAGGAAAAGGGCCTTTCCGTCCTCAGC
CGTCGCTTCATGTGACTCCACGGAGTACGGGCGCCGTCCAGGCACCTCGATTAGT
TCTCGAGCTTTTGGAGTACGTCGTCTTTAGGTTGGGGGGAGGGGTTTTATGCGATG
GAGTTTCCCCACACTGAGTGGGTGGAGACTGAAGTTAGGCCAGCTTGGCACTTGA
TGTAATTCTCCTTGGAATTTGCCCTTTTTGAGTTTGGATCTTGGTTCATTCTCAAGC
CTCAGACAGTGGTTCAAAGTTTTTTCTTCCATTTCAGGTGTCGTGA-3')(SEQ ID
NO: 4).

Functional test for lentivirus CDH-shCCR5-1: The ability of the miR CCR5 sequences to knock-down CCR5 expression was determined by transducing CEM-CCR5 T cells and measuring cell surface CCR5 expression after staining with a fluorescently-labeled monoclonal antibody against CCR5 and measuring the intensity of staining, that is directly proportional to the number of cell surface CCR5 molecules, by analytical flow cytometry. The most effective shRNA sequence for targeting CCR5 was CCR5 shRNA sequence #1. However, the most effective CCR5 targeting sequence for constructing the synthetic microRNA sequence was overlapping with CCR5 sequence #5; this conclusion was based on sequence alignments and experience with miRNA construction. Finally, the miR30 hairpin sequence was used to construct the synthetic miR30 CCR5 sequence which is (5'-
AGGTATATTGCTGTTGACAGTGAGCGACTGTAAACTGAGCTTGCTCTACTGTGAAG
CCACAGATGGGTAGAGCAAGCACAGTTTACCGCTGCCTACTGCCTCGGACTTCAA
GGGGCTT-3')(SEQ ID NO: 1). The miR CCR5 target sequence is (5'-
GAGCAAGCTCAGTTTACA-3')(SEQ ID NO: 5). At multiplicity of infection equal to 5, generating on average 1.25 genome copies of integrated lentivirus per cell, CCR5 expression levels were reduce by ≥90% indicating potent inhibition of CCR5 mRNA by the miR30CCR5 micro RNA construct in a lentivirus vector.

Conclusion: The miR30CCR5 construct is potent for reducing CCR5 cell surface expression and is a lead candidate for a therapeutic lentivirus for HIV.

| 13 | shVif | Lentiviral vector | microRNA sequence | Vif protein reduction >80% | Lead |

Vector Construction: A Vif microRNA was constructed with oligonucleotide sequences containing BsrGI and NotI restriction sites that were synthesized by MWG Operon. Oligonucleotide sequences were inserted into the pCDH lentiviral vector (System Biosciences) containing an EF-1 promoter. Based on sequence alignments and experience with constructing synthetic miRNA, the miR21 hairpin sequence was used to construct the synthetic miR21 Vif sequence which is (5'-
CATCTCCATGGCTGTACCACCTTGTCGGGGGATGTGTACTTCTGAACTTGTGTTGA
ATCTCATGGAGTTCAGAAGAACACATCCGCACTGACATTTTGGTATCTTTCATCTG
ACCA-3')(SEQ ID NO: 2). The miR Vif target sequence is (5'-
GGGATGTGTACTTCTGAACTT-3')(SEQ ID NO: 6).

Functional test for potency of miR21Vif: The ability of the miR Vif sequence to knock-down Vif expression was determined by measuring Vif protein expression by immunoblot analysis using an anti-Vif monoclonal antibody to identify the Vif protein.

Conclusion: the miR21Vif reduced Vif protein expression by ≥ 10-fold as determined by quantitative image analysis of immunoblot data. This was sufficient to justify miR21Vif as a lead candidate for our therapeutic lentivirus.

| 14 | shTat | Lentiviral vector | microRNA sequence | Tat RNA reduction >80% | Lead |

Vector Construction: A Tat microRNA was constructed with oligonucleotide sequences containing BsrGI and NotI restriction sites that were synthesized by MWG Operon. The microRNA cluster was inserted into the pCDH lentiviral vector (System Biosciences)

TABLE 2-continued

Development of HIV Vectors

| Internal Code | Material | Description | Remarks | Decision |
|---|---|---|---|---| containing an EF-1 promoter. Based on sequence alignments and experience in the construction of synthetic miRNA, the miR185 hairpin sequence was selected for constructing a synthetic miR185 Tat sequence which is (5'-
GGGCCTGGCTCGAGCAGGGGGCGAGGGATTCCGCTTCTTCCTGCCATAGCGTGGT
CCCCTCCCCTATGGCAGGCAGAAGCGGCACCTTCCCTCCCAATGACCGCGTCTTCG
TCG-3'). The miR Tat target sequence is (5'-TCCGCTTCTTCCTGCCATAG-3')(SEQ ID NO: 7).

Functional test for potency of miR185Tat: The ability of miR Tat to knock-down Tat expression was determined by measuring Tat mRNA expression by RT-PCR analysis using Tat specific primers. We compared the miR185Tat with a similar miR155Tat on the basis of reducing the relative levels of Tat mRNA.

Conclusion: The miR185Tat was approximately twice as potent for reducing Tat mRNA compare to miR155Tat, and was selected as the lead candidate for our therapeutic lentivirus.

| Internal Code | Material | Description | Remarks | Decision |
|---|---|---|---|---|
| 15 | shCCR5-shVif-shTat | Lentiviral vector | microRNA cluster sequence | CCR5 reduction >90%, Vif protein reduction >80%, RNA reduction >80%, >95% inhibition of HIV replication | Candidate Tat |

Vector Construction: A miR30CCR5 miR21Vif miR185Tat microRNA cluster sequence was constructed with a synthetic DNA fragment containing BsrGI and NotI restriction sites that was synthesized by MWG Operon. The DNA fragment was inserted into the pCDH lentiviral vector (System Biosciences) containing the EF-1 promoter. The miR cluster sequence is (5'-
AGGTATATTGCTGTTGACAGTGAGCGACTGTAAACTGAGCTTGCTCTACTGTGAAG
CCACAGATGGGTAGAGCAAGCACAGTTTACCGCTGCCTACTGCCTCGGACTTCAA
GGGGCTTCCCGGGCATCTCCATGGCTGTACCACCTTGTCGGGGATGTGTACTTCT
GAACTTGTGTTGAATCTCATGGAGTTCAGAAGAACACATCCGCACTGACATTTTGG
TATCTTTCATCTGACCAGCTAGCGGGCCTGGCTCGAGCAGGGGGCGAGGGATTCC
GCTTCTTCCTGCCATAGCGTGGTCCCCTCCCCTATGGCAGGCAGAAGCGGCACCTT
CCCTCCCAATGACCGCGTCTTCGTC-3')(SEQ ID NO: 31) and incorporates Test Material 12, Test Material 13 and Test Material 14 into a single cluster that can be expressed under control of the EF-1 promoter.

Functional test for potency of the Lentivirus Vector AGT103 containing the microRNA cluster of miR30CCR5, miR21Vif and miR185Tat: The AGT103 vector was tested for potency against CCR5 using the assay for reduction in cell surface CCR5 expression (Test Material 12). The AGT103 vector was tested for potency against Vif using the assay for reduction in cell surface Vif expression (Test Material 13). The AGT103 vector was tested for potency against Tat using the assay for reduction in cell surface Tat expression (Test Material 14).

Conclusion: Potency for reducing CCR5 expression by the miRNA cluster was similar to potency observed for the miR30CCR5 alone. Potency for reducing Vif expression by the miRNA cluster was similar to potency observed for the miR21Vif alone. Potency for reducing Tat expression by the miRNA cluster was similar to potency observed for the miR185Tat alone. The miRNA cluster is potent for reducing cell surface CCR5 levels and for inhibiting two HIV genes. Thus, AGT103 containing this miRNA cluster was selected as the therapeutic vector construct for our HIV functional cure program.

Functional Assays. Individual lentivirus vectors containing CCR5, Tat or Vif shRNA sequences and, for experimental purposes, expressing green fluorescent protein (GFP) under control of the CMV Immediate Early Promoter, and designated AGT103/CMV-GFP were tested for their ability to knockdown CCR5, Tat or Vif expression. Mammalian cells were transduced with lentiviral particles either in the presence or absence of polybrene. Cells were collected after 2-4 days; protein and RNA were analyzed for CCR5, Tat or Vif expression. Protein levels were tested by Western blot assay or by labeling cells with specific fluorescent antibodies (CCR5 assay), followed by analytical flow cytometry comparing modified and unmodified cell fluorescence using either the CCR5-specific or isotype control antibodies.

Starting Testing of Lentivirus. T cell culture medium was made using RPMI 1640 supplemented with 10% FBS and 1% penicillin-streptomycin. Cytokine stocks of IL-2 10,000 units/ml, IL-12 1 µg/ml, IL-7 1 µg/ml, IL-15 1 µg/ml were also prepared in advance.

Prior to transduction with the lentivirus, an infectious viral titer was determined and used to calculate the amount of virus to add for the proper multiplicity of infection (MOI).

Day 0-12: Antigen-specific enrichment. On day 0, cryopreserved PBMC were thawed, washed with 10 ml 37° C. medium at 1200 rpm for 10 minutes and resuspended at a concentration of $2 \times 10^6$/ml in 37° C. medium. The cells were cultured at 0.5 ml/well in a 24-well plate at 37° C. in 5% CO2. To define the optimal stimulation conditions, cells were stimulated with combinations of reagents as listed in Table 3 below:

TABLE 3

| 1 | 2 | 3 | 4 | 5 | 6 |
|---|---|---|---|---|---|
| IL-2 + IL-12 | IL-7 + IL-15 | Peptides + IL-2 + IL-12 | Peptides + IL-7 + IL-15 | MVA + IL-2 + IL-12 | MVA + IL-7 + IL-15 |

Final concentrations: IL-2=20 units/ml, IL-12=10 ng/ml, IL-7=10 ng/ml, IL-15=10 ng/ml, peptides=5 pg/ml individual peptide, MVA MOI=1.

On days 4 and 8, 0.5 ml fresh medium and cytokine at listed concentrations (all concentrations indicate the final concentration in the culture) were added to the stimulated cells.

Day 12-24: non-specific expansion and lentivirus transduction. On day 12, the stimulated cells were removed from the plate by pipetting and resuspended in fresh T cell culture medium at a concentration of $1 \times 10^6$/ml. The resuspended cells were transferred to T25 culture flasks and stimulated with DYNABEADS® Human T-Activator CD3/CD28 following the manufacturer's instruction plus cytokine as listed above; flasks were incubated in the vertical position.

On day 14, AGT103/CMV-GFP was added at MOI 20 and cultures were returned to the incubator for 2 days. At this time, cells were recovered by pipetting, collected by centrifugation at 1300 rpm for 10 minutes, resuspended in the same volume of fresh medium, and centrifuged again to form a loose cell pellet. That cell pellet was resuspended in fresh medium with the same cytokines used in previous steps, with cells at $0.5 \times 10^6$ viable cells per ml.

From days 14 to 23, the number of the cells was evaluated every 2 days and the cells were diluted to $0.5 \times 10^6$/ml with fresh media. Cytokines were added every time.

On day 24, the cells were collected and the beads were removed from the cells. To remove the beads, cells were transferred to a suitable tube that was placed in the sorting magnet for 2 minutes. Supernatant containing the cells was transferred to a new tube. Cells were then cultured for 1 day in fresh medium at $1 \times 10^6$/ml. Assays were performed to determine the frequencies of antigen-specific T cells and lentivirus transduced cells.

To prevent possible viral outgrowth, amprenavir (0.5 ng/ml) was added to the cultures on the first day of stimulation and every other day during the culture.

Examine antigen-specific T cells by intracellular cytokine staining for IFN-gamma.

Cultured cells after peptide stimulation or after lentivirus transduction at $1 \times 10^6$ cells/ml were stimulated with medium alone (negative control), Gag peptides (5 pg/ml individual peptide), or PHA (5 pg/ml, positive control). After 4 hours, BD GolgiPlug™ (1:1000, BD Biosciences) was added to block Golgi transport. After 8 hours, cells were washed and stained with extracellular (CD3, CD4 or CD8; BD Biosciences) and intracellular (IFN-gamma; BD Biosciences) antibodies with BD Cytofix/Cytoperm™ kit following the manufacturer's instruction. Samples were analyzed on a BD FACSCalibur™ Flow Cytometer. Control samples labeled with appropriate isotype-matched antibodies were included in each experiment. Data were analyzed using Flowjo software.

Lentivirus transduction rate was determined by the frequency of GFP+ cells. The transduced antigen-specific T cells are determined by the frequency of CD3+CD4+GFP+ IFN gamma+ cells; tests for CD3+CD8+GFP+IFN gamma+ cells are included as a control.

These results indicate that CD4 T cells, the target T cell population, can be transduced with lentiviruses that are designed to specifically knock down the expression of HIV-specific proteins, thus producing an expandable population of T cells that are immune to the virus. This example serves as a proof of concept indicating that the disclosed lentiviral constructs can be used in combination with vaccination to produce a functional cure in HIV patients.

Example 4: CCR5 Knockdown with Experimental Vectors

AGTc120 is a Hela cell line that stably expresses large amounts of CD4 and CCR5. AGTc120 was transduced with or without LV-CMV-mCherry (the red fluorescent protein mCherry expressed under control of the CMV Immediate Early Promoter) or AGT103/CMV-mCherry. Gene expression of the mCherry fluorescent protein was controlled by a CMV (cytomegalovirus immediate early promoter) expression cassette. The LV-CMV-mCherry vector lacked a microRNA cluster, while AGT103/CMV-mCherry expressed therapeutic miRNA against CCR5, Vif, and Tat.

Figure 9A:
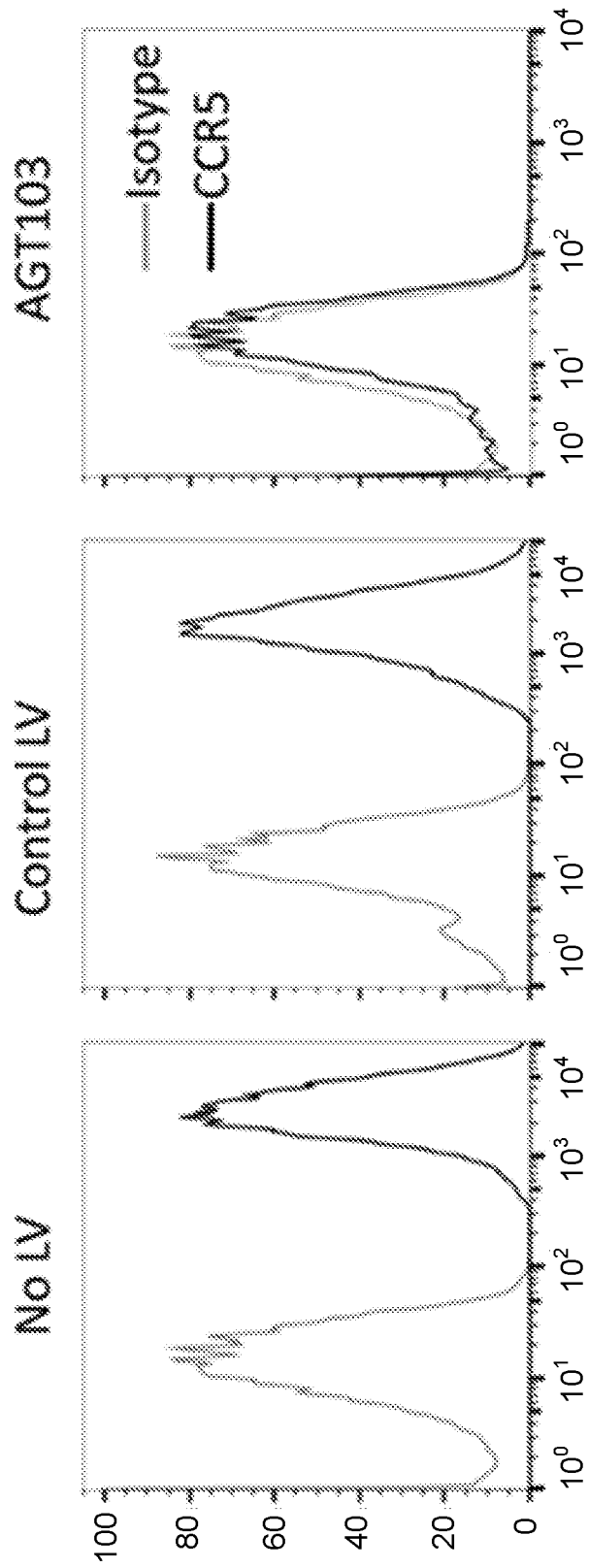
FIG. 9 shows knockdown of CCR5 by an experimental vector and corresponding prevention of R5-tropic HIV infection in AGTc120 cells. (A) shows CCR5 expression in AGTc120 cells with or without AGT103 lentivirus vector. (B) shows the sensitivity of transduced AGTc120 cells to infection with a HIV BaL virus stock that was expressing green fluorescent protein (GFP) fused to the Nef gene of HIV.

As shown in FIG. 9A, transduction efficiency was >90%. After 7 days, cells were collected and stained with fluorescent monoclonal antibody against CCR5 and subjected to analytical flow cytometry. Isotype controls are shown in gray on these histograms plotting Mean Fluorescence Intensity of CCR5 APC (x axis) versus cell number normalized to mode (y axis). After staining for cell surface CCR5, cells treated with no lentivirus or control lentivirus (expressing only the mCherry marker) showed no changes in CCR5 density while AGT103 (right section) reduced CCR5 staining intensity to nearly the levels of isotype control. After 7 days, cells were infected with or without R5-tropic HIV reporter virus Bal-GFP. 3 days later, cells were collected and analyzed by flow cytometry. More than 90% of cells were transduced. AGT103-CMV/CMVmCherry reduced CCR5 expression in transduced AGTc120 cells and blocked R5-tropic HIV infection compared with cells treated with the Control vector.

Figure 9B:
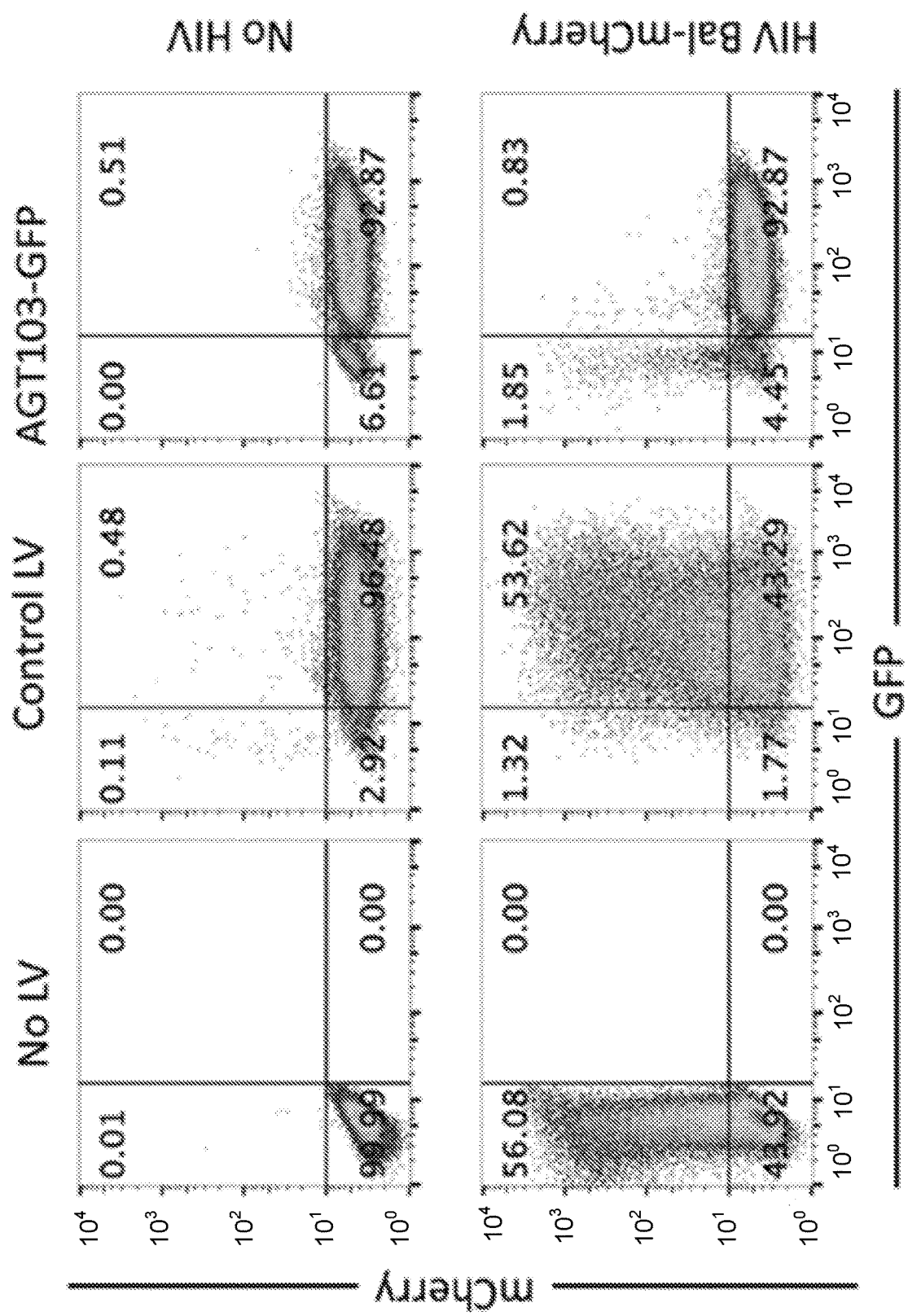

FIG. 9B shows the relative insensitivity of transfected AGTc120 cells to infection with HIV. As above, the lentivirus vectors express mCherry protein and a transduced cell that was also infected with HIV (expressing GFP) would appear as a double positive cell in the upper right quadrant of the false color flow cytometry dot plots. In the absence of HIV (upper panels), there were no GFP+ cells under any condition. After HIV infection (lower panels), 56% of cells were infected in the absence of lentivirus transduction and 53.6% of cells became infected in AGTc120 cells transduced with the LV-CMV-mCherry. When cells were transduced with the therapeutic AGT103/CMV-mCherry vector, only 0.83% of cells appeared in the double positive quadrant indicating they were transduced and infected.

Dividing 53.62 (proportion of double positive cells with control vector) by 0.83 (the proportion of double positive cells with the therapeutic vector) shows that AGT103 provided greater than 65-fold protection against HIV in this experimental system.

Example 5: Regulation of CCR5 Expression by shRNA Inhibitor Sequences in a Lentiviral Vector Inhibitory RNA Design. The sequence of *Homo sapiens* chemokine receptor CCR5 (CCR5, NC 000003.12) was used to search for potential siRNA or shRNA candidates to knockdown CCR5 levels in human cells. Potential RNA interference sequences were chosen from candidates selected by siRNA or shRNA design programs such as from the Broad Institute or the BLOCK-IT RNA iDesigner from Thermo Scientific. A shRNA sequence may be inserted into a plasmid immediately after a RNA polymerase III promoter such as H1, U6, or 7SK to regulate shRNA expression. The shRNA sequence may also be inserted into a lentiviral vector using similar promoters or embedded within a microRNA backbone to allow for expression by an RNA polymerase II promoter such as CMV or EF-1 alpha. The RNA sequence may also be synthesized as a siRNA oligonucleotide and utilized independently of a plasmid or lentiviral vector.

Plasmid Construction. For CCR5 shRNA, oligonucleotide sequences containing BamHI and EcoRI restriction sites were synthesized by MWG Operon. Oligonucleotide sequences were annealed by incubating at 70° C. then cooled to room temperature. Annealed oligonucleotides were digested with the restriction enzymes BamHI and EcoRI for one hour at 37° C., then the enzymes were inactivated at 70° C. for 20 minutes. In parallel, plasmid DNA was digested with the restriction enzymes BamHI and EcoRI for one hour at 37° C. The digested plasmid DNA was purified by agarose gel electrophoresis and extracted from the gel using a DNA gel extraction kit from Invitrogen. The DNA concentration was determined and the plasma to oligonucleotide sequence was ligated in the ratio 3:1 insert to vector. The ligation reaction was done with T4 DNA ligase for 30 minutes at room temperature. 2.5 µL of the ligation mix were added to 25 µL of STBL3 competent bacterial cells. Transformation required heat shock at 42° C. Bacterial cells were spread on agar plates containing ampicillin and colonies were expanded in L broth. To check for insertion of the oligo sequences, plasmid DNA was extracted from harvested bacterial cultures using the Invitrogen DNA Miniprep kit and tested by restriction enzyme digestion. Insertion of the shRNA sequence into the plasmid was verified by DNA sequencing using a primer specific for the promoter used to regulate shRNA expression.

Functional Assay for CCR5 mRNA Reduction: The assay for inhibition of CCR5 expression required co-transfection of two plasmids. The first plasmid contains one of five different shRNA sequences directed against CCR5 mRNA. The second plasmid contains the cDNA sequence for human CCR5 gene. Plasmids were co-transfected into 293T cells. After 48 hours, cells were lysed and RNA was extracted using the RNeasy kit from Qiagen. cDNA was synthesized from RNA using a Super Script Kit from Invitrogen. The samples were then analyzed by quantitative RT-PCR using an Applied Biosystems Step One PCR machine. CCR5 expression was detected with SYBR Green from Invitrogen using the forward primer (5'-AGGAATT-GATGGCGAGAAGG-3') (SEQ ID NO: 93) and reverse primer (5'-CCCCAAAGAAGGTCAAGGTAATCA-3') (SEQ ID NO: 94) with standard conditions for polymerase chain reaction analysis. The samples were normalized to the mRNA for beta actin gene expression using the forward primer (5'-AGCGCGGCTACAGCTTCA-3') (SEQ ID NO: 95) and reverse primer (5'-GGCGACGTAGCACAGCTTCT-3') (SEQ ID NO: 96) with standard conditions for polymerase chain reaction analysis.

The relative expression of CCR5 mRNA was determined by its Ct value normalized to the level of actin messenger RNA for each sample. The results are shown in FIG. 10.

Figure 10A:
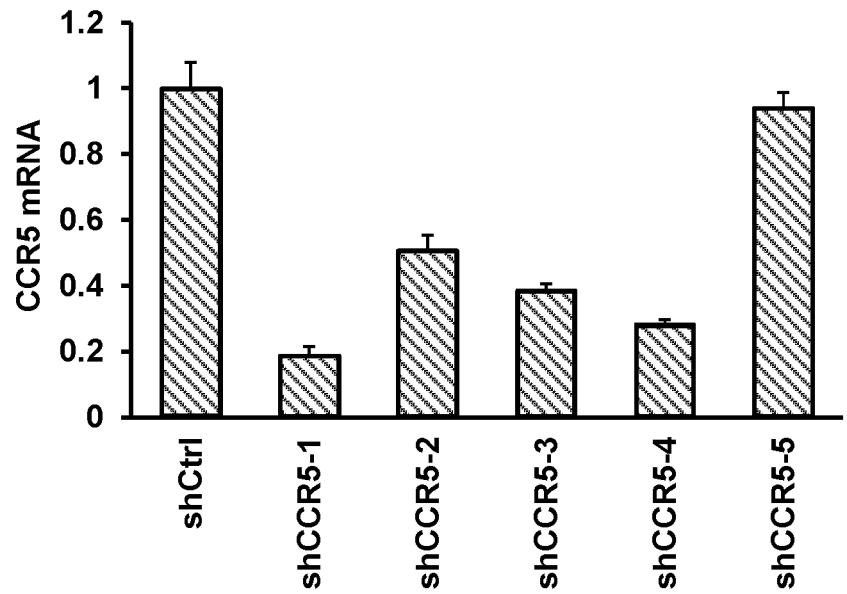
FIG. 10 depicts data demonstrating regulation of CCR5 expression by shRNA inhibitor sequences in a lentiviral vector of the present disclosure. (A) Screening data for potential candidates is shown. (B) CCR5 knock-down data following transduction with CCR5 shRNA-1 (SEQ ID NO: 16) is shown.
Figure 10B:
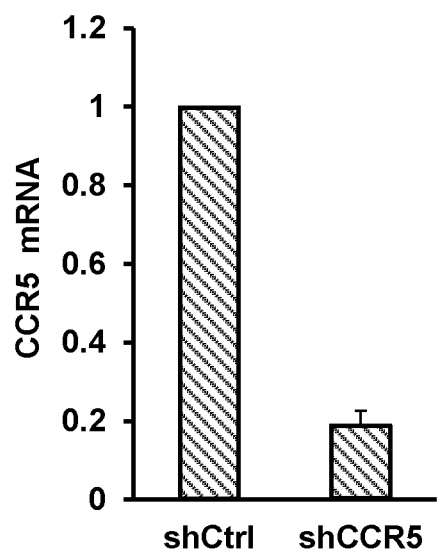

As shown in FIG. 10A, CCR5 knock-down was tested in 293T cells by co-transfection of the CCR5 shRNA construct and a CCR5-expressing plasmid. Control samples were transfected with a scrambled shRNA sequence that did not target any human gene and the CCR5-expressing plasmid. After 60 hours post-transfection, samples were harvested and CCR5 mRNA levels were measured by quantitative PCR. Further, as shown in FIG. 10B, CCR5 knock-down after transduction with lentivirus expressing CCR5 shRNA-1 (SEQ ID NO: 16).

Example 6: Regulation of HIV Components by shRNA Inhibitor Sequences in a Lentiviral Vector Inhibitory RNA Design.

The sequences of HIV type 1 Rev/Tat (5'-GCGGA-GACAGCGACGAAGAGC-3') (SEQ ID NO: 9) and Gag (5'-GAAGAAATGATGACAGCAT-3') (SEQ ID NO: 11) were used to design:

Rev/Tat:
(5'GCGGAGACAGCGACGAAGAGCTT-CAAGAGAGCTCTTCGTCGCTGTCTCCGCTTT TT-3') (SEQ ID NO: 10) and Gag:
(5'GAAGAAATGATGACAGCATTT-CAAGAGAATGCTGTCATCATTTCTTCTTTTT-3') (SEQ ID NO: 12) shRNA that were synthesized and cloned into plasmids as described above.

Plasmid Construction. The Rev/Tat or Gag target sequences were inserted into the 3'UTR (untranslated region) of the firefly luciferase gene used commonly as a reporter of gene expression in cells or tissues. Additionally, one plasmid was constructed to express the Rev/Tat shRNA and a second plasmid was constructed to express the Gag shRNA. Plasmid constructions were as described above.

Functional assay for shRNA targeting of Rev Tat or Gag mRNA: Using plasmid co-transfection we tested whether a shRNA plasmid was capable of degrading luciferase messenger RNA and decreasing the intensity of light emission in co-transfected cells. A shRNA control (scrambled sequence) was used to establish the maximum yield of light from luciferase transfected cells. When the luciferase construct containing a Rev/Tat target sequence inserted into the 3'-UTR (untranslated region of the mRNA) was co-transfected with the Rev/Tat shRNA sequence there was nearly a 90% reduction in light emission indicating strong function of the shRNA sequence. A similar result was obtained when a luciferase construct containing a Gag target sequence in the 3'-UTR was co-transfected with the Gag shRNA sequence. These results indicate potent activity of the shRNA sequences.

Figure 11A:
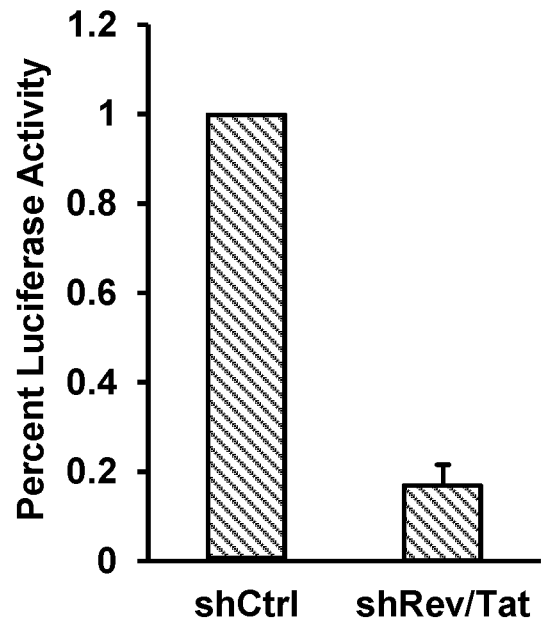
FIG. 11 depicts data demonstrating regulation of HIV components by shRNA inhibitor sequences in a lentiviral vector of the present disclosure. (A) Knock-down data for the rev/tat target gene is shown. (B) Knock-down data for the gag target gene is shown.
Figure 11B:
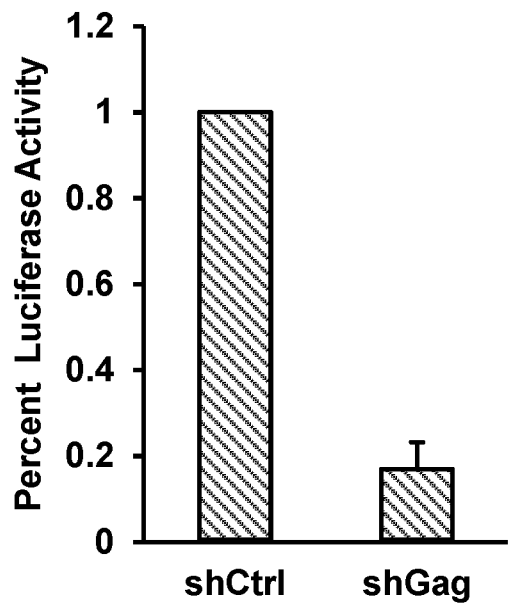

As shown in FIG. 11A, knock-down of the Rev/Tat target gene was measured by a reduction of luciferase activity, which was fused with the target mRNA sequence in the 3'UTR, by transient transfection in 293T cells. As shown in FIG. 11B, knock-down of the Gag target gene sequence fused with the luciferase gene. The results are displayed as the mean±SD of three independent transfection experiments, each in triplicate.

Example 7: AGT103 Decreases Expression of Tat and Vif

Cells were transfected with exemplary vector AGT103/CMV-GFP. AGT103 and other exemplary vectors are defined in Table 3 below.

TABLE 3

| Vector Designation | Composition |
| --- | --- |
| AGT103 | EF1-miR30CCR5-miR21Vif-miR185-Tat-WPRE |
| Control-mCherry | CMV-mCherry |
| AGT103/CMV-mCherry | CMV-mCherry-EF1-miR30CCR5-miR21Vif-miR185-Tat-WPRE- |
| Control-GFP | CMV-mCherry |
| AGT103/CMV-GFP | CMV-GFP-EF1-miR30CCR5-miR21Vif-miR185-Tat-WPRE- |

Figure 12:
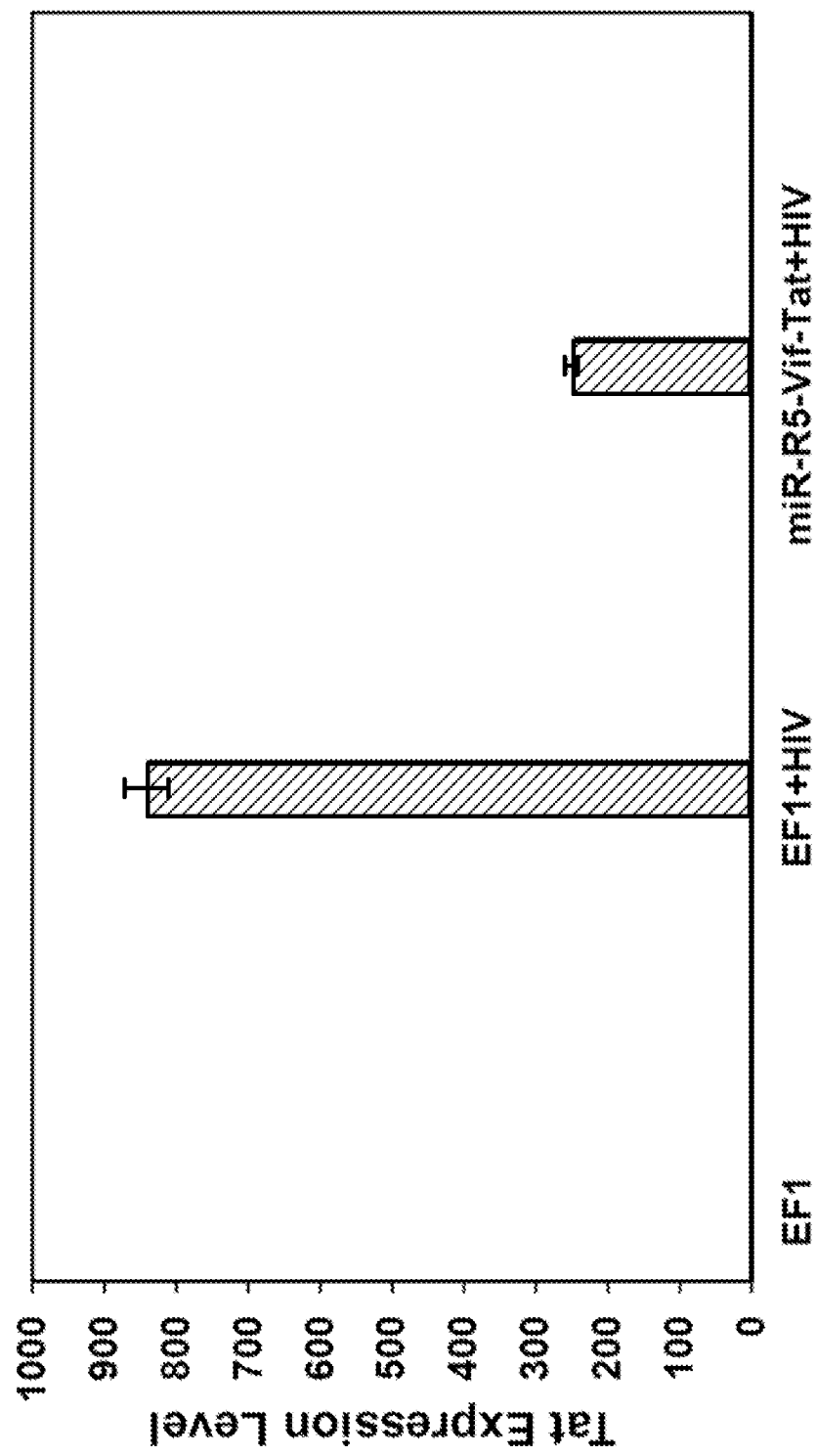
FIG. 12 depicts data demonstrating that AGT103 reduces expression of Tat protein expression in cells transfected with an HIV expression plasmid, as described herein.

Abbreviations:
EF-1: elongation factor 1 transcriptional promoter
miR30CCR5 - synthetic microRNA capable of reducing CCR5 protein on cell surfaces
miR21Vif - synthetic microRNA capable of reducing levels of HIV RNA and Vif protein expression
miR185Tat - synthetic micro RNA capable of reducing levels of HIV RNA and Tat protein expression
CMV - Immediate early transcriptional promoter from human cytomegalovirus
mCherry - coding region for the mCherry red fluorescent protein
GFP - coding region for the green fluorescent protein
WPRE - Woodchuck hepatitis virus post transcriptional regulatory element A T lymphoblastoid cell line (CEM; CCRF-CEM; American Type Culture Collection Catalogue number CCL119) was transduced with AGTT03/CMV-GFP. 48 hours later the cells were transfected with an HIV expression plasmid encoding the entire viral sequence. After 24 hours, RNA was extracted from cells and tested for levels of intact Tat sequences using reverse transcriptase polymerase chain reaction. Relative expression levels for intact Tat RNA were reduced from approximately 850 in the presence of control lentivirus vector, to approximately 200 in the presence of AGTT03/CMV-GFP for a total reduction of >4 fold, as shown in FIG. 12.

Example 8: Regulation of HIV Components by Synthetic MicroRNA Sequences in a Lentiviral Vector Inhibitory RNA Design. The sequence of HIV-1 Tat and Vif genes were used to search for potential siRNA or shRNA candidates to knockdown Tat or Vif levels in human cells. Potential RNA interference sequences were chosen from candidates selected by siRNA or shRNA design programs such as from the Broad Institute or the BLOCK-IT RNA iDesigner from Thermo Scientific. The selected shRNA sequences most potent for Tat or Vif knockdown were embedded within a microRNA backbone to allow for expression by an RNA polymerase II promoter such as CMV or EF-I alpha. The RNA sequence may also be synthesized as a siRNA oligonucleotide and used independently of a plasmid or lentiviral vector.

Plasmid Construction. The Tat target sequence (5'-TCCGCTTCTTCCTGCCATAG-3') (SEQ ID NO: 7) was incorporated into the miR185 backbone to create a Tat miRNA (5'-GGGCCTGGCTCGAGCAGGGGGCGAGG-GATTCCGCTTCTTCCTGCCATAGCGTGGT CCCCTCCCC-TATGGCAGGCAGAAGCGGCACCTTCCCTCC-CAATGACCGCGTCTTCG TCG-3') (SEQ ID NO: 3) that was inserted into a lentivirus vector and expressed under control of the EF-1 alpha promoter. Similarly, the Vif target sequence (5'-GGGATGTGTACTTCTGAACTT-3') (SEQ ID NO: 6) was incorporated into the miR21 backbone to create a Vif miRNA (5'-CATCTCCATGGCTGTAC-CACCTTGTCGGGGGATGTGTACTTCT-GAACTTGTGTTGA ATCTCATG-GAGTTCAGAAGAACACATCCGCACTGACATTTTGG-TATCTTTCATCTG ACCA-3') (SEQ ID NO: 2) that was inserted into a lentivirus vector and expressed under control of the EF-1 alpha promoter. The resulting Vif/Tat miRNA-expressing lentivirus vectors were produced in 293T cells using a lentiviral vector packaging system. The Vif and Tat miRNA were embedded into a microRNA cluster consisting of miR CCR5, miR Vif, and miR Tat all expressed under control of the EF-1 promoter.

Functional assay for miR185Tat inhibition of Tat mRNA accumulation. A lentivirus vector expressing miR185 Tat (LV-EF1-miR-CCR5-Vif-Tat) was used at a multiplicity of infection equal to 5 for transducing 293T cells. 24 hours after transduction the cells were transfected with a plasmid expressing HIV strain NL4-3 (pNL4-3) using Lipofectamine2000 under standard conditions. 24 hours later RNA was extracted and levels of Tat messenger RNA were tested by RT-PCR using Tat-specific primers and compared to actin mRNA levels for a control.

Functional assay for miR21 Vif inhibition of Vif protein accumulation. A lentivirus vector expressing miR21 Vif (LV-EF1-miR-CCR5-Vif-Tat) was used at a multiplicity of infection equal to 5 for transducing 293T cells. 24 hours after transduction, the cells were transfected with a plasmid expressing HIV strain NL4-3 (pNL4-3) using Lipofectamine2000. 24 hours later cells were lysed and total soluble protein was tested to measure the content of Vif protein. Cell lysates were separated by SDS-PAGE according to established techniques. The separated proteins were transferred to nylon membranes and probed with a Vif-specific monoclonal antibody or actin control antibody.

Figure 13A:
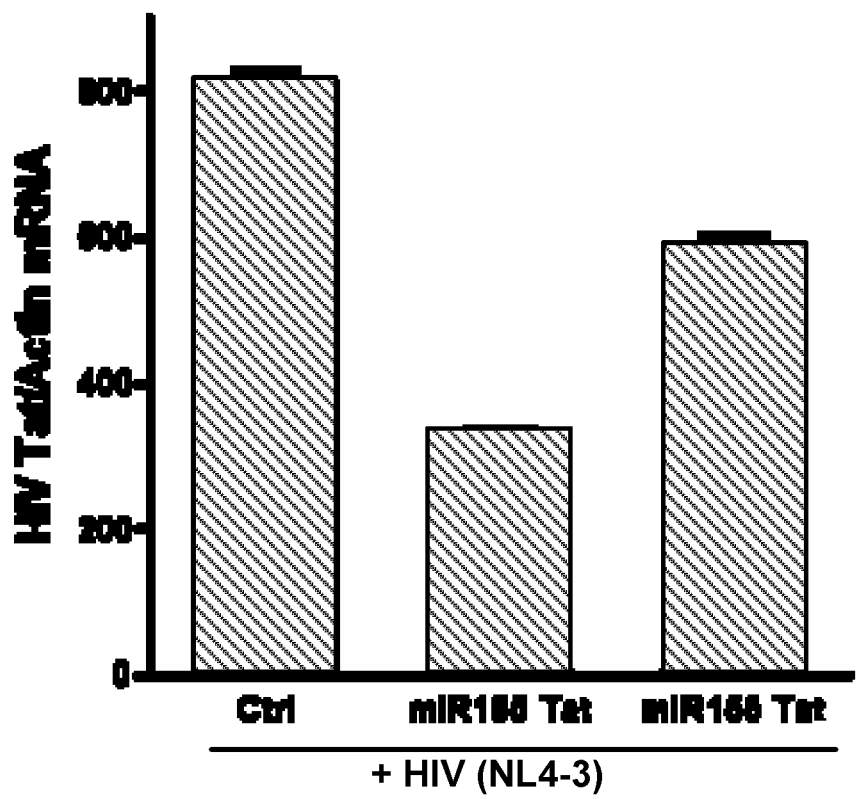
FIG. 13 depicts data demonstrating regulation of HIV components by synthetic microRNA sequences in a lentiviral vector of the present disclosure. (A) Tat knock-down data is shown. (B) Vif knock-down data is shown.
Figure 13B:
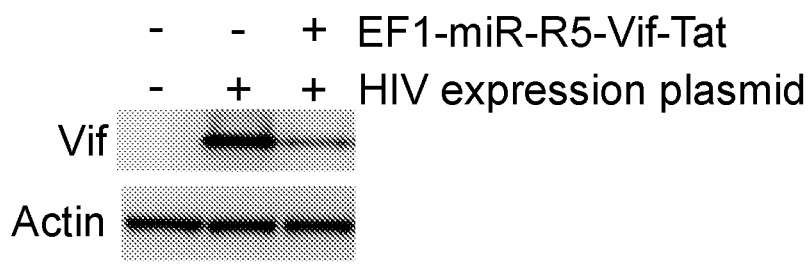

As shown in FIG. 13A, Tat knock-down was tested in 293T cells transduced with either a control lentiviral vector or a lentiviral vector expressing either synthetic miR185 Tat or miR155 Tat microRNA. After 24 hours, the HIV vector pNL4-3 was transfected with Lipofectamine2000 for 24 hours and then RNA was extracted for qPCR analysis with primers for Tat. As shown in FIG. 13B, Vif knock-down was tested in 293T cells transduced with either a control lentiviral vector or a lentiviral vector expressing a synthetic miR21 Vif microRNA. After 24 hours, the HIV vector pNL4-3 was transfected with Lipofectamine2000 for 24 hours and then protein was extracted for immunoblot analysis with an antibody for HIV Vif.

Example 9: Regulation of CCR5 Expression by Synthetic microRNA Sequences in a Lentiviral Vector CEM-CCR5 cells were transduced with a lentiviral vector containing a synthetic miR30 sequence for CCR5 (AGT103: TGTAAACTGAGCTTGCTCTA (SEQ ID NO: 97), AGT103-R5-1: TGTAAACTGAGCTTGCTCGC (SEQ ID NO: 98), or AGT103-R5-2: CATAGATTGGACTTGACAC (SEQ ID NO: 99). After 6 days, CCR5 expression was determined by FACS analysis with an APC-conjugated CCR5 antibody and quantified by mean fluorescence intensity (MFI). CCR5 levels were expressed as % CCR5 with LV-Control set at 100%. The target sequence of AGT103 and AGT103-R5-1 is in the same region as CCR5 target sequence #5. The target sequence of AGT103-R5-2 is the same as CCR5 target sequence #1. AGT103 (2% of total CCR5) is most effective at reducing CCR5 levels as compared with AGT103-R5-1 (39% of total CCR5) and AGT103-R5-2 which does not reduce CCR5 levels. The data is demonstrated in FIG. 14 herein.

Example 10: Regulation of CCR5 Expression by Synthetic microRNA Sequences in a Lentiviral Vector Containing Either a Long or Short WPRE Sequence Vector Construction. Lentivirus vectors often require an RNA regulatory element for optimal expression of therapeutic genes or genetic constructs. A common choice is to use the Woodchuck hepatitis virus post transcriptional regulatory element (WPRE). We compared AGT103 that contains a full-length WPRE:

```
                                          (SEQ ID NO: 32)
(5'AATCAACCTCTGATTACAAAATTTGTGAAAGATTGACTGGTATTCTT

AACTATGTTGCTCCTTTTACGCTATGTGGATACGCTGCTTTAATGCCTTT

GTATCATGCTATTGCTTCCCGTATGGCTTTCATTTTCTCCTCCTTGTATA

AATCCTGGTTGCTGTCTCTTTATGAGGAGTTGTGGCCCGTTGTCAGGCAA

CGTGGCGTGGTGTGCACTGTGTTTGCTGACGCAACCCCCACTGGTTGGGG

CATTGCCACCACCTGTCAGCTCCTTTCCGGGACTTTCGCTTTCCCCCTCC

CTATTGCCACGGCGGAACTCATCGCCGCCTGCCTTGCCCGCTGCTGGACA

GGGGCTCGGCTGTTGGGCACTGACAATTCCGTGGTGTTGTCGGGGAAATC

ATCGTCCTTTCCTTGGCTGCTCGCCTGTGTTGCCACCTGGATTCTGCGCG

GGACGTCCTTCTGCTACGTCCCTTCGGCCCTCAATCCAGCGGACCTTCCT

TCCCGCGGCCTGCTGCCGGCTCTGCGGCCTCTTCCGCGTCTTCGCCTTCG

CCCTCAGACGAGTCGGATCTCCCTTTGGGCCGCCTCCCCGCCT-3')
``` with a modified AGT103 vector containing a shortened WPRE element

```
                                          (SEQ ID NO: 80)
(5'AATCAACCTCTGGATTACAAAATTTGTGAAAGATTGACTGATATTCT

TAACTATGTTGCTCCTTTTACGCTGTGTGGATATGCTGCTTTAATGCCTC

TGTATCATGCTATTGCTTCCCGTACGGCTTTCGTTTTCTCCTCCTTGTAT

AAATCCTGGTTGCTGTCTCTTTATGAGGAGTTGTGGCCCGTTGTCCGTCA

ACGTGGCGTGGTGTGCTCTGTGTTTGCTGACGCAACCCCCACTGGCTGGG

GCATTGCCACCACCTGTCAACTCCTTTCTGGGACTTTCGCTTTCCCCCTC

CCGATCGCCACGGCAGAACTCATCGCCGCCTGCCTTGCCCGCTGCTGGAC

AGGGGCTAGGTTGCTGGGCACTGATAATTCCGTGGTGTTGTC-3').
```

Functional assay for modulating cell surface CCR5 expression as a function of long versus short WPRE element in the vector sequence. AGT103 containing long or short WPRE elements were used for transducing CEM-CCR5 T cells a multiplicity of infection equal to 5. Six days after transduction cells were collected and stained with a monoclonal antibody capable of detecting cell surface CCR5 protein. The antibody was conjugated to a fluorescent marker and the intensity of staining is directly proportional to the level of CCR5 on the cell surface. A control lentivirus had no effect on cell surface CCR5 levels resulting in a single population with a mean fluorescence intensity of 73.6 units. The conventional AGT103 with a long WPRE element reduced CCR5 expression to a mean fluorescence intensity level of 11 units. AGT103 modified to incorporate a short WPRE element resulted in a single population of cells with mean fluorescence intensity of 13 units. Accordingly, substituting a short WPRE element had little or no effect on the capacity for AGT103 to reduce cell surface CCR5 expression.

Figure 14:
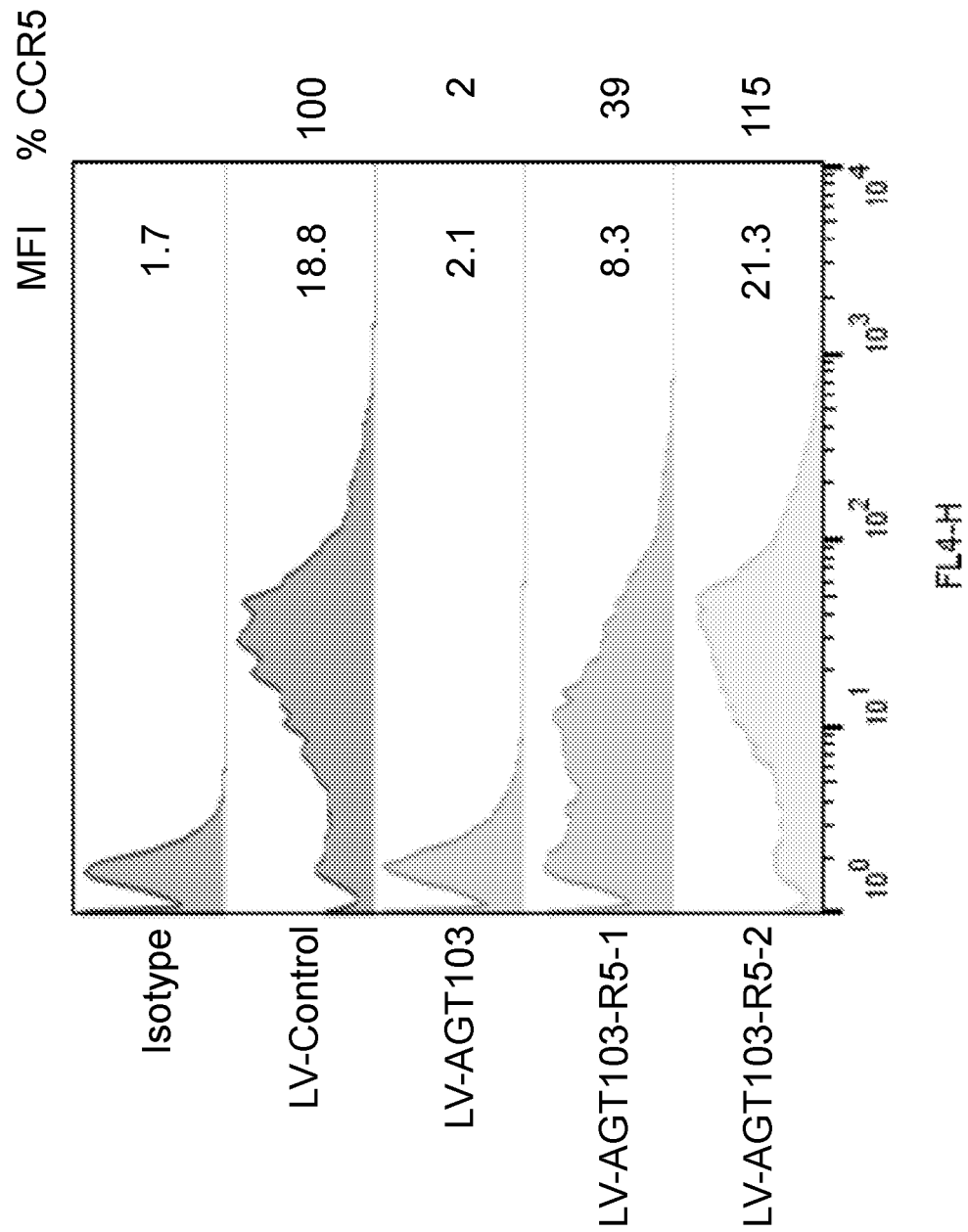
FIG. 14 depicts data demonstrating regulation of CCR5 expression by synthetic microRNA sequences in a lentiviral vector of the present disclosure.
Figure 15:
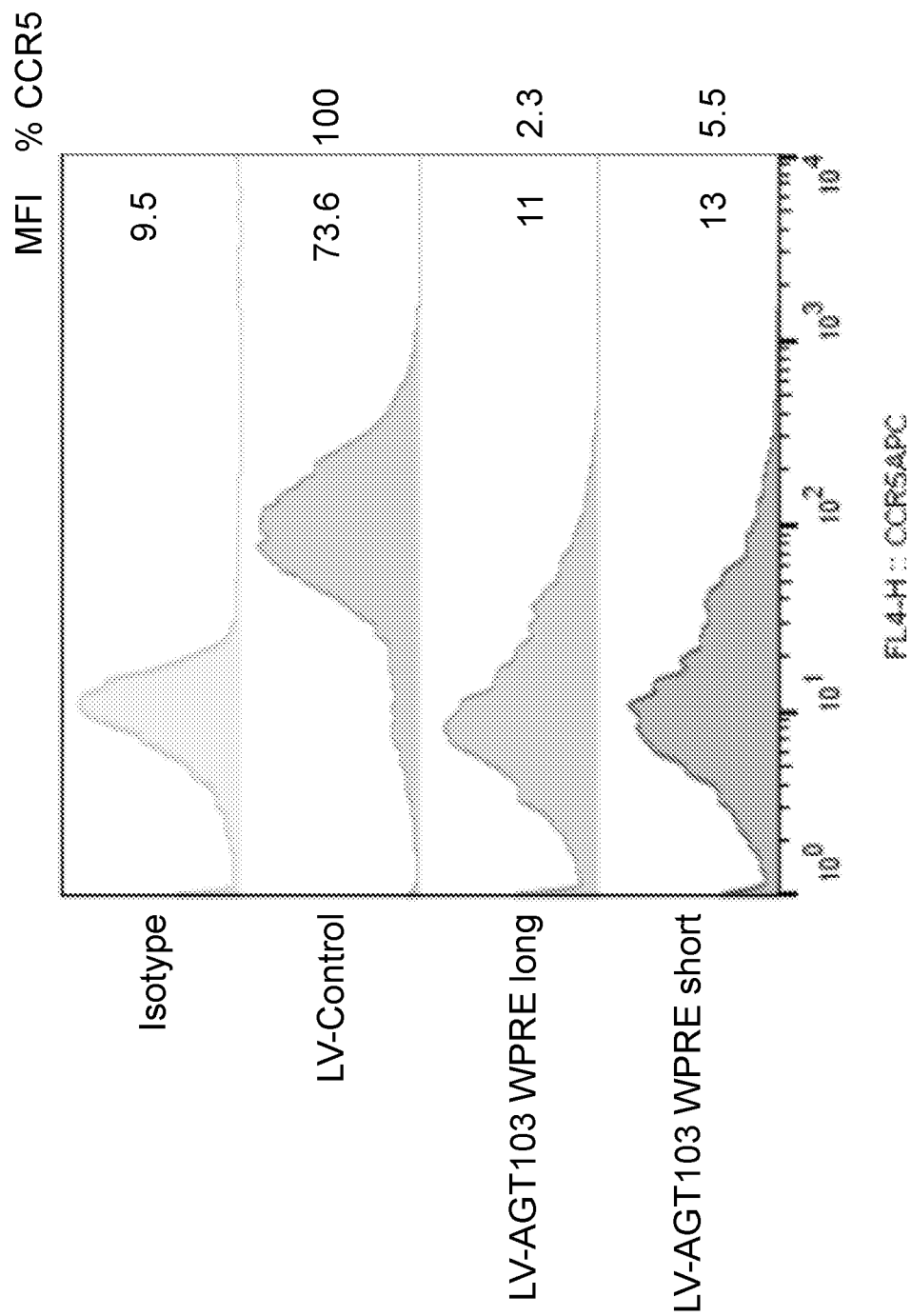
FIG. 15 depicts data demonstrating regulation of CCR5 expression by synthetic microRNA sequences in a lentiviral vector of the present disclosure containing either a long or short WPRE sequence.

As shown in FIG. 14, CEM-CCR5 cells were transduced with AGT103 containing either a long or short WPRE sequence. After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. The reduction in CCR5 levels was similar for AGT103 with either the short (5.5% of total CCR5) or long (2.3% of total CCR5) WPRE sequence.

Example 11: Regulation of CCR5 Expression by Synthetic microRNA Sequences in a Lentiviral Vector with or without a WPRE Sequence Vector construction. In order to test whether WPRE was required for AGT103 down regulation of CCR5 expression we constructed a modified vector without WPRE element sequences.

Functional assay for modulating cell surface CCR5 expression as a function of including or not including a long WPRE element in the AGT103 vector. In order to test whether WPRE was required for AGT103 modulation of CCR5 expression levels we transduced CEM-CCR5 T cells with AGT103 or a modified vector lacking WPRE using a multiplicity of infection equal to 5. Six days after transduction cells were collected and stained with a monoclonal antibody capable of recognizing cell surface CCR5 protein. The monoclonal antibody was directly conjugated to a fluorescent marker and the intensity of staining is directly proportional to the number of CCR5 molecules per cell surface. A lentivirus control vector had no effect on cell surface CCR5 levels resulting in a uniform population with mean fluorescence intensity of 164. The lentivirus vector (AGT103 with a long WPRE and also expressing GFP marker protein), AGT103 lacking GFP but containing a long WPRE element, or AGT103 lacking both GFP and WPRE all were similarly effective for modulating cell surface CCR5 expression. After removing GFP, AGT103 with or without WPRE elements were indistinguishable in terms of their capacity for modulating cell surface CCR5 expression.

Figure 16:
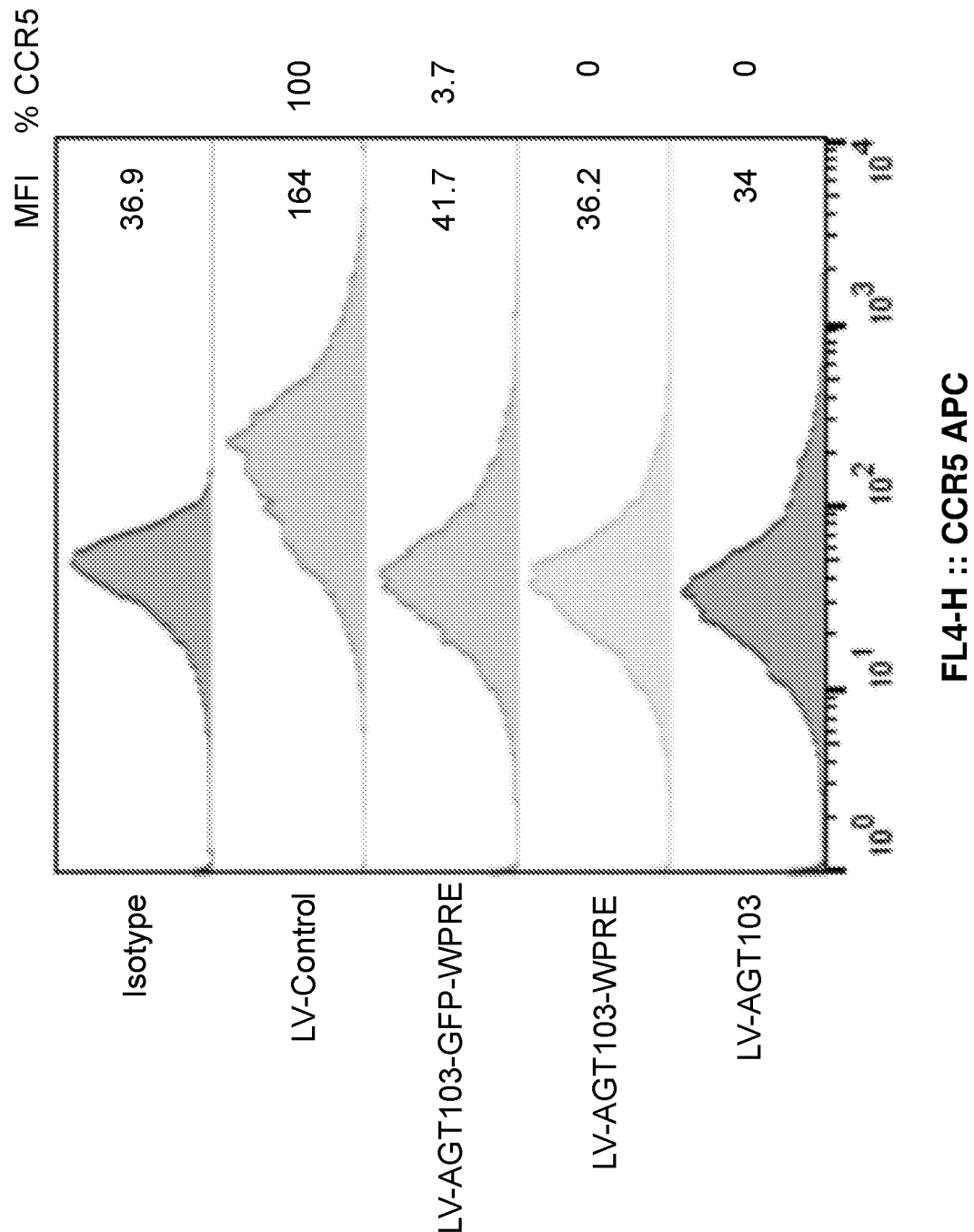
FIG. 16 depicts data demonstrating regulation of CCR5 expression by synthetic microRNA sequences in a lentiviral vector of the present disclosure with or without a WPRE sequence.

CEM-CCR5 cells were transduced with AGT103 with or without GFP and WPRE. After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. The reduction in CCR5 levels was similar for AGT103 with (0% of total CCR5) or without (0% of total CCR5) the WPRE sequence. This data is demonstrated in FIG. 16.

Example 12: Regulation of CCR5 Expression by a CD4 Promoter Regulating Synthetic microRNA Sequences in a Lentiviral Vector Vector Construction. A modified version of AGT103 was constructed to test the effect of substituting alternate promoters for expressing the microRNA cluster that suppresses CCR5, Vif and Tat gene expression. In place of the normal EF-1 promoter we substituted the T cell-specific promoter for CD4 glycoprotein expression using the sequence:

```
                                          (SEQ ID NO: 30)
(5'TGTTGGGGTTCAAATTTGAGCCCCAGCTGTTAGCCCTCTGCAAAGAA

AAAAAAAAAAAAAAAGAACAAAGGGCCTAGATTTCCCTTCTGAGCCCCA

CCCTAAGATGAAGCCTCTTCTTTCAAGGGAGTGGGGTTGGGGTGGAGGCG

GATCCTGTCAGCTTTGCTCTCTCTGTGGCTGGCAGTTTCTCCAAAGGGTA
```

-continued

```
ACAGGTGTCAGCTGGCTGAGCCTAGGCTGAACCCTGAGACATGCTACCTC

TGTCTTCTCATGGCTGGAGGCAGCCTTTGTAAGTCACAGAAAGTAGCTGA

GGGGCTCTGGAAAAAAGACAGCCAGGGTGGAGGTAGATTGGTCTTTGACT

CCTGATTTAAGCCTGATTCTGCTTAACTTTTTCCCTTGACTTTGGCATTT

TCACTTTGACATGTTCCCTGAGAGCCTGGGGGTGGGGAACCCAGCTCCA

GCTGGTGACGTTTGGGGCCGGCCCAGGCCTAGGGTGTGGAGGAGCCTTGC

CATCGGGCTTCCTGTCTCTCTTCATTTAAGCACGACTCTGCAGA-3').
```

Functional assay comparing EF-1 and CD4 gene promoters in terms of potency for reducing cell surface CCR5protein expression. AGT103 modified by substituting the CD4 gene promoter for the normal EF-1 promoter was used for transducing CEM-CCR5 T cells. Six days after transduction cells were collected and stained with a monoclonal antibody capable of recognizing cell surface CCR5 protein. The monoclonal antibody was conjugated to a fluorescent marker and staining intensity is directly proportional to the level of cell surface CCR5 protein. A control lentivirus transduction resulted in a population of CEM-CCR5 T cells that were stained with a CCR5-specific monoclonal antibody and produced a mean fluorescence intensity of 81.7 units. The modified AGT103 using a CD4 gene promoter in place of the EF-1 promoter for expressing microRNA showed a broad distribution of staining with a mean fluorescence intensity roughly equal to 17.3 units. Based on this result, the EF-1 promoter is at least similar and likely superior to the CD4 gene promoter for microRNA expression. Depending on the desired target cell population, the EF-1 promoter is universally active in all cell types and the CD4 promoter is only active in T-lymphocytes.

Figure 17:
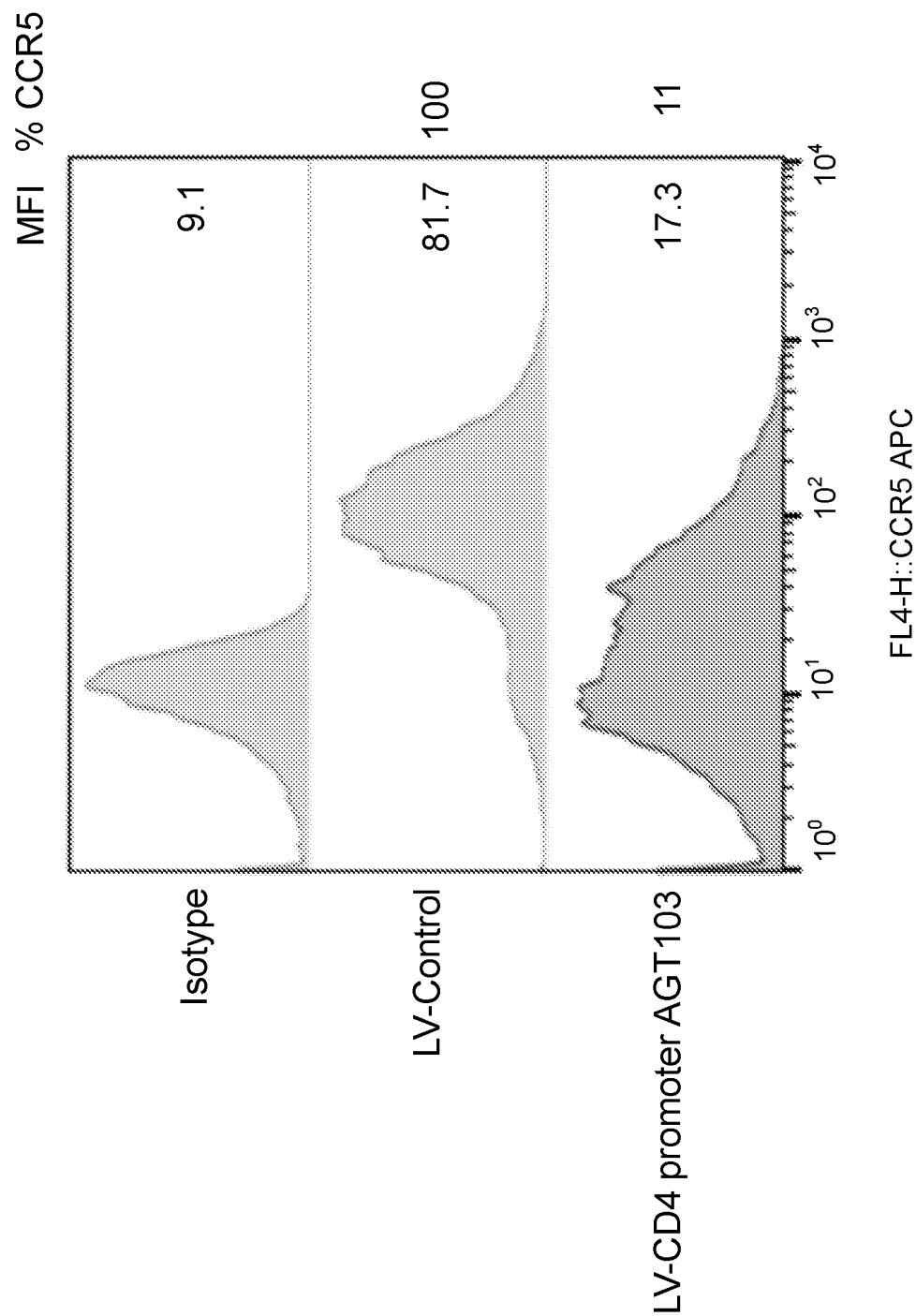
FIG. 17 depicts data demonstrating regulation of CCR5 expression by a CD4 promoter regulating synthetic microRNA sequences in a lentiviral vector of the present disclosure.

CEM-CCR5 cells were transduced with a lentiviral vector containing a CD4 promoter regulating a synthetic microRNA sequence for CCR5, Vif, and Tat (AGT103). After 6 days, CCR5 expression was determined by FACS analysis with an APC-conjugated CCR5 antibody and quantified as mean fluorescence intensity (MFI). CCR5 levels were expressed as % CCR5 with LV-Control set at 100%. In cells transduced with LV-CD4-AGT103, CCR5 levels were 11% of total CCR5. This is comparable to that observed for LV-AGT103 which contains the EF1 promoter. This data is demonstrated in FIG. 17.

Example 13: Detecting HIV Gag-Specific CD4 T Cells

Cells and reagents. Viable frozen peripheral blood mononuclear cells (PBMC) were obtained from a vaccine company. Data were obtained with a representative specimen from an HIV+ individual who was enrolled into an early stage clinical trial (TRIAL REGISTRATION: clinicaltrials.gov NCT01378156) testing a candidate HIV therapeutic vaccine. Two specimens were obtained for the "Before vaccination" and "After vaccination" studies. Cell culture products, supplements and cytokines were from commercial suppliers. Cells were tested for responses to recombinant Modified Vaccinia Ankara 62B from Geovax Corporation as described in Thompson et al. (2016). "DNA/MVA Vaccination of HIV-1 Infected Participants with Viral Suppression on Antiretroviral Therapy, followed by Treatment Interruption: Elicitation of Immune Responses without Control of Re-Emergent Virus." PLoS One 11(10): e0163164. Synthetic peptides representing the entire HIV-1 Gag polyprotein were obtained from GeoVax the HIV (GAG) Ultra peptide sets were obtained from JPT Peptide Technologies GmbH (www.jpt.com), Berlin, Germany. HIV (GAG) Ultra contains 150 peptides each being 15 amino acids in length and overlapping by 11 amino acids. They were chemically synthesized then purified and analyzed by liquid chromatography—mass spectrometry. Collectively these peptides represent major immunogenic regions of the HIV Gag polyprotein and are designed for average coverage of 57.8% among known HIV strains. Peptide sequences are based on the HIV sequence database from the Los Alamos National Laboratory (http://www.hiv.lanl.gov/content/sequence/NEWALIGN/align.html). Peptides are provided as dried trifluoroacetate salts, 25 micrograms per peptide, and are dissolved in approximately 40 microliters of DMSO then diluted with PBS to final concentration. Monoclonal antibodies for detecting CD4 and cytoplasmic IFN-gamma were obtained from commercial sources and intracellular staining was done with the BD Pharmingen Intracellular Staining Kit for interferon-gamma. Peptides were resuspended in DMSO and we include a DMSO only control condition.

Functional assay for detecting HIV-specific CD4+ T cells. Frozen PBMC were thawed, washed and resuspended in RPMI medium containing 10% fetal bovine serum, supplements and cytokines. Cultured PBMC collected before or after vaccination were treated with DMSO control, MVA GeoVax (multiplicity of infection equal to 1 plaque forming unit per cell), Peptides GeoVax (1 microgram/ml) or HIV (GAG) Ultra peptide mixture (1 microgram/ml) for 20 hours in the presence of Golgi Stop reagent. Cells were collected, washed, fixed, permeabilized and stained with monoclonal antibodies specific for cell surface CD4 or intracellular interferon-gamma. Stained cells were analyzed with a FACSCalibur analytical flow cytometer and data were gated on the CD4+ T cell subset. Cells highlighted within boxed regions are double-positive and designated HIV-specific CD4 T cells on the basis of interferon-gamma expression after MVA or peptide stimulation. Numbers within the boxed regions show the percentage of total CD4 that were identified as HIV-specific. We did not detect strong responses to DMSO or MVA. Peptides from GeoVax elicited fewer responding cells compared to HIV (GAG) Ultra peptide mixture from JPT but differences were small and not significant.

Figure 18:
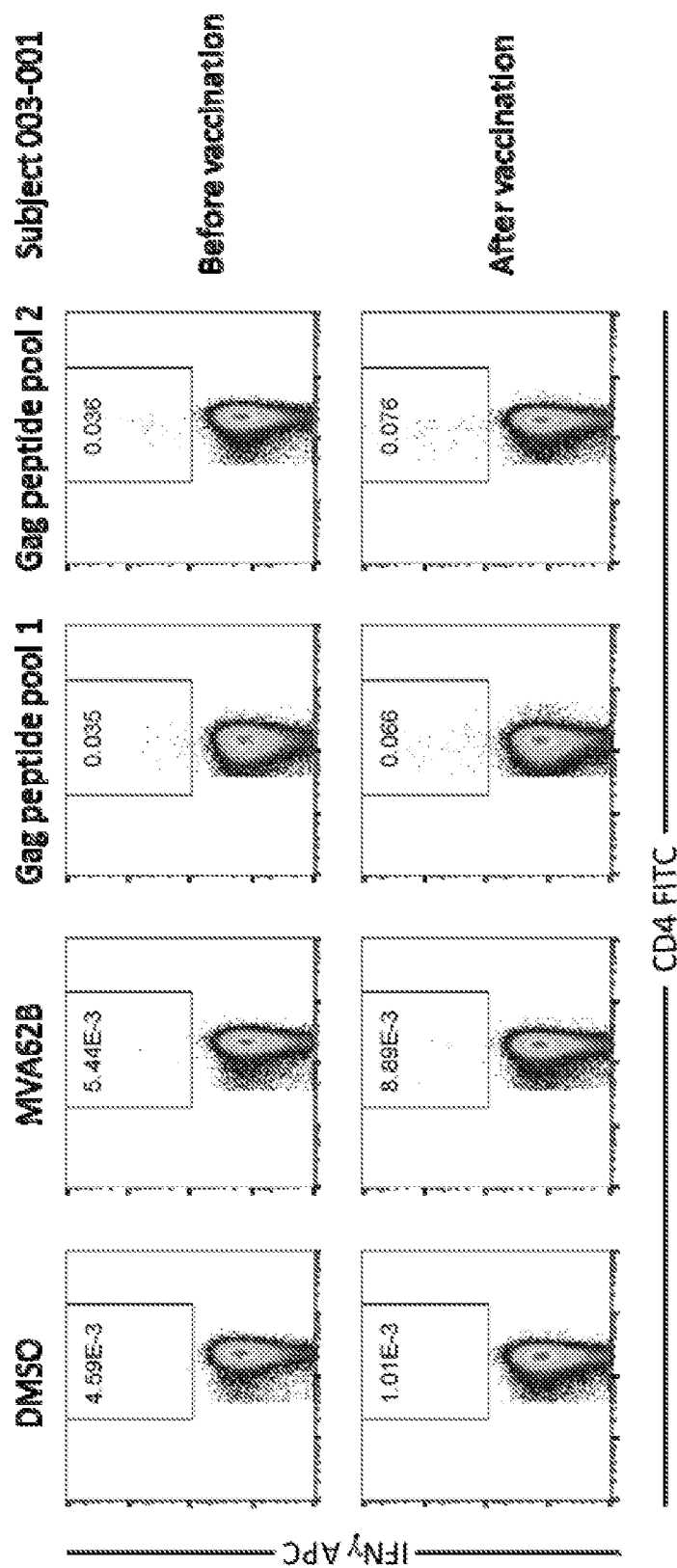
FIG. 18 depicts data demonstrating detection of HIV Gag-specific CD4 T cells.
Figure 19A:
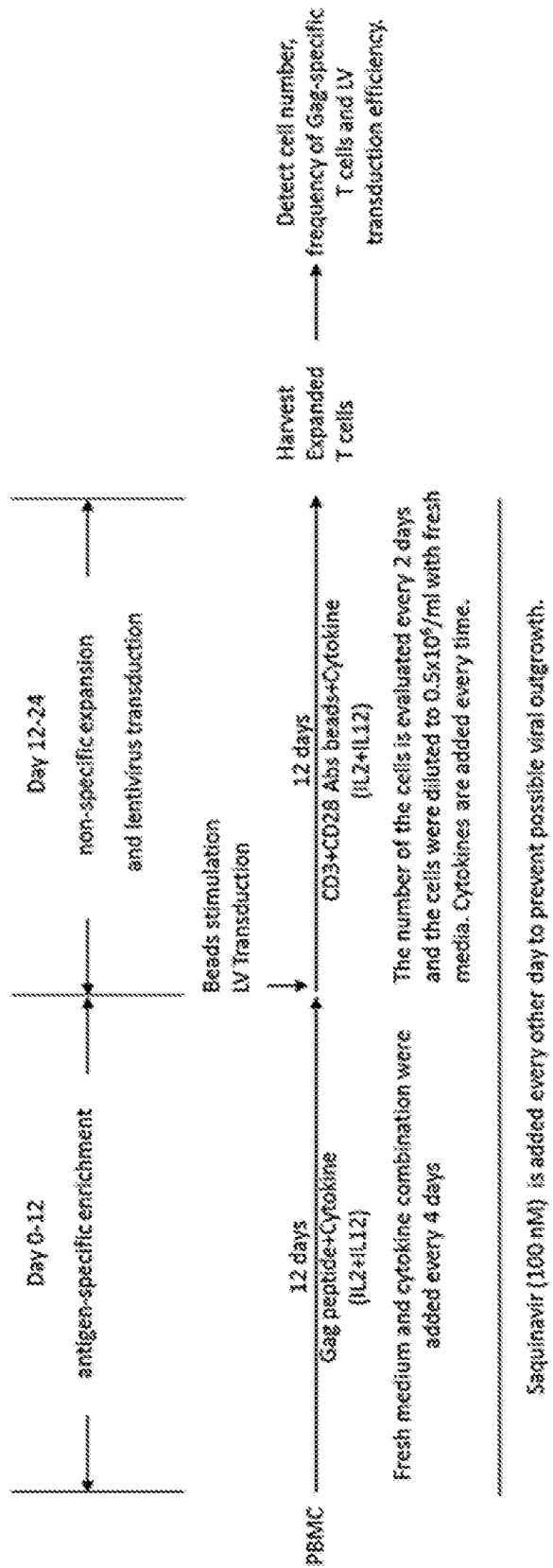
FIG. 19 depicts data demonstrating HIV-specific CD4 T cell expansion and lentivirus transduction. (A) An exemplary schedule of treatment is shown. (B) IFN-gamma production in CD4-gated T cells is shown, as described herein. (C) IFN-gamma production and GFP expression in CD4-gated T cells is shown, as described herein. (D) Frequency of HIV-specific CD4+ T cells is shown, as described herein. (E) IFN-gamma production from PBMCs post-vaccination and following ex vivo peptide and expansion is shown, as described herein.
Figure 19B:
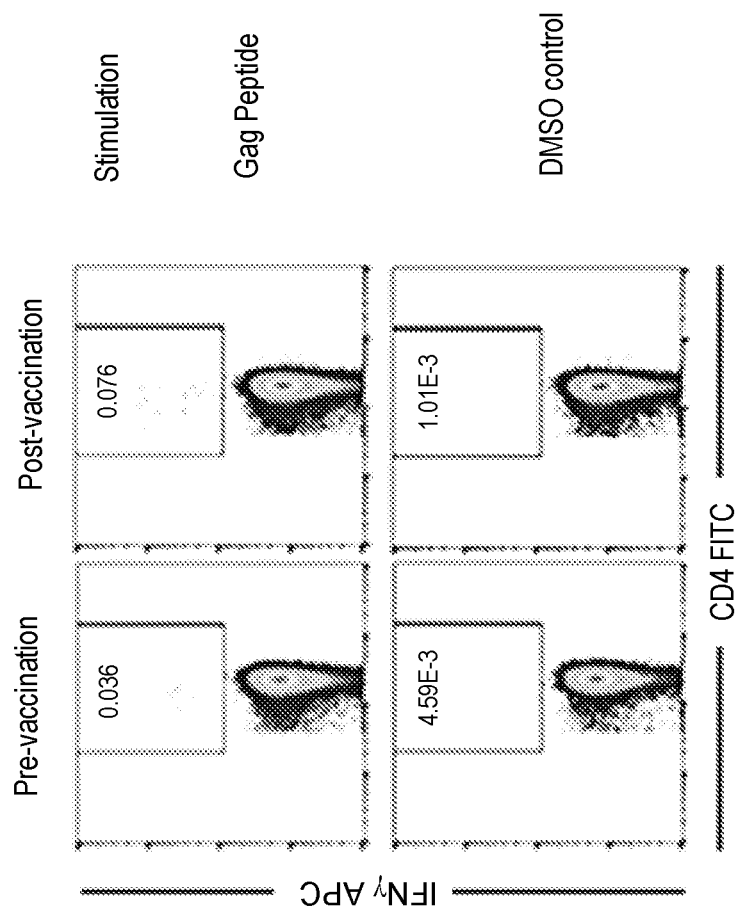
Figure 19C:
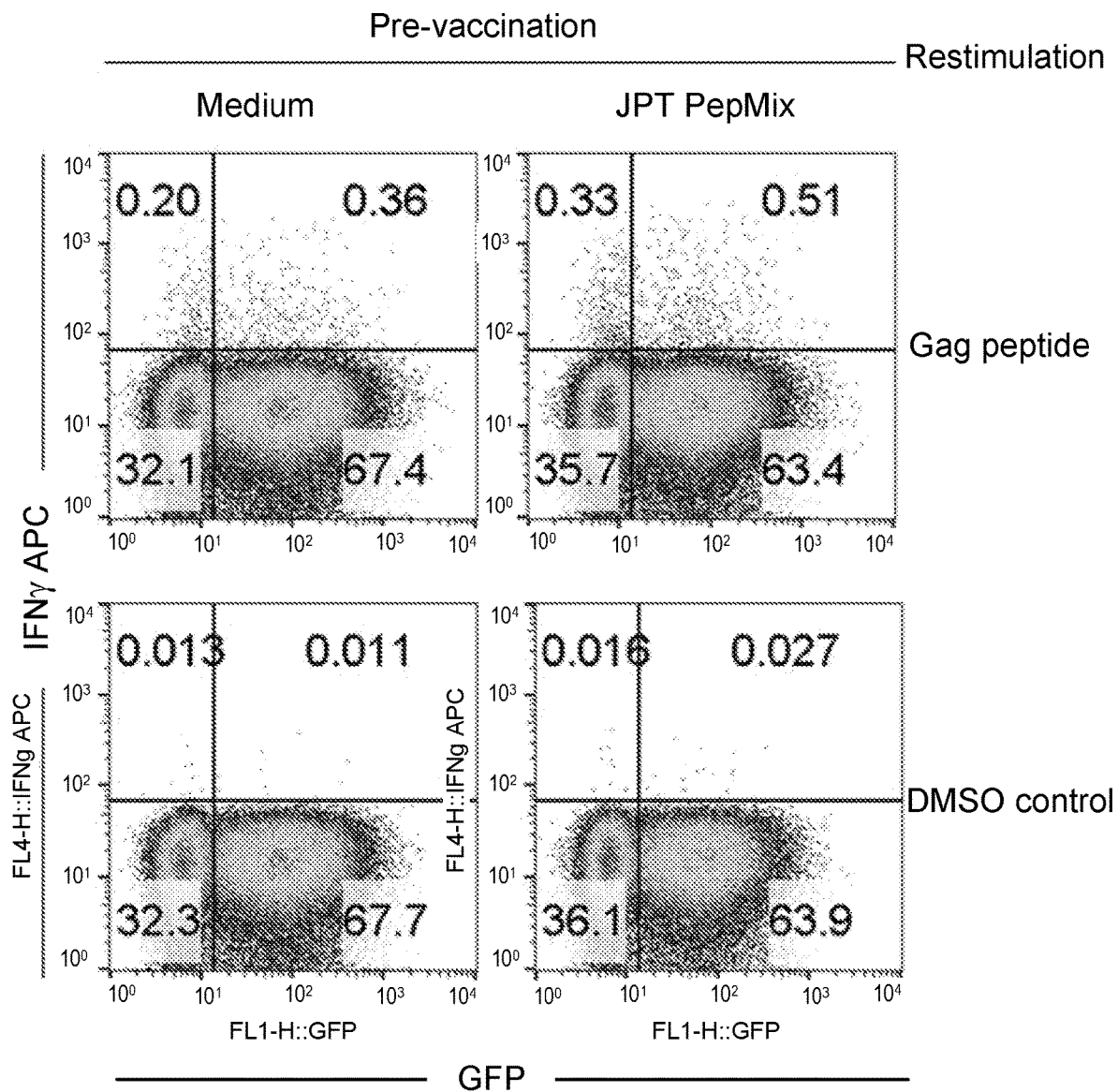
Figure 19C:
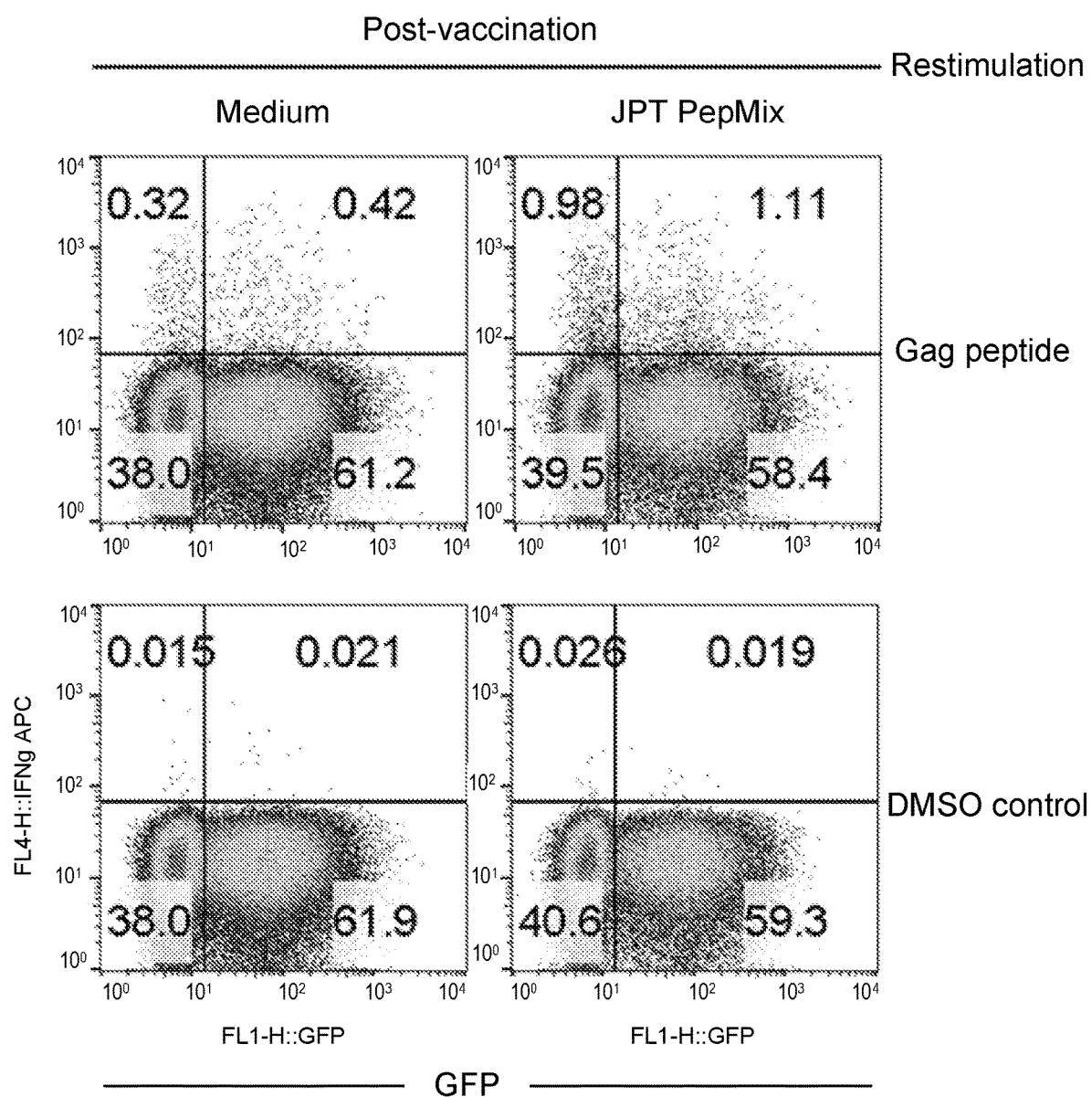
Figure 19D:
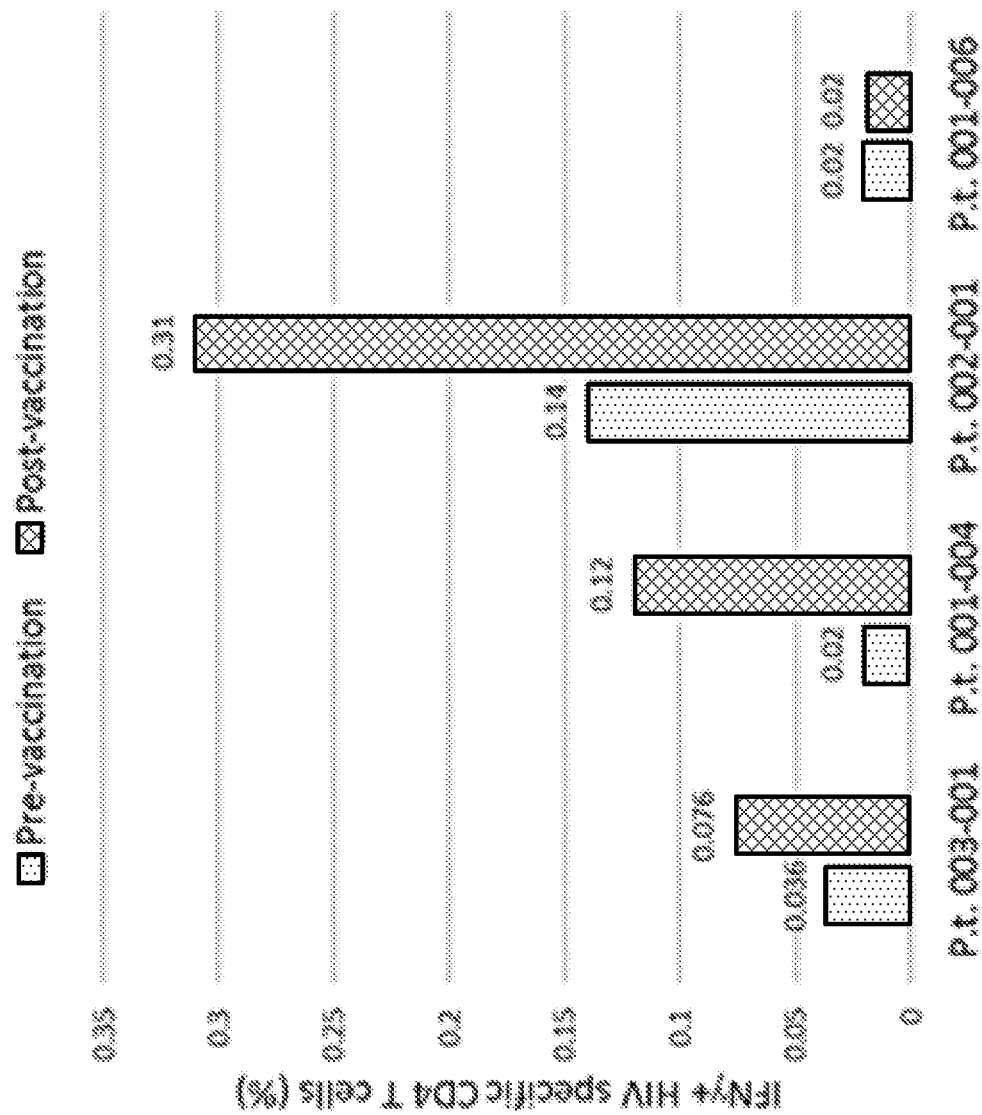
Figure 19E:
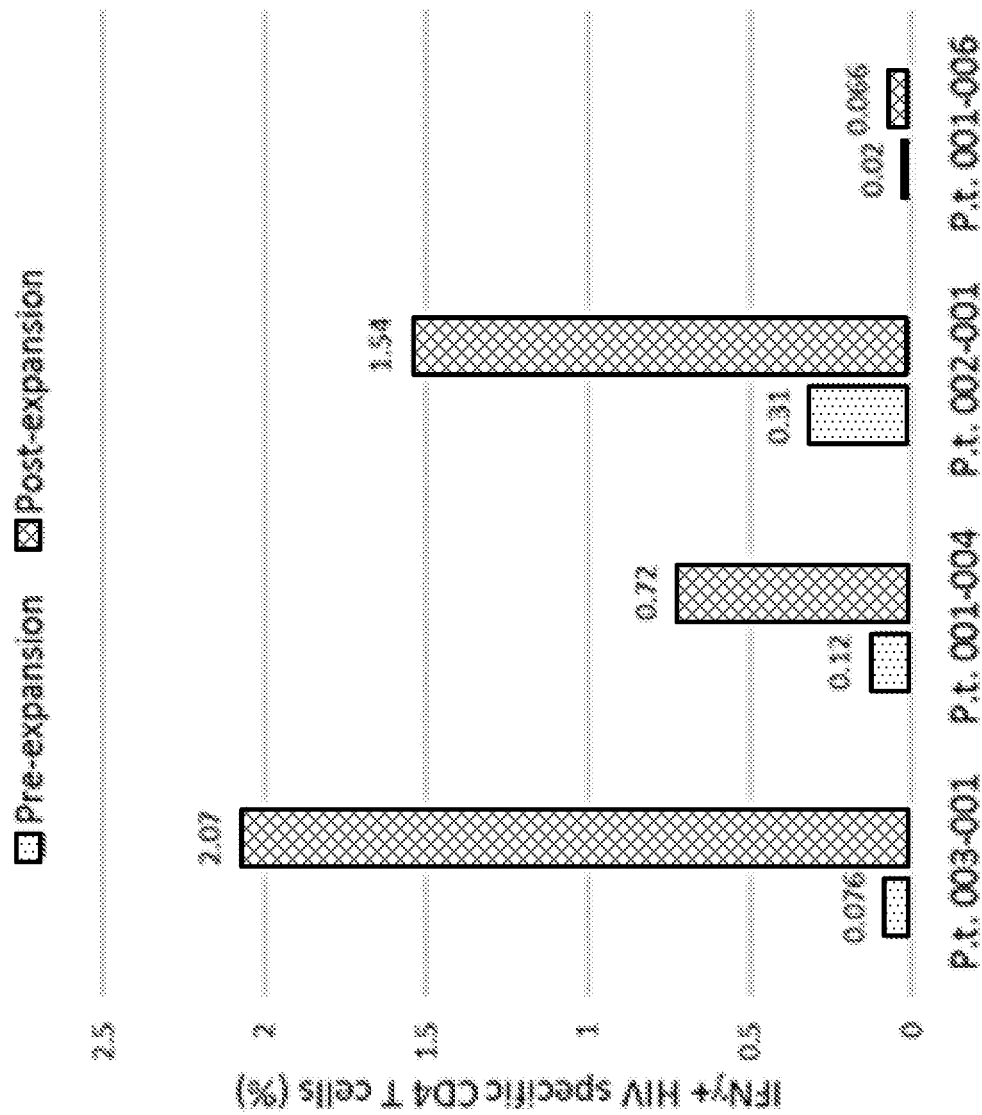

As shown in FIG. 18, PBMCs from a HIV-positive patient before or after vaccination were stimulated with DMSO (control), recombinant MVA expressing HIV Gag from GeoVax (MVA GeoVax), Gag peptide from GeoVax (Pep GeoVax, also referred to herein as Gag peptide pool 1) or Gag peptides from JPT (HIV (GAG) Ultra, also referred to herein as Gag peptide pool 2) for 20 hours. IFNg production was detected by intracellular staining and flow cytometry using standard protocols. Flow cytometry data were gated on CD4 T cells. Numbers captured in boxes are the percentage of total CD4 T cells designated "HIV-specific" on the basis of cytokine response to antigen-specific stimulation.

Example 14: HIV-Specific CD4 T Cell Expansion and Lentivirus Transduction

Designing and testing methods for enriching PBMC to increase the proportion of HIV-specific CD4 T cells and transducing these cells with AGT103 to produce the cellular product AGT103T.

The protocol was designed for ex vivo culture of PBMC (peripheral blood mononuclear cells) from HIV-positive patients who had received a therapeutic HIV vaccine. In this example, the therapeutic vaccine consisted of three doses of plasmid DNA expressing HIV Gag, Pol and Env genes followed by two doses of MVA 62-B (modified vaccinia Ankara number 62-B) expressing the same HIV Gag, Pol, and Env genes. The protocol is not specific for a vaccine product and only requires a sufficient level of HIV-specific CD4+ T cells after immunization. Venous blood was collected and PBMC were purified by Ficoll-Paque density gradient centrifugation. Alternately, PBMC or defined cellular tractions can be prepared by positive or negative selection methods using antibody cocktails and fluorescence activated or magnetic bead sorting. The purified PBMC are washed and cultured in standard medium containing supplements, antibiotics and fetal bovine serum. To these cultures, a pool of synthetic peptides was added representing possible T cell epitopes within the HIV Gag polyprotein. Cultures are supplemented by adding cytokines interleukin-2 and interleukin-12 that were selected after testing combinations of interleukin-2 and interleukin-12, interleukin 2 and interleukin-7, interleukin 2 and interleukin-15. Peptide stimulation is followed by a culture interval of approximately 12 days. During the 12 days culture, fresh medium and fresh cytokine supplements were added approximately once every four days.

The peptide stimulation interval is designed to increase the frequency of HIV-specific CD4 T cells in the PBMC culture. These HIV-specific CD4 T cells were activated by prior therapeutic immunization and can be re-stimulated and caused to proliferate by synthetic peptide exposure. Our goal is to achieve greater than or equal to 1% of total CD4 T cells being HIV-specific by end of the peptide stimulation culture period.

On approximately day 12 of culture cells are washed to remove residual materials then stimulated with synthetic beads decorated with antibodies against CD4 T cell surface proteins CD3 and CD28. This well-established method for polyclonal stimulation of T cells will reactivate the cells and make them more susceptible for AGT103 lentivirus transduction. The lentivirus transduction is performed on approximately day 13 of culture and uses a multiplicity of infection between 1 and 5. After transduction cells are washed to remove residual lentivirus vector and cultured in media containing interleukin-2 and interleukin-12 with fresh medium and cytokines added approximately once every four days until approximately day 24 of culture.

Throughout the culture interval the antiretroviral drug Saquinavir is added at a concentration of approximately 100 nM to suppress any possible outgrowth of HIV.

On approximately day 24 of culture cells are harvested, washed, a sample is set aside for potency and release assay, then the remaining cells are suspended in cryopreservation medium before freezing in single aliquots of approximately $1 \times 10^{10}$ cells per dose that will contain approximately $1 \times 10^8$ HIV-specific CD4 T cells that are transduced with AGT103.

Potency of the cell product (AGT103T) is tested in one of two alternate potency assays. Potency assay 1 tests for the average number of genome copies (integrated AGT103 vector sequences) per CD4 T cell. The minimum potency is approximately 0.5 genome copies per CD4 T cell in order to release the product. The assay is performed by positive selection of CD3 positive/CD4 positive T cells using magnetic bead labeled monoclonal antibodies, extracting total cellular DNA and using a quantitative PCR reaction to detect sequences unique to the AGT103 vector. Potency assay 2 tests for the average number of genome copies of integrated AGT103 within the subpopulation of HIV-specific CD4 T cells. This essay is accomplished by first stimulating the PBMC with the pool of synthetic peptides representing HIV Gag protein. Cells are then stained with a specific antibody reagent capable of binding to the CD4 T cell and also capturing secreted interferon-gamma cytokine. The CD4 positive/interferon-gamma positive cells are captured by magnetic bead selection, total cellular DNA is prepared, and the number of genome copies of AGT103 per cell is determined with a quantitative PCR reaction. Release criterion based on potency using Assay 2 require that greater than or equal to 0.5 genome copies per HIV-specific CD4 T-cell are present in the AGT103 cell product.

Functional test for enriching and transducing HIV-specific CD4 T cells from PBMC of HIV-positive patients that received a therapeutic HIV vaccine. The impact of therapeutic vaccination on the frequency of HIV-specific CD4 T cells was tested by a peptide stimulation assay (FIG. 19, Panel B). Before vaccination the frequency of HIV-specific CD4 T cells was 0.036% in this representative individual. After vaccination, the frequency of HIV-specific CD4 T cells was increased approximately 2-fold to the value of 0.076%. Responding cells (HIV-specific) identified by accumulation of cytoplasmic interferon-gamma, were only detected after specific peptide stimulation.

We also tested whether peptide stimulation to enrich for HIV-specific CD4 T cells followed by AGT103 transduction would reach our goal of generating approximately 1% of total CD4 T cells in culture that were both HIV-specific and transduced by AGT103. In this case, we used an experimental version of AGT103 that expresses green fluorescence protein (see GFP). In FIG. 19, Panel C the post-vaccination culture after peptide stimulation (HIV (GAG) Ultra) and AGT103 transduction demonstrated that 1.11% of total CD4 T cells were both HIV-specific (based on expressing interferon-gamma in response to peptide stimulation) and AGT103 transduced (based on expression of GFP).

Several patients from a therapeutic HIV vaccine study were tested to assess the range of responses to peptide stimulation and to begin defining eligibility criteria for entering a gene therapy arm in a future human clinical trial. FIG. 19 Panel D show the frequency of HIV-specific CD4 T cells in 4 vaccine trial participants comparing their pre- and post-vaccination specimens. In three cases the post-vaccination specimens show a value of HIV-specific CD4 T cells that was greater than or equal to 0.076% of total CD4 T cells. The ability to reach this value was not predicted by the pre-vaccination specimens as patient 001-004 and patient 001-006 both started with pre-vaccination values of 0.02% HIV-specific CD4 T cells but one reached an eventual post-vaccination value of 0.12% HIV-specific CD4 T cells while the other individual fail to increase this value after vaccination. The same three patients that responded well to vaccine, in terms of increasing the frequency of HIV-specific CD4 T cells, also showed substantial enrichment of HIV-specific CD4 T cells after peptide stimulation and culture. In the three cases shown in FIG. 19 Panel E, peptide stimulation and subsequent culture generated samples where 2.07%, 0.72% or 1.54% respectively of total CD4 T cells were HIV-specific. These values indicate that a majority of individuals responding to a therapeutic HIV vaccine will have a sufficiently large ex vivo response to peptide stimulation in order to enable our goal of achieving approximately 1% of total CD4 T cells that are HIV-specific and transduced with AGT103 in the final cell product.

As shown in FIG. 19, Panel A describes the schedule of treatment. Panel B demonstrates that PBMCs were stimulated with Gag peptide or DMSO control for 20 hours. IFN gamma production was detected by intracellular staining by FACS. CD4+ T cells were gated for analysis. Panel C demonstrates CD4+ T cells were expanded and transduced with AGT103-GFP using the method as shown in Panel A. Expanded CD4+ T cells were rested in fresh medium without any cytokine for 2 days and re-stimulated with Gag peptide or DMSO control for 20 hours. IFN gamma production and GFP expression was detected by FACS. CD4+ T cells were gated for analysis. Panel D demonstrates frequency of HIV-specific CD4+ T cells (IFN gamma positive, pre- and post-vaccination) were detected from 4 patients. Panel E demonstrates Post-vaccination PBMCs from 4 patients were expanded and HIV-specific CD4+ T cells were examined.

Example 15: Dose Response

Vector Construction. A modified version of AGT103 was constructed to test the dose response for increasing AGT103 and its effects on cell surface CCR5 levels. The AGT103 was modified to include a green fluorescent protein (GFP) expression cassette under control of the CMV promoter. Transduced cells expression the miR30CCR5 miR21Vif miR185Tat micro RNA cluster and emit green light due to expressing GFP.

Functional assay for dose response of increasing AGT103-GFP and inhibition of CCR5 expression. CEM-CCR5 T cells were transduced with AGT103-GFP using multiplicity of infection per cell from 0 to 5. Transduced cells were stained with a fluorescently conjugated (APC) monoclonal antibody specific for cell surface CCR5. The intensity of staining is proportional to the number of CCR5 molecules per cell surface. The intensity of green fluorescence is proportional to the number of integrated AGT103-GFP copies per cell.

Figure 20A:
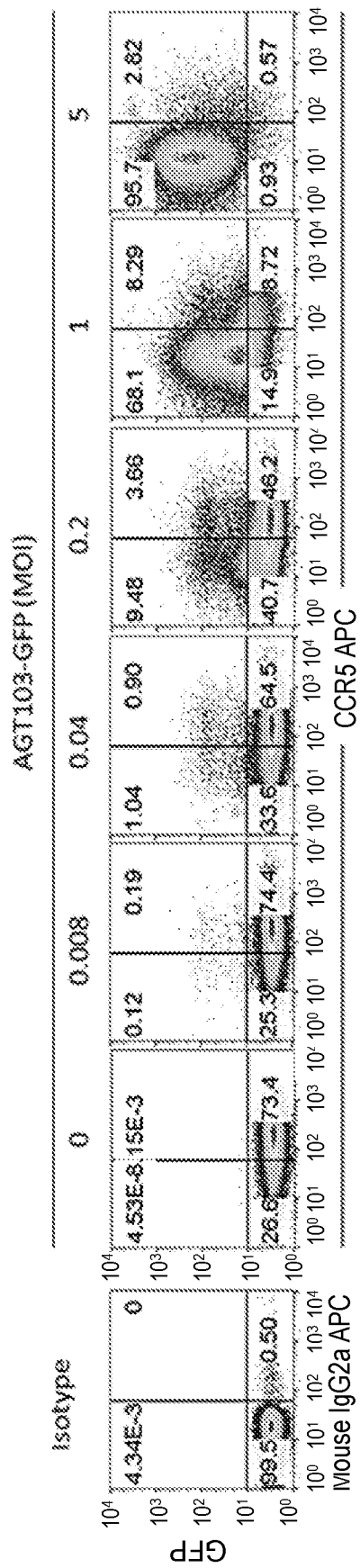
FIG. 20 depicts data demonstrating a functional assay for a dose response of increasing AGT103-GFP and inhibition of CCR5 expression. (A) Dose response data for increasing amounts of AGT103-GFP is shown. (B) Normally distributed populations in terms of CCR5 expression are shown and a left shift of the population average indicates decreasing CCR5 expression due to AGT103-GFP transduction. (C) Percentage inhibition of CCR5 expression with increasing doses of AGT103-GFP is shown.
Figure 20B:
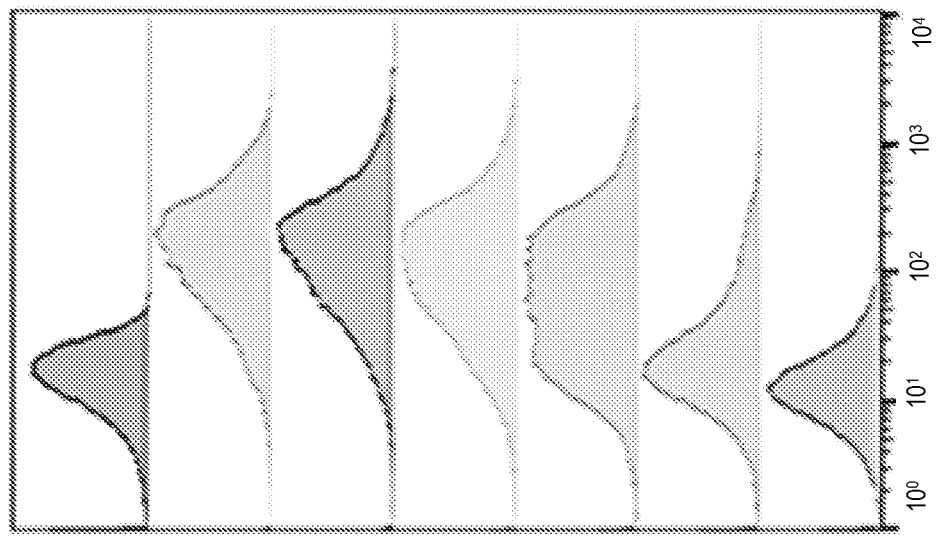
Figure 20C:
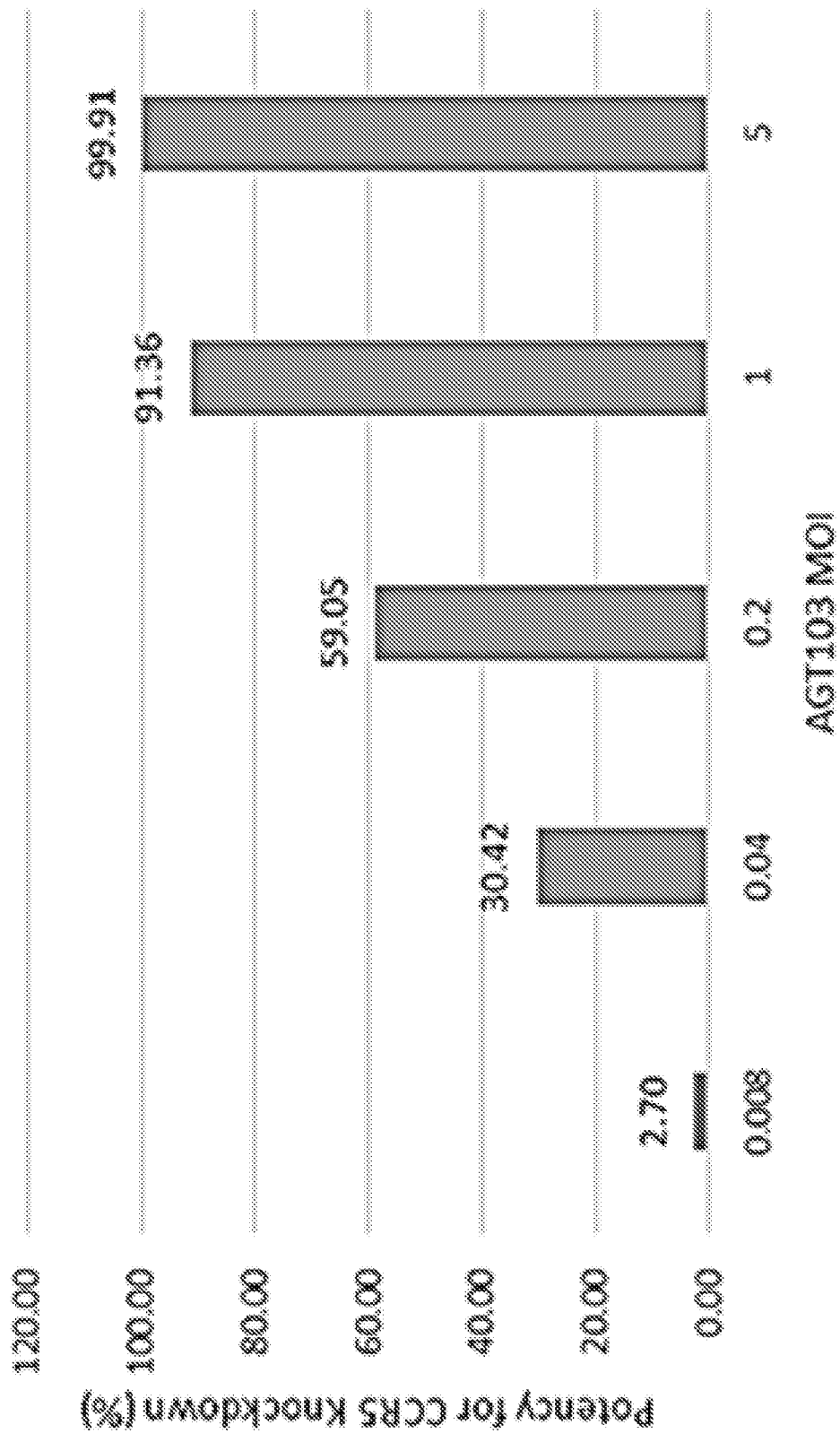

As shown in FIG. 20, Panel A demonstrates the dose response for increasing AGT103-GFP and its effects on cell surface CCR5 expression. At multiplicity of infection equal to 0.4 only 1.04% of cells are both green (indicating transduction) and showing significantly reduced CCR5 expression. At multiplicity of infection equal to 1 the number of CCR5low, GFP+ cells increases to 68.1%/ At multiplicity of infection equal to 5 the number of CCR5low, GFP+ cells increased to 95.7%. These data are presented in histogram form in FIG. 20, Panel B that shows a normally distribution population in terms of CCR5 staining, moving toward lower mean fluorescence intensity with increasing doses of AGT103-GFP. The potency of AGT103-GFP is presented in graphical form in FIG. 20, Panel C showing the percentage inhibition of CCR5 expression with increasing doses of AGT103-GFP. At multiplicity of infection equal to 5, there was greater than 99% reduction in CCR5 expression levels.

Example 16: AGT103 Efficiently Transduces Primary Human CD4' T Cells

Transducing primary CD4 T cells with AGT103 lentivirus vector. A modified AGT103 vector containing the green fluorescence protein marker (GFP) was used at multiplicities of infection between 0.2 and 5 for transducing purified, primary human CD4 T cells.

Figure 21A:
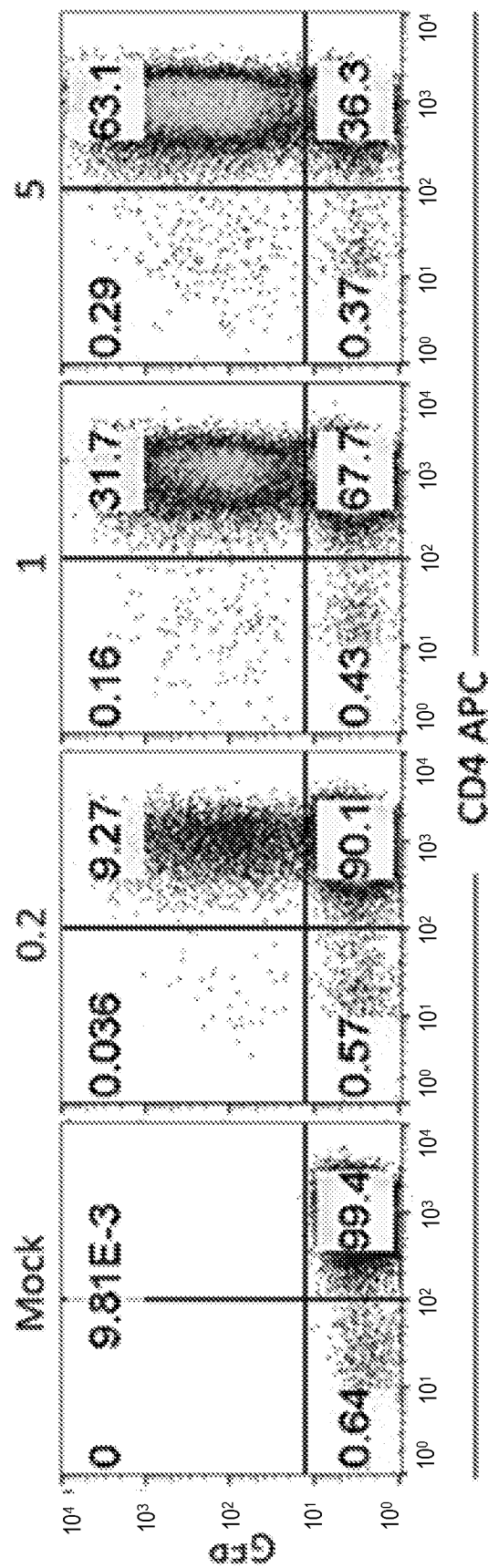
FIG. 21 depicts data demonstrating AGT103 transduction efficiency for primary human CD4+ T cells. (A) Frequency of transduced cells (GFP-positive) is shown by FACS, as described herein. (B) Number of vector copies per cell is shown, as described herein.
Figure 21B:
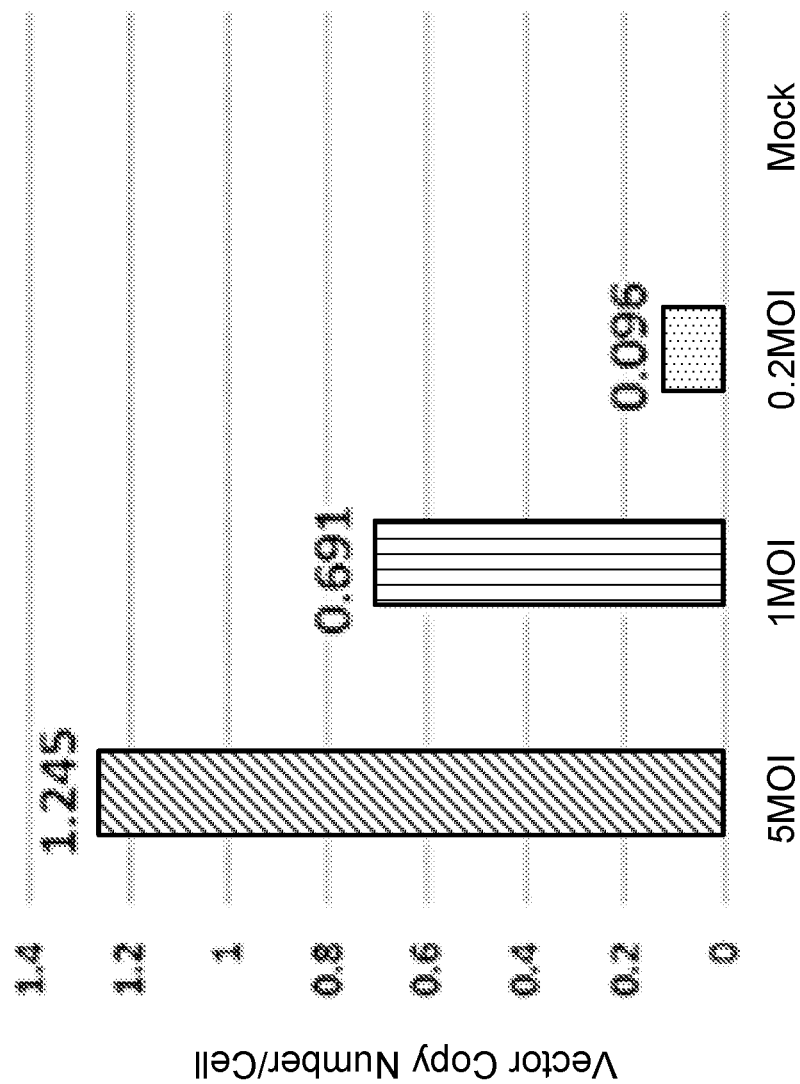

Functional assay for transduction efficiency of AGT103 in primary human CD4 T cells. CD4 T cells were isolated from human PBMC (HIV-negative donor) using magnetic bead labeled antibodies and standard procedures. The purified CD4 T cells were stimulated ex vivo with CD3/CD28 beads and cultured in media containing interleukin-2 for 1 day before AGT103 transduction. The relationship between lentivirus vector dose (the multiplicity of infection) and transduction efficiency is demonstrated in FIG. 21, Panel A showing that multiplicity of infection equal to 0.2 resulted in 9.27% of CD4 positive T cells being transduced by AGT103 and that value was increased to 63.1% of CD4 positive T cells being transduced by AGT103 with a multiplicity of infection equal to 5. In addition to achieving efficient transduction of primary CD4 positive T cells it is also necessary to quantify the number of genome copies per cell. In FIG. 21, Panel B total cellular DNA from primary human CD4 T cells transduced at several multiplicities of infection were tested by quantitative PCR to determine the number of genome copies per cell. In a multiplicity of infection equal to 0.2 we measured 0.096 genome copies per cell that was in good agreement with 9.27% GFP positive CD4 T cells in panel A. Multiplicity of infection equal to 1 generated 0.691 genome copies per cell and multiplicity of infection equal to 5 generated 1.245 genome copies per cell.

As shown in FIG. 21, CD4+ T cells isolated from PBMC were stimulated with CD3/CD28 beads plus IL-2 for 1 day and transduced with AGT103 at various concentrations. After 2 days, beads were removed and CD4+ T cells were collected. As shown in Panel A, frequency of transduced cells (GFP positive) were detected by FACS. As shown in Panel B, the number of vector copies per cell was determined by qPCR. At a multiplicity of infection (MOI) of 5, 63% of CD4+ T cells were transduced with an average of 1 vector copy per cell.

Example 17: AGT103 Inhibits HIV Replication in Primary CD4+ T Cells

Protecting primary human CD4 positive T cells from HIV infection by transducing cells with AGT103. Therapeutic lentivirus AGT103 was used for transducing primary human CD4 positive T cells at multiplicities of infection between 0.2 and 5 per cell. The transduced cells were then challenged with a CXCR4-tropic HIV strain NL4.3 that does not require cell surface CCR5 for penetration. This assay tests the potency of microRNA against Vif and Tat genes of HIV in terms of preventing productive infection in primary CD4 positive T cells, but uses an indirect method to detect the amount of HIV released from infected, primary human CD4 T cells.

Functional assay for AGT103 protection against CXCR4-tropic HIV infection of primary human CD4 positive T cells. CD4 T cells were isolated from human PBMC (HIV-negative donor) using magnetic bead labeled antibodies and standard procedures. The purified CD4 T cells were stimulated ex vivo with CD3/CD28 beads and cultured in media containing interleukin-2 for 1 day before AGT103 transduction using multiplicities of infection between 0.2 and 5. Two days after transduction the CD4 positive T cell cultures were challenged with HIV strain NL4.3 that was engineered to express the green fluorescent protein (GFP). The transduced and HIV-exposed primary CD4 T cell cultures were maintained for 7 days before collecting cell-free culture fluids containing HIV. The cell-free culture fluids were used to infect a highly permissive T cell line C8166 for 2 days. The proportion of HIV-infected C8166 cells was determined by flow cytometry detecting GFP fluorescence. With a mock lentivirus infection, the dose of 0.1 multiplicity of infection for NL4.3 HIV resulted in an amount of HIV being released into culture fluids that was capable of establishing productive infection in 15.4% of C8166 T cells. With the dose 0.2 multiplicity of infection for AGT103, this value for HIV infection of C8166 cells is reduced to 5.3% and multiplicity of infection equal to 1 for AGT103 resulted in only 3.19% of C8166 T cells being infected by HIV. C8166 infection was reduced further to 0.62% after AGT103 transduction using a multiplicity of infection equal to 5. There is a clear dose response relationship between the amount of AGT103 used for transduction and the amount of HIV released into the culture medium.

Figure 22:
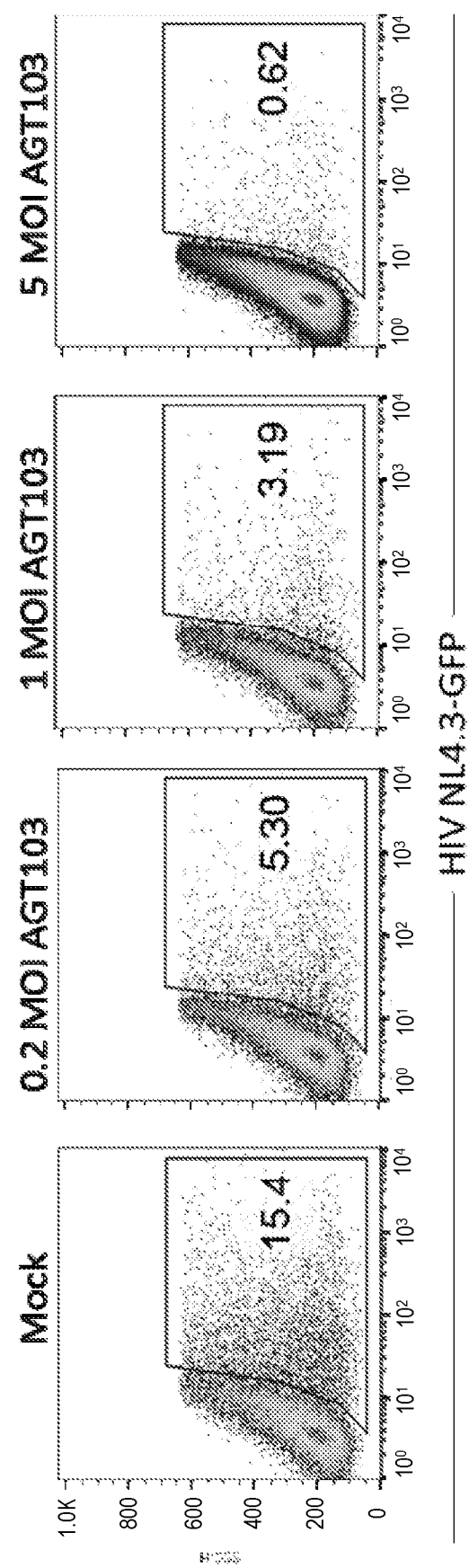
FIG. 22 depicts data demonstrating AGT103 inhibition of HIV replication in primary CD4+ T cells, as described herein.

As shown in FIG. 22, CD4+ T cells isolated from PBMC were stimulated with CD3/CD28 beads plus IL-2 for 1 day and transduced with AGT103 at various concentrations (MOI). After 2 days, beads were removed and CD4+ T cells were infected with 0.1 MOI of HIV NL4.3-GFP. 24 hours later, cells were washed 3 times with PBS and cultured with IL-2 (30U/ml) for 7 days. At the end of the culture, supernatant was collected to infect the HIV permissive cell line C8166 for 2 days. HIV-infected C8166 cells (GFP positive) were detected by FACS. There was a reduction in viable HIV with an increase in the multiplicity of infection of AGT103 as observed by less infection of C8166 cells MOI 0.2=65.6%, MOI 1=79.3%, and MOI 5=96%).

Example 18: AGT103 Protects Primary Human CD4+ T Cells from HIV-Induced Depletion AGT103 transduction of primary human CD4 T cells to protect against HIV-mediated cytopathology and cell depletion. PBMC were obtained from healthy, HIV-negative donors and stimulated with CD3/CD28 beads then cultured for 1 day in medium containing interleukin-2 before AGT103 transduction using multiplicities of infection between 0.2 and 5.

Functional assay for AGT103 protection of primary human CD4 T cells against HIV-mediated cytopathology. AGT103-transduced primary human CD4 T cells were infected with HIV NL 4.3 strain (CXCR4-tropic) that does not require CCR5 for cellular entry. When using the CXCR4-tropic NL 4.3, only the effect of Vif and Tat microRNA on HIV replication is being tested. The dose of HIV NL 4.3 was 0.1 multiplicity of infection. One day after HIV infection, cells were washed to remove residual virus and cultured in medium plus interleukin-2. Cells were collected every three days during a 14-day culture then stained with a monoclonal antibody that was specific for CD4 and directly conjugated to a fluorescent marker to allow measurement of the proportion of CD4 positive T cells in PBMC. Untreated CD4 T cells or CD4 T cells transduced with the control lentivirus vector were highly susceptible to HIV challenge and the proportion of CD4 positive T cells in PBMC fell below 10% by day 14 culture. In contrast, there was a dose-dependent effect of AGT103 on preventing cell depletion by HIV challenge. With a AGT103 dose of 0.2 multiplicity of infection more than 20% of PBMC were CD4 T cells by day 14 of culture and this value increased to more than 50% of PBMC being CD4 positive T cells by day 14 of culture with a AGT103 dose of multiplicity of infection equal to 5. Again, there is a clear dose response effect of AGT103 on HIV cytopathogenicity in human PBMC.

Figure 23:
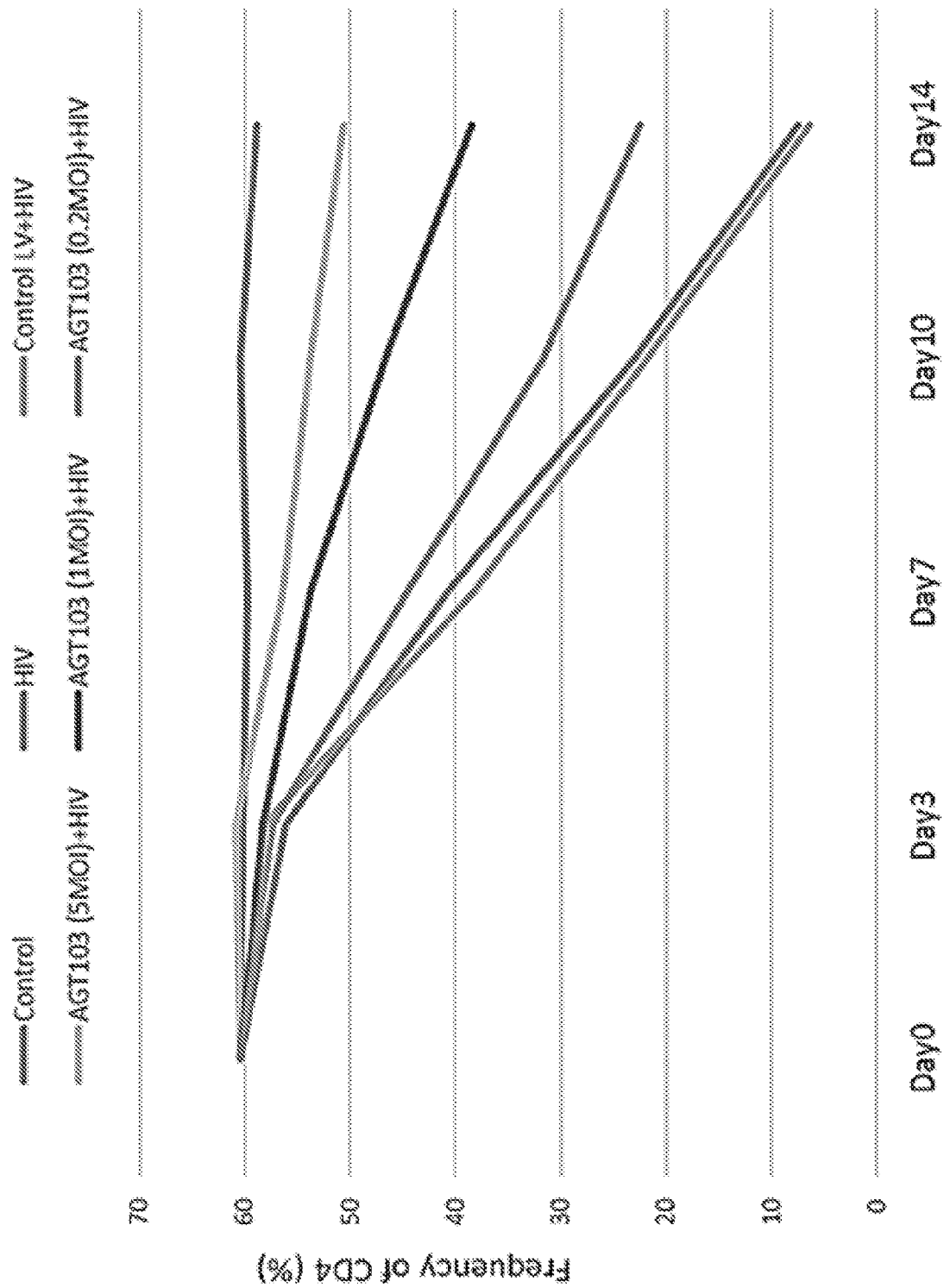
FIG. 23 depicts data demonstrating AGT103 protection of primary human CD4+ T cells from HIV-induced depletion.

As shown in FIG. 23, PBMCs were stimulated with CD3/CD28 beads plus IL-2 for 1 day and transduced with AGT103 at various concentrations (MOI). After 2 days, beads were removed and cells were infected with 0.1 MOI of HIV NL4.3. 24 hours later, cells were washed 3 times with PBS and cultured with IL-2 (30U/ml). Cells were collected every 3 days and the frequency of CD4+ T cells were analyzed by FACS. After 14 days of exposure to HIV, there was an 87% reduction in CD4+ T cells transduced with LV-Control, a 60% reduction with AGT103 MOI 0.2, a 37% reduction with AGT103 MOI 1, and a 17% reduction with AGT103 MOI 5.

Figure 24A:
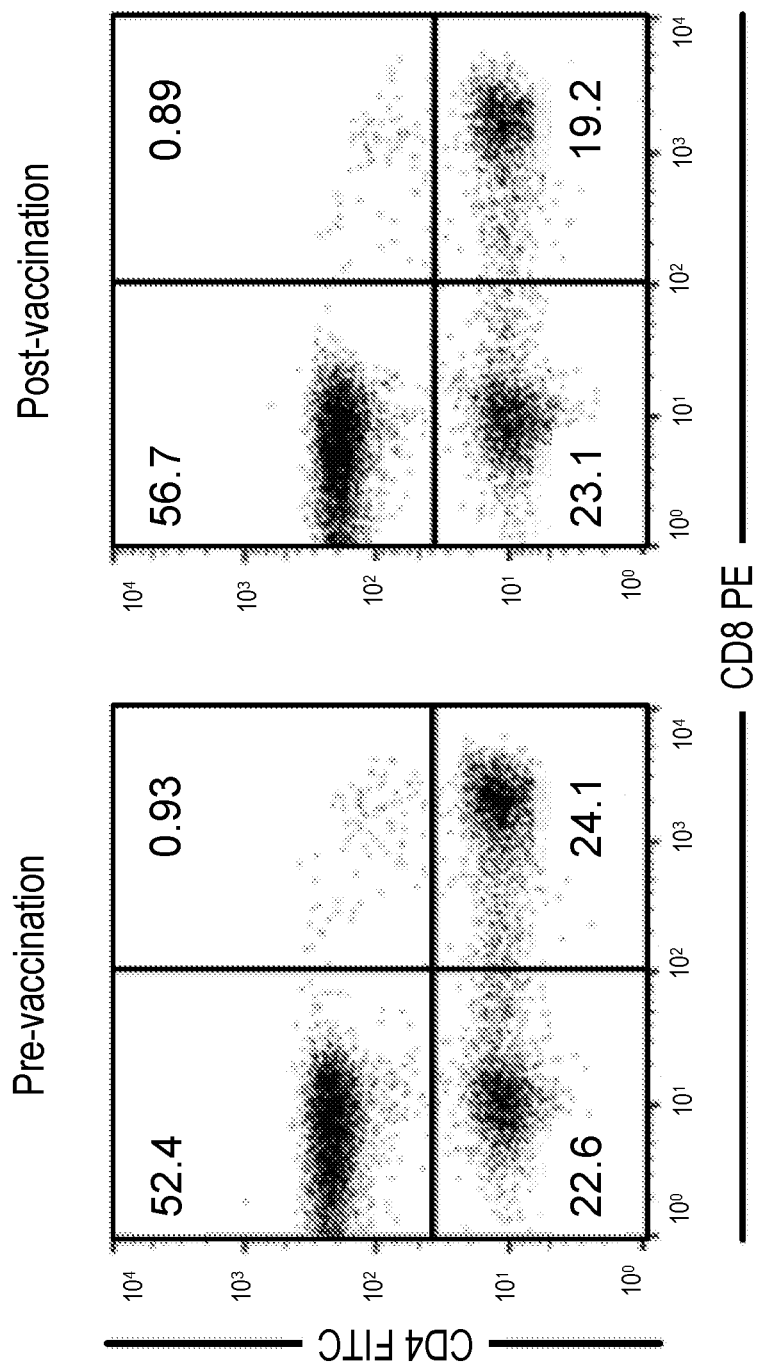
FIG. 24 depicts data demonstrating generation of a CD4+ T cell population that is highly enriched for HIV-specific, AGT103-transduced CD4 T cells. (A) shows CD4 and CD8 expression profiles for cell populations, as described herein. (B) shows CD4 and CD8 expression profiles for cell populations, as described herein. (C) shows IFN-gamma and CD4 expression profiles for cell populations, as described herein. (D) shows IFN-gamma and GFP expression profiles for cell populations, as described herein.

Example 19: Generating a Population of CD4+ T Cells Enriched for HIV-Specificity and Transduced with AGT103/CMV-GFP Therapeutic vaccination against HIV had minimal effect on the distribution of CD4+, CD8+ and CD4+/CD8+ T cells. As shown in FIG. 24A, the CD4 T cell population is shown in the upper left quadrant of the analytical flow cytometry dot plots, and changes from 52% to 57% of total T cells after the vaccination series. These are representative data.

Figure 24B:
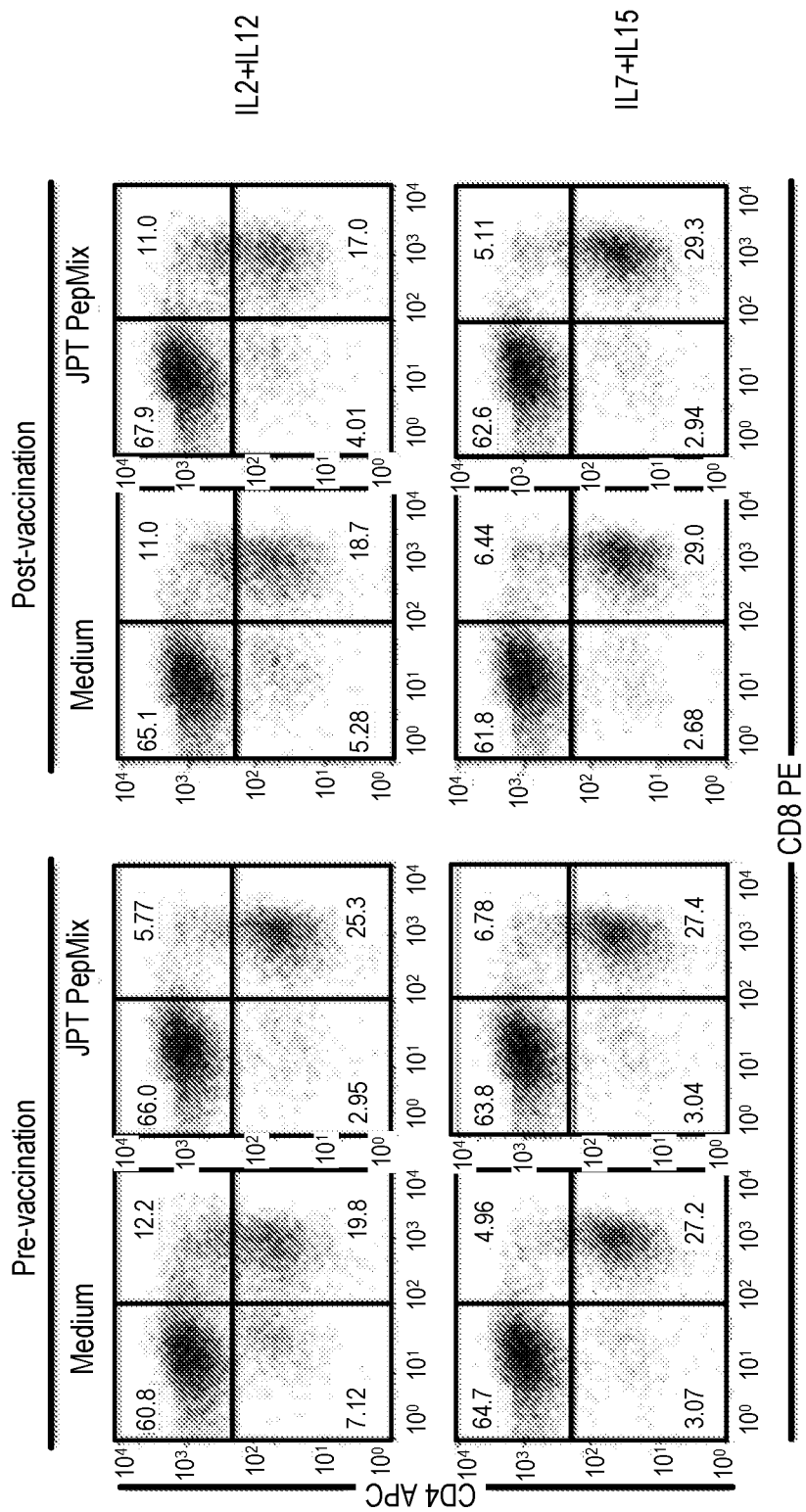

Peripheral blood mononuclear cells from a participant in an HIV therapeutic vaccine trial were cultured for 12 days in medium +/− interleukin-2/interleukin-12 or +/− interleukin-7/interleukin-15. Some cultures were stimulated with overlapping peptides representing the entire p55 Gag protein of HIV-1 (HIV (GAG) Ultra peptide mixture) as a source of epitope peptides for T cell stimulation. These peptides are 10-20 amino acids in length and overlap by 20-50% of their length to represent the entire Gag precursor protein (p55) from HIV-1 BaL strain. The composition and sequence of individual peptides can be adjusted to compensate for regional variations in the predominant circulating HIV sequences or when detailed sequence information is available for an individual patient receiving this therapy. At culture end, cells were recovered and stained with anti-CD4 or anti-CD8 monoclonal antibodies and the CD3+ population was gated and displayed here. The HIV (GAG) Ultra peptide mixture stimulation for either pre- or post-vaccination samples was similar to the medium control indicating that HIV (GAG) Ultra peptide mixture was not toxic to cells and was not acting as a polyclonal mitogen. The results of this analysis can be found in FIG. 24B.

Figure 24C:
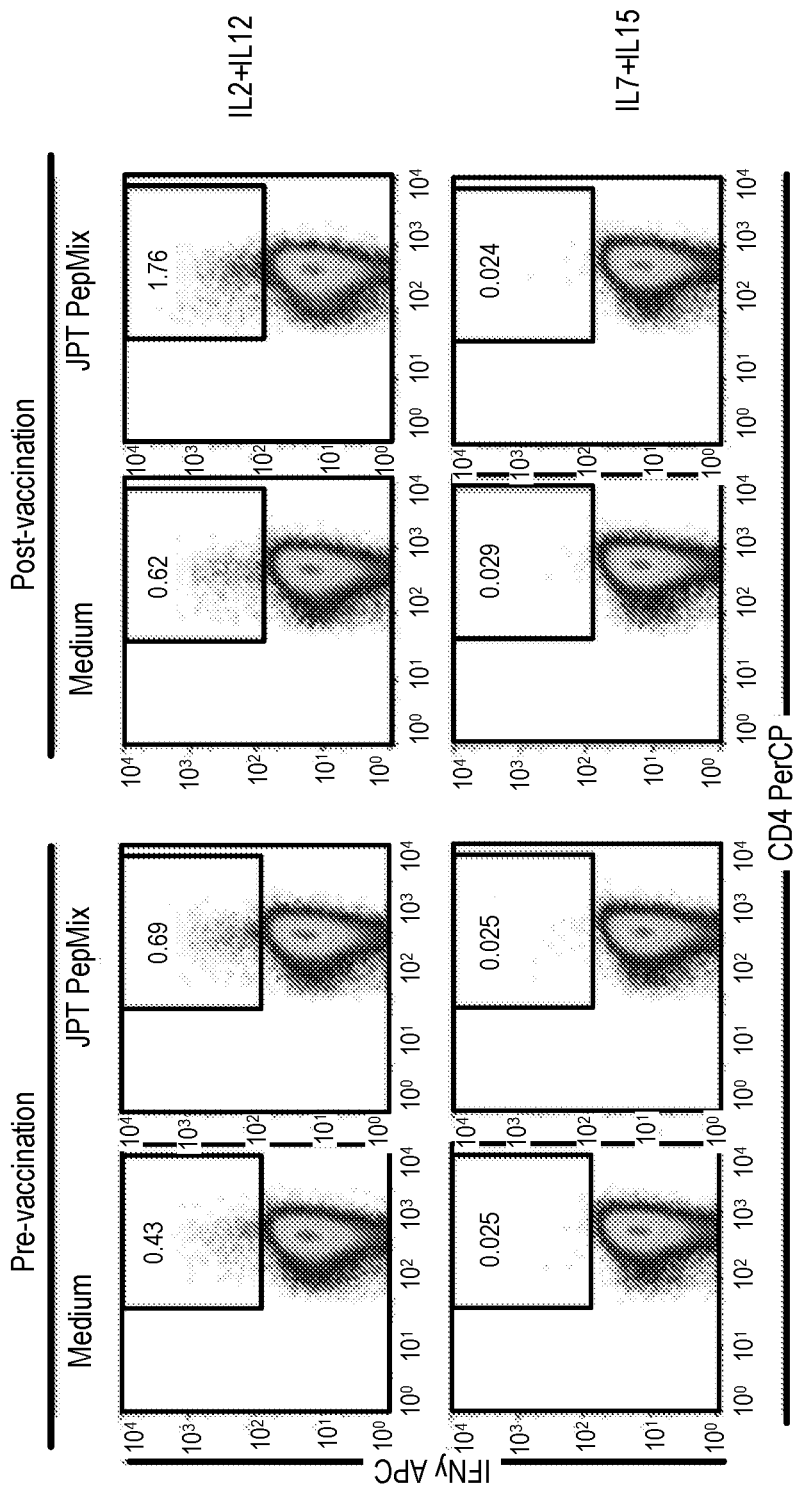

HIV (GAG) Ultra peptide mixture and interleukin-2/interleukin-12 provided for optimal expansion of antigen-specific CD4 T cells. As shown in the upper panels of FIG. 24C, there was an increase in cytokine (interferon-gamma) secreting cells in post-vaccination specimens exposed to HIV (GAG) Ultra peptide mixture. In the pre-vaccination sample, cytokine secreting cells increased from 0.43 to 0.69% as a result of exposure to antigenic peptides. In contrast, the post-vaccination samples showed an increase of cytokine secreting cells from 0.62 to 1.76% of total CD4 T cells as a result of peptide stimulation. These data demonstrate the strong impact of vaccination on the CD4 T cell responses to HIV antigen.

Figure 24D:
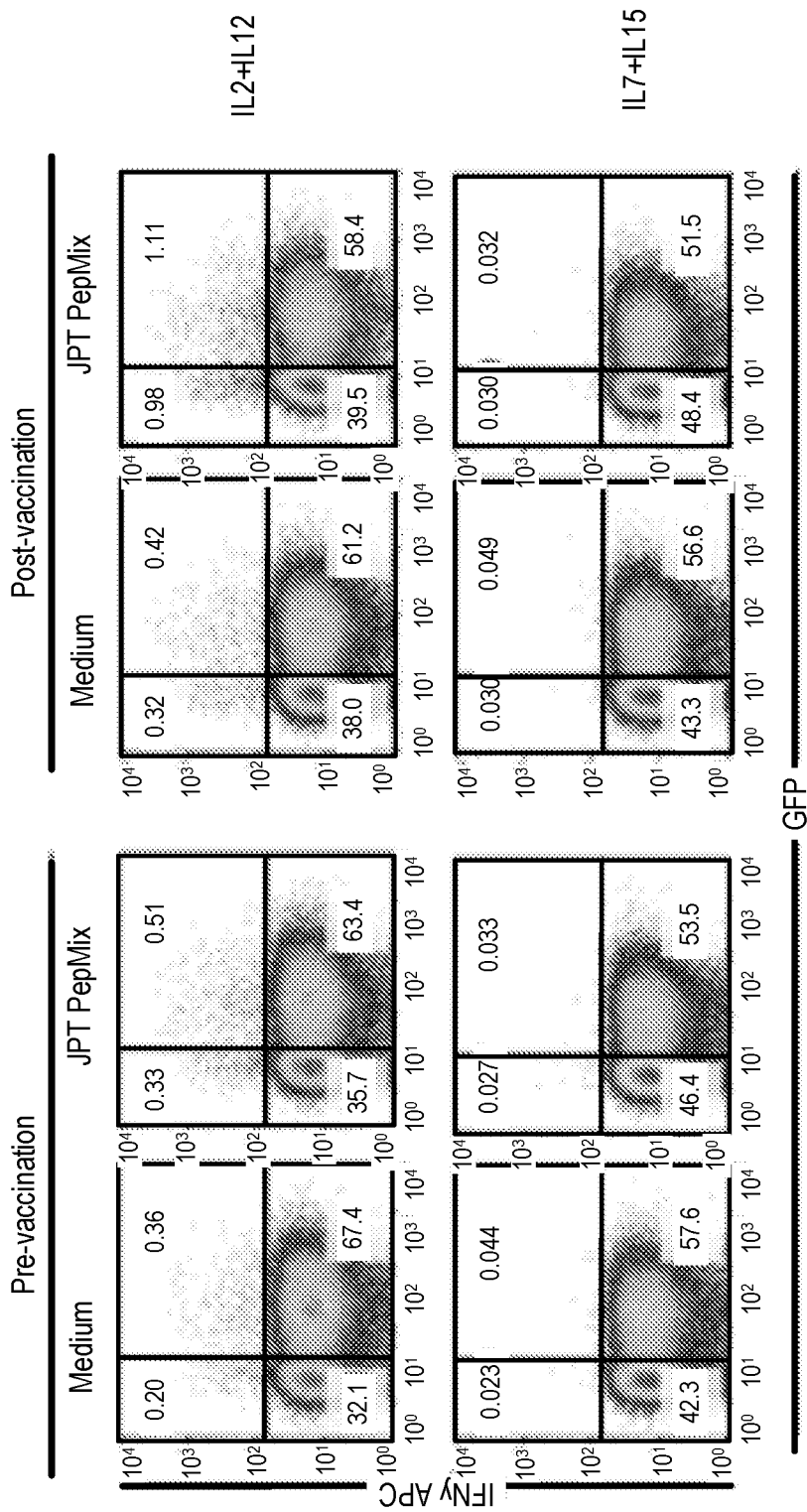

Finally, AGT103/CMV-GFP transduction of antigen-expanded CD4 T cells produced HIV-specific and HIV-resistant helper CD4 T cells that are needed for infusion into patients as part of a functional cure for HIV (in accordance with other various aspects and embodiments, AGT103 alone is used; for example, clinical embodiments may not include the CMV-GFP segment). The upper panels of FIG. 24D show the results of analyzing the CD4+ T cell population in culture. The x axis of FIG. 24D shows Green Fluorescent Protein (GFP) emission indicating that individual cells were transduced with the AGT103/CMV-GFP. As shown in FIG. 24D, in the post-vaccination samples 1.11% of total CD4 T cells that were both cytokine secreting was recovered, indicating that the cells are responding specifically to HIV antigen, and transduced with AGT103/CMV-GFP. This is the target cell population and the clinical product intended for infusion and functional cure of HIV. With the efficiency of cell expansion during the antigen stimulation and subsequent polyclonal expansion phases of ex vivo culture, $4\times10^8$ antigen-specific, lentivirus transduced CD4 T cells can be produced. This exceeds the target for cell production by 4-fold and will allow achievement of a count of antigen-specific and HIV-resistant CD4 T cells of approximately 40 cells/microliter of blood or around 5.7% of total circulating CD4 T cells.

Table 4 below shows the results of the ex vivo production of HIV-specific and HIV-resistant CD4 T cells using the disclosed vectors and methods.

TABLE 4

| Material/manipulation | Total CD4 T cells | Percentage HIV-specific | Percentage HIV-specific and HIV-resistant |
|---|---|---|---|
| Leukapheresis pack from HIV + patient | $\sim 7 \times 10^8$ | ~0.12 | N/A |
| Peptide expansion ex vivo | $\sim 8 \times 10^8$ | ~2.4 | N/A |
| Mitogen expansion | $\sim 1.5 \times 10^{10}$ | ~2.4 | N/A |
| Lentivirus transduction | $\sim 1.5 \times 10^{10}$ | ~2.4 | ~1.6 |

Example 20: Clinical Study for Treatment of HIV

AGT103T is a genetically modified autologous PBMC containing >$5\times10^7$ HIV-specific CD4 T cells that are also transduced with AGT103 lentivirus vector.

A Phase I clinical trial will test the safety and feasibility of infusing ex vivo modified autologous CD4 T cells (AGT103T) in adult research participants with confirmed HIV infection, CD4+ T-cell counts >600 cells per mm$^3$ of blood and stable virus suppression below 200 copies per ml of plasma while on cART. All study participants will continue receiving their standard antiretroviral medications through the Phase I clinical trial. Up to 40 study participants receive two doses by intramuscular injection 8 weeks apart, of recombinant modified vaccinia Ankara (rMVA) expressing HIV Gag, Pol and Env proteins. Seven to 10 days after the second immunization a blood sample is collected for in vitro testing to measure the frequency of CD4+ T-cells that respond to stimulation with a pool of overlapping, synthetic peptides representing the HIV-1 Gag polyprotein. Subjects in the upper half of vaccine responders, based on measuring the frequency of Gag-specific CD4 T cells are enrolled in the gene therapy arm and subjects in the lower half of responders do not continue in the study. We anticipate that the cut-off for higher responders is a HIV-specific CD4+ T cell frequency ≥0.065% of total CD4 T cells. Subjects enrolled into the gene therapy arm of our trial undergo leukapheresis followed by purification of PBMC (using Ficoll density gradient centrifugation or negative selection with antibodies) that are cultured ex vivo and stimulated with HIV Gag peptides plus interleukin-2 and interleukin-12 for 12 days, then stimulated again with beads decorated with CD3/CD28 bispecific antibody. The antiretroviral drug Saquinavir is included at 100 nM to prevent emergence of autologous HIV during ex vivo culture. One day after CD3/CD28 stimulation cells are transduced with AGT103 at multiplicity of infection between 1 and 10. The transduced cells are cultured for an additional 7-14 days during which time they expand by polyclonal proliferation. The culture period is ended by harvesting and washing cells, setting aside aliquots for potency and safety release assays, and resuspending the remaining cells in cryopreservation medium. A single dose is ≤$1\times10^{10}$ autologous PBMC. The potency assay measures the frequency of CD4 T cells that respond to peptide stimulation by expressing interferon-gamma. Other release criteria include the product must include ≥$0.5\times10^7$ HIV-specific CD4 T cells that are also transduced with AGT103. Another release criterion is that the number of AGT103 genome copies per cell must not exceed 3. Five days before infusion with AGT103T subjects receive one dose of busulfuram (or Cytoxan) conditioning regimen followed by infusion of ≤$1\times10^{10}$ PBMC containing genetically modified CD4 T cells.

A Phase II study will evaluate efficacy of AGT103T cell therapy. Phase II study participants include individuals enrolled previously in our Phase I study who were judged to have successful and stable engraftment of genetically modified, autologous, HIV-specific CD4 T cells and clinical responses defined as positive changes in parameters monitored as described in efficacy assessments (1.3.). Study participants will be asked to add Maraviroc to their existing regimen of antiretroviral medication. Maraviroc is a CCR5 antagonist that will enhance the effectiveness of genetic therapy directed at reducing CCR5 levels. Once the Maraviroc regimen is in place subjects will be asked to discontinue the previous antiretroviral drug regimen and only maintain Maraviroc monotherapy for 28 days or until plasma viral RNA levels exceed 10,000 per ml on 2 sequential weekly blood draws. Persistently high viremia requires participants to return to their original antiretroviral drug regimen with or without Maraviroc according to recommendations of their HIV care physician.

If participants remain HIV suppressed (below 2,000 vRNA copies per ml of plasma) for >28 days on Maraviroc monotherapy, they will be asked to gradually reduce Maraviroc dosing over a period of 4 weeks followed by intensive monitoring for an additional 28 days. Subjects who maintained HIV suppression with Maraviroc monotherapy are considered to have a functional cure. Subjects who maintain HIV suppression even after Maraviroc withdrawal also have a functional cure. Monthly monitoring for 6 months followed by less intensive monitoring will establish the durability of functional cure.

Patient Selection

Inclusion Criteria:

Aged between 18 and 60 years.

Documented HIV infection prior to study entry.

Must be willing to comply with study-mandated evaluations; including not changing their antiretroviral regimen (unless medically indicated) during the study period.

CD4+ T-cell count >500 cell per millimeter cubed (cells/mm3)

CD4+ T-cell nadir of >400 cells/mm3

HIV viral load <1,000 copies per milliliter (mL)

Exclusion Criteria:

Any viral hepatitis

Acute HIV infection

HIV viral load >1,000 copies/mL

Active or recent (prior 6 months) AIDS defining complication

Any change in HIV medications within 12 weeks of entering the study

Cancer or malignancy that has not been in remission for at least 5 years with the exception of successfully treated basal cell carcinoma of the skin Current diagnosis of NYHA grade 3 or 4 congestive heart failure or uncontrolled angina or arrhythmias History of bleeding problems Use of chronic steroids in past 30 days Pregnant or breast feeding
Active drug or alcohol abuse
Serious illness in past 30 days
Currently participating in another clinical trial or any prior gene therapy Safety Assessments
Acute infusion reaction
Post-infusion safety follow-up Efficacy Assessments—Phase I
Number and frequency of modified CD4 T cells.
Durability of modified CD4 T cells.
In vitro response to Gag peptide restimulation (ICS assay) as a measure of memory T cell function.
Polyfunctional anti-HIV CD8 T cell responses compare to pre- and post-vaccination time points.
Frequency of CD4 T cells making doubly spliced HIV mRNA after in vitro stimulation.

Efficacy Assessments—Phase II
Number and frequency of genetically modified CD4 T cells.
Maintenance of viral suppression (<2,000 vRNA copies per ml but 2 consecutive weekly draws not exceeding 5×10$^4$ vRNA copies per ml are permitted) with Maraviroc monotherapy.
Continued virus suppression during and after Maraviroc withdrawal.
Stable CD4 T cell count.

AGTI03T consists of up to $1\times10^{10}$ genetically modified, autologous CD4+ T cells containing $\geq 5\times10^7$ HIV-specific CD4 T cells that are also transduced with AGT103 lentivirus vector. A Phase I clinical trial will test the safety and feasibility of infusing ex vivo modified autologous CD4 T cells (AGT103T) in adult research participants with confirmed HIV infection, CD4+ T-cell counts >600 cells per mm$^3$ of blood and stable virus suppression below 200 copies per ml of plasma while on cART. Up to 40 study participants receive two doses by intramuscular injection 8 weeks apart, of recombinant modified vaccinia Ankara (rMVA) expressing HIV Gag, Pol and Env proteins. Seven to 10 days after the second immunization a blood sample is collected for in vitro testing to measure the frequency of CD4+ T-cells that respond to stimulation with a pool of overlapping, synthetic peptides representing the HIV-1 Gag polyprotein. Subjects in the upper half of vaccine responders, based on measuring the frequency of Gag-specific CD4 T cells are enrolled in the gene therapy arm and subjects in the lower half of responders do not continue in the study. We anticipate that the cut-off for higher responders is a HIV-specific CD4+ T cell frequency $\geq 0.065\%$ of total CD4 T cells. Subjects enrolled into the gene therapy arm of our trial undergo leukapheresis and the CD4+ T cells are enriched by negative selection. The enriched CD4 subset is admixed with 10% the number of cells from the CD4-negative subset to provide a source and antigen-presenting cells. The enriched CD4 T cells are stimulated with HIV Gag peptides plus interleukin-2 and interleukin-12 for 12 days, then stimulated again with beads decorated with CD3/CD28 bispecific antibody. The antiretroviral drug Saquinavir is included at 100 nM to prevent emergence of autologous HIV during ex vivo culture. One day after CD3/CD28 stimulation cells are transduced with AGT103 at multiplicity of infection between 1 and 10. The transduced cells are cultured for an additional 7-14 days during which time they expand by polyclonal proliferation. The culture period is ended by harvesting and washing cells, setting aside aliquots for potency and safety release assays, and resuspending the remaining cells in cryopreservation medium. A single dose is $\leq 1\times10^{10}$ autologous cells enriched for the CD4+ T cell subset. The potency assay measures the frequency of CD4 T cells that respond to peptide stimulation by expressing interferon-gamma. Other release criteria include that the product must include $\geq 0.5\times10^7$ HIV-specific CD4 T cells that are also transduced with AGT103. Another release criterion is that the number of AGT103 genome copies per cell must not exceed 3. Five days before infusion with AGT103T subjects receive one dose of busulfuram (or Cytoxan) conditioning regimen followed by infusion of $\leq 1\times10^{10}$ enriched and genetically modified CD4 T cell.

A Phase II study will evaluate efficacy of AGT103T cell therapy. Phase II study participants include individuals enrolled previously in our Phase I study who were judged to have successful and stable engraftment of genetically modified, autologous, HIV-specific CD4 T cells and clinical responses defined as positive changes in parameters monitored as described in efficacy assessments (1.3.). Study participants will be asked to add Maraviroc to their existing regimen of antiretroviral medication. Maraviroc is a CCR5 antagonist that will enhance the effectiveness of genetic therapy directed at reducing CCR5 levels. Once the Maraviroc regimen is in place subjects will be asked to discontinue the previous antiretroviral drug regimen and only maintain Maraviroc monotherapy for 28 days or until plasma viral RNA levels exceed 10,000 per ml on 2 sequential weekly blood draws. Persistently high viremia requires participants to return to their original antiretroviral drug regimen with or without Maraviroc according to recommendations of their HIV care physician.

If participants remain HIV suppressed (below 2,000 vRNA copies per ml of plasma) for >28 days on Maraviroc monotherapy, they will be asked to gradually reduce Maraviroc dosing over a period of 4 weeks followed by intensive monitoring for an additional 28 days. Subjects who maintained HIV suppression with Maraviroc monotherapy are considered to have a functional cure. Subjects who maintain HIV suppression even after Maraviroc withdrawal also have a functional cure. Monthly monitoring for 6 months followed by less intensive monitoring will establish the durability of functional cure.

Sequences

The following sequences are referred to herein:

| SEQ ID NO: | Description | Sequence |
|---|---|---|
| 1 | miR30 CCR5 | AGGTATATTGCTGTTGACAGTGAGCGACTGTAAACTGAGCT TGCTCTACTGTGAAGCCACAGATGGGTAGAGCAAGCACAG TTTACCGCTGCCTACTGCCTCGGACTTCAAGGGGCTT |
| 2 | miR21 Vif | CATCTCCATGGCTGTACCACCTTGTCGGGGATGTGTACTT CTGAACTTGTGTTGAATCTCATGGAGTTCAGAAGAACACAT CCGCACTGACATTTTGGTATCTTTCATCTGACCA |

-continued

| SEQ ID NO: | Description | Sequence |
|---|---|---|
| 3 | miR185 Tat | GGGCCTGGCTCGAGCAGGGGGCGAGGGATTCCGCTTCTTC CTGCCATAGCGTGG TCCCCTCCCCTATGGCAGGCAGAAGCGGCACCTTCCCTCCC AATGACCGCGTCTTCGTCG |
| 4 | Elongation Factor-1 alpha (EF1-alpha) promoter | CCGGTGCCTAGAGAAGGTGGCGCGGGGTAAACTGGGAAAG TGATGTCGTGTACTGGCTCCGCCTTTTTCCCGAGGGTGGGG GAGAACCGTATATAAGTGCAGTAGTCGCCGTGAACGTTCTT TTTCGCAACGGGTTTGCCGCCAGAACACAGGTAAGTGCCGT GTGTGGTTCCCGCGGGCCTGGCCTCTTTACGGGTTATGGCC CTTGCGTGCCTTGAATTACTTCCACGCCCCTGGCTGCAGTA CGTGATTCTTGATCCCGAGCTTCGGGTTGGAAGTGGGTGGG AGAGTTCGAGGCCTTGCGCTTAAGGAGCCCCTTCGCCTCGT GCTTGAGTTGAGGCCTGGCCTGGGCGCTGGGGCCGCCGCG TGCGAATCTGGTGGCACCTTCGCGCCTGTCTCGCTGCTTTC GATAAGTCTCTAGCCATTTAAAATTTTTGATGACCTGCTGC GACGCTTTTTTTCTGGCAAGATAGTCTTGTAAATGCGGGCC AAGATCTGCACACTGGTATTTCGGTTTTTGGGGCCGCGGGG GGCGACGGGCCCGTGCGTCCCAGCGCACATGTTCGGCGA GGCGGGGCCTGCGAGCGCGGCCACCGAGAATCGGACGGGG GTAGTCTCAAGCTGGCCGGCCTGCTCTGGTGCCTGGCCTCG CGCCGCCGTGTATCGCCCCGCCCTGGGCGGCAAGGCTGGC CCGGTCGGCACCAGTTGCGTGAGCGGAAAGATGGCCGCTT CCCGGCCCTGCTGCAGGGAGCTCAAAATGGAGGACGCGGC GCTCGGGAGAGCGGGCGGGTGAGTCACCCACACAAAGGAA AAGGGCCTTTCCGTCCTCAGCCGTCGCTTCATGTGACTCCA CGGAGTACCGGGCGCCGTCCAGGCACCTCGATTAGTTCTCG AGCTTTTGGAGTACGTCGTCTTTAGGTTGGGGGAGGGGTT TTATGCGATGGAGTTTCCCCACACTGAGTGGGTGGAGACTG AAGTTAGGCCAGCTTGGCACTTGATGTAATTCTCCTTGGAA TTTGCCCTTTTTGAGTTTGGATCTTGGTTCATTCTCAAGCCT CAGACAGTGGTTCAAAGTTTTTTTCTTCCATTTCAGGTGTCG TGA |
| 5 | CCR5 target sequence | GAGCAAGCTCAGTTTACA |
| 6 | Vif target sequence | GGGATGTGTACTTCTGAACTT |
| 7 | Tat target sequence | TCCGCTTCTTCCTGCCATAG |
| 8 | TAR decoy sequence | CTTGCAATGATGTCGTAATTTGCGTCTTACCTCGTTCTCGAC AGCGACCAGATCTGAGCCTGGGAGCTCTCTGGCTGTCAGTA AGCTGGTACAGAAGGTTGACGAAAATTCTTACTGAGCAAG AAA |
| 9 | Rev/Tat target sequence | GCGGAGACAGCGACGAAGAGC |
| 10 | Rev/Tat shRNA sequence | GCGGAGACAGCGACGAAGAGCTTCAAGAGAGCTCTTCGTC GCTGTCTCCGCTTTTT |
| 11 | Gag target sequence | GAAGAAATGATGACAGCAT |
| 12 | Gag shRNA sequence | GAAGAAATGATGACAGCATTTCAAGAGAATGCTGTCATCA TTTCTTCTTTTT |
| 13 | Pol target sequence | CAGGAGCAGATGATACAG |
| 14 | Pol shRNA sequence | CAGGAGATGATACAGTTCAAGAGACTGTATCATCTGCTCCT GTTTTT |
| 15 | CCR5 target sequence #1 | GTGTCAAGTCCAATCTATG |
| 16 | CCR5 shRNA sequence #1 | GTGTCAAGTCCAATCTATGTTCAAGAGACATAGATTGGACT TGACACTTTTT |
| 17 | CCR5 target sequence #2 | GAGCATGACTGACATCTAC |

| SEQ ID NO: | Description | Sequence |
|---|---|---|
| 18 | CCR5 shRNA sequence #2 | GAGCATGACTGACATCTACTTCAAGAGAGTAGATGTCAGT CATGCTCTTTTT |
| 19 | CCR5 target sequence #3 | GTAGCTCTAACAGGTTGGA |
| 20 | CCR5 shRNA sequence #3 | GTAGCTCTAACAGGTTGGATTCAAGAGATCCAACCTGTTAG AGCTACTTTTT |
| 21 | CCR5 target sequence #4 | GTTCAGAAACTACCTCTTA |
| 22 | CCR5 shRNA sequence #4 | GTTCAGAAACTACCTCTTATTCAAGAGATAAGAGGTAGTTT CTGAACTTTTT |
| 23 | CCR5 target sequence #5 | GAGCAAGCTCAGTTTACACC |
| 24 | CCR5 shRNA sequence #5 | GAGCAAGCTCAGTTTACACCTTCAAGAGAGGTGTAAACTG AGCTTGCTCTTTTT |
| 25 | *Homo sapiens* CCR5 gene, sequence 1 | ATGGATTATCAAGTGTCAAGTCCAATCTATGACATCAATTA TTATACATCGGAGCCCTGCCAAAAAATCAATGTGAAGCAA ATCGCAGCCCGCCTCCTGCCTCCGCTCTACTCACTGGTGTT CATCTTTGGTTTTGTGGGC |
| 26 | *Homo sapiens* CCR5 gene, sequence 2 | AACATGCTGGTCATCCTCATCCTGATAAACTGCAAAAGGCT GAAGAGCATGACTGACATCTACCTGCTCAACCTGGCCATCT CTGACCTGTTTTTCCTTCTTACTGTCCCCTTCTGGGCTCACT ATGCTGCCGCCCAGTGGGACTTTGGAAATACAATGTGTCAA CTCTTGACAGGGCTCTATTTTATAGGCTTCTTCTCTGGAATC TTCTTCATCATCCTCCTGACAATCGATAGGTACCTGGCTGT CGTCCATGCTGTGTTTGCTTTAAAAGCCAGGACGGTCACCT TTGGGGTGGTGACAAGTGTGATCACTTGGGTGGTGGCTGTG TTTGCGTCTCTCCCAGGAATCATCTTTACCAGATCTCAAAA AGAAGGTCTTCATTACACCTGCAGCTCTCATTTTCCATACA GTCAGTATCAATTCTGGAAGAATTTCCAGACATTAAAGATA GTCATCTTGGGGCTGGTCCTGCCGCTGCTTGTCATGGTCAT CTGCTACTCGGGAATCCTAAAAACTCTGCTTCGGTGTCGAA ATGAGAAGAAGAGGCACAGGGCTGTGAGGCTTATCTTCAC CATCATGATTGTTTATTTTCTCTTCTGGGCTCCCTACAACAT TGTCCTTCTCCTGAAC |
| 27 | *Homo sapiens* CCR5 gene, sequence 3 | ACCTTCCAGGAATTCTTTGGCCTGAATAATTGCAGTAGCTC TAACAGGTTGGACCAAGCTATGCAGGTGA |
| 28 | *Homo sapiens* CCR5 gene, sequence 4 | CAGAGACTCTTGGGATGACGCACTGCTGCATCAACCCCATC ATCTATGCCTTTGTCGGGGAGAAGTTCAGAAACTACCTCTT AGTCTTCTTCCAAAAGCACATTGCCAAACGCTTCTGCAAAT GCTGTTCTATTTTCCAG |
| 29 | *Homo sapiens* CCR5 gene, sequence 5 | CAAGAGGCTCCCGAGCGAGCAAGCTCAGTTTACACCCGAT CCACTGGGGAGCAGGAAATATCTGTGGGCTTGTGA |
| 30 | CD4 promoter sequence | TGTTGGGGTTCAAATTTGAGCCCCAGCTGTTAGCCCTCTGC AAAGAAAAAAAAAAAAAAAAAGAACAAAGGGCCTAGAT TTCCCTTCTGAGCCCCACCCTAAGATGAAGCCTCTTCTTTCA AGGGAGTGGGGTTGGGGTGGAGGCGGATCCTGTCAGCTTT GCTCTCTCTGTGGCTGGCAGTTTCTCCAAAGGGTAACAGGT GTCAGCTGGCTGAGCCTAGGCTGAACCCTGAGACATGCTA CCTCTGTCTTCTCATGGCTGGAGGCAGCCTTTGTAAGTCAC AGAAAGTAGCTGAGGGGCTCTGGAAAAAAGACAGCCAGG GTGGAGGTAGATTGGTCTTTGACTCCTGATTTAAGCCTGAT TCTGCTTAACTTTTTCCCTTGACTTTGGCATTTTCACTTTGA CATGTTCCCTGAGAGCCTGGGGGTGGGGAACCCAGCTCC AGCTGGTGACGTTTGGGGCCGGCCCAGGCCTAGGGTGTGG AGGAGCCTTGCCATCGGGCTTCCTGTCTCTCTTCATTTAAG CACGACTCTGCAGA |

| SEQ ID NO: | Description | Sequence |
|---|---|---|
| 31 | miR30-CCR5/miR21-Vif/miR185 Tat microRNA cluster sequence | AGGTATATTGCTGTTGACAGTGAGCGACTGTAAACTGAGCT TGCTCTACTGTGAAGCCACAGATGGGTAGAGCAAGCACAG TTTACCGCTGCCTACTGCCTCGGACTTCAAGGGGCTTCCCG GGCATCTCCATGGCTGTACCACCTTGTCGGGGGATGTGTAC TTCTGAACTTGTGTTGAATCTCATGGAGTTCAGAAGAACAC ATCCGCACTGACATTTTGGTATCTTTCATCTGACCAGCTAG CGGGGCCTGGCTCGAGCAGGGGGCGAGGGATTCCGCTTCTT CCTGCCATAGCGTGGTCCCCTCCCCTATGGCAGGCAGAAGC GGCACCTTCCCTCCCAATGACCGCGTCTTCGTC |
| 32 | Long WPRE sequence | AATCAACCTCTGATTACAAAATTTGTGAAAGATTGACTGGT ATTCTTAACTATGTTGCTCCTTTTACGCTATGTGGATACGCT GCTTTAATGCCTTTGTATCATGCTATTGCTTCCCGTATGGCT TTCATTTTCTCCTCCTTGTATAAATCCTGGTTGCTGTCTCTTT ATGAGGAGTTGTGGCCCGTTGTCAGGCAACGTGGCGTGGT GTGCACTGTGTTTGCTGACGCAACCCCCACTGGTTGGGGCA TTGCCACCACCTGTCAGCTCCTTTCCGGGACTTTCGCTTTCC CCCTCCCTATTGCCACGGCGGAACTCATCGCCGCCTGCCTT GCCCGCTGCTGGACAGGGGCTCGGCTGTTGGGCACTGACA ATTCCGTGGTGTTGTCGGGGAAATCATCGTCCTTTCCTTGG CTGCTCGCCTGTGTTGCCACCTGGATTCTGCGCGGGACGTC CTTCTGCTACGTCCCTTCGGCCCTCAATCCAGCGGACCTTC CTTCCCGCGGCCTGCTGCCGGCTCTGCGGCCTCTTCCGCGT CTTCGCCTTCGCCCTCAGACGAGTCGGATCTCCCTTTGGGC CGCCTCCCCGCCT |
| 33 | Elongation Factor-1 alpha (EF1-alpha) promoter; miR30CCR5; miR21Vif; miR185Tat | CCGGTGCCTAGAGAAGGTGGCGCGGGGTAAACTGGGAAAG TGATGTCGTGTACTGGCTCCGCCTTTTTCCCGAGGGTGGGG GAGAACCGTATATAAGTGCAGTAGTCGCCGTGAACGTTCTT TTTCGCAACGGGTTTGCCGCCAGAACACAGGTAAGTGCCGT GTGTGGTTCCCGCGGGCCTGGCCTCTTTACGGGTTATGGCC CTTGCGTGCCTTGAATTACTTCCACGCCCCTGGCTGCAGTA CGTGATTCTTGATCCCGAGCTTCGGGTTGGAAGTGGGTGGG AGAGTTCGAGGCCTTGCGCTTAAGGAGCCCCTTCGCCTCGT GCTTGAGTTGAGGCCTGGCCTGGGCGCTGGGGCCGCCGCG TGCGAATCTGGTGGCACCTTCGCGCCTGTCTCGCTGCTTTC GATAAGTCTCTAGCCATTTAAAATTTTTGATGACCTGCTGC GACGCTTTTTTTCTGGCAAGATAGTCTTGTAAATGCGGGCC AAGATCTGCACACTGGTATTTCGGTTTTTGGGGCCGCGGGC GGCGACGGGGCCCGTGCGTCCCAGCGCACATGTTCGGCGA GGCGGGGCCTGCGAGCGCGGCCACCGAGAATCGGACGGGG GTAGTCTCAAGCTGGCCGGCCTGCTCTGGTGCCTGGCCTCG CGCCGCCGTGTATCGCCCCGCCCTGGGCGGCAAGGCTGGC CCGGTCGGCACCAGTTGCGTGAGCGGAAAGATGGCCGCTT CCCGGCCCTGCTGCAGGGAGCTCAAAATGGAGGACGCGGC GCTCGGGAGAGCGGGCGGGTGAGTCACCCACACAAAGGAA AAGGGCCTTTCCGTCCTCAGCCGTCGCTTCATGTGACTCCA CGGAGTACCGGGCGCCGTCCAGGCACCTCGATTAGTTCTCG AGCTTTTGGAGTACGTCGTCTTTAGGTTGGGGGGAGGGGTT TTATGCGATGGAGTTTCCCCACACTGAGTGGGTGGAGACTG AAGTTAGGCCAGCTTGGCACTTGATGTAATTCTCCTTGGAA TTTGCCCTTTTTGAGTTTGGATCTTGGTTCATTCTCAAGCCT CAGACAGTGGTTCAAAGTTTTTTTCTTCCATTTCAGGTGTCG TGATGTACA<br>AGGTATATTGCTGTTGACAGTGAGCGACTGTAAACTGAGCT TGCTCTACTGTGAAGCCACAGATGGGTAGAGCAAGCACAG TTTACCGCTGCCTACTGCCTCGGACTTCAAGGGGCTTCCCG GGCATCTCCATGGCTGTACCACCTTGTCGGGGGATGTGTAC TTCTGAACTTGTGTTGAATCTCATGGAGTTCAGAAGAACAC ATCCGCACTGACATTTTGGTATCTTTCATCTGACCAGCTAG CGGGGCCTGGCTCGAGCAGGGGGCGAGGGATTCCGCTTCTT CCTGCCATAGCGTGGTCCCCTCCCCTATGGCAGGCAGAAGC GGCACCTTCCCTCCCAATGACCGCGTCTTCGTC |
| 34 | Rous Sarcoma virus (RSV) promoter | GTAGTCTTATGCAATACTCTTGTAGTCTTGCAACATGGTAA CGATGAGTTAGCAACATGCCTTACAAGGAGAGAAAAAGCA CCGTGCATGCCGATTGGTGGAAGTAAGGTGGTACGATCGT GCCTTATTAGGAAGGCAACAGACGGGTCTGACATGGATTG GACGAACCACTGAATTGCCGCATTGCAGAGATATTGTATTT AAGTGCCTAGCTCGATACAATAAACG |

| SEQ ID NO: | Description | Sequence |
|---|---|---|
| 35 | 5' Long terminal repeat (LTR) | GGTCTCTCTGGTTAGACCAGATCTGAGCCTGGGAGCTCTCT GGCTAACTAGGGAACCCACTGCTTAAGCCTCAATAAAGCTT GCCTTGAGTGCTTCAAGTAGTGTGTGCCCGTCTGTTGTGTG ACTCTGGTAACTAGAGATCCCTCAGACCCTTTTAGTCAGTG TGGAAAATCTCTAGCA |
| 36 | Psi Packaging signal | TACGCCAAAAATTTTGACTAGCGGAGGCTAGAAGGAGAGA G |
| 37 | Rev response element (RRE) | AGGAGCTTTGTTCCTTGGGTTCTTGGGAGCAGCAGGAAGCA CTATGGGCGCAGCCTCAATGACGCTGACGGTACAGGCCAG ACAATTATTGTCTGGTATAGTGCAGCAGCAGAACAATTTGC TGAGGGCTATTGAGGCGCAACAGCATCTGTTGCAACTCAC AGTCTGGGGCATCAAGCAGCTCCAGGCAAGAATCCTGGCT GTGGAAAGATACCTAAAGGATCAACAGCTCC |
| 38 | Central polypurine tract (cPPT) | TTTTAAAAGAAAAGGGGGGATTGGGGGGTACAGTGCAGGG GAAAGAATAGTAGACATAATAGCAACAGACATACAAACTA AAGAATTACAAAAACAAATTACAAAATTCAAAATTTTA |
| 39 | 3' delta LTR | TGGAAGGGCTAATTCACTCCCAACGAAGATAAGATCTGCTT TTTGCTTGTACTGGGTCTCTCTGGTTAGACCAGATCTGAGC CTGGGAGCTCTCTGGCTAACTAGGGAACCCACTGCTTAAGC CTCAATAAAGCTTGCCTTGAGTGCTTCAAGTAGTGTGTGCC CGTCTGTTGTGTGACTCTGGTAACTAGAGATCCCTCAGACC CTTTTAGTCAGTGTGGAAAATCTCTAGCAGTAGTAGTTCAT GTCA |
| 40 | Helper/Rev; CMV early (CAG) enhancer; Enhance Transcription | TAGTTATTAATAGTAATCAATTACGGGGTCATTAGTTCATA GCCCATATATGGAGTTCCGCGTTACATAACTTACGGTAAAT GGCCCGCCTGGCTGACCGCCCAACGACCCCCGCCCATTGAC GTCAATAATGACGTATGTTCCCATAGTAACGCCAATAGGG ACTTTCCATTGACGTCAATGGGTGGACTATTTACGGTAAAC TGCCCACTTGGCAGTACATCAAGTGTATCATATGCCAAGTA CGCCCCCTATTGACGTCAATGACGGTAAATGGCCCGCCTGG CATTATGCCCAGTACATGACCTTATGGGACTTTCCTACTTG GCAGTACATCTACGTATTAGTCATC |
| 41 | Helper/Rev; Chicken beta actin (CAG) promoter; Transcription | GCTATTACCATGGGTCGAGGTGAGCCCCACGTTCTGCTTCA CTCTCCCCATCTCCCCCCCCTCCCCACCCCCAATTTTGTATT TATTTATTTTTTAATTATTTTGTGCAGCGATGGGGGCGGGG GGGGGGGGGGGCGCGCGCCAGGCGGGGCGGGGCGGGGCGA GGGGCGGGGCGGGGCGAGGCGGAGAGGTGCGGCGGCAGC CAATCAGAGCGGCGCGCTCCGAAAGTTTCCTTTTATGGCGA GGCGGCGGCGGCGGCCCTATAAAAAGCGAAGCGCGCG GCGGGCG |
| 42 | Helper/Rev; Chicken beta actin intron; Enhance gene expression | GGAGTCGCTGCGTTGCCTTCGCCCCGTGCCCCGCTCCGCGC CGCCTCGCGCCGCCCGCCCCGGCTCTGACTGACCGCGTTAC TCCCACAGGTGAGCGGGCGGGACGGCCCTTCTCCTCCGGG CTGTAATTAGCGCTTGGTTTAATGACGGCTCGTTTCTTTTCT GTGGCTGCGTGAAAGCCTTAAAGGGCTCCGGGAGGGCCCT TTGTGCGGGGGGGAGCGGCTCGGGGGGTGCGTGCGTGTGT GTGTGCGTGGGGAGCGCCGCGTGCGGCCCGCGCTGCCCGG CGGCTGTGAGCGCTGCGGGCGCGGCGCGGGGCTTTGTGCG CTCCGCGTGTGCGCGAGGGGAGCGCGGCCGGGGGCGGTGC CCCGCGGTGCGGGGGGGCTGCGAGGGGAACAAAGGCTGCG TGCGGGGTGTGTGCGTGGGGGGGTGAGCAGGGGGTGTGGG CGCGGCGGTCGGGCTGTAACCCCCCCCTGCACCCCCCTCCC CGAGTTGCTGAGCACGGCCCGGCTTCGGGTGCGGGGCTCC GTGCGGGCGTGGCGCGGGGCTCGCCGTGCCGGGCGGGGG GTGGCGGCAGGTGGGGGTGCCGGGCGGGGCGGGGCCGCCT CGGGCCGGGGAGGGCTCGGGGGAGGGGCGCGGCGGCCCC GGAGCGCCGGCGGCTGTCGAGGCGCGGCGAGCCGCAGCCA TTGCCTTTTATGGTAATCGTGCGAGAGGGCGCAGGGACTTC CTTTGTCCCAAATCTGGCGGAGCCGAAATCTGGGAGGCGC CGCCGCACCCCCTCTAGCGGGCGCGGGCGAAGCGGTGCGG CGCCGGCAGGAAGGAAATGGGCGGGAGGGCCTTCGTGCG TCGCCGCGCCGCCGTCCCCTTCTCCATCTCCAGCCTCGGGG CTGCCGCAGGGGACGGCTGCCTTCGGGGGGACGGGGCA GGGCGGGGTTCGGCTTCTGGCGTGTGACCGGCGG |

| SEQ ID NO: | Description | Sequence |
|---|---|---|
| 43 | Helper/Rev; HIV Gag; Viral capsid | ATGGGTGCGAGAGCGTCAGTATTAAGCGGGGGAGAATTAG ATCGATGGGAAAAAATTCGGTTAAGGCCAGGGGGAAAGAA AAAATATAAATTAAAACATATAGTATGGGCAAGCAGGGAG CTAGAACGATTCGCAGTTAATCCTGGCCTGTTAGAAACATC AGAAGGCTGTAGACAAATACTGGGACAGCTACAACCATCC CTTCAGACAGGATCAGAAGAACTTAGATCATTATATAATAC AGTAGCAACCCTCTATTGTGTGCATCAAAGGATAGAGATA AAAGACACCAAGGAAGCTTTAGACAAGATAGAGGAAGAG CAAAACAAAAGTAAGAAAAAAGCACAGCAAGCAGCAGCT GACACAGGACACAGCAATCAGGTCAGCCAAAATTACCCTA TAGTGCAGAACATCCAGGGGCAAATGGTACATCAGGCCAT ATCACCTAGAACTTTAAATGCATGGGTAAAAGTAGTAGAA GAGAAGGCTTTCAGCCCAGAAGTGATACCCATGTTTTCAGC ATTATCAGAAGGAGCCACCCCACAAGATTTAAACACCATG CTAAACACAGTGGGGGGACATCAAGCAGCCATGCAAATGT TAAAAGAGACCATCAATGAGGAAGCTGCAGAATGGGATAG AGTGCATCCAGTGCATGCAGGGCCTATTGCACCAGGCCAG ATGAGAGAACCAAGGGGAAGTGACATAGCAGGAACTACTA GTACCCTTCAGGAACAAATAGGATGGATGACACATAATCC ACCTATCCCAGTAGGAGAAATCTATAAAAGATGGATAATC CTGGGATTAAATAAAATAGTAAGAATGTATAGCCCTACCA GCATTCTGGACATAAGACAAGGACCAAAGGAACCCTTTAG AGACTATGTAGACCGATTCTATAAAACTCTAAGAGCCGAG CAAGCTTCACAAGAGGTAAAAAATTGGATGACAGAAACCT TGTTGGTCCAAAATGCGAACCCAGATTGTAAGACTATTTTA AAAGCATTGGGACCAGGAGCGACACTAGAAGAAATGATGA CAGCATGTCAGGGAGTGGGGGGACCCGGCCATAAAGCAAG AGTTTTGGCTGAAGCAATGAGCCAAGTAACAAATCCAGCT ACCATAATGATACAGAAAGGCAATTTTAGGAACCAAAGAA AGACTGTTAAGTGTTTCAATTGTGGCAAAGAAGGGCACAT AGCCAAAAATTGCAGGGCCCCTAGGAAAAAGGGCTGTTGG AAATGTGGAAAGGAAGGACACCAAATGAAAGATTGTACTG AGAGACAGGCTAATTTTTTAGGGAAGATCTGGCCTTCCCAC AAGGGAAGGCCAGGGAATTTTCTTCAGAGCAGACCAGAGC CAACAGCCCCACCAGAAGAGAGCTTCAGGTTTGGGGAAGA GACAACAACTCCCTCTCAGAAGCAGGAGCCGATAGACAAG GAACTGTATCCTTTAGCTTCCCTCAGATCACTCTTTGGCAG CGACCCCTCGTCACAATAA |
| 44 | Helper/Rev; HIV Pol; Protease and reverse transcriptase | ATGAATTTGCCAGGAAGATGGAAACCAAAAATGATAGGGG GAATTGGAGGTTTTATCAAAGTAGGACAGTATGATCAGAT ACTCATAGAAATCTGCGGACATAAAGCTATAGGTACAGTA TTAGTAGGACCTACACCTGTCAACATAATTGGAAGAAATCT GTTGACTCAGATTGGCTGCACTTTAAATTTTCCCATTAGTCC TATTGAGACTGTACCAGTAAAATTAAAGCCAGGAATGGAT GGCCCAAAAGTTAAACAATGGCCATTGACAGAAGAAAAAA TAAAAGCATTAGTAGAAATTTGTACAGAAATGGAAAAGGA AGGAAAAATTTCAAAAATTGGGCCTGAAAATCCATACAAT ACTCCAGTATTTGCCATAAAGAAAAAAGACAGTACTAAAT GGAGAAAATTAGTAGATTTCAGAGAACTTAATAAGAGAAC TCAAGATTTCTGGGAAGTTCAATTAGGAATACCACATCCTG CAGGGTTAAAACAGAAAAAATCAGTAACAGTACTGGATGT GGGCGATGCATATTTTTCAGTTCCCTTAGATAAAGACTTCA GGAAGTATACTGCATTTACCATACCTAGTATAAACAATGAG ACACCAGGGATTAGATATCAGTACAATGTGCTTCCACAGG GATGGAAAGGATCACCAGCAATATTCCAGTGTAGCATGAC AAAAATCTTAGAGCCTTTTAGAAAACAAAATCCAGACATA GTCATCTATCAATACATGGATGATTTGTATGTAGGATCTGA CTTAGAAATAGGGCAGCATAGAACAAAAATAGAGGAACTG AGACAACATCTGTTGAGGTGGGGATTTACCACACCAGACA AAAAACATCAGAAAGAACCTCCATTCCTTTGGATGGGTTAT GAACTCCATCCTGATAAATGGACAGTACAGCCTATAGTGCT GCCAGAAAAGGACAGCTGGACTGTCAATGACATACAGAAA TTAGTGGGAAAATTGAATTGGGCAAGTCAGATTTATGCAG GGATTAAAGTAAGGCAATTATGTAAACTTCTTAGGGGAAC CAAAGCACTAACAGAAGTAGTACCACTAACAGAAGAAGCA GAGCTAGAACTGGCAGAAAACAGGGAGATTCTAAAAGAAC CGGTACATGGAGTGTATTATGACCCATCAAAAGACTTAATA GCAGAAATACAGAAGCAGGGGCAAGGCCAATGGACATATC AAATTTATCAAGAGCCATTTAAAAATCTGAAAACAGGAAA ATATGCAAGAATGAAGGGTGCCCACACTAATGATGTGAAA CAATTAACAGAGGCAGTACAAAAAATAGCCACAGAAAGCA TAGTAATATGGGGAAAGACTCCTAAATTTAAATTACCCATA CAAAAGGAAACATGGGAAGCATGGTGGACAGAGTATTGGC |

| SEQ ID NO: | Description | Sequence |
|---|---|---|
| | | AAGCCACCTGGATTCCTGAGTGGGAGTTTGTCAATACCCCT<br>CCCTTAGTGAAGTTATGGTACCAGTTAGAGAAAGAACCCA<br>TAATAGGAGCAGAAACTTTCTATGTAGATGGGGCAGCCAA<br>TAGGGAAACTAAATTAGGAAAAGCAGGATATGTAACTGAC<br>AGAGGAAGACAAAAGTTGTCCCCCTAACGGACACAACAA<br>ATCAGAAGACTGAGTTACAAGCAATTCATCTAGCTTTGCAG<br>GATTCGGGATTAGAAGTAAACATAGTGACAGACTCACAAT<br>ATGCATTGGGAATCATTCAAGCACAACCAGATAAGAGTGA<br>ATCAGAGTTAGTCAGTCAAATAATAGAGCAGTTAATAAAA<br>AAGGAAAAAGTCTACCTGGCATGGGTACCAGCACACAAAG<br>GAATTGGAGGAAATGAACAAGTAGATGGGTTGGTCAGTGC<br>TGGAATCAGGAAAGTACTA |
| 45 | Helper Rev; HIV Integrase; Integration of viral RNA | TTTTTAGATGGAATAGATAAGGCCCAAGAAGAACATGAGA<br>AATATCACAGTAATTGGAGAGCAATGGCTAGTGATTTTAAC<br>CTACCACCTGTAGTAGCAAAAGAAATAGTAGCCAGCTGTG<br>ATAAATGTCAGCTAAAAGGGGAAGCCATGCATGGACAAGT<br>AGACTGTAGCCCAGGAATATGGCAGCTAGATTGTACACAT<br>TTAGAAGGAAAAGTTATCTTGGTAGCAGTTCATGTAGCCAG<br>TGGATATATAGAAGCAGAAGTAATTCCAGCAGAGACAGGG<br>CAAGAAACAGCATACTTCCTCTTAAAATTAGCAGGAAGAT<br>GGCCAGTAAAAACAGTACATACAGACAATGGCAGCAATTT<br>CACCAGTACTACAGTTAAGGCCGCCTGTTGGTGGGCGGGG<br>ATCAAGCAGGAATTTGGCATTCCCTACAATCCCCAAAGTCA<br>AGGAGTAATAGAATCTATGAATAAAGAATTAAAGAAAATT<br>ATAGGACAGGTAAGAGATCAGGCTGAACATCTTAAGACAG<br>CAGTACAAATGGCAGTATTCATCCACAATTTTAAAAGAAA<br>AGGGGGGATTGGGGGGTACAGTGCAGGGGAAAGAATAGT<br>AGACATAATAGCAACAGACATACAAACTAAAGAATTACAA<br>AAACAAATTACAAAAATTCAAAATTTTCGGGTTTATTACAG<br>GGACAGCAGAGATCCAGTTTGGAAAGGACCAGCAAAGCTC<br>CTCTGGAAAGGTGAAGGGGCAGTAGTAATACAAGATAATA<br>GTGACATAAAAGTAGTGCCAAGAAGAAAAGCAAAGATCAT<br>CAGGGATTATGGAAAACAGATGGCAGGTGATGATTGTGTG<br>GCAAGTAGACAGGATGAGGATTAA |
| 46 | Helper/Rev; HIV RRE; Binds Rev element | AGGAGCTTTGTTCCTTGGGTTCTTGGGAGCAGCAGGAAGCA<br>CTATGGGCGCAGCGTCAATGACGCTGACGGTACAGGCCAG<br>ACAATTATTGTCTGGTATAGTGCAGCAGCAGAACAATTTGC<br>TGAGGGCTATTGAGGCGCAACAGCATCTGTTGCAACTCAC<br>AGTCTGGGGCATCAAGCAGCTCCAGGCAAGAATCCTGGCT<br>GTGGAAAGATACCTAAAGGATCAACAGCTCCT |
| 47 | Helper/Rev; HIV Rev; Nuclear export and stabilize viral mRNA | ATGGCAGGAAGAAGCGGAGACAGCGACGAAGAACTCCTC<br>AAGGCAGTCAGACTCATCAAGTTTCTCTATCAAAGCAACCC<br>ACCTCCCAATCCCGAGGGGACCCGACAGGCCCGAAGGAAT<br>AGAAGAAGAAGGTGGAGAGAGAGACAGAGACAGATCCAT<br>TCGATTAGTGAACGGATCCTTAGCACTTATCTGGGACGATC<br>TGCGGAGCCTGTGCCTCTTCAGCTACCACCGCTTGAGAGAC<br>TTACTCTTGATTGTAACGAGGATTGTGGAACTTCTGGGACG<br>CAGGGGGTGGGAAGCCCTCAAATATTGGTGGAATCTCCTA<br>CAATATTGGAGTCAGGAGCTAAAGAATAG |
| 48 | Helper/Rev; Rabbit beta globin poly A; RNA stability | AGATCTTTTTCCCTCTGCCAAAAATTATGGGGACATCATGA<br>AGCCCCTTGAGCATCTGACTTCTGGCTAATAAAGGAAATTT<br>ATTTTCATTGCAATAGTGTGTTGGAATTTTTTGTGTCTCTCA<br>CTCGGAAGGACATATGGGAGGGCAAATCATTTAAAACATC<br>AGAATGAGTATTTGGTTTAGAGTTTGGCAACATATGCCATA<br>TGCTGGCTGCCATGAACAAAGGTGGCTATAAAGAGGTCAT<br>CAGTATATGAAACAGCCCCCTGCTGTCCATTCCTTATTCCA<br>TAGAAAAGCCTTGACTTGAGGTTAGATTTTTTTATATTTTG<br>TTTTGTGTTATTTTTTCTTTAACATCCCTAAAATTTTCCTTA<br>CATGTTTTACTAGCCAGATTTTTCCTCCTCCTGACTACTC<br>CCAGTCATAGCTGTCCCTCTTCTCTTATGAAGATC |
| 49 | Helper; CMV early (CAG) enhancer; Enhance transcription | TAGTTATTAATAGTAATCAATTACGGGGTCATTAGTTCATA<br>GCCCATATATGGAGTTCCGCGTTACATAACTTACGGTAAAT<br>GGCCCGCCTGGCTGACCGCCCAACGACCCCCGCCCATTGAC<br>GTCAATAATGACGTATGTTCCCATAGTAACGCCAATAGGG<br>ACTTTCCATTGACGTCAATGGGTGGACTATTTACGGTAAAC<br>TGCCCACTTGGCAGTACATCAAGTGTATCATATGCCAAGTA<br>CGCCCCCTATTGACGTCAATGACGGTAAATGGCCCGCCTGG<br>CATTATGCCCAGTACATGACCTTATGGGACTTTCCTACTTG<br>GCAGTACATCTACGTATTAGTCATC |

| SEQ ID NO: | Description | Sequence |
|---|---|---|
| 50 | Helper; Chicken beta actin (CAG) promoter; Transcription | GCTATTACCATGGGTCGAGGTGAGCCCCACGTTCTGCTTCA CTCTCCCCATCTCCCCCCCCTCCCCACCCCCAATTTTGTATT TATTTATTTTTTAATTATTTTGTGCAGCGATGGGGGCGGGG GGGGGGGGGCGCGCGCCAGGCGGGGCGGGGCGGGGCGA GGGGCGGGGCGGGGCGAGGCGGAGAGGTGCGGCGGCAGC CAATCAGAGCGGCGCGCTCCGAAAGTTTCCTTTTATGGCGA GGCGGCGGCGGCGGCGGCCCTATAAAAAGCGAAGCGCGCG GCGGGCG |
| 51 | Helper; Chicken beta actin intron; Enhance gene expression | GGAGTCGCTGCGTTGCCTTCGCCCCGTGCCCCGCTCCGCGC CGCCTCGCGCCGCCCGCCCCGGCTCTGACTGACCGCGTTAC TCCCACAGGTGAGCGGGCGGGACGGCCCTTCTCCTCCGGG CTGTAATTAGCGCTTGGTTTAATGACGGCTCGTTTCTTTTCT GTGGCTGCGTGAAAGCCTTAAAGGGCTCCGGGAGGGCCCT TTGTGCGGGGGGGAGCGGCTCGGGGGGTGCGTGCGTGTGT GTGTGCGTGGGGAGCGCCGCGTGCGGCCCGCGCTGCCCGG CGGCTGTGAGCGCTGCGGGCGCGGCGCGGGGCTTTGTGCG CTCCGCGTGTGCGCGAGGGGAGCGCGGCCGGGGGCGGTGC CCCGCGGTGCGGGGGGGCTGCGAGGGGAACAAAGGCTGCG TGCGGGGTGTGTGCGTGGGGGGGTGAGCAGGGGGTGTGGG CGCGGCGGTCGGGCTGTAACCCCCCCCTGCACCCCCCTCCC CGAGTTGCTGAGCACGGCCCGGCTTCGGGTGCGGGGCTCC GTGCGGGGCGTGGCGCGGGGCTCGCCGTGCCGGGCGGGGG GTGGCGGCAGGTGGGGGTGCCGGGCGGGGCGGGGCCGCCT CGGGCCGGGGAGGGCTCGGGGGAGGGGCGCGGCGGCCCC GGAGCGCCGGCGGCTGTCGAGGCGCGGCGAGCCGCAGCCA TTGCCTTTTATGGTAATCGTGCGAGAGGGCGCAGGGACTTC CTTTGTCCCAAATCTGGCGGAGCCGAAATCTGGGAGGCGC CGCCGCACCCCCTCTAGCGGGCGCGGGCGAAGCGGTGCGG CGCCGGCAGGAAGGAAATGGGCGGGGAGGGCCTTCGTGCG TCGCCGCGCCGCCGTCCCCTTCTCCATCTCCAGCCTCGGGG CTGCCGCAGGGGACGGCTGCCTTCGGGGGGGACGGGGCA GGGCGGGGTTCGGCTTCTGGCGTGTGACCGGCGG |
| 52 | Helper; HIV Gag; Viral capsid | ATGGGTGCGAGAGCGTCAGTATTAAGCGGGGGAGAATTAG ATCGATGGGAAAAAATTCGGTTAAGGCCAGGGGGAAAGAA AAAATATAAATTAAAACATATAGTATGGGCAAGCAGGGAG CTAGAACGATTCGCAGTTAATCCTGGCCTGTTAGAAACATC AGAAGGCTGTAGACAAATACTGGGACAGCTACAACCATCC CTTCAGACAGGATCAGAAGAACTTAGATCATTATATAATAC AGTAGCAACCCTCTATTGTGTGCATCAAAGGATAGAGATA AAAGACACCAAGGAAGCTTTAGACAAGATAGAGGAAGAG CAAAACAAAAGTAAGAAAAAAGCACAGCAAGCAGCAGCT GACACAGGACACAGCAATCAGGTCAGCCAAAATTACCCTA TAGTGCAGAACATCCAGGGGCAAATGGTACATCAGGCCAT ATCACCTAGAACTTTAAATGCATGGGTAAAAGTAGTAGAA GAGAAGGCTTTCAGCCCAGAAGTGATACCCATGTTTTCAGC ATTATCAGAAGGAGCCACCCCACAAGATTTAAACACCATG CTAAACACAGTGGGGGGACATCAAGCAGCCATGCAAATGT TAAAAGAGACCATCAATGAGGAAGCTGCAGAATGGGATAG AGTGCATCCAGTGCATGCAGGGCCTATTGCACCAGGCCAG ATGAGAGAACCAAGGGGAAGTGACATAGCAGGAACTACTA GTACCCTTCAGGAACAAATAGGATGGATGACACATAATCC ACCTATCCCAGTAGGAGAAATCTATAAAAGATGGATAATC CTGGGATTAAATAAAATAGTAAGAATGTATAGCCCTACCA GCATTCTGGACATAAGACAAGGACCAAAGGAACCCTTTAG AGACTATGTAGACCGATTCTATAAAACTCTAAGAGCCGAG CAAGCTTCACAAGAGGTAAAAAATTGGATGACAGAAACCT TGTTGGTCCAAAATGCGAACCCAGATTGTAAGACTATTTTA AAAGCATTGGGACCAGGAGCGACACTAGAAGAAATGATGA CAGCATGTCAGGGAGTGGGGGGACCCGGCCATAAAGCAAG AGTTTTGGCTGAAGCAATGAGCCAAGTAACAAATCCAGCT ACCATAATGATACAGAAAGGCAATTTTAGGAACCAAAGAA AGACTGTTAAGTGTTTCAATTGTGGCAAAGAAGGGCACAT AGCCAAAAATTGCAGGGCCCCTAGGAAAAAGGGCTGTTGG AAATGTGGAAAGGAAGGACACCAAATGAAAGATTGTACTG AGAGACAGGCTAATTTTTTAGGGAAGATCTGGCCTTCCCAC AAGGGAAGGCCAGGGAATTTTCTTCAGAGCAGACCAGAGC CAACAGCCCCACCAGAAGAGAGCTTCAGGTTTGGGGAAGA GACAACAACTCCCTCTCAGAAGCAGGAGCCGATAGACAAG GAACTGTATCCTTTAGCTTCCCTCAGATCACTCTTTGGCAG CGACCCCTCGTCACAATAA |

| SEQ ID NO: | Description | Sequence |
|---|---|---|
| 53 | Helper; HIV Pol; Protease and reverse transcriptase | ATGAATTTGCCAGGAAGATGGAAACCAAAAATGATAGGGG GAATTGGAGGTTTTATCAAAGTAGGACAGTATGATCAGAT ACTCATAGAAATCTGCGGACATAAAGCTATAGGTACAGTA TTAGTAGGACCTACACCTGTCAACATAATTGGAAGAAATCT GTTGACTCAGATTGGCTGCACTTTAAATTTTCCCATTAGTCC TATTGAGACTGTACCAGTAAAATTAAAGCCAGGAATGGAT GGCCCAAAAGTTAAACAATGGCCATTGACAGAAGAAAAA TAAAAGCATTAGTAGAAATTTGTACAGAAATGGAAAAGGA AGGAAAAATTTCAAAAATTGGGCCTGAAAATCCATACAAT ACTCCAGTATTTGCCATAAAGAAAAAAGACAGTACTAAAT GGAGAAAATTAGTAGATTTCAGAGAACTTAATAAGAGAAC TCAAGATTTCTGGGAAGTTCAATTAGGAATACCACATCCTG CAGGGTTAAAACAGAAAAAATCAGTAACAGTACTGGATGT GGGGCGATGCATATTTTTCAGTTCCCTTAGATAAAGACTTCA GGAAGTATACTGCATTTACCATACCTAGTATAAACAATGAG ACACCAGGGATTAGATATCAGTACAATGTGCTTCCACAGG GATGGAAAGGATCACCAGCAATATTCCAGTGTAGCATGAC AAAAATCTTAGAGCCTTTTAGAAAACAAAATCCAGACATA GTCATCTATCAATACATGGATGATTTGTATGTAGGATCTGA CTTAGAAATAGGGCAGCATAGAACAAAAATAGAGGAACTG AGACAACATCTGTTGAGGTGGGGATTTACCACACCAGACA AAAAACATCAGAAAGAACCTCCATTCCTTTGGATGGGTTAT GAACTCCATCCTGATAAATGGACAGTACAGCCTATAGTGCT GCCAGAAAAGGACAGCTGGACTGTCAATGACATACAGAAA TTAGTGGGAAAATTGAATTGGGCAAGTCAGATTTATGCAG GGATTAAAGTAAGGCAATTATGTAAACTTCTTAGGGGAAC CAAAGCACTAACAGAAGTAGTACCACTAACAGAAGAAGCA GAGCTAGAACTGGCAGAAAACAGGGAGATTCTAAAAGAAC CGGTACATGGAGTGTATTATGACCCATCAAAAGACTTAATA GCAGAAATACAGAAGCAGGGGCAAGGCCAATGGACATATC AAATTTATCAAGAGCCATTTAAAAATCTGAAAACAGGAAA ATATGCAAGAATGAAGGGTGCCCACACTAATGATGTGAAA CAATTAACAGAGGCAGTACAAAAAATAGCCACAGAAAGCA TAGTAATATGGGGAAAGACTCCTAAATTTAAATTACCCATA CAAAAGGAAACATGGGAAGCATGGTGGACAGAGTATTGGC AAGCCACCTGGATTCCTGAGTGGGAGTTTGTCAATACCCCT CCCTTAGTGAAGTTATGGTACCAGTTAGAGAAAGAACCCA TAATAGGAGCAGAAACTTTCTATGTAGATGGGGCAGCCAA TAGGGAAACTAAATTAGGAAAAGCAGGATATGTAACTGAC AGAGGAAGACAAAAAGTTGTCCCCCTAACGGACACAACAA ATCAGAAGACTGAGTTACAAGCAATTCATCTAGCTTTGCAG GATTCGGGATTAGAAGTAAACATAGTGACAGACTCACAAT ATGCATTGGGAATCATTCAAGCACAACCAGATAAGAGTGA ATCAGAGTTAGTCAGTCAAATAATAGAGCAGTTAATAAAA AAGGAAAAGTCTACCTGGCATGGGTACCAGCACACAAAG GAATTGGAGGAAATGAACAAGTAGATGGGTTGGTCAGTGC TGGAATCAGGAAAGTACTA |
| 54 | Helper; HIV Integrase; Integration of viral RNA | TTTTTAGATGGAATAGATAAGGCCCAAGAAGAACATGAGA AATATCACAGTAATTGGAGAGCAATGGCTAGTGATTTTAAC CTACCACCTGTAGTAGCAAAAGAAATAGTAGCCAGCTGTG ATAAATGTCAGCTAAAAGGGGAAGCCATGCATGGACAAGT AGACTGTAGCCCAGGAATATGGCAGCTAGATTGTACACAT TTAGAAGGAAAAGTTATCTTGGTAGCAGTTCATGTAGCCAG TGGATATATAGAAGCAGAAGTAATTCCAGCAGAGACAGGG CAAGAAACAGCATACTTCCTCTTAAAATTAGCAGGAAGAT GGCCAGTAAAAACAGTACATACAGACAATGGCAGCAATTT CACCAGTACTACAGTTAAGGCCGCCTGTTGGTGGGCGGGG ATCAAGCAGGAATTTGGCATTCCCTACAATCCCCAAAGTCA AGGAGTAATAGAATCTATGAATAAAGAATTAAAGAAAATT ATAGGACAGGTAAGAGATCAGGCTGAACATCTTAAGACAG CAGTACAAATGGCAGTATTCATCCACAATTTTAAAAGAAA AGGGGGGATTGGGGGGTACAGTGCAGGGGAAAGAATAGT AGACATAATAGCAACAGACATACAAACTAAAGAATTACAA AAACAAATTACAAAAATTCAAAATTTTCGGGTTTATTACAG GGACAGCAGAGATCCAGTTTGGAAAGGACCAGCAAAGCTC CTCTGGAAAGGTGAAGGGGCAGTAGTAATACAAGATAATA GTGACATAAAAGTAGTGCCAAGAAGAAAAGCAAAGATCAT CAGGGATTATGGAAAACAGATGGCAGGTGATGATTGTGTG GCAAGTAGACAGGATGAGGATTAA |

| SEQ ID NO: | Description | Sequence |
|---|---|---|
| 55 | Helper; HIV RRE; Binds Rev element | AGGAGCTTTGTTCCTTGGGTTCTTGGGAGCAGCAGGAAGCA CTATGGGCGCAGCGTCAATGACGCTGACGGTACAGGCCAG ACAATTATTGTCTGGTATAGTGCAGCAGCAGAACAATTTGC TGAGGGCTATTGAGGCGCAACAGCATCTGTTGCAACTCAC AGTCTGGGGCATCAAGCAGCTCCAGGCAAGAATCCTGGCT GTGGAAAGATACCTAAAGGATCAACAGCTCCT |
| 56 | Helper; Rabbit beta globin poly A; RNA stability | AGATCTTTTTCCCTCTGCCAAAAATTATGGGGACATCATGA AGCCCCTTGAGCATCTGACTTCTGGCTAATAAAGGAAATTT ATTTTCATTGCAATAGTGTGTTGGAATTTTTTGTGTCTCTCA CTCGGAAGGACATATGGGAGGGCAAATCATTTAAAACATC AGAATGAGTATTTGGTTTAGAGTTTGGCAACATATGCCATA TGCTGGCTGCCATGAACAAAGGTGGCTATAAAGAGGTCAT CAGTATATGAAACAGCCCCCTGCTGTCCATTCCTTATTCCA TAGAAAAGCCTTGACTTGAGGTTAGATTTTTTTTATATTTTG TTTTGTGTTATTTTTTCTTTAACATCCCTAAAATTTTCCTTA CATGTTTTACTAGCCAGATTTTTCCTCCTCTCCTGACTACTC CCAGTCATAGCTGTCCCTCTTCTCTTATGAAGATC |
| 57 | Rev; RSV promoter; Transcription | ATGGCAGGAAGAAGCGGAGACAGCGACGAAGAACTCCTC AAGGCAGTCAGACTCATCAAGTTTCTCTATCAAAGCAACCC ACCTCCCAATCCCGAGGGGACCCGACAGGCCCGAAGGAAT AGAAGAAGAAGGTGGAGAGAGAGACAGAGACAGATCCAT TCGATTAGTGAACGGATCCTTAGCACTTATCTGGGACGATC TGCGGAGCCTGTGCCTCTTCAGCTACCACCGCTTGAGAGAC TTACTCTTGATTGTAACGAGGATTGTGGAACTTCTGGGACG CAGGGGGTGGAAGCCCTCAAATATTGGTGGAATCTCCTA CAATATTGGAGTCAGGAGCTAAAGAATAG |
| 58 | Rev; HIV Rev; Nuclear export and stabilize viral mRNA | ATGGCAGGAAGAAGCGGAGACAGCGACGAAGAACTCCTC AAGGCAGTCAGACTCATCAAGTTTCTCTATCAAAGCAACCC ACCTCCCAATCCCGAGGGGACCCGACAGGCCCGAAGGAAT AGAAGAAGAAGGTGGAGAGAGAGACAGAGACAGATCCAT TCGATTAGTGAACGGATCCTTAGCACTTATCTGGGACGATC TGCGGAGCCTGTGCCTCTTCAGCTACCACCGCTTGAGAGAC TTACTCTTGATTGTAACGAGGATTGTGGAACTTCTGGGACG CAGGGGGTGGAAGCCCTCAAATATTGGTGGAATCTCCTA CAATATTGGAGTCAGGAGCTAAAGAATAG |
| 59 | Rev; Rabbit beta globin poly A; RNA stability | AGATCTTTTTCCCTCTGCCAAAAATTATGGGGACATCATGA AGCCCCTTGAGCATCTGACTTCTGGCTAATAAAGGAAATTT ATTTTCATTGCAATAGTGTGTTGGAATTTTTTGTGTCTCTCA CTCGGAAGGACATATGGGAGGGCAAATCATTTAAAACATC AGAATGAGTATTTGGTTTAGAGTTTGGCAACATATGCCCAT ATGCTGGCTGCCATGAACAAAGGTTGGCTATAAAGAGGTC ATCAGTATATGAAACAGCCCCCTGCTGTCCATTCCTTATTC CATAGAAAAGCCTTGACTTGAGGTTAGATTTTTTTTATATTT TGTTTTGTGTTATTTTTTCTTTAACATCCCTAAAATTTTCCT TACATGTTTTACTAGCCAGATTTTTCCTCCTCTCCTGACTAC TCCCAGTCATAGCTGTCCCTCTTCTCTTATGGAGATC |
| 60 | Envelope; CMV promoter; Transcription | ACATTGATTATTGACTAGTTATTAATAGTAATCAATTACGG GGTCATTAGTTCATAGCCCATATATGGAGTTCCGCGTTACA TAACTTACGGTAAATGGCCCGCCTGGCTGACCGCCCAACG ACCCCCGCCCATTGACGTCAATAATGACGTATGTTCCCATA GTAACGCCAATAGGGACTTTCCATTGACGTCAATGGGTGG AGTATTTACGGTAAACTGCCCACTTGGCAGTACATCAAGTG TATCATATGCCAAGTACGCCCCCTATTGACGTCAATGACGG TAAATGGCCCGCCTGGCATTATGCCCAGTACATGACCTTAT GGGACTTTCCTACTTGGCAGTACATCTACGTATTAGTCATC GCTATTACCATGGTGATGCGGTTTTGGCAGTACATCAATGG GCGTGGATAGCGGTTTGACTCACGGGGATTTCCAAGTCTCC ACCCCATTGACGTCAATGGGAGTTTGTTTTGGCACCAAAAT CAACGGGACTTTCCAAAATGTCGTAACAACTCCGCCCCATT GACGCAAATGGGCGGTAGGCGTGTACGGTGGGAGGTCTAT ATAAGC |
| 61 | Envelope; Beta globin intron; Enhance gene expression | GTGAGTTTGGGGACCCTTGATTGTTCTTTCTTTTTCGCTATT GTAAAATTCATGTTATATGGAGGGGGCAAAGTTTTCAGGGT GTTGTTTAGAATGGGAAGATGTCCCTTGTATCACCATGGAC CCTCATGATAATTTTGTTCTTTCACTTTCTACTCTGTTGAC AACCATTGTCTCCTCTTATTTTCTTTTCATTTTCTGTAACTTT TTCGTTAAACTTTAGCTTGCATTTGTAACGAATTTTTAAATT CACTTTTGTTTATTTGTCAGATTGTAAGTACTTTCTCTAATC |

-continued

| SEQ ID NO: | Description | Sequence |
|---|---|---|
| | | ACTTTTTTTTCAAGGCAATCAGGGTATATTATATTGTACTTC AGCACAGTTTTAGAGAACAATTGTTATAATTAAATGATAAG GTAGAATATTTCTGCATATAAATTCTGGCTGGCGTGGAAAT ATTCTTATTGGTAGAAACAACTACACCCTGGTCATCATCCT GCCTTTCTCTTTATGGTTACAATGATATACACTGTTTGAGAT GAGGATAAAATACTCTGAGTCCAAACCGGGCCCCTCTGCT AACCATGTTCATGCCTTCTTCTCTTTCCTACAG |
| 62 | Envelope; VSV-G; Glycoprotein envelope-cell entry | ATGAAGTGCCTTTTGTACTTAGCCTTTTTATTCATTGGGGTG AATTGCAAGTTCACCATAGTTTTTCCACACAACCAAAAAGG AAACTGGAAAAATGTTCCTTCTAATTACCATTATTGCCCGT CAAGCTCAGATTTAAATTGGCATAATGACTTAATAGGCACA GCCTTACAAGTCAAAATGCCCAAGAGTCACAAGGCTATTC AAGCAGACGGTTGGATGTGTCATGCTTCCAAATGGGTCACT ACTTGTGATTTCCGCTGGTATGGACCGAAGTATATAACACA TTCCATCCGATCCTTCACTCCATCTGTAGAACAATGCAAGG AAAGCATTGAACAAACGAAACAAGGAACTTGGCTGAATCC AGGCTTCCCTCCTCAAAGTTGTGGATATGCAACTGTGACGG ATGCCGAAGCAGTGATTGTCCAGGTGACTCCTCACCATGTG CTGGTTGATGAATACACAGGAGAATGGGTTGATTCACAGTT CATCAACGGAAAATGCAGCAATTACATATGCCCCACTGTCC ATAACTCTACAACCTGGCATTCTGACTATAAGGTCAAAGGG CTATGTGATTCTAACCTCATTTCCATGGACATCACCTTCTTC TCAGAGGACGGAGAGCTATCATCCCTGGGAAAGGAGGGCA CAGGGTTCAGAAGTAACTACTTTGCTTATGAAACTGGAGGC AAGGCCTGCAAAATGCAATACTGCAAGCATTGGGGAGTCA GACTCCCATCAGGTGTCTGGTTCGAGATGGCTGATAAGGAT CTCTTTGCTGCAGCCAGATTCCCTGAATGCCCAGAAGGGTC AAGTATCTCTGCTCCATCTCAGACCTCAGTGGATGTAAGTC TAATTCAGGACGTTGAGAGGATCTTGGATTATTCCCTCTGC CAAGAAACCTGGAGCAAAATCAGAGCGGGTCTTCCAATCT CTCCAGTGGATCTCAGCTATCTTGCTCCTAAAAACCCAGGA ACCGGTCCTGCTTTCACCATAATCAATGGTACCCTAAAATA CTTTGAGACCAGATACATCAGAGTCGATATTGCTGCTCCAA TCCTCTCAAGAATGGTCGGAATGATCAGTGGAACTACCAC AGAAAGGGAACTGTGGGATGACTGGGCACCATATGAAGAC GTGGAAATTGGACCCAATGGAGTTCTGAGGACCAGTTCAG GATATAAGTTTCCTTTATACATGATTGGACATGGTATGTTG GACTCCGATCTTCATCTTAGCTCAAAGGCTCAGGTGTTCGA ACATCCTCACATTCAAGACGCTGCTTCGCAACTTCCTGATG ATGAGAGTTTATTTTTTGGTGATACTGGGCTATCCAAAAAT CCAATCGAGCTTGTAGAAGGTTGGTTCAGTAGTTGGAAAA GCTCTATTGCCTCTTTTTTCTTTATCATAGGGTTAATCATTG GACTATTCTTGGTTCTCCGAGTTGGTATCCATCTTTGCATTA AATTAAAGCACACCAAGAAAAGACAGATTTATACAGACAT AGAGATGA |
| 63 | Envelope; Rabbit beta globin poly A; RNA stability | AGATCTTTTTCCCTCTGCCAAAAATTATGGGGACATCATGA AGCCCCTTGAGCATCTGACTTCTGGCTAATAAAGGAAATTT ATTTTCATTGCAATAGTGTGTTGGAATTTTTTGTGTCTCTCA CTCGGAAGGACATATGGAGGGCAAATCATTTAAAACATC AGAATGAGTATTTGGTTTAGAGTTTGGCAACATATGCCCAT ATGCTGGCTGCCATGAACAAAGGTTGGCTATAAAGAGGTC ATCAGTATATGAAACAGCCCCCTGCTGTCCATTCCTTATTC CATAGAAAAGCCTTGACTTGAGGTTAGATTTTTTTTATATTT TGTTTTGTGTTATTTTTTCTTTAACATCCCTAAAATTTTCCT TACATGTTTTACTAGCCAGATTTTTCCTCCTCTCCTGACTAC TCCCAGTCATAGCTGTCCCTCTTCTCTTATGGAGATC |
| 64 | Promoter; EF-1 | CCGGTGCCTAGAGAAGGTGGCGCGGGGTAAACTGGGAAAG TGATGTCGTGTACTGGCTCCGCCTTTTTCCCGAGGGTGGGG GAGAACCGTATATAAGTGCAGTAGTCGCCGTGAACGTTCTT TTTCGCAACGGGTTTGCCGCCAGAACACAGGTAAGTGCCGT GTGTGGTTCCCGCGGGCCTGGCCTCTTTACGGGTTATGGCC CTTGCGTGCCTTGAATTACTTCCACGCCCCTGGCTGCAGTA CGTGATTCTTGATCCCGAGCTTCGGGTTGGAAGTGGGTGGG AGAGTTCGAGGCCTTGCGCTTAAGGAGCCCCTTCGCCTCGT GCTTGAGTTGAGGCCTGGCCTGGGCGCTGGGGCCGCCGCG TGCGAATCTGGTGGCACCTTCGCGCCTGTCTCGCTGCTTTC GATAAGTCTCTAGCCATTTAAAATTTTTGATGACCTGCTGC GACGCTTTTTTTCTGGCAAGATAGTCTTGTAAATGCGGGCC AAGATCTGCACACTGGTATTTCGGTTTTTGGGGCCGCGGGC GGCGACGGGCCCGTGCGTCCCAGCGCACATGTTCGGCGA GGCGGGGCCTGCGAGCGCGGCCACCGAGAATCGGACGGG GTAGTCTCAAGCTGGCCGGCCTGCTCTGGTGCCTGGCCTCG |

-continued

| SEQ ID NO: | Description | Sequence |
|---|---|---|
| | | CGCCGCCGTGTATCGCCCCGCCCTGGGCGGCAAGGCTGGC CCGGTCGGCACCAGTTGCGTGAGCGGAAAGATGGCCGCTT CCCCGGCCCTGCTGCAGGGAGCTCAAAATGGAGGACGCGGC GCTCGGGAGAGCGGGCGGGTGAGTCACCCACACAAAGGAA AAGGGCCTTTCCGTCCTCAGCCGTCGCTTCATGTGACTCCA CGGAGTACCGGGCGCCGTCCAGGCACCTCGATTAGTTCTCG AGCTTTTGGAGTACGTCGTCTTTAGGTTGGGGGGAGGGGTT TTATGCGATGGAGTTTCCCCACACTGAGTGGGTGGAGACTG AAGTTAGGCCAGCTTGGCACTTGATGTAATTCTCCTTGGAA TTTGCCCTTTTTGAGTTTGGATCTTGGTTCATTCTCAAGCCT CAGACAGTGGTTCAAAGTTTTTTTCTTCCATTTCAGGTGTCG TGA |
| 65 | Promoter; PGK | GGGGTTGGGGTTGCGCCTTTTCCAAGGCAGCCCTGGGTTTG CGCAGGGACGCGGCTGCTCTGGGCGTGGTTCCGGGAAACG CAGCGGCGCCGACCCTGGGTCTCGCACATTCTTCACGTCCG TTCGCAGCGTCACCCGGATCTTCGCCGCTACCCTTGTGGGC CCCCCGGCGACGCTTCCTGCTCCCCCCTAAGTCGGGAAGG TTCCTTGCGGTTCGCGGCGTGCCGGACGTGACAAACGGAA GCCGCACGTCTCACTAGTACCCTCGCAGACGGACAGCGCC AGGGAGCAATGGCAGCGCGCCGACCGCGATGGGCTGTGGC CAATAGCGGCTGCTCAGCAGGGCGCGCCGAGAGCAGCGGC CGGGAAGGGGCGGTGCGGGAGGCGGGGTGTGGGGCGGTA GTGTGGGCCCTGTTCCTGCCCGCGCGGTGTTCCGCATTCTG CAAGCCTCCGGAGCGCACGTCGGCAGTCGGCTCCCTCGTTG ACCGAATCACCGACCTCTCTCCCCAG |
| 66 | Promoter; UbC | GCGCCGGGTTTTGGCGCCTCCCGCGGGCGCCCCCCTCCTCA CGGCGAGCGCTGCCACGTCAGACGAAGGGCGCAGGAGCGT TCCTGATCCTTCCGCCCGGACGCTCAGGACAGCGGCCCGCT GCTCATAAGACTCGGCCTTAGAACCCCAGTATCAGCAGAA GGACATTTTAGGACGGGACTTGGGTGACTCTAGGGCACTG GTTTTCTTTCCAGAGAGCGGAACAGGCGAGGAAAAGTAGT CCCTTCTCGGCGATTCTGCGGAGGGATCTCCGTGGGGCGGT GAACGCCGATGATTATATAAGGACGCGCCGGGTGTGGCAC AGCTAGTTCCGTCGCAGCCGGGATTTGGGTCGCGGTTCTTG TTTGTGGATCGCTGTGATCGTCACTTGGTGAGTTGCGGGCT GCTGGGCTGGCCGGGGCTTTCGTGGCCGCCGGGCCGCTCG GTGGGACGGAAGCGTGTGGAGAGACCGCCAAGGGCTGTAG TCTGGGTCCGCGAGCAAGGTTGCCCTGAACTGGGGGTTGG GGGGAGCGCACAAAATGGCGGCTGTTCCCGAGTCTTGAAT GGAAGACGCTTGTAAGGCGGGCTGTGAGGTCGTTGAAACA AGGTGGGGGGCATGGTGGGCGGCAAGAACCCAAGGTCTTG AGGCCTTCGCTAATGCGGGAAAGCTCTTATTCGGGTGAGAT GGGCTGGGGCACCATCTGGGGACCCTGACGTGAAGTTTGT CACTGACTGGAGAACTCGGGTTTGTCGTCTGGTTGCGGGGG CGGCAGTTATGCGGTGCCGTTGGGCAGTGCACCCGTACCTT TGGGAGCGCGCGCCTCGTCGTGTCGTGACGTCACCCGTTCT GTTGGCTTATAATGCAGGGTGGGGCCACCTGCCGGTAGGT GTGCGGTAGGCTTTTCTCCGTCGCAGGACGCAGGGTTCGGG CCTAGGGTAGGCTCTCCTGAATCGACAGGCGCCGGACCTCT GGTGAGGGGAGGGATAAGTGAGGCGTCAGTTTCTTTGGTC GGTTTTATGTACCTATCTTCTTAAGTAGCTGAAGCTCCGGTT TTGAACTATGCGCTCGGGGTTGGCGAGTGTGTTTTGTGAAG TTTTTTAGGCACCTTTTGAAATGTAATCATTTGGGTCAATAT GTAATTTTCAGTGTTAGACTAGTAAA |
| 67 | Poly A; SV40 | GTTTATTGCAGCTTATAATGGTTACAAATAAAGCAATAGCA TCACAAATTTCACAAATAAAGCATTTTTTTCACTGCATTCT AGTTGTGGTTTGTCCAAACTCATCAATGTATCTTATCA |
| 68 | Poly A; bGH | GACTGTGCCTTCTAGTTGCCAGCCATCTGTTGTTTGCCCCTC CCCCGTGCCTTCCTTGACCCTGGAAGGTGCCACTCCCACTG TCCTTTCCTAATAAAATGAGGAAATTGCATCGCATTGTCTG AGTAGGTGTCATTCTATTCTGGGGGGTGGGGTGGGGCAGG ACAGCAAGGGGGAGGATTGGGAAGACAATAGCAGGCATG CTGGGGATGCGGTGGGCTCTATGG |
| 69 | HIV Gag; Bal | ATGGGTGCGAGAGCGTCAGTATTAAGCGGGGGAGAATTAG ATAGGTGGGAAAAAATTCGGTTAAGGCCAGGGGGAAAGA AAAAATATAGATTAAAACATATAGTATGGGCAAGCAGGGA ACTAGAAAGATTCGCAGTCAATCCTGGCCTGTTAGAAACAT CAGAAGGCTGCAGACAAATACTGGGACAGCTACAACCATC CCTTCAGACAGGATCAGAAGAACTTAGATCATTATATAATA CAGTAGCAACCCTCTATTGTGTACATCAAAAGATAGAGGT |

| SEQ ID NO: | Description | Sequence |
|---|---|---|
| | | AAAAGACACCAAGGAAGCTTTAGACAAAATAGAGGAAGA<br>GCAAAACAAATGTAAGAAAAAGGCACAGCAAGCAGCAGC<br>TGACACAGGAAACAGCGGTCAGGTCAGCCAAAATTTCCCT<br>ATAGTGCAGAACCTCCAGGGGCAAATGGTACATCAGGCCA<br>TATCACCTAGAACTTTAAATGCATGGGTAAAAGTAATAGA<br>AGAGAAAGCTTTCAGCCCAGAAGTAATACCCATGTTTTCAG<br>CATTATCAGAAGGAGCCACCCCACAAGATTTAAACACCAT<br>GCTAAACACAGTGGGGGGACATCAAGCAGCCATGCAAATG<br>TTAAAAGAACCCATCAATGAGGAAGCTGCAAGATGGGATA<br>GATTGCATCCCGTGCAGGCAGGGCCTGTTGCACCAGGCCA<br>GATAAGAGATCCAAGGGGAAGTGACATAGCAGGAACTACC<br>AGTACCCTTCAGGAACAAATAGGATGGATGACAAGTAATC<br>CACCTATCCCAGTAGGAGAAATCTATAAAAGATGGATAAT<br>CCTGGGATTAAATAAAATAGTAAGGATGTATAGCCCTACC<br>AGCATTTTGGACATAAGACAAGGACCAAAGGAACCCTTTA<br>GAGACTATGTAGACCGGTTCTATAAAACTCTAAGAGCCGA<br>GCAAGCTTCACAGGAGGTAAAAAATTGGATGACAGAAACC<br>TTGTTGGTCCAAAATGCGAACCCAGATTGTAAGACTATTTT<br>AAAAGCATTGGGACCAGCAGCTACACTAGAAGAAATGATG<br>ACAGCATGTCAGGGAGTGGGAGGACCCAGCCATAAAGCAA<br>GAATTTTGGCAGAAGCAATGAGCCAAGTAACAAATTCAGC<br>TACCATAATGATGCAGAAAGGCAATTTTAGGAACCAAAGA<br>AAGATTGTTAAATGTTTCAATTGTGGCAAAGAAGGGCACA<br>TAGCCAGAAACTGCAGGGCCCCTAGGAAAAGGGGCTGTTG<br>GAAATGTGGAAAGGAAGGACACCAAATGAAAGACTGTACT<br>GAGAGACAGGCTAATTTTTTAGGGAAAATCTGGCCTTCCCA<br>CAAAGGAAGGCCAGGGAATTTCCTTCAGAGCAGACCAGAG<br>CCAACAGCCCCACCAGCCCCACCAGAAGAGAGCTTCAGGT<br>TTGGGGAAGAGACAACAACTCCCTCTCAGAAGCAGGAGCT<br>GATAGACAAGGAACTGTATCCTTTAGCTTCCCTCAGATCAC<br>TCTTTGGCAACGACCCCTCGTCACAATAA |
| 70 | HIV Pol; Bal | ATGAATTTGCCAGGAAGATGGAAACCAAAAATGATAGGGG<br>GAATTGGAGGTTTTATCAAAGTAAGACAGTATGATCAGAT<br>ACTCATAGAAATCTGTGGACATAAAGCTATAGGTACAGTA<br>TTAATAGGACCTACACCTGTCAACATAATTGGAAGAAATCT<br>GTTGACTCAGATTGGTTGCACTTTAAATTTTCCCATTAGTCC<br>TATTGAAACTGTACCAGTAAAATTAAAACCAGGAATGGAT<br>GGCCCAAAAGTTAAACAATGGCCACTGACAGAAGAAAAAA<br>TAAAAGCATTAATGGAAATCTGTACAGAAATGGAAAAGGA<br>AGGGAAAATTTCAAAAATTGGGCCTGAAAATCCATACAAT<br>ACTCCAGTATTTGCCATAAAGAAAAAAGACAGTACTAAAT<br>GGAGAAAATTAGTAGATTTCAGAGAACTTAATAAGAAAAC<br>TCAAGACTTCTGGGAAGTACAATTAGGAATACACATCCCG<br>CAGGGGTTAAAAAAGAAAAAATCAGTAACAGTACTGGATG<br>TGGGTGATGCATATTTTTCAGTTCCCTTAGATAAAGAATTC<br>AGGAAGTATACTGCATTTACCATACCTAGTATAAACAATGA<br>AACACCAGGGATCAGATATCAGTACAATGTACTTCCACAG<br>GGATGGAAAGGATCACCAGCAATATTTCAAAGTAGCATGA<br>CAAGAATCTTAGAGCCTTTTAGAAAACAAAATCCAGAAAT<br>AGTTGATCTATCAATACATGGATGATTTGTATGTAGGATCT<br>ACTTAGAAATAGGGCAGCATAGAACAAAAATAGAGGAACT<br>GAGACAACATCTGTTGAGGTGGGGATTTACCACACCAGAC<br>AAAAAACATCAGAAAGAACCTCCATTCCTTTGGATGGGTT<br>ATGAACTCCATCCTGATAAATGGACAGTACAGCCTATAGTG<br>CTGCCAGAAAAAGACAGCTGGACTGTCAATGACATACAGA<br>AGTTAGTGGGAAAATTGAATTGGGCAAGTCAGATTTACCC<br>AGGAATTAAAGTAAAGCAATTATGTAGGCTCCTTAGGGGA<br>ACCAAGGCATTAACAGAAGTAATACCACTAACAAAAGAAA<br>CAGAGCTAGAACTGGCAGAGAACAGGGAAATTCTAAAAGA<br>ACCAGTACATGGGGTGTATTATGACCCATCAAAAGACTTA<br>ATAGCAGAAATACAGAAGCAGGGGCAAGGCCAATGGACA<br>TATCAAATTTATCAAGAGCCATTTAAAAATCTGAAAACAG<br>GAAAATATGCAAGAATGAGGGGTGCCCACACTAATGATGT<br>AAAACAATTAACAGAGGCAGTGCAAAAAATAACCACAGA<br>AAGCATAGTAATATGGGGAAAGACTCCTAAATTTAAACTA<br>CCCATACAAAAGGAAACATGGGAAACATGGTGGACAGAGT<br>ATTGGCAAGCCACCTGGATTCCTGAGTGGGAGTTTGTCAAT<br>ACCCCTCCCTTAGTGAAATTATGGTACCAGTTAGAGAAAGA<br>ACCCATAATAGGAGCAGAAACATTCTATGTAGATGGAGCA<br>GCTAACCGGGAGACTAAATTAGGAAAAGCAGGATATGTTA<br>CTAACAGAGGAAGACAAAAAGTTGTCTCCCTAACTGACAC<br>AACAAATCAGAAGACTGAGTTACAAGCAATTCATCTAGCT<br>TTACAAGATTCAGGATTAGAAGTAAACATAGTAACAGACT<br>CACAATATGCATTAGGAATCATTCAAGCACAACCAGATAA |

| SEQ ID NO: | Description | Sequence |
|---|---|---|
| | | AAGTGAATCAGAGTTAGTCAGTCAAATAATAGAACAGTTA<br>ATAAAAAAGGAAAAGGTCTACCTGGCATGGGTACCAGCGC<br>ACAAAGGAATTGGAGGAAATGAACAAGTAGATAAATTAGT<br>CAGTACTGGAATCAGGAAAGTACTA |
| 71 | HIV Integrase; Bal | TTTTTAGATGGAATAGATATAGCCCAAGAAGAACATGAGA<br>AATATCACAGTAATTGGAGAGCAATGGCTAGTGATTTTAAC<br>CTGCCACCTGTGGTAGCAAAAGAAATAGTAGCCAGCTGTG<br>ATAAATGTCAGCTAAAAGGAGAAGCCATGCATGGACAAGT<br>AGACTGTAGTCCAGGAATATGGCAACTAGATTGTACACATT<br>TAGAAGGAAAAATTATCCTGGTAGCAGTTCATGTAGCCAG<br>TGGATATATAGAAGCAGAAGTTATTCCAGCAGAGACAGGG<br>CAGGAAACAGCATACTTTCTCTTAAAATTAGCAGGAAGAT<br>GGCCAGTAAAAACAATACATACAGACAATGGCAGCAATTT<br>CACTAGTACTACAGTCAAGGCCGCCTGTTGGTGGGCGGGG<br>ATCAAGCAGGAATTTGGCATTCCCTACAATCCCCAAAGTCA<br>GGGAGTAGTAGAATCTATAAATAAAGAATTAAAGAAAATT<br>ATAGGACAGGTAAGAGATCAGGCTGAACATCTTAAAACAG<br>CAGTACAAATGGCAGTATTCATCCACAATTTTAAAAGAAA<br>AGGGGGGATTGGGGGGTATAGTGCAGGGGAAAGAATAGT<br>AGACATAATAGCAACAGACATACAAACTAAAGAATTACAA<br>AAACAAATTACAAAAATTCAAAATTTTCGGGTTTATTACAG<br>GGACAGCAGAGATCCACTTTGGAAAGGACCAGCAAAGCTT<br>CTCTGGAAAGGTGAAGGGGCAGTAGTAATACAAGATAATA<br>GTGACATAAAAGTAGTACCAAGAAGAAAAGCAAAGATCAT<br>TAGGGATTATGGAAAACAGATGGCAGGTGATGATTGTGTG<br>GCAAGTAGACAGGATGAGGATTAG |
| 72 | Envelope; RD114 | ATGAAACTCCCAACAGGAATGGTCATTTTATGTAGCCTAAT<br>AATAGTTCGGGCAGGGTTTGACGACCCCCGCAAGGCTATC<br>GCATTAGTACAAAAACAACATGGTAAACCATGCGAATGCA<br>GCGGAGGGCAGGTATCCGAGGCCCCACCGAACTCCATCCA<br>ACAGGTAACTTGCCCAGGCAAGACGGCCTACTTAATGACC<br>AACCAAAAATGGAAATGCAGAGTCACTCCAAAAAATCTCA<br>CCCCTAGCGGGGGAGAACTCCAGAACTGCCCCTGTAACAC<br>TTTCCAGGACTCGATGCACAGTTCTTGTTATACTGAATACC<br>GGCAATGCAGGGCGAATAATAAGACATACTACACGGCCAC<br>CTTGCTTAAAATACGGTCTGGGAGCCTCAACGAGGTACAG<br>ATATTACAAAACCCCAATCAGCTCCTACAGTCCCCTTGTAG<br>GGGCTCTATAAATCAGCCCGTTTGCTGGAGTGCCACAGCCC<br>CCATCCATATCTCCGATGGTGGAGGACCCCTCGATACTAAG<br>AGAGTGTGGACAGTCCAAAAAAGGCTAGAACAAATTCATA<br>AGGCTATGCATCCTGAACTTCAATACCACCCCTTAGCCCTG<br>CCCAAAGTCAGAGATGACCCTTAGCCTTGATGCACGGACTTT<br>TGATATCCTGAATACCACTTTTAGGTTACTCCAGATGTCCA<br>ATTTTAGCCTTGCCCAAGATTGTTGGCTCTGTTTAAAACTA<br>GGTACCCCTACCCCTCTTGCGATACCCACTCCCTCTTTAACC<br>TACTCCCTAGCAGACTCCCTAGCGAATGCCTCCTGTCAGAT<br>TATACCTCCCCTCTTGGTTCAACCGATGCAGTTCTCCAACTC<br>GTCCTGTTTATCTTCCCCTTTCATTAACGATACGGAACAAA<br>TAGACTTAGGTGCAGTCACCTTTACTAACTGCACCTCTGTA<br>GCCAATGTCAGTAGTCCTTTATGTGCCCTAAACGGGTCAGT<br>CTTCCTCTGTGGAAATAACATGGCATACACCTATTTACCCC<br>AAAACTGGACAGGACTTTGCGTCCAAGCCTCCCTCCTCCCC<br>GACATTGACATCATCCCGGGGGATGAGCCAGTCCCCATTCC<br>TGCCATTGATCATTATATACATAGACCTAAACGAGCTGTAC<br>AGTTCATCCCTTTACTAGCTGGACTGGGAATCACCGCAGCA<br>TTCACCACCGGAGCTACAGGCCTAGGTGTCTCCGTCACCCA<br>GTATACAAAATTATCCCATCAGTTAATATCTGATGTCCAAG<br>TCTTATCCGGTACCATACAAGATTTACAAGACCAGGTAGAC<br>TCGTTAGCTGAAGTAGTTCTCCAAAATAGGAGGGGACTGG<br>ACCTACTAACGGCAGAACAAGGAGGAATTTGTTTAGCCTT<br>ACAAGAAAATGCTGTTTTTATGCTAACAAGTCAGGAATTG<br>TGAGAAACAAAATAAGAACCCTACAAGAAGAATTACAAAA<br>ACGCAGGGAAAGCCTGGCATCCAACCCTCTCTGGACCGGG<br>CTGCAGGGCTTTCTTCCGTACCTCCTACCTCTCCTGGGACCC<br>CTACTCACCCTCCTACTCATACTAACCATTGGGCCATGCGT<br>TTTCAATCGATTGGTCCAATTTGTTAAAGACAGGATCTCAG<br>TGGTCCAGGCTCTGGTTTTGACTCAGCAATATCACCAGCTA<br>AAACCCATAGAGTACGAGCCATGA |
| 73 | Envelope; GALV | ATGCTTCTCACCTCAAGCCCGCACCACCTTCGGCACCAGAT<br>GAGTCCTGGGAGCTGGAAAAGACTGATCATCCTCTTAAGCT<br>GCGTATTCGGAGACGGCAAAACGAGTCTGCAGAATAAGAA<br>CCCCCACCAGCCTGTGACCCTCACCTGGCAGGTACTGTCCC |

| SEQ ID NO: | Description | Sequence |
|---|---|---|
| | | AAACTGGGGACGTTGTCTGGGACAAAAAGGCAGTCCAGCC<br>CCTTTGGACTTGGTGGCCCTCTCTTACACCTGATGTATGTGC<br>CCTGGCGGCCGGTCTTGAGTCCTGGGATATCCCGGGATCCG<br>ATGTATCGTCCTCTAAAAGAGTTAGACCTCCTGATTCAGAC<br>TATACTGCCGCTTATAAGCAAATCACCTGGGGAGCCATAG<br>GGTGCAGCTACCCTCGGGCTAGGACCAGGATGGCAAATTC<br>CCCCTTCTACGTGTGTCCCCGAGCTGGCCGAACCCATTCAG<br>AAGCTAGGAGGTGTGGGGGGCTAGAATCCCTATACTGTAA<br>AGAATGGAGTTGTGAGACCACGGGTACCGTTTATTGGCAA<br>CCCAAGTCCTCATGGGACCTCATAACTGTAAAATGGGACC<br>AAAATGTGAAATGGGAGCAAAAATTTCAAAAGTGTGAACA<br>AACCGGCTGGTGTAACCCCCTCAAGATAGACTTCACAGAA<br>AAAGGAAAACTCTCCAGAGATTGGATAACGGAAAAAACCT<br>GGGAATTAAGGTTCTATGTATATGGACACCCAGGCATACA<br>GTTGACTATCCGCTTAGAGGTCACTAACATGCCGGTTGTGG<br>CAGTGGGCCCAGACCCTGTCCTTGCGGAACAGGGACCTCCT<br>AGCAAGCCCCTCACTCTCCCTCTCTCCCCACGGAAAGCGCC<br>GCCCACCCCTCTACCCCCGGCGGCTAGTGAGCAAACCCCTG<br>CGGTGCATGGAGAAACTGTTACCCTAAACTCTCCGCCTCCC<br>ACCAGTGGCGACCGACTCTTTGGCCTTGTGCAGGGGGCCTT<br>CCTAACCTTGAATGCTACCAACCCAGGGGCCACTAAGTCTT<br>GCTGGCTCTGTTTGGGCATGAGCCCCCCTTATTATGAAGGG<br>ATAGCCTCTTCAGGAGAGGTCGCTTATACCTCCAACCATAC<br>CCGATGCCACTGGGGGGCCCAAGGAAAGCTTACCCTCACT<br>GAGGTCTCCGGACTCGGGTCATGCATAGGGAAGGTGCCTC<br>TTACCCATCAACATCTTTGCAACCAGACCTTACCCATCAAT<br>TCCTCTAAAAACCATCAGTATCTGCTCCCCTCAAACCATAG<br>CTGGTGGGCCTGCAGCACTGGCCTCACCCCCTGCCTCTCCA<br>CCTCAGTTTTTAATCAGTCTAAAGACTTCTGTGTCCAGGTC<br>CAGCTGATCCCCCGCATCTATTACCATTCTGAAGAAACCTT<br>GTTACAAGCCTATGACAAATCACCCCCCAGGTTTAAAAGA<br>GAGCCTGCCTCACTTACCCTAGCTGTCTTCCTGGGGTTAGG<br>GATTGCGGCAGGTATAGGTACTGGCTCAACCGCCCTAATTA<br>AAGGGCCCATAGACCTCCAGCAAGGCCTAACCAGCCTCCA<br>AATCGCCATTGACGCTGACCTCCGGGCCCTTCAGGACTCAA<br>TCAGCAAGCTAGAGGACTCACTGACTTCCCTATCTGAGGTA<br>GTACTCCAAAATAGGAGAGGCCTTGACTTACTATTCCTTAA<br>AGAAGGAGGCCTCTGCGCGGCCCTAAAAGAAGAGTGCTGT<br>TTTTATGTAGACCACTCAGGTGCAGTACGAGACTCCATGAA<br>AAAACTTAAAGAAAGACTAGATAAAAGACAGTTAGAGCGC<br>CAGAAAAACCAAAACTGGTATGAAGGGTGGTTCAATAACT<br>CCCCTTGGTTTACTACCCTACTATCAACCATCGCTGGGCCC<br>CTATTGCTCCTCCTTTTGTTACTCACTCTTGGGCCCTGCATC<br>ATCAATAAATTAATCCAATTCATCAATGATAGGATAAGTGC<br>AGTCAAAATTTTAGTCCTTAGACAGAAATATCAGACCCTAG<br>ATAACGAGGAAAACCTTTAA |
| 74 | Envelope;<br>FUG | ATGGTTCCGCAGGTTCTTTTGTTTGTACTCCTTCTGGGTTTT<br>TCGTTGTGTTTCGGGAAGTTCCCCATTTACACGATACCAGA<br>CGAACTTGGTCCCTGGAGCCCTATTGACATACACCATCTCA<br>GCTGTCCAAATAACCTGGTTGTGGAGGATGAAGGATGTAC<br>CAACCTGTCCGAGTTCTCCTACATGGAACTCAAAGTGGGAT<br>ACATCTCAGCCATCAAAGTGAACGGGTTCACTTGCACAGGT<br>GTTGTGACAGAGGCAGAGACCTACACCAACTTTGTTGGTTA<br>TGTCACAACCACATTCAAGAGAAAGCATTTCCGCCCCACCC<br>CAGACGCATGTAGAGCCGCGTATAACTGGAAGATGGCCGG<br>TGACCCCAGATATGAAGAGTCCCTACACAATCCATACCCCG<br>ACTACCACTGGCTTCGAACTGTAAGAACCACCAAAGAGTC<br>CCTCATTATCATATCCCCAAGTGTGACAGATTTGGACCCAT<br>ATGACAAATCCCTTCACTCAAGGGTCTTCCCTGGCGGAAAG<br>TGCTCAGGAATAACGGTGTCCTCTACCTACTGCTCAACTAA<br>CCATGATTACACCATTTGGATGCCCGAGAATCCGAGACCA<br>AGGACACCTTGTGACATTTTTACCAATAGCAGAGGGAAGA<br>GAGCATCCAACGGGAACAAGACTTGCGGCTTTGTGGATGA<br>AAGAGGCCTGTATAAGTCTCTAAAAGGAGCATGCAGGCTC<br>AAGTTATGTGGAGTTCTTGGACTTAGACTTATGGATGGAAC<br>ATGGGTCGCGATGCAAACATCAGATGAGACCAAATGGTGC<br>CCTCCAGATCAGTTGGTGAATTTGCACGACTTTCGCTCAGA<br>CGAGATCGAGCATCTCGTTGTGGAGGAGTTAGTTAAGAAA<br>AGAGAGGAATGTCTGGATGCATTAGAGTCCATCATGACCA<br>CCAAGTCAGTAAGTTTCAGACGTCTCAGTCACCTGAGAAA<br>ACTTGTCCCAGGGTTTGGAAAAGCATATACCATATTCAACA<br>AAACCTTGATGGAGGCTGATGCTCACTACAAGTCAGTCCG<br>GACCTGGAATGAGATCATCCCCTCAAAAGGGTGTTTGAAA<br>GTTGGAGGAAGGTGCCATCCTCATGTGAACGGGGTGTTTTT |

| SEQ ID NO: | Description | Sequence |
|---|---|---|
| | | CAATGGTATAATATTAGGGCCTGACGACCATGTCCTAATCC<br>CAGAGATGCAATCATCCCTCCTCCAGCAACATATGGAGTTG<br>TTGGAATCTTCAGTTATCCCCCTGATGCACCCCCTGGCAGA<br>CCCTTCTACAGTTTTCAAAGAAGGTGATGAGGCTGAGGATT<br>TTGTTGAAGTTCACCTCCCCGATGTGTACAAACAGATCTCA<br>GGGGTTGACCTGGGTCTCCCGAACTGGGGAAAGTATGTATT<br>GATGACTGCAGGGGCCATGATTGGCCTGGTGTTGATATTTT<br>CCCTAATGACATGGTGCAGAGTTGGTATCCATCTTTGCATT<br>AAATTAAAGCACACCAAGAAAAGACAGATTTATACAGACA<br>TAGAGATGAACCGACTTGGAAAGTAA |
| 75 | Envelope; LCMV | ATGGGTCAGATTGTGACAATGTTTGAGGCTCTGCCTCACAT<br>CATCGATGAGGTGATCAACATTGTCATTATTGTGCTTATCG<br>TGATCACGGGTATCAAGGCTGTCTACAATTTTGCCACCTGT<br>GGGATATTCGCATTGATCAGTTTCCTACTTCTGGCTGGCAG<br>GTCCTGTGGCATGTACGGTCTTAAGGGACCCGACATTTACA<br>AAGGAGTTTACCAATTTAAGTCAGTGGAGTTTGATATGTCA<br>CATCTGAACCTGACCATGCCCAACGCATGTTCAGCCAACAA<br>CTCCCACCATTACATCAGTATGGGGACTTCTGGACTAGAAT<br>TGACCTTCACCAATGATTCCATCATCAGTCACAACTTTTGC<br>AATCTGACCTCTGCCTTCAACAAAAGACCTTTGACCACAC<br>ACTCCATGAGTATAGTTTCGAGCCTACACCTCAGTATCAGAG<br>GGAACTCCAACTATAAGGCAGTATCCTGCGACTTCAACAAT<br>GGCATAACCATCCAATACAACTTGACATTCTCAGATCGACA<br>AAGTGCTCAGAGCCAGTGTAGAACCTTCAGAGGTAGAGTC<br>CTAGATATGTTTAGAACTGCCTTCGGGGGGAAATACATGA<br>GGAGTGGCTGGGGCTGGACAGGCTCAGATGGCAAGACCAC<br>CTGGTGTAGCCAGACGAGTTACCAATACCTGATTATACAAA<br>ATAGAACCTGGGAAAACCACTGCACATATGCAGGTCCTTTT<br>GGGATGTCCAGGATTCTCCTTTCCCAAGAGAAGACTAAGTT<br>CTTCACTAGGAGACTAGCGGGCACATTCACCTGGACTTTGT<br>CAGACTCTTCAGGGGTGGAGAATCCAGGTGGTTATTGCCTG<br>ACCAAATGGATGATTCTTGCTGCAGAGCTTAAGTGTTTCGG<br>GAACACAGCAGTTGCGAAATGCAATGTAAATCATGATGCC<br>GAATTCTGTGACATGCTGCGACTAATTGACTACAACAAGGC<br>TGCTTTGAGTAAGTTCAAAGAGGACGTAGAATCTGCCTTGC<br>ACTTATTCAAAACAACAGTGAATTCTTTGATTTCAGATCAA<br>CTACTGATGAGGAACCACTTGAGAGATCTGATGGGGGTGC<br>CATATTGCAATTACTCAAAGTTTTGGTACCTAGAACATGCA<br>AAGACCGGCGAAACTAGTGTCCCCAAGTGCTGGCTTGTCA<br>CCAATGGTTCTTACTTAAATGAGACCCACTTCAGTGATCAA<br>ATCGAACAGGAAGCCGATAACATGATTACAGAGATGTTGA<br>GGAAGGATTACATAAAGAGGCAGGGGAGTACCCCCCTAGC<br>ATTGATGGACCTTCTGATGTTTTCCACATCTGCATATCTAGT<br>CAGCATCTTCCTGCACCTTGTCAAAATACCAACACACAGGC<br>ACATAAAAGGTGGCTCATGTCCAAAGCCACACCGATTAAC<br>CAACAAAGGAATTTGTAGTTGTGGTGCATTTAAGGTGCCTG<br>GTGTAAAAACCGTCTGGAAAAGACGCTGA |
| 76 | Envelope; FPV | ATGAACACTCAAATCCTGGTTTTCGCCCTTGTGGCAGTCAT<br>CCCCACAAATGCAGACAAAATTTGTCTTGGACATCATGCTG<br>TATCAAATGGCACCAAAGTAAACACACTCACTGAGAGAGG<br>AGTAGAAGTTGTCAATGCAACGGAAACAGTGGAGCGGACA<br>AACATCCCCAAAATTTGCTCAAAAGGGAAAAGAACCACTG<br>ATCTTGGCCAATGCGGACTGTTAGGGACCATTACCGGACCA<br>CCTCAATGCGACCAATTTCTAGAATTTTCAGCTGATCTAAT<br>AATCGAGAGACGAGAAGGAAATGATGTTTGTTACCCGGGG<br>AAGTTTGTTAATGAAGAGGCATTGCGACAAATCCTCAGAG<br>GATCAGGTGGGATTGACAAAGAAACAATGGGATTCACATA<br>TAGTGGAATAAGGACCAACGGAACAACTAGTGCATGTAGA<br>AGATCAGGGTCTTCATTCTATGCAGAAATGGAGTGGCTCCT<br>GTCAAATACAGACAATGCTGCTTTCCCACAAATGACAAAA<br>TCATACAAAAACACAAGGAGAGAATCAGCTCTGATAGTCT<br>GGGGAATCCACCATTCAGGATCAACCACCGAACAGACCAA<br>ACTATATGGGAGTGGAAATAAACTGATAACAGTCGGGAGT<br>TCCAAATATCATCAATCTTTTGTGCCGAGTCCAGGAACACG<br>ACCGCAGATAAATGGCCAGTCCGGACGGATTGATTTTCATT<br>GGTTGATCTTGGATCCCAATGATACAGTTACTTTTAGTTTC<br>AATGGGGCTTTCATAGCTCCAAATCGTGCCAGCTTCTTGAG<br>GGGAAAGTCCATGGGGATCCAGAGCGATGTGCAGGTTGAT<br>GCCAATTGCGAAGGGGAATGCTACCACAGTGGAGGGACTA<br>TAACAAGCAGATTGCCTTTTCAAAACATCAATAGCAGAGC<br>AGTTGGCAAATGCCCAAGATATGTAAAACAGGAAAGTTTA<br>TTATTGGCAACTGGGATGAAGAACGTTCCCGAACCTTCCAA<br>AAAAAGGAAAAAAGAGGCCTGTTTGGCGCTATAGCAGGG |

-continued

| SEQ ID NO: | Description | Sequence |
|---|---|---|
| | | TTTATTGAAAATGGTTGGGAAGGTCTGGTCGACGGGTGGTA CGGTTTCAGGCATCAGAATGCACAAGGAGAAGGAACTGCA GCAGACTACAAAAGCACCCAATCGGCAATTGATCAGATAA CCGGAAAGTTAAATAGACTCATTGAGAAAACCAACCAGCA ATTTGAGCTAATAGATAATGAATTCACTGAGGTGGAAAAG CAGATTGGCAATTTAATTAACTGGACCAAAGACTCCATCAC AGAAGTATGGTCTTACAATGCTGAACTTCTTGTGGCAATGG AAAACCAGCACACTATTGATTTGGCTGATTCAGAGATGAA CAAGCTGTATGAGCGAGTGAGGAAACAATTAAGGGAAAAT GCTGAAGAGGATGGCACTGGTTGCTTTGAAATTTTTCATAA ATGTGACGATGATTGTATGGCTAGTATAAGGAACAATACTT ATGATCACAGCAAATACAGAGAAGAAGCGATGCAAAATAG AATACAAATTGACCCAGTCAAATTGAGTAGTGGCTACAAA GATGTGATACTTTGGTTTAGCTTCGGGGCATCATGCTTTTTG CTTCTTGCCATTGCAATGGGCCTTGTTTTCATATGTGTGAAG AACGGAAACATGCGGTGCACTATTTGTATATAA |
| 77 | Envelope; RRV | AGTGTAACAGAGCACTTTAATGTGTATAAGGCTACTAGACC ATACCTAGCACATTGCGCCGATTGCGGGGACGGGTACTTCT GCTATAGCCCAGTTGCTATCGAGGAGATCCGAGATGAGGC GTCTGATGGCATGCTTAAGATCCAAGTCTCCGCCCAAATAG GTCTGGACAAGGCAGGCACCCACGCCCACACGAAGCTCCG ATATATGGCTGGTCATGATGTTCAGGAATCTAAGAGAGATT CCTTGAGGGTGTACACGTCCGCAGCGTGCTCCATACATGGG ACGATGGGACACTTCATCGTCGCACACTGTCCACCAGGCG ACTACCTCAAGGTTTCGTTCGAGGACGCAGATTCGCACGTG AAGGCATGTAAGGTCCAATACAAGCACAATCCATTGCCGG TGGGTAGAGAGAAGTTCGTGGTTAGACCACACTTTGGCGT AGAGCTGCCATGCACCTCATACCAGCTGACAACGGCTCCC ACCGACGAGGAGATTGACATGCATACACCGCCAGATATAC CGGATCGCACCCTGCTATCACAGACGGCGGGCAACGTCAA AATAACAGCAGGCGGCAGGACTATCAGGTACAACTGTACC TGCGGCCGTGACAACGTAGGCACTACCAGTACTGACAAGA CCATCAACACATGCAAGATTGACCAATGCCATGCTGCCGTC ACCAGCCATGACAAATGGCAATTTACCTCTCCATTTGTTCC CAGGGCTGATCAGACAGCTAGGAAAGGCAAGGTACACGTT CCGTTCCCTCTGACTAACGTCACCTGCCGAGTGCCGTTGGC TCGAGCGCCGGATGCCACCTATGGTAAGAAGGAGGTGACC CTGAGATTACACCCAGATCATCCGACGCTCTTCTCCTATAG GAGTTTAGGAGCCGAACCGCACCCGTACGAGGAATGGGTT GACAAGTTCTCTGAGCGCATCATCCCAGTGACGGAAGAAG GGATTGAGTACCAGTGGGGCAACAACCCGCCGGTCTGCCT GTGGGCGCAACTGACGACCGAGGGCAAACCCCATGGCTGG CCACATGAAATCATTCAGTACTATTATGGACTATACCCCGC CGCCACTATTGCCGCAGTATCCGGGGCGAGTCTGATGGCCC TCCTAACTCTGGCGGCCACATGCTGCATGCTGGCCACCGCG AGGAGAAAGTGCCTAACACCGTACGCCCTGACGCCAGGAG CGGTGGTACCGTTGACACTGGGGCTGCTTTGCTGCGCACCG AGGGCGAATGCA |
| 78 | Envelope; MLV 10A1 | AGTGTAACAGAGCACTTTAATGTGTATAAGGCTACTAGACC ATACCTAGCACATTGCGCCGATTGCGGGGACGGGTACTTCT GCTATAGCCCAGTTGCTATCGAGGAGATCCGAGATGAGGC GTCTGATGGCATGCTTAAGATCCAAGTCTCCGCCCAAATAG GTCTGGACAAGGCAGGCACCCACGCCCACACGAAGCTCCG ATATATGGCTGGTCATGATGTTCAGGAATCTAAGAGAGATT CCTTGAGGGTGTACACGTCCGCAGCGTGCTCCATACATGGG ACGATGGGACACTTCATCGTCGCACACTGTCCACCAGGCG ACTACCTCAAGGTTTCGTTCGAGGACGCAGATTCGCACGTG AAGGCATGTAAGGTCCAATACAAGCACAATCCATTGCCGG TGGGTAGAGAGAAGTTCGTGGTTAGACCACACTTTGGCGT AGAGCTGCCATGCACCTCATACCAGCTGACAACGGCTCCC ACCGACGAGGAGATTGACATGCATACACCGCCAGATATAC CGGATCGCACCCTGCTATCACAGACGGCGGGCAACGTCAA AATAACAGCAGGCGGCAGGACTATCAGGTACAACTGTACC TGCGGCCGTGACAACGTAGGCACTACCAGTACTGACAAGA CCATCAACACATGCAAGATTGACCAATGCCATGCTGCCGTC ACCAGCCATGACAAATGGCAATTTACCTCTCCATTTGTTCC CAGGGCTGATCAGACAGCTAGGAAAGGCAAGGTACACGTT CCGTTCCCTCTGACTAACGTCACCTGCCGAGTGCCGTTGGC TCGAGCGCCGGATGCCACCTATGGTAAGAAGGAGGTGACC CTGAGATTACACCCAGATCATCCGACGCTCTTCTCCTATAG GAGTTTAGGAGCCGAACCGCACCCGTACGAGGAATGGGTT GACAAGTTCTCTGAGCGCATCATCCCAGTGACGGAAGAAG GGATTGAGTACCAGTGGGGCAACAACCCGCCGGTCTGCCT |

| SEQ ID NO: | Description | Sequence |
|---|---|---|
| | | GTGGGCGCAACTGACGACCGAGGGCAAACCCCATGGCTGG<br>CCACATGAAATCATTCAGTACTATTATGGACTATACCCCGC<br>CGCCACTATTGCCGCAGTATCCGGGGCGAGTCTGATGGCCC<br>TCCTAACTCTGGCGGCCACATGCTGCATGCTGGCCACCGCG<br>AGGAGAAAGTGCCTAACACCGTACGCCCTGACGCCAGGAG<br>CGGTGGTACCGTTGACACTGGGGCTGCTTTGCTGCGCACCG<br>AGGGCGAATGCA |
| 79 | Envelope; Ebola | ATGGGTGTTACAGGAATATTGCAGTTACCTCGTGATCGATT<br>CAAGAGGACATCATTCTTTCTTTGGGTAATTATCCTTTTCCA<br>AAGAACATTTTCCATCCCACTTGGAGTCATCCACAATAGCA<br>CATTACAGGTTAGTGATGTCGACAAACTGGTTTGCCGTGAC<br>AAACTGTCATCCACAAATCAATTGAGATCAGTTGGACTGA<br>ATCTCGAAGGGAATGGAGTGGCAACTGACGTGCCATCTGC<br>AACTAAAAGATGGGGCTTCAGGTCCGGTGTCCCACCAAAG<br>GTGGTCAATTATGAAGCTGGTGAATGGGCTGAAAACTGCT<br>ACAATCTTGAAATCAAAAAACCTGACGGGAGTGAGTGTCT<br>ACCAGCAGCGCCAGACGGGATTCGGGGCTTCCCCCGGTGC<br>CGGTATGTGCACAAAGTATCAGGAACGGGACCGTGTGCCG<br>GAGACTTTGCCTTCCACAAAGAGGGTGCTTTCTTCCTGTAT<br>GACCGACTTGCTTCCACAGTTATCTACCGAGGAACGACTTT<br>CGCTGAAGGTGTCGTTGCATTTCTGATACTGCCCCAAGCTA<br>AGAAGGACTTCTTCAGCTCACACCCCTTGAGAGAGCCGGTC<br>AATGCAACGGAGGACCCGTCTAGTGGCTACTATTCTACCAC<br>AATTAGATATCAAGCTACCGGTTTTGGAACCAATGAGACA<br>GAGTATTTGTTCGAGGTTGACAATTTGACCTACGTCCAACT<br>TGAATCAAGATTCACACCACAGTTTCTGCTCCAGCTGAATG<br>AGACAATATATACAAGTGGGAAAAGGAGCAATACCACGGG<br>AAAACTAATTTGGAAGGTCAACCCCGAAATTGATACAACA<br>ATCGGGGAGTGGGCCTTCTGGGAAACTAAAAAAACCTCAC<br>TAGAAAAATTCGCAGTGAAGAGTTGTCTTTCACAGCTGTAT<br>CAAACAGAGCCAAAAACATCAGTGGTCAGAGTCCGGCGCG<br>AACTTCTTCCGACCCAGGGACCAACACAACAACTGAAGAC<br>CACAAAATCATGGCTTCAGAAAATTCCTCTGCAATGGTTCA<br>AGTGCACAGTCAAGGAAGGGAAGCTGCAGTGTCGCATCTG<br>ACAACCCTTGCCACAATCTCCACGAGTCCTCAACCCCCCAC<br>AACCAAACCAGGTCCGGACAACAGCACCCACAATACACCC<br>GTGTATAAACTTGACATCTCTGAGGCAACTCAAGTTGAACA<br>ACATCACCGCAGAACAGACAACGACAGCACAGCCTCCGAC<br>ACTCCCCCCGCCACGACCGCAGCCGGACCCCTAAAAGCAG<br>AGAACACCAACACGAGCAAGGGTACCGACCTCCTGGACCC<br>CGCCACCACAACAAGTCCCCAAAAACCACAGCGAGACCGCT<br>GGCAACAACAACACTCATCACCAAGATACCGGAGAAGAGA<br>GTGCCAGCAGCGGGAAGCTAGGCTTAATTACCAATACTATT<br>GCTGGAGTCGCAGGACTGATCACAGGCGGGAGGAGAGCTC<br>GAAGAGAAGCAATTGTCAATGCTCAACCCAAATGCAACCC<br>TAATTTACATTACTGGACTACTCAGGATGAAGGTGCTGCAA<br>TCGGACTGGCCTGGATACCATATTTCGGGCCAGCAGCCGA<br>GGGAATTTACATAGAGGGGCTGATGCACAATCAAGATGGT<br>TTAATCTGTGGGTTGAGACAGCTGGCCAACGAGACGACTC<br>AAGCTCTTCAACTGTTCCTGAGAGCCACAACCGAGCTACGC<br>ACCTTTTCAATCCTCAACCGTAAGGCAATTGATTTCTTGCT<br>GCAGCGATGGGGCGGCACATGCCACATTTTGGGACCGGAC<br>TGCTGTATCGAACCACATGATTGGACCAAGAACATAACAG<br>ACAAAATTGATCAGATTATTCATGATTTTGTTGATAAAACC<br>CTTCCGGACCAGGGGGACAATGACAATTGGTGGACAGGAT<br>GGAGACAATGGATACCGGCAGGTATTGGAGTTACAGGCGT<br>TATAATTGCAGTTATCGCTTTATTCTGTATATGCAAATTTGT<br>CTTTTAG |
| 80 | Short WPRE sequence | AATCAACCTCTGGATTACAAAATTTGTGAAAGATTGACTGA<br>TATTCTTAACTATGTTGCTCCTTTTACGCTGTGTGGATATGC<br>TGCTTTAATGCCTCTGTATCATGCTATTGCTTCCCGTACGGC<br>TTTCGTTTTCTCCTCCTTGTATAAATCCTGGTTGCTGTCTCTT<br>TATGAGGAGTTGTGGCCCGTTGTCCGTCAACGTGGCGTGGT<br>GTGCTCTGTGTTTGCTGACGCAACCCCCACTGGCTGGGGCA<br>TTGCCACCACCTGTCAACTCCTTTCTGGGACTTTCGCTTTCC<br>CCCTCCCGATCGCCACGGCAGAACTCATCGCCGCCTGCCTT<br>GCCCGCTGCTGGACAGGGGCTAGGTTGCTGGGCACTGATA<br>ATTCCGTGGTGTTGTC |
| 81 | Primer | TAAGCAGAATTCATGAATTTGCCAGGAAGAT |
| 82 | Primer | CCATACAATGAATGGACACTAGGCGGCCGCACGAAT |

-continued

| SEQ ID NO: | Description | Sequence |
|---|---|---|
| 83 | Gag, Pol, Integrase fragment | GAATTCATGAATTTGCCAGGAAGATGGAAACCAAAAATGA TAGGGGGAATTGGAGGTTTTATCAAAGTAAGACAGTATGA TCAGATACTCATAGAAATCTGCGGACATAAAGCTATAGGT ACAGTATTAGTAGGACCTACACCTGTCAACATAATTGGAA GAAATCTGTTGACTCAGATTGGCTGCACTTTAAATTTTCCC ATTAGTCCTATTGAGACTGTACCAGTAAAATTAAAGCCAGG AATGGATGGCCCAAAAGTTAAACAATGGCCATTGACAGAA GAAAAAATAAAAGCATTAGTAGAAATTTGTACAGAAATGG AAAAGGAAGGAAAAATTTCAAAAATTGGGCCTGAAAATCC ATACAATACTCCAGTATTTGCCATAAAGAAAAAAGACAGT ACTAAATGGAGAAAATTAGTAGATTTCAGAGAACTTAATA AGAGAACTCAAGATTTCTGGGAAGTTCAATTAGGAATACC ACATCCTGCAGGGTTAAAACAGAAAAAATCAGTAACAGTA CTGGATGTGGGCGATGCATATTTTTCAGTTCCCTTAGATAA AGACTTCAGGAAGTATACTGCATTTACCATACCTAGTATAA ACAATGAGACACCAGGGATTAGATATCAGTACAATGTGCT TCCACAGGGATGGAAAGGATCACCAGCAATATTCCAGTGT AGCATGACAAAAATCTTAGAGCCTTTTAGAAAACAAAATC CAGACATAGTCATCTATCAATACATGGATGATTTGTATGTA GGATCTGACTTAGAAATAGGGCAGCATAGAACAAAAATAG AGGAACTGAGACAACATCTGTTGAGGTGGGGATTTACCAC ACCAGACAAAAAACATCAGAAAGAACCTCCATTCCTTTGG ATGGGTTATGAACTCCATCCTGATAAATGGACAGTACAGCC TATAGTGCTGCCAGAAAAGGACAGCTGGACTGTCAATGAC ATACAGAAATTAGTGGGAAAATTGAATTGGGCAAGTCAGA TTTATGCAGGGATTAAAGTAAGGCAATTATGTAAACTTCTT AGGGGAACCAAAGCACTAACAGAAGTAGTACCACTAACAG AAGAAGCAGAGCTAGAACTGGCAGAAAACAGGGAGATTCT AAAAGAACCGGTACATGGAGTGTATTATGACCCATCAAAA GACTTAATAGCAGAAATACAGAAGCAGGGGCAAGGCCAAT GGACATATCAAATTTATCAAGAGCCATTTAAAAATCTGAA AACAGGAAAGTATGCAAGAATGAAGGGTGCCCACACTAAT GATGTGAAACAATTAACAGAGGCAGTACAAAAAATAGCCA CAGAAAGCATAGTAATATGGGGAAAGACTCCTAAATTTAA ATTACCCATACAAAAGGAAACATGGGAAGCATGGTGGACA GAGTATTGGCAAGCCACCTGGATTCCTGAGTGGGAGTTTGT CAATACCCCTCCCTTAGTGAAGTTATGGTACCAGTTAGAGA AAGAACCCATAATAGGAGCAGAAACTTTCTATGTAGATGG GGCAGCCAATAGGGAAACTAAATTAGGAAAAGCAGGATAT GTAACTGACAGAGGAAGACAAAAAGTTGTCCCCCTAACGG ACACAACAAATCAGAAGACTGAGTTACAAGCAATTCATCT AGCTTTGCAGGATTCGGGATTAGAAGTAAACATAGTGACA GACTCACAATATGCATTGGGAATCATTCAAGCACAACCAG ATAAGAGTGAATCAGAGTTAGTCAGTCAAATAATAGAGCA GTTAATAAAAAAGGAAAAAGTCTACCTGGCATGGGTACCA GCACACAAAGGAATTGGAGGAAATGAACAAGTAGATAAAT TGGTCAGTGCTGGAATCAGGAAAGTACTATTTTTAGATGGA ATAGATAAGGCCCAAGAAGAACATGAGAAATATCACAGTA ATTGGAGAGCAATGGCTAGTGATTTTAACCTACCACCTGTA GTAGCAAAAGAAATAGTAGCCAGCTGTGATAAATGTCAGC TAAAAGGGGAAGCCATGCATGGACAAGTAGACTGTAGCCC AGGAATATGGCAGCTAGATTGTACACATTTAGAAGGAAAA GTTATCTTGGTAGCAGTTCATGTAGCCAGTGGATATATAGA AGCAGAAGTAATTCCAGCAGAGACAGGGCAAGAAACAGC ATACTTCCTCTTAAAATTAGCAGGAAGATGGCCAGTAAAA ACAGTACATACAGACAATGGCAGCAATTTCACCAGTACTA CAGTTAAGGCCGCCTGTTGGTGGGCGGGATCAAGCAGGA ATTTGGCATTCCCTACAATCCCCAAAGTCAAGGAGTAATAG AATCTATGAATAAAGAATTAAAGAAAATTATAGGACAGGT AAGAGATCAGGCTGAACATCTTAAGACAGCAGTACAAATG GCAGTATTCATCCACAATTTTAAAAGAAAAGGGGGGATTG GGGGGTACAGTGCAGGGGAAAGAATAGTAGACATAATAGC AACAGACATACAAACTAAAGAATTACAAAAACAAATTACA AAAATTCAAAATTTTCGGGTTTATTACAGGGACAGCAGAG ATCCAGTTTGGAAAGGACCAGCAAAGCTCCTCTGGAAAGG TGAAGGGGCAGTAGTAATACAAGATAATAGTGACATAAAA GTAGTGCCAAGAAGAAAAGCAAAGATCATCAGGGATTATG GAAAACAGATGGCAGGTGATGATTGTGTGGCAAGTAGACA GGATGAGGATTAA |

| SEQ ID NO: | Description | Sequence |
|---|---|---|
| 84 | DNA Fragment containing Rev, RRE and rabbit beta globin poly A | TCTAGAATGGCAGGAAGAAGCGGAGACAGCGACGAAGAG CTCATCAGAACAGTCAGACTCATCAAGCTTCTCTATCAAAG CAACCCACCTCCCAATCCCGAGGGGACCCGACAGGCCCGA AGGAATAGAAGAAGAAGGTGGAGAGAGAGACAGAGACAG ATCCATTCGATTAGTGAACGGATCCTTGGCACTTATCTGGG ACGATCTGCGGAGCCTGTGCCTCTTCAGCTACCACCGCTTG AGAGACTTACTCTTGATTGTAACGAGGATTGTGGAACTTCT GGGACGCAGGGGGTGGGAAGCCCTCAAATATTGGTGGAAT CTCCTACAATATTGGAGTCAGGAGCTAAAGAATAGAGGAG CTTTGTTCCTTGGGTTCTTGGGAGCAGCAGGAAGCACTATG GGCGCAGCGTCAATGACGCTGACGGTACAGGCCAGACAAT TATTGTCTGGTATAGTGCAGCAGCAGAACAATTTGCTGAGG GCTATTGAGGCGCAACAGCATCTGTTGCAACTCACAGTCTG GGGCATCAAGCAGCTCCAGGCAAGAATCCTGGCTGTGGAA AGATACCTAAAGGATCAACAGCTCCTAGATCTTTTTCCCTC TGCCAAAAATTATGGGGACATCATGAAGCCCCTTGAGCAT CTGACTTCTGGCTAATAAAGGAAATTTATTTTCATTGCAAT AGTGTGTTGGAATTTTTTGTGTCTCTCACTCGGAAGGACAT ATGGGAGGGCAAATCATTTAAAACATCAGAATGAGTATTT GGTTTAGAGTTTGGCAACATATGCCATATGCTGGCTGCCAT GAACAAAGGTGGCTATAAAGAGGTCATCAGTATATGAAAC AGCCCCCTGCTGTCCATTCCTTATTCCATAGAAAAGCCTTG ACTTGAGGTTAGATTTTTTTTATATTTTGTTTTGTGTTATTTT TTTCTTTAACATCCCTAAAATTTTCCTTACATGTTTTACTAG CCAGATTTTTCCTCCTCTCCTGACTACTCCCAGTCATAGCTG TCCCTCTTCTCTTATGAAGATCCCTCGACCTGCAGCCCAAG CTTGGCGTAATCATGGTCATAGCTGTTTCCTGTGTGAAATT GTTATCCGCTCACAATTCCACACAACATACGAGCCGGAAG CATAAAGTGTAAAGCCTGGGGTGCCTAATGAGTGAGCTAA CTCACATTAATTGCGTTGCGCTCACTGCCCGCTTTCCAGTC GGGAAACCTGTCGTGCCAGCGGATCCGCATCTCAATTAGTC AGCAACCATAGTCCCGCCCCTAACTCCGCCCATCCCGCCCC TAACTCCGCCCAGTTCCGCCCATTCTCCGCCCCATGGCTGA CTAATTTTTTTATTTATGCAGAGGCCGAGGCCGCCTCGGC CTCTGAGCTATTCCAGAAGTAGTGAGGAGGCTTTTTTGGAG GCCTAGGCTTTTGCAAAAAGCTAACTTGTTTATTGCAGCTT ATAATGGTTACAAATAAAGCAATAGCATCACAAATTTCAC AAATAAAGCATTTTTTCACTGCATTCTAGTTGTGGTTTGTC CAAACTCATCAATGTATCTTATCAGCGGCCGCCCCGGG |
| 85 | DNA fragment containing the CAG enhancer/ promoter/intron sequence | ACGCGTTAGTTATTAATAGTAATCAATTACGGGGTCATTAG TTCATAGCCCATATATGGAGTTCCGCGTTACATAACTTACG GTAAATGGCCCGCCTGGCTGACCGCCCAACGACCCCCGCC CATTGACGTCAATAATGACGTATGTTCCCATAGTAACGCCA ATAGGGACTTTCCATTGACGTCAATGGGTGGACTATTTACG GTAAACTGCCCACTTGGCAGTACATCAAGTGTATCATATGC CAAGTACGCCCCCTATTGACGTCAATGACGGTAAATGGCCC GCCTGGCATTATGCCCAGTACATGACCTTATGGGACTTTCC TACTTGGCAGTACATCTACGTATTAGTCATCGCTATTACCA TGGGTCGAGGTGAGCCCCACGTTCTGCTTCACTCTCCCCAT CTCCCCCCCCTCCCCACCCCCAATTTTGTATTTATTTATTTT TTAATTATTTTGTGCAGCGATGGGGGCGGGGGGGGGGGG GCGCGCGCCAGGCGGGGCGGGCGGGCGAGGGGCGGGG CGGGGCGAGGCGGAGAGGTGCGGCGGCAGCCAATCAGAG CGGCGCGCTCCGAAAGTTTCCTTTTATGGCGAGGCGGCGGC GGCGGCGGCCCTATAAAAAGCGAAGCGCGCGGCGGGCGG GAGTCGCTGCGTTGCCTTCGCCCCGTGCCCCGCTCCGCGCC GCCTCGCGCCGCCCGCCCCGGCTCTGACTGACCGCGTTACT CCCACAGGTGAGCGGGCGGGACGGCCCTTCTCCTCCGGGC TGTAATTAGCGCTTGGTTTAATGACGGCTCGTTTCTTTTCTG TGGCTGCGTGAAAGCCTTAAAGGGCTCCGGGAGGGCCCTT TGTGCGGGGGGAGCGGCTCGGGGGTGCGTGCGTGTGTG TGTGCGTGGGGAGCGCCGCGTGCGGCCCGCGCTGCCCGGC GGCTGTGAGCGCTGCGGGCGCGGCGCGGGGCTTTGTGCGC TCCGCGTGTGCGCGAGGGGAGCGCGGCCGGGGCGGTGCC CCGCGGTGCGGGGGGCTGCGAGGGGAACAAAGGCTGCGT GCGGGGTGTGTGCGTGGGGGGTGAGCAGGGGGTGTGGGC GCGGCGGTCGGGCTGTAACCCCCCCCTGCACCCCCCTCCCC GAGTTGCTGAGCACGGCCCGGCTTCGGGTGCGGGGCTCCG TGCGGGGCGTGGCGCGGGGCTCGCCGTGCCGGGCGGGGGG TGGCGGCAGGTGGGGGTGCCGGGCGGGGCGGGGCCGCTC GGGCCGGGGAGGGCTCGGGGAGGGGCGCGGCGGCCCCG GAGCGCCGGCGGCTGTCGAGGCGCGGCGAGCCGCAGCCAT TGCCTTTTATGGTAATCGTGCGAGAGGGCGCAGGGACTTCC |

| SEQ ID NO: | Description | Sequence |
|---|---|---|
| | | TTTGTCCCAAATCTGGCGGAGCCGAAATCTGGGAGGCGCC<br>GCCGCACCCCCTCTAGCGGGCGCGGGCGAAGCGGTGCGGC<br>GCCGGCAGGAAGGAAATGGGCGGGGAGGGCCTTCGTGCGT<br>CGCCGCGCCGCCGTCCCCTTCTCCATCTCCAGCCTCGGGGC<br>TGCCGCAGGGGGACGGCTGCCTTCGGGGGGGACGGGGCAG<br>GGCGGGGTTCGGCTTCTGGCGTGTGACCGGCGGGAATTC |
| 86 | DNA fragment containing VSV-G | GAATTCATGAAGTGCCTTTTGTACTTAGCCTTTTTATTCATT<br>GGGGTGAATTGCAAGTTCACCATAGTTTTTCCACACAACCA<br>AAAAGGAAACTGGAAAAATGTTCCTTCTAATTACCATTATT<br>GCCCGTCAAGCTCAGATTTAAATTGGCATAATGACTTAATA<br>GGCACAGCCTTACAAGTCAAAATGCCCAAGAGTCACAAGG<br>CTATTCAAGCAGACGGTTGGATGTGTCATGCTTCCAAATGG<br>GTCACTACTTGTGATTTCCGCTGGTATGGACCGAAGTATAT<br>AACACATTCCATCCGATCCTTCACTCCATCTGTAGAACAAT<br>GCAAGGAAAGCATTGAACAAACGAAACAAGGAACTTGGCT<br>GAATCCAGGCTTCCCTCCTCAAAGTTGTGGATATGCAACTG<br>TGACGGATGCCGAAGCAGTGATTGTCCAGGTGACTCCTCAC<br>CATGTGCTGGTTGATGAATACACAGGAGAATGGGTTGATTC<br>ACAGTTCATCAACGGAAAATGCAGCAATTACATATGCCCC<br>ACTGTCCATAACTCTACAACCTGGCATTCTGACTATAAGGT<br>CAAAGGGCTATGTGATTCTAACCTCATTTCCATGGACATCA<br>CCTTCTTCTCAGAGGACGGAGAGCTATCATCCCTGGGAAAG<br>GAGGGCACAGGGTTCAGAAGTAACTACTTTGCTTATGAAA<br>CTGGAGGCAAGGCCTGCAAAATGCAATACTGCAAGCATTG<br>GGGAGTCAGACTCCCATCAGGTGTCTGGTTCGAGATGGCTG<br>ATAAGGATCTCTTTGCTGCAGCCAGATTCCCTGAATGCCCA<br>GAAGGGTCAAGTATCTCTGCTCCATCTCAGACCTCAGTGGA<br>TGTAAGTCTAATTCAGGACGTTGAGAGGATCTTGGATTATT<br>CCCTCTGCCAAGAAACCTGGAGCAAAATCAGAGCGGGTCT<br>TCCAATCTCTCCAGTGGATCTCAGCTATCTTGCTCCTAAAA<br>ACCCAGGAACCGGTCCTGCTTTCACCATAATCAATGGTACC<br>CTAAAATACTTTGAGACCAGATACATCAGAGTCGATATTGC<br>TGCTCCAATCCTCTCAAGAATGGTCGGAATGATCAGTGGAA<br>CTACCACAGAAAGGGAACTGTGGGATGACTGGGCACCATA<br>TGAAGACGTGGAAATTGGACCCAATGGAGTTCTGAGGACC<br>AGTTCAGGATATAAGTTTCCTTTATACATGATTGGACATGG<br>TATGTTGGACTCCGATCTTCATCTTAGCTCAAAGGCTCAGG<br>TGTTCGAACATCCTCACATTCAAGACGCTGCTTCGCAACTT<br>CCTGATGATGAGAGTTTATTTTTGGTGATACTGGGCTATC<br>CAAAAATCCAATCGAGCTTGTAGAAGGTTGGTTCAGTAGTT<br>GGAAAAGCTCTATTGCCTCTTTTTTCTTTATCATAGGGTTAA<br>TCATTGGACTATTCTTGGTTCTCCGAGTTGGTATCCATCTTT<br>GCATTAAATTAAAGCACACCAAGAAAAGACAGATTTATAC<br>AGACATAGAGATGAGAATTC |
| 87 | Helper plasmid containing RRE and rabbit beta globin poly A | TCTAGAAGGAGCTTTGTTCCTTGGGTTCTTGGGAGCAGCAG<br>GAAGCACTATGGGCGCAGCGTCAATGACGCTGACGGTACA<br>GGCCAGACAATTATTGTCTGGTATAGTGCAGCAGCAGAAC<br>AATTTGCTGAGGGCTATTGAGGCGCAACAGCATCTGTTGCA<br>ACTCACAGTCTGGGGCATCAAGCAGCTCCAGGCAAGAATC<br>CTGGCTGTGGAAAGATACCTAAAGGATCAACAGCTCCTAG<br>ATCTTTTTCCCTCTGCCAAAAATTATGGGGACATCATGAAG<br>CCCCTTGAGCATCTGACTTCTGGCTAATAAAGGAAATTTAT<br>TTTCATTGCAATAGTGTGTTGGAATTTTTTGTGTCTCTCACT<br>CGGAAGGACATATGGGAGGGCAAATCATTTAAAACATCAG<br>AATGAGTATTTGGTTTAGAGTTTGGCAACATATGCCATATG<br>CTGGCTGCCATGAACAAAGGTGGCTATAAAGAGGTCATCA<br>GTATATGAAACAGCCCCTGCTGTCCATTCCTTATTCCATA<br>GAAAAGCCTTGACTTGAGGTTAGATTTTTTTATATTTTGTT<br>TTGTGTTATTTTTTCTTTAACATCCCTAAAATTTTCCTTAC<br>ATGTTTTACTAGCCAGATTTTTCCTCCTCTCCTGACTACTCC<br>CAGTCATAGCTGTCCCTCTTCTCTTATGAAGATCCCTCGAC<br>CTGCAGCCCAAGCTTGGCGTAATCATGGTCATAGCTGTTTC<br>CTGTGTGAAATTGTTATCCGCTCACAATTCCACACAACATA<br>CGAGCCGGAAGCATAAAGTGTAAAGCCTGGGGTGCCTAAT<br>GAGTGAGCTAACTCACATTAATTGCGTTGCGCTCACTGCCC<br>GCTTTCCAGTCGGGAAACCTGTCGTGCCAGCGGATCCGCAT<br>CTCAATTAGTCAGCAACCATAGTCCCGCCCCTAACTCCGCC<br>CATCCCGCCCCTAACTCCGCCCAGTTCCGCCCATTCTCCGC<br>CCCATGGCTGACTAATTTTTTTATTTATGCAGAGGCCGAG<br>GCCGCCTCGGCCTCTGAGCTATTCCAGAAGTAGTGAGGAG<br>GCTTTTTTGGAGGCCTAGGCTTTTGCAAAAAGCTAACTTGT |

| SEQ ID NO: | Description | Sequence |
|---|---|---|
| | | TTATTGCAGCTTATAATGGTTACAAATAAAGCAATAGCATC<br>ACAAATTTCACAAATAAAGCATTTTTTTCACTGCATTCTAG<br>TTGTGGTTTGTCCAAACTCATCAATGTATCTTATCACCCGG<br>G |
| 88 | RSV promoter and HIV Rev | CAATTGCGATGTACGGGCCAGATATACGCGTATCTGAGGG<br>GACTAGGGTGTGTTTAGGCGAAAAGCGGGGCTTCGGTTGT<br>ACGCGGTTAGGAGTCCCCTCAGGATATAGTAGTTTCGCTTT<br>TGCATAGGGAGGGGAAATGTAGTCTTATGCAATACACTT<br>GTAGTCTTGCAACATGGTAACGATGAGTTAGCAACATGCCT<br>TACAAGGAGAGAAAAGCACCGTGCATGCCGATTGGTGGA<br>AGTAAGGTGGTACGATCGTGCCTTATTAGGAAGGCAACAG<br>ACAGGTCTGACATGGATTGGACGAACCACTGAATTCCGCA<br>TTGCAGAGATAATTGTATTTAAGTGCCTAGCTCGATACAAT<br>AAACGCCATTTGACCATTCACCACATTGGTGTGCACCTCCA<br>AGCTCGAGCTCGTTTAGTGAACCGTCAGATCGCCTGGAGAC<br>GCCATCCACGCTGTTTTGACCTCCATAGAAGACACCGGGAC<br>CGATCCAGCCTCCCCTCGAAGCTAGCGATTAGGCATCTCCT<br>ATGGCAGGAAGAAGCGGAGACAGCGACGAAGAACTCCTC<br>AAGGCAGTCAGACTCATCAAGTTTCTCTATCAAAGCAACCC<br>ACCTCCCAATCCCGAGGGGACCCGACAGGCCCGAAGGAAT<br>AGAAGAAGAAGGTGGAGAGAGAGACAGAGACAGATCCAT<br>TCGATTAGTGAACGGATCCTTAGCACTTATCTGGGACGATC<br>TGCGGAGCCTGTGCCTCTTCAGCTACCACCGCTTGAGAGAC<br>TTACTCTTGATTGTAACGAGGATTGTGGAACTTCTGGGACG<br>CAGGGGGTGGGAAGCCCTCAAATATTGGTGGAATCTCCTA<br>CAATATTGGAGTCAGGAGCTAAAGAATAGTCTAGA |
| 89 | Target sequence | ATGGCAGGAAGAAGCGGAG |
| 90 | shRNA sequence | ATGGCAGGAAGAAGCGGAGTTCAAGAGACTCCGCTTCTTC<br>CTGCCATTTTTT |
| 91 | H1 promoter and shRT sequence | GAACGCTGACGTCATCAACCCGCTCCAAGGAATCGCGGGC<br>CCAGTGTCACTAGGCGGGAACACCCAGCGCGCGTGCGCCC<br>TGGCAGGAAGATGGCTGTGAGGGACAGGGGAGTGGCGCCC<br>TGCAATATTTGCATGTCGCTATGTGTTCTGGGAAATCACCA<br>TAAACGTGAAATGTCTTTGGATTTGGGAATCTTATAAGTTC<br>TGTATGAGACCACTTGGATCCGCGGAGACAGCGACGAAGA<br>GCTTCAAGAGAGCTCTTCGTCGCTGTCTCCGCTTTTT |
| 92 | H1 CCR5 sequence | GAACGCTGACGTCATCAACCCGCTCCAAGGAATCGCGGGC<br>CCAGTGTCACTAGGCGGGAACACCCAGCGCGCGTGCGCCC<br>TGGCAGGAAGATGGCTGTGAGGGACAGGGGAGTGGCGCCC<br>TGCAATATTTGCATGTCGCTATGTGTTCTGGGAAATCACCA<br>TAAACGTGAAATGTCTTTGGATTTGGGAATCTTATAAGTTC<br>TGTATGAGACCACTTGGATCCGTGTCAAGTCCAATCTATGT<br>TCAAGAGACATAGATTGGACTTGACACTTTTT |
| 93 | Primer | AGGAATTGATGGCGAGAAGG |
| 94 | Primer | CCCCAAAGAAGGTCAAGGTAATCA |
| 95 | Primer | AGCGCGGCTACAGCTTCA |
| 96 | Primer | GGCGACGTAGCACAGCTTCT |
| 97 | AGT103 CCR5 miR30 | TGTAAACTGAGCTTGCTCTA |
| 98 | AGT103-R5-1 | TGTAAACTGAGCTTGCTCGC |
| 99 | AGT103-R5-2 | CATAGATTGGACTTGACAC |
| 100 | CAG promoter | TAGTTATTAATAGTAATCAATTACGGGGTCATTAGTTCATA<br>GCCCATATATGGAGTTCCGCGTTACATAACTTACGGTAAAT<br>GGCCCGCCTGGCTGACCGCCCAACGACCCCCGCCCATTGAC<br>GTCAATAATGACGTATGTTCCCATAGTAACGCCAATAGGG<br>ACTTTCCATTGACGTCAATGGGTGGACTATTTACGGTAAAC<br>TGCCCACTTGGCAGTACATCAAGTGTATCATATGCCAAGTA<br>CGCCCCCTATTGACGTCAATGACGGTAAATGGCCCGCCTGG<br>CATTATGCCCAGTACATGACCTTATGGGACTTTCCTACTTG |

| SEQ ID NO: | Description | Sequence |
|---|---|---|
| | | GCAGTACATCTACGTATTAGTCATCGCTATTACCATGGGTC<br>GAGGTGAGCCCCACGTTCTGCTTCACTCTCCCCATCTCCCC<br>CCCCTCCCCACCCCCAATTTTGTATTTATTTATTTTTTAATT<br>ATTTTGTGCAGCGATGGGGGCGGGGGGGGGGGGGCGCGC<br>GCCAGGCGGGGCGGGGCGGGGCGAGGGGCGGGGCGGGGC<br>GAGGCGGAGAGGTGCGGCGGCAGCCAATCAGAGCGGCGC<br>GCTCCGAAAGTTTCCTTTTATGGCGAGGCGGCGGCGGCGGC<br>GGCCCTATAAAAAGCGAAGCGCGCGGCGGGCG |
| 101 | H1 element | GAACGCTGACGTCATCAACCCGCTCCAAGGAATCGCGGGC<br>CCAGTGTCACTAGGCGGGAACACCCAGCGCGCGTGCGCCC<br>TGGCAGGAAGATGGCTGTGAGGGACAGGGGAGTGGCGCCC<br>TGCAATATTTGCATGTCGCTATGTGTTCTGGGAAATCACCA<br>TAAACGTGAAATGTCTTTGGATTTGGGAATCTTATAAGTTC<br>TGTATGAGACCACTT |
| 102 | 3' LTR | TGGAAGGGCTAATTCACTCCCAACGAAGATAAGATCTGCTT<br>TTTGCTTGTACTGGGTCTCTCTGGTTAGACCAGATCTGAGC<br>CTGGGAGCTCTCTGGCTAACTAGGGAACCCACTGCTTAAGC<br>CTCAATAAAGCTTGCCTTGAGTGCTTCAAGTAGTGTGTGCC<br>CGTCTGTTGTGTGACTCTGGTAACTAGAGATCCCTCAGACC<br>CTTTTAGTCAGTGTGGAAAATCTCTAGCAGTAGTAGTTCAT<br>GTCA |
| 103 | 7SK promoter | CTGCAGTATTTAGCATGCCCCACCCATCTGCAAGGCATTCT<br>GGATAGTGTCAAAACAGCCGGAAATCAAGTCCGTTTATCTC<br>AAACTTTAGCATTTTGGGAATAAATGATATTTGCTATGCTG<br>GTTAAATTAGATTTTAGTTAAATTTCCTGCTGAAGCTCTAG<br>TACGATAAGCAACTTGACCTAAGTGTAAAGTTGAGATTTCC<br>TTCAGGTTTATATAGCTTGTGCGCCGCCTGGCTACCTC |
| 104 | miR155 Tat | CTGGAGGCTTGCTGAAGGCTGTATGCTGTCCGCTTCTTCCT<br>GCCATAGGGTTTTGGCCACTGACTGACCCTATGGGAAGA<br>AGCGGACAGGACACAAGGCCTGTTACTAGCACTCACATGG<br>AACAAATGGCC |
| 105 | pRSV Rev | AGCGCCCAATACGCAAACCGCCTCTCCCCGCGCGTTGGCCG<br>ATTCATTAATGCAGCTGGCACGACAGGTTTCCCGACTGGAA<br>AGCGGGCAGTGAGCGCAACGCAATTAATGTGAGTTAGCTC<br>ACTCATTAGGCACCCCAGGCTTTACACTTTATGCTTCCGGC<br>TCGTATGTTGTGTGGAATTGTGAGCGGATAACAATTTCACA<br>CAGGAAACAGCTATGACCATGATTACGAATTCGATGTACG<br>GGCCAGATATACGCGTATCTGAGGGGACTAGGGTGTGTTT<br>AGGCGAAAAGCGGGGCTTCGGTTGTACGCGGTTAGGAGTC<br>CCCTCAGGATATAGTAGTTTCGCTTTTGCATAGGGAGGGGG<br>AAATGTAGTCTTATGCAATACACTTGTAGTCTTGCAACATG<br>GTAACGATGAGTTAGCAACATGCCTTACAAGGAGAGAAAA<br>AGCACCGTGCATGCCGATTGGTGGAAGTAAGGTGGTACGA<br>TCGTGCCTTATTAGGAAGGCAACAGACAGGTCTGACATGG<br>ATTGGACGAACCACTGAATTCCGCATTGCAGAGATAATTGT<br>ATTTAAGTGCCTAGCTCGATACAATAAACGCCATTTGACCA<br>TTCACCACATTGGTGTGCACCTCCAAGCTCGAGCTCGTTTA<br>GTGAACCGTCAGATCGCCTGGAGACGCCATCCACGCTGTTT<br>TGACCTCCATAGAAGACACCGGGACCGATCCAGCCTCCCCT<br>CGAAGCTAGTCGATTAGGCATCTCCTATGGCAGGAAGAAG<br>CGGAGACAGCGACGAAGACCTCCTCAAGGCAGTCAGACTC<br>ATCAAGTTTCTCTATCAAAGCAACCCACCTCCCAATCCCGA<br>GGGGACCCGACAGGCCCGAAGGAATAGAAGAAGAAGGTG<br>GAGAGAGAGACAGAGACAGATCCATTCGATTAGTGAACGG<br>ATCCTTAGCACTTATCTGGGACGATCTGCGGAGCCTGTGCC<br>TCTTCAGCTACCACCGCTTGAGAGACTTACTCTTGATTGTA<br>ACGAGGATTGTGGAACTTCTGGGACGCAGGGGGTGGGAAG<br>CCCTCAAATATTGGTGGAATCTCCTACAATATTGGAGTCAG<br>GAGCTAAAGAATAGTGCTGTTAGCTTGCTCAATGCCACAGC<br>TATAGCAGTAGCTGAGGGGACAGATAGGGTTATAGAAGTA<br>GTACAAGAAGCTTGGCACTGGCCGTCGTTTTACATGATCTG<br>AGCCTGGGAGATCTCTGGCTAACTAGGGAACCCACTGCTTA<br>AGCCTCAATAAAGCTTGCCTTGAGTGCTTCAAGTAGTGTGT<br>GCCCGTCTGTTGTGTGACTCTGGTAACTAGAGATCACAAAG<br>CAACCATAGTACGCGCCCTGTAGCGGCGCATTAAGCGCGG<br>CGGGTGTGGTGGTTACGCGCAGCGTGACCGCTACACTTGCC<br>AGCGCCCTAGCGCCCGCTCCTTTCGCTTTCTTCCCTTCCTTT<br>CTCGCCACGTTCGCCGGCTTTCCCCGTCAAGCTCTAAATCG<br>GGGGCTCCCTTTAGGGTTCCGATTTAGTGCTTTACGGCACC<br>TCGACCCCAAAAAACTTGATTTGGGTGATGGTTCACGTAGT |

-continued

| SEQ ID NO: | Description | Sequence |
|---|---|---|
| | | GGGCCATCGCCCTGATAGACGGTTTTTCGCCCTTTGACGTT GGAGTCCACGTTCTTTAATAGTGGACTCTTGTTCCAAACTG GAACAACACTCAACCCTATCTCGGGCTATTCTTTTGATTTA TAAGGGATTTTGCCGATTTCGGCCTATTGGTTAAAAAATGA GCTGATTTAACAAAAATTTAACGCGAATTTTAACAAAATAT TAACGTTTACAATTTTATGGTGCACTCTCAGTACAATCTGC TCTGATGCCGCATAGTTAAGCCAGCCCCGACACCCGCCAAC ACCCGCTGACGCGCCCTGACGGGCTTGTCTGCTCCCGGCAT CCGCTTACAGACAAGCTGTGACCGTCTCCGGGAGCTGCATG TGTCAGAGGTTTTCACCGTCATCACCGAAACGCGCGAGAC GAAAGGGCCTCGTGATACGCCTATTTTTATAGGTTAATGTC ATGATAATAATGGTTTCTTAGACGTCAGGTGGCACTTTTCG GGGAAATGTGCGCGGAACCCCTATTTGTTTATTTTTCTAAA TACATTCAAATATGTATCCGCTCATGAGACAATAACCCTGA TAAATGCTTCAATAATATTGAAAAAGGAAGAGTATGAGTA TTCAACATTTCCGTGTCGCCCTTATTCCCTTTTTTGCGGCAT TTTGCCTTCCTGTTTTTGCTCACCCAGAAACGCTGGTGAAA GTAAAAGATGCTGAAGATCAGTTGGGTGCACGAGTGGGTT ACATCGAACTGGATCTCAACAGCGGTAAGATCCTTGAGAG TTTTCGCCCCGAAGAACGTTTTCCAATGATGAGCACTTTTA AAGTTCTGCTATGTGGCGCGGTATTATCCCGTATTGACGCC GGGCAAGAGCAACTCGGTCGCCGCATACACTATTCTCAGA ATGACTTGGTTGAGTACTCACCAGTCACAGAAAAGCATCTT ACGGATGGCATGACAGTAAGAGAATTATGCAGTGCTGCCA TAACCATGAGTGATAACACTGCGGCCAACTTACTTCTGACA ACGATCGGAGGACCGAAGGAGCTAACCGCTTTTTTGCACA ACATGGGGGATCATGTAACTCGCCTTGATCGTTGGGAACCG GAGCTGAATGAAGCCATACCAAACGACGAGCGTGACACCA CGATGCCTGTAGCAATGGCAACAACGTTGCGCAAACTATT AACTGGCGAACTACTTACTCTAGCTTCCCGGCAACAATTAA TAGACTGGATGGAGGCGGATAAAGTTGCAGGACCACTTCT GCGCTCGGCCCTTCCGGCTGGCTGGTTTATTGCTGATAAAT CTGGAGCCGGTGAGCGTGGGTCTCGCGGTATCATTGCAGC ACTGGGGCCAGATGGTAAGCCCTCCCGTATCGTAGTTATCT ACACGACGGGGAGTCAGGCAACTATGGATGAACGAAATAG ACAGATCGCTGAGATAGGTGCCTCACTGATTAAGCATTGGT AACTGTCAGACCAAGTTTACTCATATATACTTTAGATTGAT TTAAAACTTCATTTTTAATTTAAAAGGATCTAGGTGAAGAT CCTTTTTGATAATCTCATGACCAAAATCCCTTAACGTGAGT TTTCGTTCCACTGAGCGTCAGACCCCGTAGAAAAGATCAAA GGATCTTCTTGAGATCCTTTTTTTCTGCGCGTAATCTGCTGC TTGCAAACAAAAAAACCACCGCTACCAGCGGTGGTTTGTTT GCCGGATCAAGAGCTACCAACTCTTTTTCCGAAGGTAACTG GCTTCAGCAGAGCGCAGATACCAAATACTGTCCTTCTAGTG TAGCCGTAGTTAGGCCACCACTTCAAGAACTCTGTAGCACC GCCTACATACCTCGCTCTGCTAATCCTGTTACCAGTGGCTG CTGCCAGTGGCGATAAGTCGTGTCTTACCGGGTTGGACTCA AGACGATAGTTACCGGATAAGGCGCAGCGGTCGGGCTGAA CGGGGGGTTCGTGCACACAGCCCAGCTTGGAGCGAACGAC CTACACCGAACTGAGATACCTACAGCGTGAGCTATGAGAA AGCGCCACGCTTCCCGAAGGGAGAAAGGCGGACAGGTATC CGGTAAGCGGCAGGGTCGGAACAGGAGAGCGCACGAGGG AGCTTCCAGGGGGAAACGCCTGGTATCTTTATAGTCCTGTC GGGTTTCGCCACCTCTGACTTGAGCGTCGATTTTTGTGATG CTCGTCAGGGGGGCGGAGCCTATGGAAAAACGCCAGCAAC GCGGCCTTTTTACGGTTCCTGGCCTTTTGCTGGCCTTTTGCT CACATGTTCTTTCCTGCGTTATCCCCTGATTCTGTGGATAAC CGTATTACCGCCTTTGAGTGAGCTGATACCGCTCGCCGCAG CCGAACGACCGAGCGCAGCGAGTCAGTGAGCGAGGAAGC GGAAG |
| 106 | pCMV-VSV-G | GAGCTTGGCCCATTGCATACGTTGTATCCATATCATAATAT GTACATTTATATTGGCTCATGTCCAACATTACCGCCATGTT GACATTGATTATTGACTAGTTATTAATAGTAATCAATTACG GGTCATTAGTTCATAGCCCATATATGGAGTTCCGCGTTAC ATAACTTACGGTAAATGGCCCGCCTGGCTGACCGCCCAAC GACCCCCGCCCATTGACGTCAATAATGACGTATGTTCCCAT AGTAACGCCAATAGGGACTTTCCATTGACGTCAATGGGTG GAGTATTTACGGTAAACTGCCCACTTGGCAGTACATCAAGT GTATCATATGCCAAGTACGCCCCCTATTGACGTCAATGACG GTAAATGGCCCGCCTGGCATTATGCCCAGTACATGACCTTA TGGGACTTTCCTACTTGGCAGTACATCTACGTATTAGTCAT CGCTATTACCATGGTGATGCGGTTTTGGCAGTACATCAATG GGCGTGGATAGCGGTTTGACTCACGGGGATTTCCAAGTCTC CACCCCATTGACGTCAATGGGAGTTTGTTTTGGCACCAAAA |

| SEQ ID NO: Description | Sequence |
|---|---|
| | TCAACGGGACTTTCCAAAATGTCGTAACAACTCCGCCCCAT |
| | TGACGCAAATGGGCGGTAGGCGTGTACGGTGGGAGGTCTA |
| | TATAAGCAGAGCTCGTTTAGTGAACCGTCAGATCGCCTGGA |
| | GACGCCATCCACGCTGTTTTGACCTCCATAGAAGACACCGG |
| | GACCGATCCAGCCTCCGGTCGACCGATCCTGAGAACTTCAG |
| | GGTGAGTTTGGGGACCCTTGATTGTTCTTTCTTTTTCGCTAT |
| | TGTAAAATTCATGTTATATGGAGGGGGCAAAGTTTTCAGGG |
| | TGTTGTTTAGAATGGGAAGATGTCCCTTGTATCACCATGGA |
| | CCCTCATGATAATTTTGTTTCTTTCACTTTCTACTCTGTTGA |
| | CAACCATTGTCTCCTCTTATTTTCTTTTCATTTTCTGTAACTT |
| | TTTCGTTAAACTTTAGCTTGCATTTGTAACGAATTTTTAAAT |
| | TCACTTTTGTTTATTTGTCAGATTGTAAGTACTTTCTCTAAT |
| | CACTTTTTTTTCAAGGCAATCAGGGTATATTATATTGTACTT |
| | CAGCACAGTTTTAGAGAACAATTGTTATAATTAAATGATAA |
| | GGTAGAATATTTCTGCATATAAATTCTGGCTGGCGTGGAAA |
| | TATTCTTATTGGTAGAAACAACTACACCCTGGTCATCATCC |
| | TGCCTTTCTCTTTATGGTTACAATGATATACACTGTTTGAGA |
| | TGAGGATAAAATACTCTGAGTCCAAACCGGGCCCCTCTGCT |
| | AACCATGTTCATGCCTTCTTCTCTTTCCTACAGCTCCTGGGC |
| | AACGTGCTGGTTGTTGTGCTGTCTCATCATTTTGGCAAAGA |
| | ATTCCTCGACGGATCCGCCATGAAGTGCCTTTTGTACTTAG |
| | CCTTTTTATTCATTGGGGTGAATTGCAAGTTCACCATAGTTT |
| | TTCCACACAACCAAAAAGGAAACTGGAAAAATGTTCCTTC |
| | TAATTACCATTATTGCCCGTCAAGCTCAGATTTAAATTGGC |
| | ATAATGACTTAATAGGCACAGCCTTACAAGTCAAAATGCC |
| | CAAGAGTCACAAGGCTATTCAAGCAGACGGTTGGATGTGT |
| | CATGCTTCCAAATGGGTCACTACTTGTGATTTCCGCTGGTA |
| | TGGACCGAAGTATATAACACATTCCATCCGATCCTTCACTC |
| | CATCTGTAGAACAATGCAAGGAAAGCATTGAACAAACGAA |
| | ACAAGGAACTTGGCTGAATCCAGGCTTCCCTCCTCAAAGTT |
| | GTGGATATGCAACTGTGACGGATGCCGAAGCAGTGATTGT |
| | CCAGGTGACTCCTCACCATGTGCTGGTTGATGAATACACAG |
| | GAGAATGGGTTGATTCACAGTTCATCAACGGAAAATGCAG |
| | CAATTACATATGCCCCACTGTCCATAACTCTACAACCTGGC |
| | ATTCTGACTATAAGGTCAAAGGGCTATGTGATTCTAACCTC |
| | ATTTCCATGGACATCACCTTCTTCTCAGAGGACGGAGAGCT |
| | ATCATCCCTGGGAAAGGAGGGCACAGGGTTCAGAAGTAAC |
| | TACTTTGCTTATGAAACTGGAGGCAAGGCCTGCAAAATGC |
| | AATACTGCAAGCATTGGGGAGTCAGACTCCCATCAGGTGT |
| | CTGGTTCGAGATGGCTGATAAGGATCTCTTTGCTGCAGCCA |
| | GATTCCCTGAATGCCCAGAAGGGTCAAGTATCTCTGCTCCA |
| | TCTCAGACCTCAGTGGATGTAAGTCTAATTCAGGACGTTGA |
| | GAGGATCTTGGATTATTCCCTCTGCCAAGAAACCTGGAGCA |
| | AAATCAGAGCGGGTCTTCCAATCTCTCCAGTGGATCTCAGC |
| | TATCTTGCTCCTAAAAACCCAGGAACCGGTCCTGCTTTCAC |
| | CATAATCAATGGTACCCTAAAATACTTTGAGACCAGATACA |
| | TCAGAGTCGATATTGCTGCTCCAATCCTCTCAAGAATGGTC |
| | GGAATGATCAGTGGAACTACCACAGAAAGGGAACTGTGGG |
| | ATGACTGGGCACCATATGAAGACGTGGAAATTGGACCCAA |
| | TGGAGTTCTGAGGACCAGTTCAGGATATAAGTTTCCTTTAT |
| | ACATGATTGGACATGGTATGTTGGACTCCGATCTTCATCTT |
| | AGCTCAAAGGCTCAGGTGTTCGAACATCCTCACATTCAAGA |
| | CGCTGCTTCGCAACTTCCTGATGATGAGAGTTTATTTTTTGG |
| | TGATACTGGGCTATCCAAAAATCCAATCGAGCTTGTAGAA |
| | GGTTGGTTCAGTAGTTGGAAAAGCTCTATTGCCTCTTTTTTC |
| | TTTATCATAGGGTTAATCATTGGACTATTCTTGGTTCTCCGA |
| | GTTGGTATCCATCTTTGCATTAAATTAAAGCACACCAAGAA |
| | AAGACAGATTTATACAGACATAGAGATGAACCGACTTGGA |
| | AAGTGATAAGGATCCGTCGAGGAATTCACTCCTCAGGTGC |
| | AGGCTGCCTATCAGAAGGTGGTGGCTGGTGTGGCCAATGC |
| | CCTGGCTCACAAATACCACTGAGATCTTTTTCCCTCTGCCA |
| | AAAATTATGGGGACATCATGAAGCCCCTTGAGCATCTGACT |
| | TCTGGCTAATAAAGGAAATTTATTTTCATTGCAATAGTGTG |
| | TTGGAATTTTTTGTGTCTCTCACTCGGAAGGACATATGGGA |
| | GGGCAAATCATTTAAAACATCAGAATGAGTATTTGGTTTAG |
| | AGTTTGGCAACATATGCCCATATGCTGGCTGCCATGAACAA |
| | AGGTTGGCTATAAAGAGGTCATCAGTATATGAAACAGCCC |
| | CCTGCTGTCCATTCCTTATTCCATAGAAAAGCCTTGACTTG |
| | AGGTTAGATTTTTTTTATATTTTGTTTTGTGTTATTTTTTCT |
| | TTAACATCCCTAAAATTTTCCTTACATGTTTTACTAGCCAGA |
| | TTTTTCCTCCTCCTGACTACTCCCAGTCATAGCTGTCCCT |
| | CTTCTCTTATGGAGATCCCTCGACGGATCGGCCGCAATTCG |
| | TAATCATGTCATAGCTGTTTCCTGTGTGAAATTGTTATCCGC |
| | TCACAATTCCACACAACATACGAGCCGGAAGCATAAAGTG |
| | TAAAGCCTGGGGTGCCTAATGAGTGAGCTAACTCACATTA |

| SEQ ID NO: | Description | Sequence |
|---|---|---|
| | | ATTGCGTTGCGCTCACTGCCCGCTTTCCAGTCGGGAAACCT<br>GTCGTGCCAGCTGCATTAATGAATCGGCCAACGCGCGGGG<br>AGAGGCGGTTTGCGTATTGGGCGCTCTTCCGCTTCCTCGCT<br>CACTGACTCGCTGCGCTCGGTCGTTCGGCTGCGGCGAGCGG<br>TATCAGCTCACTCAAAGGCGGTAATACGGTTATCCACAGA<br>ATCAGGGGATAACGCAGGAAAGAACATGTGAGCAAAAGG<br>CCAGCAAAAGGCCAGGAACCGTAAAAAGGCCGCGTTGCTG<br>GCGTTTTTCCATAGGCTCCGCCCCCCTGACGAGCATCACAA<br>AAATCGACGCTCAAGTCAGAGGTGGCGAAACCCGACAGGA<br>CTATAAAGATACCAGGCGTTTCCCCCTGGAAGCTCCCTCGT<br>GCGCTCTCCTGTTCCGACCCTGCCGCTTACCGGATACCTGT<br>CCGCCTTTCTCCCTTCGGGAAGCGTGGCGCTTTCTCATAGC<br>TCACGCTGTAGGTATCTCAGTTCGGTGTAGGTCGTTCGCTC<br>CAAGCTGGGCTGTGTGCACGAACCCCCCGTTCAGCCCGACC<br>GCTGCGCCTTATCCGGTAACTATCGTCTTGAGTCCAACCCG<br>GTAAGACACGACTTATCGCCACTGGCAGCAGCCACTGGTA<br>ACAGGATTAGCAGAGCGAGGTATGTAGGCGGTGCTACAGA<br>GTTCTTGAAGTGGTGGCCTAACTACGGCTACACTAGAAGA<br>ACAGTATTTGGTATCTGCGCTCTGCTGAAGCCAGTTACCTT<br>CGGAAAAAGAGTTGGTAGCTCTTGATCCGGCAAACAAACC<br>ACCGCTGGTAGCGGTGGTTTTTTTGTTTGCAAGCAGCAGAT<br>TACGCGCAGAAAAAAAGGATCTCAAGAAGATCCTTTGATC<br>TTTTCTACGGGGTCTGACGCTCAGTGGAACGAAAACTCACG<br>TTAAGGGATTTTGGTCATGAGATTATCAAAAAGGATCTTCA<br>CCTAGATCCTTTTAAATTAAAAATGAAGTTTTAAATCAATC<br>TAAAGTATATATGAGTAAACTTGGTCTGACAGTTACCAATG<br>CTTAATCAGTGAGGCACCTATCTCAGCGATCTGTCTATTTC<br>GTTCATCCATAGTTGCCTGACTCCCCGTCGTGTAGATAACT<br>ACGATACGGGAGGGCTTACCATCTGGCCCCAGTGCTGCAA<br>TGATACCGCGAGACCCACGCTCACCGGCTCCAGATTTATCA<br>GCAATAAACCAGCCAGCCGGAAGGGCCGAGCGCAGAAGT<br>GGTCCTGCAACTTTATCCGCCTCCATCCAGTCTATTAATTGT<br>TGCCGGGAAGCTAGAGTAAGTAGTTCGCCAGTTAATAGTTT<br>GCGCAACGTTGTTGCCATTGCTACAGGCATCGTGGTGTCAC<br>GCTCGTCGTTTGGTATGGCTTCATTCAGCTCCGGTTCCCAA<br>CGATCAAGGCGAGTTACATGATCCCCCATGTTGTGCAAAA<br>AAGCGGTTAGCTCCTTCGGTCCTCCGATCGTTGTCAGAAGT<br>AAGTTGGCCGCAGTGTTATCACTCATGGTTATGGCAGCACT<br>GCATAATTCTCTTACTGTCATGCCATCCGTAAGATGCTTTTC<br>TGTGACTGGTGAGTACTCAACCAAGTCATTCTGAGAATAGT<br>GTATGCGGCGACCGAGTTGCTCTTGCCCGGCGTCAATACGG<br>GATAATACCGCGCCACATAGCAGAACTTTAAAAGTGCTCA<br>TCATTGGAAAACGTTCTTCGGGGCGAAAACTCTCAAGGATC<br>TTACCGCTGTTGAGATCCAGTTCGATGTAACCCACTCGTGC<br>ACCCAACTGATCTTCAGCATCTTTTACTTTCACCAGCGTTTC<br>TGGGTGAGCAAAAACAGGAAGGCAAAATGCCGCAAAAAA<br>GGGAATAAGGGCGACACGGAAATGTTGAATACTCATACTC<br>TTCCTTTTTCAATATTATTGAAGCATTTATCAGGGTTATTGT<br>CTCATGAGCGGATACATATTTGAATGTATTTAGAAAAATAA<br>ACAAATAGGGGTTCCGCGCACATTTCCCCGAAAAGTGCCA<br>CCTAAATTGTAAGCGTTAATATTTTGTTAAAATTCGCGTTA<br>AATTTTTGTTAAATCAGCTCATTTTTTAACCAATAGGCCGA<br>AATCGGCAAAATCCCTTATAAATCAAAAGAATAGACCGAG<br>ATAGGGTTGAGTGTTGTTCCAGTTTGGAACAAGAGTCCACT<br>ATTAAAGAACGTGGACTCCAACGTCAAAGGGCGAAAAACC<br>GTCTATCAGGGCGATGGCCCACTACGTGAACCATCACCCTA<br>ATCAAGTTTTTTGGGGTCGAGGTGCCGTAAAGCACTAAATC<br>GGAACCCTAAAGGGAGCCCCCGATTTAGAGCTTGACGGGG<br>AAAGCCGGCGAACGTGGCGAGAAAGGAAGGGAAGAAAGC<br>GAAAGGAGCGGGCGCTAGGGCGCTGGCAAGTGTAGCGGTC<br>ACGCTGCGCGTAACCACCACACCCGCCGCGCTTAATGCGCC<br>GCTACAGGGCGCGTCCCATTCGCCATTCAGGCTGCGCAACT<br>GTTGGGAAGGGCGATCGGTGCGGGCCTCTTCGCTATTACGC<br>CAGCTGGCGAAAGGGGGATGTGCTGCAAGGCGATTAAGTT<br>GGGTAACGCCAGGGTTTTCCCAGTCACGACGTTGTAAAAC<br>GACGGCCAGTGAGCGCGCGTAATACGACTCACTATAGGGC<br>GAATTGGAGCTCCACCGCGGTGGCGGCCGCTCTAGA |
| 107 | PSPAX2 delta Rev | GTCGACATTGATTATTGACTAGTTATTAATAGTAATCAATT<br>ACGGGGTCATTAGTTCATAGCCCATATATGGAGTTCCGCGT<br>TACATAACTTACGGTAAATGGCCCGCCTGGCTGACCGCCCA<br>ACGACCCCCGCCCATTGACGTCAATAATGACGTATGTTCCC<br>ATAGTAACGCCAATAGGGACTTTCCATTGACGTCAATGGGT<br>GGACTATTTACGGTAAACTGCCCACTTGGCAGTACATCAAG<br>TGTATCATATGCCAAGTACGCCCCCTATTGACGTCAATGAC |

| SEQ ID NO: Description | Sequence |
|---|---|
| | GGTAAATGGCCCGCCTGGCATTATGCCCAGTACATGACCTT
ATGGGACTTTCCTACTTGGCAGTACATCTACGTATTAGTCA
TCGCTATTACCATGGGTCGAGGTGAGCCCCACGTTCTGCTT
CACTCTCCCCATCTCCCCCCCCTCCCCACCCCCAATTTTGTA
TTTATTTATTTTTTAATTATTTTGTGCAGCGATGGGGCGGG
GGGGGGGGGGCGCGCGCCAGGCGGGGCGGGGCGGGGCG
AGGGGCGGGGCGGGGCGAGGCGGAGAGGTGCGGCGGCAG
CCAATCAGAGCGGCGCGCTCCGAAAGTTTCCTTTTATGGCG
AGGCGGCGGCGGCGGCGGCCCTATAAAAAGCGAAGCGCGC
GGCGGGCGGGAGTCGCTGCGTTGCCTTCGCCCCGTGCCCCG
CTCCGCGCCGCCTCGCGCCGCCCGCCCGGCTCTGACTGAC
CGCGTTACTCCCACAGGTGAGCGGGCGGGACGGCCCTTCTC
CTCCGGGCTGTAATTAGCGCTTGGTTTAATGACGGCTCGTT
TCTTTTCTGTGGCTGCGTGAAAGCCTTAAAGGGCTCCGGGA
GGGCCCTTTGTGCGGGGGGGAGCGGCTCGGGGGGTGCGTG
CGTGTGTGTGCGTGGGGAGCGCCGCGTGCGGCCCGCGC
TGCCCGGCGGCTGTGAGCGCTGCGGGCGCGGCGCGGGGCT
TTGTGCGCTCCGCGTGTGCGCGAGGGGAGCGCGGCCGGGG
GCGGTGCCCCGCGGTGCGGGGGGCTGCGAGGGGAACAAA
GGCTGCGTGCGGGTGTGTGCGTGGGGGGTGAGCAGGGG
GTGTGGGCGCGGCGGTCGGGCTGTAACCCCCCCTGCACCC
CCCTCCCCGAGTTGCTGAGCACGGCCCGGCTTCGGGTGCGG
GGCTCCGTGCGGGGCGTGGCGCGGGGCTCGCCGTGCCGGG
CGGGGGGTGGCGGCAGGTGGGGGTGCCGGGCGGGGCGGG
GCCGCCTCGGGCCGGGAGGGCTCGGGGAGGGGCGCGGC
GGCCCCGGAGCGCCGGCGGCTGTCGAGGCGCGGCGAGCCG
CAGCCATTGCCTTTTATGGTAATCGTGCGAGAGGGCGCAGG
GACTTCCTTTGTCCCAAATCTGGCGGAGCCGAAATCTGGGA
GGCGCCGCCGCACCCCCTCTAGCGGGCGCGGGCGAAGCGG
TGCGGCGCCGGCAGGAAGGAAATGGGCGGGAGGGCCTTC
GTGCGTCGCCGCGCCGCCGTCCCCTTCTCCATCTCCAGCCT
CGGGGCTGCCGCAGGGGGACGGCTGCCTTCGGGGGGGACG
GGGCAGGGCGGGGTTCGGCTTCTGGCGTGTGACCGGCGGC
TCTAGAGCCTCTGCTAACCATGTTCATGCCTTCTTCTTTTTC
CTACAGCTCCTGGGCAACGTGCTGGTTATTGTGCTGTCTCA
TCATTTTGGCAAAGAATTCGGGCCGGCCGCGTTGACGCGCA
CGGCAAGAGGCGAGGGGCGGCGACTGGTGAGAGATGGGT
GCGAGAGCGTCAGTATTAAGCGGGGGAGAATTAGATCGAT
GGGAAAAAATTCGGTTAAGGCCAGGGGGAAAGAAAAAAT
ATAAATTAAAACATATAGTATGGGCAAGCAGGGAGCTAGA
ACGATTCGCAGTTAATCCTGGCCTGTTAGAAACATCAGAAG
GCTGTAGACAAATACTGGGACAGCTACAACCATCCCTTCA
GACAGGATCAGAAGAACTTAGATCATTATATAATACAGTA
GCAACCCTCTATTGTGTGCATCAAAGGATAGAGATAAAAG
ACACCAAGGAAGCTTTAGACAAGATAGAGGAAGAGCAAA
ACAAAAGTAAGAAAAAAGCACAGCAAGCAGCAGCTGACA
CAGGACACAGCAATCAGGTCAGCCAAAATTACCCTATAGT
GCAGAACATCCAGGGGCAAATGGTACATCAGGCCATATCA
CCTAGAACTTTAAATGCATGGGTAAAAGTAGTAGAAGAGA
AGGCTTTCAGCCCAGAAGTGATACCCATGTTTTCAGCATTA
TCAGAAGGAGCCACCCCACAAGATTTAAACACCATGCTAA
ACACAGTGGGGGACATCAAGCAGCCATGCAAATGTTAAA
AGAGACCATCAATGAGGAAGCTGCAGAATGGGATAGAGTG
CATCCAGTGCATGCAGGGCCTATTGCACCAGGCCAGATGA
GAGAACCAAGGGGAAGTGACATAGCAGGAACTACTAGTAC
CCTTCAGGAACAAATAGGATGGATGACACATAATCCACCT
ATCCCAGTAGGAGAAATCTATAAAAGATGGATAATCCTGG
GATTAAATAAAATAGTAAGAATGTATAGCCCTACCAGCAT
TCTGGACATAAGACAAGGACCAAAGGAACCCTTTAGAGAC
TATGTAGACCGATTCTATAAAACTCTAAGAGCCGAGCAAG
CTTCACAAGAGGTAAAAAATTGGATGACAGAAACCTTGTT
GGTCCAAAATGCGAACCCAGATTGTAAGACTATTTTAAAA
GCATTGGGACCAGGAGCGACACTAGAAGAAATGATGACAG
CATGTCAGGGAGTGGGGGGACCCGGCCATAAAGCAAGAGT
TTTGGCTGAAGCAATGAGCCAAGTAACAAATCCAGCTACC
ATAATGATACAGAAAGGCAATTTTAGGAACCAAAGAAAGA
CTGTTAAGTGTTTCAATTGTGGCAAAGAAGGGCACATAGCC
AAAAATTGCAGGGCCCCTAGGAAAAAGGGCTGTTGGAAAT
GTGGAAAGGAAGGACACCAAATGAAAGATTGTACTGAGAG
ACAGGCTAATTTTTTAGGGAAGATCTGGCCTTCCCACAAGG
GAAGGCCAGGGAATTTTCTTCAGAGCAGACCAGAGCCAAC
AGCCCCACCAGAAGAGAGCTTCAGGTTTGGGGAAGAGACA
ACAACTCCCTCTCAGAAGCAGGAGCCGATAGACAAGGAAC
TGTATCCTTTAGCTTCCCTCAGATCACTCTTTGGCAGCGACC
CCTCGTCACAATAAAGATAGGGGGGCAATTAAAGGAAGCT |

| SEQ ID NO: Description | Sequence |
|---|---|
| | CTATTAGATACAGGAGCAGATGATACAGTATTAGAAGAAA |
| | TGAATTTGCCAGGAAGATGGAAACCAAAAATGATAGGGGG |
| | AATTGGAGGTTTTATCAAAGTAGGACAGTATGATCAGATA |
| | CTCATAGAAATCTGCGGACATAAAGCTATAGGTACAGTATT |
| | AGTAGGACCTACACCTGTCAACATAATTGGAAGAAATCTG |
| | TTGACTCAGATTGGCTGCACTTTAAATTTTCCCATTAGTCCT |
| | ATTGAGACTGTACCAGTAAAATTAAAGCCAGGAATGGATG |
| | GCCCAAAAGTTAAACAATGGCCATTGACAGAAGAAAAAAT |
| | AAAAGCATTAGTAGAAATTTGTACAGAAATGGAAAAGGAA |
| | GGAAAAATTTCAAAAATTGGGCCTGAAAATCCATACAATA |
| | CTCCAGTATTTGCCATAAAGAAAAAAGACAGTACTAAATG |
| | GAGAAAATTAGTAGATTTCAGAGAACTTAATAAGAGAACT |
| | CAAGATTTCTGGGAAGTTCAATTAGGAATACCACATCCTGC |
| | AGGGTTAAAACAGAAAAAATCAGTAACAGTACTGGATGTG |
| | GGCGATGCATATTTTTCAGTTCCCTTAGATAAAGACTTCAG |
| | GAAGTATACTGCATTTACCATACCTAGTATAAACAATGAGA |
| | CACCAGGGATTAGATATCAGTACAATGTGCTTCCACAGGG |
| | ATGGAAAGGATCACCAGCAATATTCCAGTGTAGCATGACA |
| | AAAATCTTAGAGCCTTTTAGAAAACAAAATCCAGACATAG |
| | TCATCTATCAATACATGGATGATTTGTATGTAGGATCTGAC |
| | TTAGAAATAGGGCAGCATAGAACAAAAATAGAGGAACTGA |
| | GACAACATCTGTTGAGGTGGGGATTTACCACACCAGACAA |
| | AAAACATCAGAAAGAACCTCCATTCCTTTGGATGGGTTATG |
| | AACTCCATCCTGATAAATGGACAGTACAGCCTATAGTGCTG |
| | CCAGAAAAGGACAGCTGGACTGTCAATGACATACAGAAAT |
| | TAGTGGGAAAATTGAATTGGGCAAGTCAGATTTATGCAGG |
| | GATTAAAGTAAGGCAATTATGTAAACTTCTTAGGGGAACC |
| | AAAGCACTAACAGAAGTAGTACCACTAACAGAAGAAGCAG |
| | AGCTAGAACTGGCAGAAAACAGGGAGATTCTAAAAGAACC |
| | GGTACATGGAGTGTATTATGACCCATCAAAAGACTTAATA |
| | GCAGAAATACAGAAGCAGGGGCAAGGCCAATGGACATATC |
| | AAATTTATCAAGAGCCATTTAAAAATCTGAAAACAGGAAA |
| | ATATGCAAGAATGAAGGGTGCCCACACTAATGATGTGAAA |
| | CAATTAACAGAGGCAGTACAAAAAATAGCCACAGAAAGCA |
| | TAGTAATATGGGGAAAGACTCCTAAATTTAAATTACCCATA |
| | CAAAAGGAAACATGGGAAGCATGGTGGACAGAGTATTGGC |
| | AAGCCACCTGGATTCCTGAGTGGGAGTTTGTCAATACCCCT |
| | CCCTTAGTGAAGTTATGGTACCAGTTAGAGAAAGAACCCA |
| | TAATAGGAGCAGAAACTTTCTATGTAGATGGGGCAGCCAA |
| | TAGGGAAACTAAATTAGGAAAAGCAGGATATGTAACTGAC |
| | AGAGGAAGACAAAAAGTTGTCCCCCTAACGGACACAACAA |
| | ATCAGAAGACTGAGTTACAAGCAATTCATCTAGCTTTGCAG |
| | GATTCGGGATTAGAAGTAAACATAGTGACAGACTCACAAT |
| | ATGCATTGGGAATCATTCAAGCACAACCAGATAAGAGTGA |
| | ATCAGAGTTAGTCAGTCAAATAATAGAGCAGTTAATAAAA |
| | AAGGAAAAAGTCTACCTGGCATGGGTACCAGCACACAAAG |
| | GAATTGGAGGAAATGAACAAGTAGATGGGTTGGTCAGTGC |
| | TGGAATCAGGAAAGTACTATTTTTAGATGGAATAGATAAG |
| | GCCCAAGAAGAACATGAGAAATATCACAGTAATTGGAGAG |
| | CAATGGCTAGTGATTTTAACCTACCACCTGTAGTAGCAAAA |
| | GAAATAGTAGCCAGCTGTGATAAATGTCAGCTAAAAGGGG |
| | AAGCCATGCATGGACAAGTAGACTGTAGCCCAGGAATATG |
| | GCAGCTAGATTGTACACATTTAGAAGGAAAAGTTATCTTGG |
| | TAGCAGTTCATGTAGCCAGTGGATATATAGAAGCAGAAGT |
| | AATTCCAGCAGAGACAGGGCAAGAAACAGCATACTTCCTC |
| | TTAAAATTAGCAGGAAGATGGCCAGTAAAAACAGTACATA |
| | CAGACAATGGCAGCAATTTCACCAGTACTACAGTTAAGGC |
| | CGCCTGTTGGTGGGCGGGATCAAGCAGGAATTTGGCATT |
| | CCCTACAATCCCCAAAGTCAAGGAGTAATAGAATCTATGA |
| | ATAAAGAATTAAAGAAAATTATAGGACAGGTAAGAGATCA |
| | GGCTGAACATCTTAAGACAGCAGTACAAATGGCAGTATTC |
| | ATCCACAATTTTAAAAGAAAAGGGGGGATTGGGGGGTACA |
| | GTGCAGGGGAAAGAATAGTAGACATAATAGCAACAGACAT |
| | ACAAACTAAAGAATTACAAAAACAAATTACAAAAATTCAA |
| | AATTTTCGGGTTTATTACAGGGACAGCAGAGATCCAGTTTG |
| | GAAAGGACCAGCAAAGCTCCTCTGGAAAGGTGAAGGGGCA |
| | GTAGTAATACAAGATAATAGTGACATAAAAGTAGTGCCAA |
| | GAAGAAAAGCAAAGATCATCAGGGATTATGGAAAACAGAT |
| | GGCAGGTGATGATTGTGTGGCAAGTAGACAGGATGAGGAT |
| | TAACACATGGAATTCTGCAACAACTGCTGTTTATCCATTTC |
| | AGAATTGGAGGAGCTTTGTTCCTTGGGTTCTTGGGAGCAGC |
| | AGGAAGCACTATGGGCGCAGCGTCAATGACGCTGACGGTA |
| | CAGGCCAGACAATTATTGTCTGGTATAGTGCAGCAGCAGA |
| | ACAATTTGCTGAGGGCTATTGAGGCGCAACAGCATCTGTTG |
| | CAACTCACAGTCTGGGGCATCAAGCAGCTCCAGGCAAGAA |

| SEQ ID NO: Description | Sequence |
|---|---|
| | TCCTGGCTGTGGAAAGATACCTAAAGGATCAACAGCTCCT |
| | GGGGATTTGGGGTTGCTCTGGAAAACTCATTTGCACCACTG |
| | CTGTGCCTTGGAATGCTAGTTGGAGTAATAAATCTCTGGAA |
| | CAGATTTGGAATCACACGACCTGGATGGAGTGGGACAGAG |
| | AAAATTAACAATTACACAAGCTTGCTAGCAGATCTTTTTCCC |
| | TCTGCCAAAAATTATGGGGACATCATGAAGCCCCTTGAGC |
| | ATCTGACTTCTGGCTAATAAAGGAAATTTATTTTCATTGCA |
| | ATAGTGTGTTGGAATTTTTTGTGTCTCTCACTCGGAAGGAC |
| | ATATGGGAGGGCAAATCATTTAAAACATCAGAATGAGTAT |
| | TTGGTTTAGAGTTTGGCAACATATGCCATATGCTGGCTGCC |
| | ATGAACAAAGGTGGCTATAAAGAGGTCATCAGTATATGAA |
| | ACAGCCCCTGCTGTCCATTCCTTATTCCATAGAAAAGCCT |
| | TGACTTGAGGTTAGATTTTTTTATATTTTGTTTTGTGTTATT |
| | TTTTTCTTTAACATCCCTAAAATTTTCCTTACATGTTTTACT |
| | AGCCAGATTTTTCCTCCTCTCCTGACTACTCCCAGTCATAGC |
| | TGTCCCTCTTCTCTTATGAAGATCCCTCGACCTGCAGCCCA |
| | AGCTTGGCGTAATCATGGTCATAGCTGTTTCCTGTGTGAAA |
| | TTGTTATCGCTCACAATTCCACACAACATACGAGCCGGAA |
| | GCATAAAGTGTAAAGCCTGGGGTGCCTAATGAGTGAGCTA |
| | ACTCACATTAATTGCGTTGCGCTCACTGCCCGCTTTCCAGT |
| | CGGGAAACCTGTCGTGCCAGCGGATCCGCATCTCAATTAGT |
| | CAGCAACCATAGTCCCGCCCCTAACTCCGCCCATCCCGCCC |
| | CTAACTCCGCCCAGTTCCGCCCATTCTCCGCCCCATGGCTG |
| | ACTAATTTTTTTTATTTATGCAGAGGCCGAGGCCGCCTCGG |
| | CCTCTGAGCTATTCCAGAAGTAGTGAGGAGGCTTTTTTGGA |
| | GGCCTAGGCTTTTGCAAAAAGCTAACTTGTTTATTGCAGCT |
| | TATAATGGTTACAAATAAAGCAATAGCATCACAAATTTCAC |
| | AAATAAAGCATTTTTTTCACTGCATTCTAGTTGTGGTTTGTC |
| | CAAACTCATCAATGTATCTTATCATGTCTGGATCCGCTGCA |
| | TTAATGAATCGGCCAACGCGCGGGGAGAGGCGGTTTGCGT |
| | ATTGGGCGCTCTTCCGCTTCCTCGCTCACTGACTCGCTGCG |
| | CTCGGTCGTTCGGCTGCGGCGAGCGGTATCAGCTCACTCAA |
| | AGGCGGTAATACGGTTATCCACAGAATCAGGGGATAACGC |
| | AGGAAAGAACATGTGAGCAAAAGGCCAGCAAAAGGCCAG |
| | GAACCGTAAAAAGGCCGCGTTGCTGGCGTTTTTCCATAGGC |
| | TCCGCCCCCCTGACGAGCATCACAAAAATCGACGCTCAAG |
| | TCAGAGGTGGCGAAACCCGACAGGACTATAAAGATACCAG |
| | GCGTTTCCCCCTGGAAGCTCCCTCGTGCGCTCTCCTGTTCCG |
| | ACCCTGCCGCTTACCGGATACCTGTCCGCCTTTCTCCCTTCG |
| | GGAAGCGTGGCGCTTTCTCAATGCTCACGCTGTAGGTATCT |
| | CAGTTCGGTGTAGGTCGTTCGCTCCAAGCTGGGCTGTGTGC |
| | ACGAACCCCCCGTTCAGCCCGACCGCTGCGCCTTATCCGGT |
| | AACTATCGTCTTGAGTCCAACCCGGTAAGACACGACTTATC |
| | GCCACTGGCAGCAGCCACTGGTAACAGGATTAGCAGAGCG |
| | AGGTATGTAGGCGGTGCTACAGAGTTCTTGAAGTGGTGGC |
| | CTAACTACGGCTACACTAGAAGGACAGTATTTGGTATCTGC |
| | GCTCTGCTGAAGCCAGTTACCTTCGGAAAAAGAGTTGGTA |
| | GCTCTTGATCCGGCAAACAAACCACCGCTGGTAGCGGTGG |
| | TTTTTTTGTTTGCAAGCAGCAGATTACGCGCAGAAAAAAAG |
| | GATCTCAAGAAGATCCTTTGATCTTTTCTACGGGGTCTGAC |
| | GCTCAGTGGAACGAAAACTCACGTTAAGGGATTTTGGTCAT |
| | GAGATTATCAAAAAGGATCTTCACCTAGATCCTTTTAAATT |
| | AAAAATGAAGTTTTAAATCAATCTAAAGTATATATGAGTA |
| | AACTTGGTCTGACAGTTACCAATGCTTAATCAGTGAGGCAC |
| | CTATCTCAGCGATCTGTCTATTTCGTTCATCCATAGTTGCCT |
| | GACTCCCCGTCGTGTAGATAACTACGATACGGGAGGGCTT |
| | ACCATCTGGCCCCAGTGCTGCAATGATACCGCGAGACCCA |
| | CGCTCACCGGCTCCAGATTTATCAGCAATAAACCAGCCAGC |
| | CGGAAGGGCCGAGCGCAGAAGTGGTCCTGCAACTTTATCC |
| | GCCTCCATCCAGTCTATTAATTGTTGCCGGGAAGCTAGAGT |
| | AAGTAGTTCGCCAGTTAATAGTTTGCGCAACGTTGTTGCCA |
| | TTGCTACAGGCATCGTGGTGTCACGCTCGTCGTTTGGTATG |
| | GCTTCATTCAGCTCCGGTTCCCAACGATCAAGGCGAGTTAC |
| | ATGATCCCCATGTTGTGCAAAAAAGCGGTTAGCTCCTTCG |
| | GTCCTCCGATCGTTGTCAGAAGTAAGTTGGCCGCAGTGTTA |
| | TCACTCATGGTTATGGCAGCACTGCATAATTCTCTTACTGT |
| | CATGCCATCCGTAAGATGCTTTTCTGTGACTGGTGAGTACT |
| | CAACCAAGTCATTCTGAGAATAGTGTATGCGGCGACCGAG |
| | TTGCTCTTGCCCGGCGTCAATACGGGATAATACCGCGCCAC |
| | ATAGCAGAACTTTAAAAGTGCTCATCATTGGAAAACGTTCT |
| | TCGGGGCGAAAACTCTCAAGGATCTTACCGCTGTTGAGATC |
| | CAGTTCGATGTAACCCACTCGTGCACCCAACTGATCTTCAG |
| | CATCTTTTACTTTCACCAGCGTTTCTGGGTGAGCAAAAACA |
| | GGAAGGCAAAATGCCGCAAAAAAGGGAATAAGGGCGACA |
| | CGGAAATGTTGAATACTCATACTCTTCCTTTTTCAATATTAT |

| SEQ ID NO: | Description | Sequence |
|---|---|---|
| | | TGAAGCATTTATCAGGGTTATTGTCTCATGAGCGGATACAT ATTTGAATGTATTTAGAAAAATAAACAAATAGGGGTTCCG CGCACATTTCCCCGAAAAGTGCCACCTG |

While certain of the preferred embodiments of the present invention have been described and specifically exemplified above, it is not intended that the invention be limited to such embodiments. Various modifications may be made thereto without departing from the scope and spirit of the present invention.

What is claimed is:

1. A method of treating cells, the method comprising:
    (a) positively selecting HIV-specific CD4+ T cells from PBMC isolated from a subject infected with HIV;
    (b) contacting the CD4+ T cells with a therapeutically effective amount of a stimulatory agent, wherein the contacting is carried out ex vivo,
       wherein the stimulatory agent comprises a peptide, a mixture of peptides, or a vaccine;
    (c) transducing the CD4+ T cells ex vivo with a viral delivery system encoding at least one genetic element, wherein the at least one genetic element comprises (i) a sequence having at least 90% sequence identity with SEQ ID NO: 6, (ii) a sequence having at least 90% sequence identity with SEQ ID NO: 7, and (iii) a sequence having at least 90% sequence identity with SEQ ID NO: 97, wherein the at least one genetic element does not comprise any small RNA targeting HIV sequences other than Vif and Tat; and
    (d) culturing the transduced CD4+ T cells for at least 1 day.

2. The method of claim 1, further comprising infusing the transduced CD4+ T cells into a subject.

3. The method of claim 1, wherein the stimulatory agent comprises a peptide.

4. The method of claim 3, wherein the peptide comprises a gag peptide.

5. The method of claim 1, wherein the stimulatory agent comprises a vaccine.

6. The method of claim 5, wherein the vaccine comprises a HIV vaccine.

7. The method of claim 6, wherein the HIV vaccine comprises a MVA/HIV62B vaccine or a variant thereof.

8. The method of claim 1, wherein the at least one genetic element comprises at least one microRNA.

9. The method of claim 8, wherein the at least one microRNA comprises a microRNA cluster.

10. The method of claim 1, wherein the at least one genetic element comprises SEQ ID NO: 6, SEQ ID NO: 7, and SEQ ID NO: 97.

11. A method of treating HIV infection in a subject, the method comprising:
    (a) immunizing the subject with an effective amount of a first stimulatory agent;
    (b) purifying peripheral blood mononuclear cells (PBMC) isolated from the subject;
    (c) positively selecting HIV-specific CD4+ T cells from the PBMC;
    (d) contacting the HIV-specific CD4+ T-cells ex vivo with a therapeutically effective amount of a second stimulatory agent,
       wherein the second stimulatory agent comprises a peptide, a mixture of peptides, or a vaccine;
    (e) transducing the HIV-specific CD4+ T-cells ex vivo with a viral delivery system encoding at least one genetic element,
       wherein the at least one genetic element comprises (i) a sequence having at least 90% sequence identity with SEQ ID NO: 6, (ii) a sequence having at least 90% sequence identity with SEQ ID NO: 7, and (iii) a sequence having at least 90% sequence identity with SEQ ID NO: 97, wherein the at least one genetic element does not comprise any small RNA targeting HIV sequences other than Vif and Tat; and
    (f) culturing the transduced HIV-specific CD4+ T-cells for at least 1 day; and
    (q) infusing the transduced HIV-specific CD4+ T-cells into the subject.

12. The method of claim 11, wherein the first and second stimulatory agents are the same.

13. The method of claim 11, wherein at least one of the first and second stimulatory agents comprises a HIV vaccine.

14. The method of claim 13, wherein the HIV vaccine comprises a MVA/HIV62B vaccine or a variant thereof.

15. The method of claim 11, wherein the viral delivery system comprises a lentiviral particle.

16. The method of claim 11, wherein the at least one genetic element comprises SEQ ID NO: 6, SEQ ID NO: 7, and SEQ ID NO: 97.

17. A method of treating HIV infection in a subject, the method comprising:
    (a) immunizing the subject with an effective amount of an HIV vaccine;
    (b) purifying peripheral blood mononuclear cells (PBMC) isolated from the subject;
    (c) positively selecting HIV-specific CD4+ T cells from the PBMC;
    (d) contacting the HIV-specific CD4+ T cells ex vivo with a therapeutically effective amount of a second stimulatory agent,
       wherein the second stimulatory agent comprises a peptide, a mixture of peptides, or a vaccine;
    (e) transducing the HIV-specific CD4+ T cells ex vivo with a viral delivery system encoding at least one genetic element,
       wherein the at least one genetic element comprises (i) a sequence having at least 90% sequence identity with SEQ ID NO: 6, (ii) a sequence having at least 90% sequence identity with SEQ ID NO: 7, and (iii) a sequence having at least 90% sequence identity with SEQ ID NO: 97, wherein the at least one genetic element does not comprise any small RNA targeting HIV sequences other than Vif and Tat; and
    (f) culturing the transduced HIV-specific CD4+ T cells for at least 1 day; and
    (q) infusing the transduced HIV-specific CD4+ T-cells into the subject.

18. The method of claim 17, wherein the at least one genetic element comprises SEQ ID NO: 6, SEQ ID NO: 7, and SEQ ID NO: 97.

* * * * *

SEQUENCE LISTING

<160> NUMBER OF SEQ ID NOS: 110

<210> SEQ ID NO 1
<211> LENGTH: 118
<212> TYPE: DNA
<213> ORGANISM: Artificial Sequence
<220> FEATURE:
<223> OTHER INFORMATION: miR30 CCR5

<400> SEQUENCE: 1
aggtatattg ctgttgacag tgagcgactg taaactgagc ttgctctact gtgaagccac     60
agatgggtag agcaagcaca gtttaccgct gcctactgcc tcggacttca aggggctt     118

<210> SEQ ID NO 2
<211> LENGTH: 116
<212> TYPE: DNA
<213> ORGANISM: Artificial Sequence
<220> FEATURE:
<223> OTHER INFORMATION: miR21 Vif

<400> SEQUENCE: 2
catctccatg gctgtaccac cttgtcgggg gatgtgtact tctgaacttg tgttgaatct     60
catggagttc agaagaacac atccgcactg acattttggt atctttcatc tgacca         116

<210> SEQ ID NO 3
<211> LENGTH: 114
<212> TYPE: DNA
<213> ORGANISM: Artificial Sequence
<220> FEATURE:
<223> OTHER INFORMATION: miR185 Tat

<400> SEQUENCE: 3
gggcctggct cgagcagggg gcgagggatt ccgcttcttc ctgccatagc gtggtcccct     60 ccctatggc aggcagaagc ggcaccttcc ctcccaatga ccgcgtcttc gtcg           114

<210> SEQ ID NO 4
<211> LENGTH: 1104
<212> TYPE: DNA
<213> ORGANISM: Artificial Sequence
<220> FEATURE:
<223> OTHER INFORMATION: Elongation Factor-1 alpha (EF1-alpha) promoter

<400> SEQUENCE: 4
ccggtgccta gagaaggtgg cgcggggtaa actgggaaag tgatgtcgtg tactggctcc     60 gccttttcc cgagggtggg ggagaaccgt atataagtgc agtagtcgcc gtgaacgttc     120
tttttcgcaa cgggtttgcc gccagaacac aggtaagtgc cgtgtgtggt tcccgcgggc     180
ctggcctctt tacgggttat ggcccttgcg tgccttgaat tacttccacg cccctggctg     240

```
cagtacgtga ttcttgatcc cgagcttcgg gttggaagtg ggtgggagag ttcgaggcct      300
tgcgcttaag gagcccctttc gcctcgtgct tgagttgagg cctggcctgg gcgctggggc     360
cgccgcgtgc gaatctggtg gcaccttcgc gcctgtctcg ctgctttcga taagtctcta     420
gccatttaaa attttttgatg acctgctgcg acgctttttt tctggcaaga tagtcttgta    480
aatgcgggcc aagatctgca cactggtatt tcggtttttg gggccgcggg cggcgacggg     540
gcccgtgcgt cccagcgcac atgttcggcg aggcggggcc tgcgagcgcg gccaccgaga     600
atcggacggg ggtagtctca agctggccgg cctgctctgg tgcctggcct cgcgccgccg     660
tgtatcgccc cgccctgggc ggcaaggctg gcccggtcgg caccagttgc gtgagcggaa     720
agatggccgc ttcccggccc tgctgcaggg agctcaaaat ggaggacgcg gcgctcggga     780
gagcgggcgg gtgagtcacc cacacaaagg aaaagggcct ttccgtcctc agccgtcgct     840
tcatgtgact ccacggagta ccgggcgccg tccaggcacc tcgattagtt ctcgagcttt     900
tggagtacgt cgtctttagg ttgggggggag gggtttttatg cgatggagtt tccccacact   960
gagtgggtgg agactgaagt taggccagct tggcacttga tgtaattctc cttgaatttt    1020
gccctttttg agtttggatc ttggttcatt ctcaagcctc agacagtggt tcaaagtttt   1080
tttcttccat ttcaggtgtc gtga                                           1104
```

<210> SEQ ID NO 5
<211> LENGTH: 18
<212> TYPE: DNA
<213> ORGANISM: Artificial Sequence
<220> FEATURE:
<223> OTHER INFORMATION: CCR5 target sequence

<400> SEQUENCE: 5

```
gagcaagctc agtttaca                                                    18
```

<210> SEQ ID NO 6
<211> LENGTH: 21
<212> TYPE: DNA
<213> ORGANISM: Artificial Sequence
<220> FEATURE:
<223> OTHER INFORMATION: Vif target sequence

<400> SEQUENCE: 6

```
gggatgtgta cttctgaact t                                                21
```

<210> SEQ ID NO 7
<211> LENGTH: 20
<212> TYPE: DNA
<213> ORGANISM: Artificial Sequence
<220> FEATURE:
<223> OTHER INFORMATION: Tat target sequence

<400> SEQUENCE: 7

```
tccgcttctt cctgccatag                                                  20
```

<210> SEQ ID NO 8
<211> LENGTH: 126
<212> TYPE: DNA
<213> ORGANISM: Artificial Sequence
<220> FEATURE:
<223> OTHER INFORMATION: TAR decoy sequence

<400> SEQUENCE: 8

```
cttgcaatga tgtcgtaatt tgcgtcttac ctcgttctcg acagcgacca gatctgagcc      60
tgggagctct ctggctgtca gtaagctggt acagaaggtt gacgaaaatt cttactgagc     120
``` aagaaa                                                          126

<210> SEQ ID NO 9
<211> LENGTH: 21
<212> TYPE: DNA
<213> ORGANISM: Artificial Sequence
<220> FEATURE:
<223> OTHER INFORMATION: Rev/Tat target sequence

<400> SEQUENCE: 9
gcggagacag cgacgaagag c                                          21

<210> SEQ ID NO 10
<211> LENGTH: 56
<212> TYPE: DNA
<213> ORGANISM: Artificial Sequence
<220> FEATURE:
<223> OTHER INFORMATION: Rev/Tat shRNA sequence

<400> SEQUENCE: 10
gcggagacag cgacgaagag cttcaagaga gctcttcgtc gctgtctccg cttttt     56

<210> SEQ ID NO 11
<211> LENGTH: 19
<212> TYPE: DNA
<213> ORGANISM: Artificial Sequence
<220> FEATURE:
<223> OTHER INFORMATION: Gag target sequence

<400> SEQUENCE: 11
gaagaaatga tgacagcat                                             19

<210> SEQ ID NO 12
<211> LENGTH: 52
<212> TYPE: DNA
<213> ORGANISM: Artificial Sequence
<220> FEATURE:
<223> OTHER INFORMATION: Gag shRNA sequence

<400> SEQUENCE: 12
gaagaaatga tgacagcatt tcaagagaat gctgtcatca tttcttcttt tt        52

<210> SEQ ID NO 13
<211> LENGTH: 18
<212> TYPE: DNA
<213> ORGANISM: Artificial Sequence
<220> FEATURE:
<223> OTHER INFORMATION: Pol target sequence

<400> SEQUENCE: 13
caggagcaga tgatacag                                              18

<210> SEQ ID NO 14
<211> LENGTH: 47
<212> TYPE: DNA
<213> ORGANISM: Artificial Sequence
<220> FEATURE:
<223> OTHER INFORMATION: Pol shRNA sequence

<400> SEQUENCE: 14
caggagatga tacagttcaa gagactgtat catctgctcc tgttttt              47

<210> SEQ ID NO 15
<211> LENGTH: 19
<212> TYPE: DNA

```
<213> ORGANISM: Artificial Sequence
<220> FEATURE:
<223> OTHER INFORMATION: CCR5 target sequence #1

<400> SEQUENCE: 15
gtgtcaagtc caatctatg                                                19

<210> SEQ ID NO 16
<211> LENGTH: 52
<212> TYPE: DNA
<213> ORGANISM: Artificial Sequence
<220> FEATURE:
<223> OTHER INFORMATION: CCR5 shRNA sequence #1

<400> SEQUENCE: 16
gtgtcaagtc caatctatgt tcaagagaca tagattggac ttgacacttt tt           52

<210> SEQ ID NO 17
<211> LENGTH: 19
<212> TYPE: DNA
<213> ORGANISM: Artificial Sequence
<220> FEATURE:
<223> OTHER INFORMATION: CCR5 target sequence #2

<400> SEQUENCE: 17
gagcatgact gacatctac                                                19

<210> SEQ ID NO 18
<211> LENGTH: 52
<212> TYPE: DNA
<213> ORGANISM: Artificial Sequence
<220> FEATURE:
<223> OTHER INFORMATION: CCR5 shRNA sequence #2

<400> SEQUENCE: 18
gagcatgact gacatctact tcaagagagt agatgtcagt catgctcttt tt           52

<210> SEQ ID NO 19
<211> LENGTH: 19
<212> TYPE: DNA
<213> ORGANISM: Artificial Sequence
<220> FEATURE:
<223> OTHER INFORMATION: CCR5 target sequence #3

<400> SEQUENCE: 19
gtagctctaa caggttgga                                                19

<210> SEQ ID NO 20
<211> LENGTH: 52
<212> TYPE: DNA
<213> ORGANISM: Artificial Sequence
<220> FEATURE:
<223> OTHER INFORMATION: CCR5 shRNA sequence #3

<400> SEQUENCE: 20
gtagctctaa caggttggat tcaagagatc caacctgtta gagctacttt tt           52

<210> SEQ ID NO 21
<211> LENGTH: 19
<212> TYPE: DNA
<213> ORGANISM: Artificial Sequence
<220> FEATURE:
<223> OTHER INFORMATION: CCR5 target sequence #4

<400> SEQUENCE: 21
gttcagaaac tacctctta                                                19
```

<210> SEQ ID NO 22
<211> LENGTH: 52
<212> TYPE: DNA
<213> ORGANISM: Artificial Sequence
<220> FEATURE:
<223> OTHER INFORMATION: CCR5 shRNA sequence #4

<400> SEQUENCE: 22
gttcagaaac tacctcttat tcaagagata agaggtagtt tctgaactttt tt        52

<210> SEQ ID NO 23
<211> LENGTH: 20
<212> TYPE: DNA
<213> ORGANISM: Artificial Sequence
<220> FEATURE:
<223> OTHER INFORMATION: CCR5 target sequence #5

<400> SEQUENCE: 23
gagcaagctc agtttacacc                                              20

<210> SEQ ID NO 24
<211> LENGTH: 54
<212> TYPE: DNA
<213> ORGANISM: Artificial Sequence
<220> FEATURE:
<223> OTHER INFORMATION: CCR5 shRNA sequence #5

<400> SEQUENCE: 24
gagcaagctc agtttacacc ttcaagagag gtgtaaactg agcttgctct tttt        54

<210> SEQ ID NO 25
<211> LENGTH: 141
<212> TYPE: DNA
<213> ORGANISM: Artificial Sequence
<220> FEATURE:
<223> OTHER INFORMATION: CCR5 gene, sequence 1

<400> SEQUENCE: 25
atggattatc aagtgtcaag tccaatctat gacatcaatt attatacatc ggagccctgc  60
caaaaaatca atgtgaagca aatcgcagcc cgcctcctgc ctccgctcta ctcactggtg  120
ttcatctttg gttttgtggg c                                            141

<210> SEQ ID NO 26
<211> LENGTH: 633
<212> TYPE: DNA
<213> ORGANISM: Artificial Sequence
<220> FEATURE:
<223> OTHER INFORMATION: CCR5 gene, sequence 2

<400> SEQUENCE: 26
aacatgctgg tcatcctcat cctgataaac tgcaaaaggc tgaagagcat gactgacatc  60
tacctgctca acctggccat ctctgacctg ttttcctc ttactgtccc cttctgggct  120
cactatgctg ccgcccagtg ggactttgga atacaatgt gtcaactctt gacagggctc  180
tattttatag gcttcttctc tggaatcttc ttcatcatcc tcctgacaat cgataggtac  240
ctggctgtcg tccatgctgt gtttgcttta aaagccagga cggtcacctt tggggtggtg  300
acaagtgtga tcacttgggt ggtggctgtg tttgcgtctc tcccaggaat catctttacc  360
agatctcaaa aagaaggtct tcattacacc tgcagctctc attttccata cagtcagtat  420
caattctgga agaatttcca gacattaaag atagtcatct tggggctggt cctgccgctg  480

```
cttgtcatgg tcatctgcta ctcgggaatc ctaaaaactc tgcttcggtg tcgaaatgag    540
aagaagaggc acagggctgt gaggcttatc ttcaccatca tgattgttta ttttctcttc    600
tgggctccct acaacattgt ccttctcctg aac                                 633
```

```
<210> SEQ ID NO 27
<211> LENGTH: 70
<212> TYPE: DNA
<213> ORGANISM: Artificial Sequence
<220> FEATURE:
<223> OTHER INFORMATION: CCR5 gene, sequence 3

<400> SEQUENCE: 27
accttccagg aattctttgg cctgaataat tgcagtagct ctaacaggtt ggaccaagct     60
atgcaggtga                                                           70
```

```
<210> SEQ ID NO 28
<211> LENGTH: 140
<212> TYPE: DNA
<213> ORGANISM: Artificial Sequence
<220> FEATURE:
<223> OTHER INFORMATION: CCR5 gene, sequence 4

<400> SEQUENCE: 28
cagagactct tgggatgacg cactgctgca tcaaccccat catctatgcc tttgtcgggg     60
agaagttcag aaactacctc ttagtcttct tccaaaagca cattgccaaa cgcttctgca    120
aatgctgttc tattttccag                                                140
```

```
<210> SEQ ID NO 29
<211> LENGTH: 75
<212> TYPE: DNA
<213> ORGANISM: Artificial Sequence
<220> FEATURE:
<223> OTHER INFORMATION: CCR5 gene, sequence 5

<400> SEQUENCE: 29
caagaggctc ccgagcgagc aagctcagtt tacacccgat ccactgggga gcaggaaata     60
tctgtgggct tgtga                                                     75
```

```
<210> SEQ ID NO 30
<211> LENGTH: 541
<212> TYPE: DNA
<213> ORGANISM: Artificial Sequence
<220> FEATURE:
<223> OTHER INFORMATION: CD4 promoter sequence

<400> SEQUENCE: 30
tgttggggtt caaatttgag ccccagctgt tagccctctg caaagaaaaa aaaaaaaaa      60 aaagaacaaa gggcctagat ttcccttctg agccccaccc taagatgaag cctcttcttt    120
caagggagtg gggttgggt ggaggcggat cctgtcagct ttgctctctc tgtggctggc    180
agtttctcca aagggtaaca ggtgtcagct ggctgagcct aggctgaacc ctgagacatg    240
ctacctctgt cttctcatgg ctggaggcag cctttgtaag tcacagaaag tagctgaggg    300
gctctggaaa aaagacagcc agggtggagg tagattggtc tttgactcct gatttaagcc    360
tgattctgct taactttttc ccttgacttt ggcattttca ctttgacatg ttccctgaga    420
gcctgggggg tggggaaccc agctccagct ggtgacgttt gggccggcc caggcctagg    480 gtgtggagga gccttgccat cgggcttcct gtctctcttc atttaagcac gactctgcag    540
a                                                                    541
```

<210> SEQ ID NO 31
<211> LENGTH: 359
<212> TYPE: DNA
<213> ORGANISM: Artificial Sequence
<220> FEATURE:
<223> OTHER INFORMATION: miR30-CCR5/miR21-Vif/miR185 Tat microRNA
      cluster sequence

<400> SEQUENCE: 31
aggtatattg ctgttgacag tgagcgactg taaactgagc ttgctctact gtgaagccac    60
agatgggtag agcaagcaca gtttaccgct gcctactgcc tcggacttca aggggcttcc   120
cgggcatctc catggctgta ccaccttgtc gggggatgtg tacttctgaa cttgtgttga   180
atctcatgga gttcagaaga acacatccgc actgacattt tggtatcttt catctgacca   240
gctagcgggc ctggctcgag caggggggcga gggattccgc ttcttcctgc catagcgtgg   300 tccccctcccc tatggcaggc agaagcggca ccttccctcc caatgaccgc gtcttcgtc   359

<210> SEQ ID NO 32
<211> LENGTH: 590
<212> TYPE: DNA
<213> ORGANISM: Artificial Sequence
<220> FEATURE:
<223> OTHER INFORMATION: Long WPRE sequence

<400> SEQUENCE: 32
aatcaacctc tgattacaaa atttgtgaaa gattgactgg tattcttaac tatgttgctc    60
cttttacgct atgtggatac gctgctttaa tgcctttgta tcatgctatt gcttcccgta   120
tggctttcat tttctcctcc ttgtataaat cctggttgct gtctctttat gaggagttgt   180
ggcccgttgt caggcaacgt ggcgtggtgt gcactgtgtt tgctgacgca accccactg    240 gttggggcat tgccaccacc tgtcagctcc tttccgggac tttcgctttc ccctcccta    300 ttgccacggc ggaactcatc gccgcctgcc ttgcccgctg ctggacaggg gctcggctgt   360
tgggcactga caattccgtg gtgttgtcgg ggaaatcatc gtccttttcct tggctgctcg   420 cctgtgttgc cacctggatt ctgcgcggga cgtccttctg ctacgtccct tcggccctca   480
atccagcgga ccttccttcc cgcggcctgc tgccggctct gcggcctctt ccgcgtcttc   540
gccttcgccc tcagacgagt cggatctccc tttgggccgc ctccccgcct              590

<210> SEQ ID NO 33
<211> LENGTH: 1469
<212> TYPE: DNA
<213> ORGANISM: Artificial Sequence
<220> FEATURE:
<223> OTHER INFORMATION: Elongation Factor-1 alpha (EF1-alpha)
      promoter - miR30CCR5 - miR21Vif - miR185 Tat

<400> SEQUENCE: 33
ccggtgccta gagaaggtgg cgcggggtaa actgggaaag tgatgtcgtg tactggctcc    60
gcctttttcc cgagggtggg ggagaaccgt atataagtgc agtagtcgcc gtgaacgttc   120
tttttcgcaa cgggtttgcc gccagaacac aggtaagtgc cgtgtgtggt tcccgcgggc   180
ctggcctctt tacgggttat ggcccttgcg tgccttgaat tacttccacg cccctggctg   240
cagtacgtga ttcttgatcc cgagcttcgg gttggaagtg ggtgggagag ttcgaggcct   300
tgcgcttaag gagccccttc gcctcgtgct tgagttgagg cctggcctgg gcgctggggc   360
cgccgcgtgc gaatctggtg gcaccttcgc gcctgtctcg ctgctttcga taagtctcta   420

```
gccatttaaa attttttgatg acctgctgcg acgcttttt  tctggcaaga tagtcttgta    480
aatgcgggcc aagatctgca cactggtatt tcggttttg  gggccgcggg cggcgacggg    540
gcccgtgcgt cccagcgcac atgttcggcg aggcggggcc tgcgagcgcg ccaccgaga     600 atcggacggg ggtagtctca agctggccgg cctgctctgg tgcctggcct cgcgccgccg   660
tgtatcgccc cgccctgggc ggcaaggctg gcccggtcgg caccagttgc gtgagcggaa   720
agatggccgc ttcccggccc tgctgcaggg agctcaaaat ggaggacgcg cgctcggga    780 gagcgggcgg gtgagtcacc cacacaaagg aaaagggcct ttccgtcctc agccgtcgct   840
tcatgtgact ccacggagta ccgggcgccg tccaggcacc tcgattagtt ctcgagcttt   900
tggagtacgt cgtctttagg ttgggggag gggttttatg cgatggagtt tccccacact    960
gagtgggtgg agactgaagt taggccagct tggcacttga tgtaattctc cttggaattt  1020
gccctttttg agtttggatc ttggttcatt ctcaagcctc agacagtggt tcaaagtttt  1080
tttcttccat ttcaggtgtc gtgatgtaca aggtatattg ctgttgacag tgagcgactg  1140
taaactgagc ttgctctact gtgaagccac agatgggtag agcaagcaca gtttaccgct  1200
gcctactgcc tcggacttca aggggcttcc cgggcatctc catggctgta ccaccttgtc  1260
gggggatgtg tacttctgaa cttgtgttga atctcatgga gttcagaaga acacatccgc  1320
actgacattt tggtatcttt catctgacca gctagcgggc ctggctcgag caggggggcga 1380 gggattccgc ttcttcctgc catagcgtgg tccctcccc tatggcaggc agaagcggca  1440
ccttccctcc caatgaccgc gtcttcgtc                                    1469

<210> SEQ ID NO 34
<211> LENGTH: 228
<212> TYPE: DNA
<213> ORGANISM: Artificial Sequence
<220> FEATURE:
<223> OTHER INFORMATION: Rous Sarcoma virus (RSV) promoter

<400> SEQUENCE: 34
gtagtcttat gcaatactct tgtagtcttg caacatggta acgatgagtt agcaacatgc   60
cttacaagga gagaaaaagc accgtgcatg ccgattggtg gaagtaaggt ggtacgatcg  120
tgccttatta ggaaggcaac agacgggtct gacatggatt ggacgaacca ctgaattgcc  180
gcattgcaga gatattgtat ttaagtgcct agctcgatac aataaacg                228

<210> SEQ ID NO 35
<211> LENGTH: 180
<212> TYPE: DNA
<213> ORGANISM: Artificial Sequence
<220> FEATURE:
<223> OTHER INFORMATION: 5' Long terminal repeat (LTR)

<400> SEQUENCE: 35
ggtctctctg gttagaccag atctgagcct gggagctctc tggctaacta gggaacccac   60
tgcttaagcc tcaataaagc ttgccttgag tgcttcaagt agtgtgtgcc cgtctgttgt   120
gtgactctgg taactagaga tccctcagac ccttttagtc agtgtggaaa atctctagca  180

<210> SEQ ID NO 36
<211> LENGTH: 41
<212> TYPE: DNA
<213> ORGANISM: Artificial Sequence
<220> FEATURE:
<223> OTHER INFORMATION: Psi Packaging signal

<400> SEQUENCE: 36
```

```
tacgccaaaa attttgacta gcggaggcta gaaggagaga g                    41
```

<210> SEQ ID NO 37
<211> LENGTH: 233
<212> TYPE: DNA
<213> ORGANISM: Artificial Sequence
<220> FEATURE:
<223> OTHER INFORMATION: Rev response element (RRE)

<400> SEQUENCE: 37

```
aggagctttg ttccttgggt tcttgggagc agcaggaagc actatgggcg cagcctcaat    60
gacgctgacg gtacaggcca gacaattatt gtctggtata gtgcagcagc agaacaattt   120
gctgagggct attgaggcgc aacagcatct gttgcaactc acagtctggg gcatcaagca   180
gctccaggca agaatcctgg ctgtggaaag atacctaaag gatcaacagc tcc          233
```

<210> SEQ ID NO 38
<211> LENGTH: 118
<212> TYPE: DNA
<213> ORGANISM: Artificial Sequence
<220> FEATURE:
<223> OTHER INFORMATION: Central polypurine tract (cPPT)

<400> SEQUENCE: 38

```
ttttaaaaga aaggggggga ttggggggta cagtgcaggg gaaagaatag tagacataat    60
agcaacagac atacaaacta agaattaca aaaacaaatt acaaaattca aaatttta     118
```

<210> SEQ ID NO 39
<211> LENGTH: 250
<212> TYPE: DNA
<213> ORGANISM: Artificial Sequence
<220> FEATURE:
<223> OTHER INFORMATION: 3' delta LTR

<400> SEQUENCE: 39

```
tggaagggct aattcactcc caacgaagat aagatctgct ttttgcttgt actgggtctc    60
tctggttaga ccagatctga gcctgggagc tctctggcta actagggaac ccactgctta   120
agcctcaata aagcttgcct tgagtgcttc aagtagtgtg tgcccgtctg ttgtgtgact   180
ctggtaacta gagatccctc agaccctttt agtcagtgtg aaaatctct agcagtagta   240
gttcatgtca                                                         250
```

<210> SEQ ID NO 40
<211> LENGTH: 352
<212> TYPE: DNA
<213> ORGANISM: Artificial Sequence
<220> FEATURE:
<223> OTHER INFORMATION: Helper/Rev - CMV early (CAG) enhancer -
      Enhance Transcription

<400> SEQUENCE: 40

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggac tatttacggt aaactgccca cttggcagta catcaagtgt atcatatgcc   240
aagtacgccc cctattgacg tcaatgacgg taaatggccc gcctggcatt atgcccagta   300
catgacctta tgggacttc ctacttggca gtacatctac gtattagtca tc            352
```

<210> SEQ ID NO 41
<211> LENGTH: 290
<212> TYPE: DNA
<213> ORGANISM: Artificial Sequence
<220> FEATURE:
<223> OTHER INFORMATION: Helper/Rev - Chicken beta actin (CAG)
      promoter - Transcription

<400> SEQUENCE: 41

```
gctattacca tgggtcgagg tgagccccac gttctgcttc actctcccca tctccccccc      60
ctccccaccc ccaattttgt atttatttat tttttaatta ttttgtgcag cgatggggc      120 gggggggggg gggcgcgcg ccaggcgggg cggggcgggg cgaggggcgg ggcggggcga      180
ggcggagagg tgcggcggca gccaatcaga gcggcgcgct ccgaaagttt ccttttatgg      240
cgaggcggcg gcggcggcgg ccctataaaa agcgaagcgc gcggcgggcg                290
```

<210> SEQ ID NO 42
<211> LENGTH: 960
<212> TYPE: DNA
<213> ORGANISM: Artificial Sequence
<220> FEATURE:
<223> OTHER INFORMATION: Helper/Rev - Chicken beta actin intron -
      Enhance gene expression

<400> SEQUENCE: 42

```
ggagtcgctg cgttgccttc gccccgtgcc ccgctccgcg ccgcctcgcg ccgcccgccc      60
cggctctgac tgaccgcgtt actcccacag gtgagcgggc gggacggccc ttctcctccg     120
ggctgtaatt agcgcttggt ttaatgacgg ctcgtttctt ttctgtggct gcgtgaaagc     180
cttaaagggc tccgggaggg cccttttgtgc gggggggagc ggctcggggg gtgcgtgcgt     240
gtgtgtgtgc gtgggggagcg ccgcgtgcgg cccgcgctgc ccggcggctg tgagcgctgc     300
gggcgcggcg cggggctttg tgcgctccgc gtgtgcgcga ggggagcgcg gccggggggcg     360 gtgccccgcg gtgcgggggg gctgcgaggg gaacaaaggc tgcgtgcggg gtgtgtgcgt     420 ggggggggtga gcaggggggtg tgggcgcggc ggtcgggctg taacccccccc ctgcaccccc     480 ctccccgagt tgctgagcac ggcccggctt cgggtgcggg gctccgtgcg gggcgtggcg     540
cggggctcgc cgtgccgggc gggggggtggc ggcaggtggg ggtgccgggc ggggcggggc     600
cgcctcgggc cggggagggc tcgggggagg ggcgcggcgg ccccggagcg ccggcggctg     660
tcgaggcgcg gcgagccgca gccattgcct tttatggtaa tcgtgcgaga gggcgcaggg     720
acttcctttg tcccaaatct ggcggagccg aaatctggga ggcgccgccg cacccctct     780 agcgggcgcg ggcgaagcgg tgcggcgccg gcaggaagga aatgggcggg gagggccttc     840
gtgcgtcgcc gcgccgccgt cccttctcc atctccagcc tcggggctgc cgcaggggga     900
cggctgcctt cggggggggac ggggcagggc ggggttcggc ttctggcgtg tgaccggcgg     960
```

<210> SEQ ID NO 43
<211> LENGTH: 1503
<212> TYPE: DNA
<213> ORGANISM: Artificial Sequence
<220> FEATURE:
<223> OTHER INFORMATION: Helper/Rev - HIV Gag - Viral capsid

<400> SEQUENCE: 43

```
atgggtgcga gagcgtcagt attaagcggg ggagaattag atcgatggga aaaaattcgg      60
ttaaggccag ggggaaagaa aaaatataaa ttaaaacata tagtatgggc aagcagggag     120
ctagaacgat tcgcagttaa tcctggcctg ttagaaacat cagaaggctg tagacaaata     180
```

| | |
|---|---|
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa aagcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtgcatcc agtgcatgca | 660 |
| gggcctattg caccaggcca gatgagagaa ccaaggggaa gtgacatagc aggaactact | 720 |
| agtacccttc aggaacaaat aggatggatg acacataatc cacctatccc agtaggagaa | 780 |
| atctataaaa gatggataat cctgggatta aataaaatag taagaatgta tagccctacc | 840 |
| agcattctgg acataagaca aggaccaaag gaaccctttta gagactatgt agaccgattc | 900 |
| tataaaactc taagagccga gcaagcttca caagaggtaa aaaattggat gacagaaacc | 960 |
| ttgttggtcc aaaatgcgaa cccagattgt aagactattt taaaagcatt gggaccagga | 1020 |
| gcgacactag aagaaatgat gacagcatgt cagggagtgg ggggacccgg ccataaagca | 1080 |
| agagttttgg ctgaagcaat gagccaagta acaaatccag ctaccataat gatacagaaa | 1140 |
| ggcaatttta ggaaccaaag aaagactgtt aagtgtttca attgtggcaa agaagggcac | 1200 |
| atagccaaaa attgcagggc ccctaggaaa aagggctgtt ggaaatgtgg aaaggaagga | 1260 |
| caccaaatga aagattgtac tgagagacag gctaattttt tagggaagat ctggccttcc | 1320 |
| cacaagggaa ggccagggaa ttttcttcag agcagaccag agccaacagc cccaccagaa | 1380 |
| gagagcttca ggtttgggga agagacaaca actccctctc agaagcagga gccgatagac | 1440 |
| aaggaactgt atcctttagc ttccctcaga tcactctttg gcagcgaccc ctcgtcacaa | 1500 |
| taa | 1503 |

<210> SEQ ID NO 44
<211> LENGTH: 1872
<212> TYPE: DNA
<213> ORGANISM: Artificial Sequence
<220> FEATURE:
<223> OTHER INFORMATION: Helper/Rev - HIV Pol - Protease and reverse
      transcriptase

<400> SEQUENCE: 44

| | |
|---|---|
| atgaatttgc caggaagatg gaaaccaaaa atgataggggg gaattggagg ttttatcaaa | 60 |
| gtaggacagt atgatcagat actcatagaa atctgcggac ataaagctat aggtacagta | 120 |
| ttagtaggac ctacacctgt caacataatt ggaagaaatc tgttgactca gattggctgc | 180 |
| actttaaatt ttcccattag tcctattgag actgtaccag taaaattaaa gccaggaatg | 240 |
| gatggcccaa aagttaaaca atggccattg acagaagaaa aaataaaagc attagtagaa | 300 |
| atttgtacag aaatggaaaa ggaaggaaaa atttcaaaaa ttgggcctga aaatccatac | 360 |
| aatactccag tatttgccat aaagaaaaaa gacagtacta atggagaaaa attagtagat | 420 |
| ttcagagaac ttaataagag aactcaagat ttctgggaag ttcaattagg aataccacat | 480 |
| cctgcagggt taaaacagaa aaaatcagta acagtactgg atgtgggcga tgcatatttt | 540 |
| tcagttccct tagataaaga cttcaggaag tatactgcat ttaccatacc tagtataaac | 600 |
| aatgagacac cagggattag atatcagtac aatgtgcttc cacagggatg gaaaggatca | 660 |

| | |
|---|---|
| ccagcaatat tccagtgtag catgacaaaa atcttagagc cttttagaaa acaaaatcca | 720 |
| gacatagtca tctatcaata catggatgat ttgtatgtag gatctgactt agaaataggg | 780 |
| cagcatagaa caaaaataga ggaactgaga caacatctgt tgaggtgggg atttaccaca | 840 |
| ccagacaaaa aacatcagaa agaacctcca ttcctttgga tgggttatga actccatcct | 900 |
| gataaatgga cagtacagcc tatagtgctg ccagaaaagg acagctggac tgtcaatgac | 960 |
| atacagaaat tagtgggaaa attgaattgg gcaagtcaga tttatgcagg gattaaagta | 1020 |
| aggcaattat gtaaacttct tagggggaacc aaagcactaa cagaagtagt accactaaca | 1080 |
| gaagaagcag agctagaact ggcagaaaac agggagattc taaaagaacc ggtacatgga | 1140 |
| gtgtattatg acccatcaaa agacttaata gcagaaatac agaagcaggg gcaaggccaa | 1200 |
| tggacatatc aaatttatca agagccattt aaaaatctga aaacaggaaa atatgcaaga | 1260 |
| atgaagggtg cccacactaa tgatgtgaaa caattaacag aggcagtaca aaaaatagcc | 1320 |
| acagaaagca tagtaatatg gggaaagact cctaaattta aattacccat acaaaaggaa | 1380 |
| acatgggaag catggtggac agagtattgg caagccacct ggattcctga gtgggagttt | 1440 |
| gtcaataccc ctcccttagt gaagttatgg taccagttag agaaagaacc cataataggga | 1500 |
| gcagaaactt tctatgtaga tggggcagcc aatagggaaa ctaaattagg aaaagcagga | 1560 |
| tatgtaactg acagaggaag acaaaaagtt gtccccctaa cggacacaac aaatcagaag | 1620 |
| actgagttac aagcaattca tctagctttg caggattcgg gattagaagt aaacatagtg | 1680 |
| acagactcac aatatgcatt gggaatcatt caagcacaac cagataagag tgaatcagag | 1740 |
| ttagtcagtc aaataataga gcagttaata aaaaaggaaa aagtctacct ggcatgggta | 1800 |
| ccagcacaca aaggaattgg aggaaatgaa caagtagatg ggttggtcag tgctggaatc | 1860 |
| aggaaagtac ta | 1872 |

<210> SEQ ID NO 45
<211> LENGTH: 867
<212> TYPE: DNA
<213> ORGANISM: Artificial Sequence
<220> FEATURE:
<223> OTHER INFORMATION: Helper Rev - HIV Integrase - Integration of viral RNA

<400> SEQUENCE: 45

| | |
|---|---|
| tttttagatg gaatagataa ggcccaagaa gaacatgaga atatcacag taattggaga | 60 |
| gcaatggcta gtgattttaa cctaccacct gtagtagcaa agaaaatagt agccagctgt | 120 |
| gataaatgtc agctaaaagg ggaagccatg catggacaag tagactgtag cccaggaata | 180 |
| tggcagctag attgtacaca tttagaagga aaagttatct tggtagcagt tcatgtagcc | 240 |
| agtggatata tagaagcaga agtaattcca gcagagacag ggcaagaaac agcatacttc | 300 |
| ctcttaaaat tagcaggaag atggccagta aaaacagtac atacagacaa tggcagcaat | 360 |
| ttcaccagta ctacagttaa ggccgcctgt tggtgggcgg ggatcaagca ggaatttggc | 420 |
| attccctaca atccccaaag tcaaggagta atagaatcta tgaataaaga attaaagaaa | 480 |
| attataggac aggtaagaga tcaggctgaa catcttaaga cagcagtaca atggcagta | 540 |
| ttcatccaca attttaaaag aaaagggggg attgggggggt acagtgcagg ggaaagaata | 600 |
| gtagacataa tagcaacaga catacaaact aaagaattac aaaaacaaat tacaaaaatt | 660 |
| caaaattttc gggtttatta cagggacagc agagatccag tttggaaagg accagcaaag | 720 |
| ctcctctgga aaggtgaagg ggcagtagta atacaagata atagtgacat aaaagtagtg | 780 |

```
ccaagaagaa aagcaaagat catcagggat tatggaaaac agatggcagg tgatgattgt    840
gtggcaagta gacaggatga ggattaa                                        867

<210> SEQ ID NO 46
<211> LENGTH: 234
<212> TYPE: DNA
<213> ORGANISM: Artificial Sequence
<220> FEATURE:
<223> OTHER INFORMATION: Helper/Rev - HIV RRE-  Binds Rev element

<400> SEQUENCE: 46
aggagctttg ttccttgggt tcttgggagc agcaggaagc actatgggcg cagcgtcaat     60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcct          234

<210> SEQ ID NO 47
<211> LENGTH: 351
<212> TYPE: DNA
<213> ORGANISM: Artificial Sequence
<220> FEATURE:
<223> OTHER INFORMATION: Helper/Rev - HIV Rev - Nuclear export and
      stabilize viral mRNA

<400> SEQUENCE: 47
atggcaggaa gaagcggaga cagcgacgaa gaactcctca aggcagtcag actcatcaag     60
tttctctatc aaagcaaccc acctcccaat cccgagggga cccgacaggc ccgaaggaat    120
agaagaagaa ggtggagaga gagacagaga cagatccatt cgattagtga acggatcctt    180
agcacttatc tgggacgatc tgcggagcct gtgcctcttc agctaccacc gcttgagaga    240
cttactcttg attgtaacga ggattgtgga acttctggga cgcagggggt gggaagccct    300
caaatattgg tggaatctcc tacaatattg gagtcaggag ctaagaaata g             351

<210> SEQ ID NO 48
<211> LENGTH: 448
<212> TYPE: DNA
<213> ORGANISM: Artificial Sequence
<220> FEATURE:
<223> OTHER INFORMATION: Helper/Rev - Rabbit beta globin poly A - RNA
      stability

<400> SEQUENCE: 48 agatctttttt ccctctgcca aaaattatgg ggacatcatg aagccccttg agcatctgac     60
ttctggctaa taaaggaaat ttattttcat tgcaatagtg tgttggaatt ttttgtgtct    120
ctcactcgga aggacatatg ggagggcaaa tcatttaaaa catcagaatg agtatttggt    180
ttagagtttg gcaacatatg ccatatgctg gctgccatga acaaaggtgg ctataaagag    240
gtcatcagta tatgaaacag ccccctgctg tccattcctt attccataga aaagccttga    300
cttgaggtta gattttttttt atattttgtt ttgtgttatt tttttcttta acatccctaa    360
aatttccctt acatgtttta ctagccagat ttttcctcct ctcctgacta ctcccagtca    420
tagctgtccc tcttctctta tgaagatc                                       448

<210> SEQ ID NO 49
<211> LENGTH: 352
<212> TYPE: DNA
<213> ORGANISM: Artificial Sequence
<220> FEATURE:
<223> OTHER INFORMATION: Helper - CMV early (CAG) enhancer - Enhance
``` transcription

<400> SEQUENCE: 49

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tc             352
```

<210> SEQ ID NO 50
<211> LENGTH: 290
<212> TYPE: DNA
<213> ORGANISM: Artificial Sequence
<220> FEATURE:
<223> OTHER INFORMATION: Helper - Chicken beta actin (CAG) promoter - Transcription

<400> SEQUENCE: 50

```
gctattacca tgggtcgagg tgagccccac gttctgcttc actctcccca tctcccccc      60
ctccccaccc ccaattttgt atttatttat tttttaatta ttttgtgcag cgatggggc     120
gggggggggg gggcgcgcg ccaggcgggg cggggcgggg cgaggggcgg ggcggggcga     180
ggcggagagg tgcggcggca gccaatcaga gcggcgcgct ccgaaagttt ccttttatgg     240
cgaggcggcg gcggcggcgg ccctataaaa agcgaagcgc gcggcgggcg                290
```

<210> SEQ ID NO 51
<211> LENGTH: 960
<212> TYPE: DNA
<213> ORGANISM: Artificial Sequence
<220> FEATURE:
<223> OTHER INFORMATION: Helper - Chicken beta actin intron - Enhance gene expression

<400> SEQUENCE: 51

```
ggagtcgctg cgttgccttc gccccgtgcc ccgctccgcg ccgcctcgcg ccgcccgccc      60
cggctctgac tgaccgcgtt actcccacag gtgagcgggc gggacggccc ttctcctccg     120
ggctgtaatt agcgcttggt ttaatgacgg ctcgtttctt ttctgtggct gcgtgaaagc     180
cttaaagggc tccgggaggg ccctttgtgc gggggggagc ggctcggggg gtgcgtgcgt     240
gtgtgtgtgc gtggggagcg ccgcgtgcgg ccgcgctgc ccggcggctg tgagcgctgc      300
gggcgcggcg cggggctttg tgcgctccgc gtgtgcgcga ggggagcgcg gccggggcg      360
gtgccccgcg gtgcggggg gctgcgaggg gaacaaaggc tgcgtgcggg gtgtgtgcgt      420
gggggggtga gcaggggtg tgggcgcggc ggtcgggctg taaccccccc ctgcaccccc      480
ctccccgagt tgctgagcac ggcccggctt cgggtgcggg gctccgtgcg gggcgtggcg     540
cggggctcgc cgtgccgggc ggggggtggc ggcaggtggg ggtgccgggc ggggcgggc      600
cgcctcgggc cggggagggc tcgggggagg ggcgcggcgg ccccggagcg ccggcggctg     660
tcgaggcgcg gcgagccgca gccattgcct tttatggtaa tcgtgcgaga gggcgcaggg     720
acttcctttg tcccaaatct ggcggagccg aaatctggga ggcgccgccg cacccctct      780
agcgggcgcg ggcgaagcgg tgcggcgccg gcaggaagga aatgggcggg gagggccttc     840
gtgcgtcgcc gcgccgccgt ccccttctcc atctccagcc tcggggctgc cgcaggggaa     900
cggctgcctt cggggggac ggggcagggc ggggttcggc ttctggcgtg tgaccggcgg      960
```

<210> SEQ ID NO 52
<211> LENGTH: 1503
<212> TYPE: DNA
<213> ORGANISM: Artificial Sequence
<220> FEATURE:
<223> OTHER INFORMATION: Helper - HIV Gag - Viral capsid

<400> SEQUENCE: 52

| | |
|---|---|
| atgggtgcga gagcgtcagt attaagcggg ggagaattag atcgatggga aaaaattcgg | 60 |
| ttaaggccag ggggaaagaa aaatataaa ttaaaacata tagtatgggc aagcagggag | 120 |
| ctagaacgat tcgcagttaa tcctggcctg ttagaaacat cagaaggctg tagacaaata | 180 |
| ctgggacagc tacaaccatc ccttcagaca ggatcagaag aacttagatc attatataat | 240 |
| acagtagcaa ccctctattg tgtgcatcaa aggatagaga taaaagacac caaggaagct | 300 |
| ttagacaaga tagaggaaga gcaaaacaaa agtaagaaaa agcacagca agcagcagct | 360 |
| gacacaggac acagcaatca ggtcagccaa aattacccta tagtgcagaa catccagggg | 420 |
| caaatggtac atcaggccat atcacctaga actttaaatg catgggtaaa agtagtagaa | 480 |
| gagaaggctt tcagcccaga agtgataccc atgttttcag cattatcaga aggagccacc | 540 |
| ccacaagatt taaacaccat gctaaacaca gtggggggac atcaagcagc catgcaaatg | 600 |
| ttaaaagaga ccatcaatga ggaagctgca gaatgggata gagtgcatcc agtgcatgca | 660 |
| gggcctattg caccaggcca gatgagagaa ccaaggggaa gtgacatagc aggaactact | 720 |
| agtacccttc aggaacaaat aggatggatg acacataatc cacctatccc agtaggagaa | 780 |
| atctataaaa gatggataat cctgggatta aataaaatag taagaatgta tagccctacc | 840 |
| agcattctgg acataagaca aggaccaaag gaacccttta gagactatgt agaccgattc | 900 |
| tataaaactc taagagccga gcaagcttca caagaggtaa aaaattggat gacagaaacc | 960 |
| ttgttggtcc aaaatgcgaa cccagattgt aagactattt taaaagcatt gggaccagga | 1020 |
| gcgacactag aagaaatgat gacagcatgt cagggagtgg ggggacccgg ccataaagca | 1080 |
| agagttttgg ctgaagcaat gagccaagta acaaatccag ctaccataat gatacagaaa | 1140 |
| ggcaatttta ggaaccaaag aaagactgtt aagtgtttca attgtggcaa agaagggcac | 1200 |
| atagccaaaa attgcagggc ccctaggaaa aagggctgtt ggaaatgtgg aaaggaagga | 1260 |
| caccaaatga aagattgtac tgagagacag gctaattttt tagggaagat ctggccttcc | 1320 |
| cacaagggaa ggccagggaa ttttcttcag agcagaccag agccaacagc cccaccagaa | 1380 |
| gagagcttca ggtttgggga agagacaaca actccctctc agaagcagga gccgatagac | 1440 |
| aaggaactgt atcctttagc ttccctcaga tcactctttg gcagcgaccc ctcgtcacaa | 1500 |
| taa | 1503 |

<210> SEQ ID NO 53
<211> LENGTH: 1872
<212> TYPE: DNA
<213> ORGANISM: Artificial Sequence
<220> FEATURE:
<223> OTHER INFORMATION: Helper - HIV Pol - Protease and reverse
      transcriptase

<400> SEQUENCE: 53

| | |
|---|---|
| atgaatttgc aggaagatg gaaaccaaaa atgataggg gaattggagg ttttatcaaa | 60 |
| gtaggacagt atgatcagat actcatagaa atctgcggac ataaagctat aggtacagta | 120 |
| ttagtaggac ctacacctgt caacataatt ggaagaaatc tgttgactca gattggctgc | 180 |

```
actttaaatt ttcccattag tcctattgag actgtaccag taaaattaaa gccaggaatg    240
gatggcccaa aagttaaaca atggccattg acagaagaaa aaataaaagc attagtagaa    300
atttgtacag aaatggaaaa ggaaggaaaa atttcaaaaa ttgggcctga aaatccatac    360
aatactccag tatttgccat aaagaaaaaa gacagtacta aatggagaaa attagtagat    420
ttcagagaac ttaataagag aactcaagat ttctgggaag ttcaattagg aataccacat    480
cctgcagggt taaaacagaa aaaatcagta acagtactgg atgtgggcga tgcatatttt    540
tcagttccct tagataaaga cttcaggaag tatactgcat ttaccatacc tagtataaac    600
aatgagacac cagggattag atatcagtac aatgtgcttc cacagggatg aaaggatca    660 ccagcaatat tccagtgtag catgacaaaa atcttagagc cttttagaaa acaaaatcca    720
gacatagtca tctatcaata catggatgat ttgtatgtag gatctgactt agaaataggg    780
cagcatagaa caaaaataga ggaactgaga caacatctgt tgaggtgggg atttaccaca    840
ccagacaaaa aacatcagaa agaacctcca ttcctttgga tgggttatga actccatcct    900
gataaatgga cagtacagcc tatagtgctg ccagaaaagg acagctggac tgtcaatgac    960
atacagaaat tagtgggaaa attgaattgg gcaagtcaga tttatgcagg gattaaagta    1020
aggcaattat gtaaacttct tagggggaacc aaagcactaa cagaagtagt accactaaca    1080
gaagaagcag agctagaact ggcagaaaac agggagattc taaaagaacc ggtacatgga    1140
gtgtattatg acccatcaaa agacttaata gcagaaatac agaagcaggg gcaaggccaa    1200
tggacatatc aaatttatca agagccattt aaaaatctga aaacaggaaa atatgcaaga    1260
atgaagggtg cccacactaa tgatgtgaaa caattaacag aggcagtaca aaaaatagcc    1320
acagaaagca tagtaatatg gggaaagact cctaaattta aattacccat acaaaaggaa    1380
acatgggaag catggtggac agagtattgg caagccacct ggattcctga gtgggagttt    1440
gtcaataccc ctcccttagt gaagttatgg taccagttag agaaagaacc cataatagga    1500
gcagaaactt tctatgtaga tggggcagcc aatagggaaa ctaaattagg aaaagcagga    1560
tatgtaactg acagaggaag acaaaaagtt gtccccctaa cggacacaac aaatcagaag    1620
actgagttac aagcaattca tctagctttg caggattcgg gattagaagt aaacatagtg    1680
acagactcac aatatgcatt gggaatcatt caagcacaac cagataagag tgaatcagag    1740
ttagtcagtc aaataataga gcagttaata aaaaaggaaa aagtctacct ggcatgggta    1800
ccagcacaca aaggaattgg aggaaatgaa caagtagatg ggttggtcag tgctggaatc    1860
aggaaagtac ta                                                        1872
```

<210> SEQ ID NO 54
<211> LENGTH: 867
<212> TYPE: DNA
<213> ORGANISM: Artificial Sequence
<220> FEATURE:
<223> OTHER INFORMATION: Helper - HIV Integrase - Integration of viral
      RNA

<400> SEQUENCE: 54

```
tttttagatg gaatagataa ggcccaagaa gaacatgaga aatatcacag taattggaga     60
gcaatggcta gtgattttaa cctaccacct gtagtagcaa aagaaatagt agccagctgt    120
gataaatgtc agctaaaagg ggaagccatg catggacaag tagactgtag cccaggaata    180
tggcagctag attgtacaca tttagaagga aaagttatct tggtagcagt tcatgtagcc    240
agtggatata tagaagcaga agtaattcca gcagagacag ggcaagaaac agcatacttc    300
```

```
ctcttaaaat tagcaggaag atggccagta aaaacagtac atacagacaa tggcagcaat    360
ttcaccagta ctacagttaa ggccgcctgt tggtgggcgg ggatcaagca ggaatttggc    420
attccctaca atccccaaag tcaaggagta atagaatcta tgaataaaga attaaagaaa    480
attataggac aggtaagaga tcaggctgaa catcttaaga cagcagtaca aatggcagta    540
ttcatccaca attttaaaag aaaagggggg attgggggt acagtgcagg ggaaagaata    600
gtagacataa tagcaacaga catacaaact aaagaattac aaaaacaaat tacaaaaatt    660
caaaattttc gggtttatta cagggacagc agagatccag tttggaaagg accagcaaag    720
ctcctctgga aaggtgaagg ggcagtagta atacaagata atagtgacat aaaagtagtg    780
ccaagaagaa aagcaaagat catcagggat tatggaaaac agatggcagg tgatgattgt    840
gtggcaagta gacaggatga ggattaa                                       867

<210> SEQ ID NO 55
<211> LENGTH: 234
<212> TYPE: DNA
<213> ORGANISM: Artificial Sequence
<220> FEATURE:
<223> OTHER INFORMATION: Helper - HIV RRE - Binds Rev element

<400> SEQUENCE: 55
aggagctttg ttccttgggt tcttgggagc agcaggaagc actatgggcg cagcgtcaat     60
gacgctgacg gtacaggcca gacaattatt gtctggtata gtgcagcagc agaacaattt    120
gctgagggct attgaggcgc aacagcatct gttgcaactc acagtctggg gcatcaagca    180
gctccaggca agaatcctgg ctgtggaaag atacctaaag gatcaacagc tcct          234

<210> SEQ ID NO 56
<211> LENGTH: 448
<212> TYPE: DNA
<213> ORGANISM: Artificial Sequence
<220> FEATURE:
<223> OTHER INFORMATION: Helper - Rabbit beta globin poly A - RNA
      stability

<400> SEQUENCE: 56 agatctttt ccctctgcca aaaattatgg ggacatcatg aagccccttg agcatctgac      60
ttctggctaa taaaggaaat ttattttcat tgcaatagtg tgttggaatt ttttgtgtct    120
ctcactcgga aggacatatg ggagggcaaa tcatttaaaa catcagaatg agtatttggt    180
ttagagtttg gcaacatatg ccatatgctg gctgccatga acaaaggtgg ctataaagag    240
gtcatcagta tatgaaacag ccccctgctg tccattcctt attccataga aaagccttga    300
cttgaggtta gattttttttt atattttgtt ttgtgttatt ttttttcttta acatccctaa    360 aattttcctt acatgtttta ctagccagat ttttcctcct ctcctgacta ctcccagtca    420
tagctgtccc tcttctctta tgaagatc                                       448

<210> SEQ ID NO 57
<211> LENGTH: 351
<212> TYPE: DNA
<213> ORGANISM: Artificial Sequence
<220> FEATURE:
<223> OTHER INFORMATION: Rev - RSV promoter - Transcription

<400> SEQUENCE: 57
atggcaggaa gaagcggaga cagcgacgaa gaactcctca aggcagtcag actcatcaag     60
tttctctatc aaagcaaccc acctcccaat cccgagggga cccgacaggc ccgaaggaat    120
```

```
agaagaagaa ggtggagaga gagacagaga cagatccatt cgattagtga acggatcctt      180
agcacttatc tgggacgatc tgcggagcct gtgcctcttc agctaccacc gcttgagaga      240
cttactcttg attgtaacga ggattgtgga acttctggga cgcaggggt gggaagccct       300 caaatattgg tggaatctcc tacaatattg gagtcaggag ctaaagaata g               351

<210> SEQ ID NO 58
<211> LENGTH: 351
<212> TYPE: DNA
<213> ORGANISM: Artificial Sequence
<220> FEATURE:
<223> OTHER INFORMATION: Rev - HIV Rev- Nuclear export and stabilize
      viral mRNA

<400> SEQUENCE: 58
atggcaggaa gaagcggaga cagcgacgaa gaactcctca aggcagtcag actcatcaag       60
tttctctatc aaagcaaccc acctcccaat cccgagggga cccgacaggc ccgaaggaat      120
agaagaagaa ggtggagaga gagacagaga cagatccatt cgattagtga acggatcctt      180
agcacttatc tgggacgatc tgcggagcct gtgcctcttc agctaccacc gcttgagaga      240
cttactcttg attgtaacga ggattgtgga acttctggga cgcaggggt gggaagccct       300 caaatattgg tggaatctcc tacaatattg gagtcaggag ctaaagaata g               351

<210> SEQ ID NO 59
<211> LENGTH: 450
<212> TYPE: DNA
<213> ORGANISM: Artificial Sequence
<220> FEATURE:
<223> OTHER INFORMATION: Rev- Rabbit beta globin poly A- RNA stability

<400> SEQUENCE: 59 agatctttt ccctctgcca aaaattatgg ggacatcatg aagccccttg agcatctgac        60
ttctggctaa taaaggaaat ttattttcat tgcaatagtg tgttggaatt ttttgtgtct      120
ctcactcgga aggacatatg ggagggcaaa tcatttaaaa catcagaatg agtatttggt      180
ttagagtttg gcaacatatg cccatatgct ggctgccatg aacaaaggtt ggctataaag      240
aggtcatcag tatatgaaac agccccctgc tgtccattcc ttattccata gaaaagcctt      300
gacttgaggt tagatttttt ttatattttg ttttgtgtta ttttttcttt aacatccct       360 aaaatttttcc ttacatgttt tactagccag attttttcctc ctctcctgac tactcccagt   420
catagctgtc cctcttctct tatggagatc                                       450

<210> SEQ ID NO 60
<211> LENGTH: 577
<212> TYPE: DNA
<213> ORGANISM: Artificial Sequence
<220> FEATURE:
<223> OTHER INFORMATION: Envelope- CMV promoter- Transcription

<400> SEQUENCE: 60
acattgatta ttgactagtt attaatagta atcaattacg gggtcattag ttcatagccc       60
atatatggag ttccgcgtta cataacttac ggtaaatggc ccgcctggct gaccgcccaa      120
cgacccccgc ccattgacgt caataatgac gtatgttccc atagtaacgc caatagggac      180
tttccattga cgtcaatggg tggagtattt acggtaaact gcccacttgg cagtacatca      240
agtgtatcat atgccaagta cgccccctat tgacgtcaat gacggtaaat ggcccgcctg      300
gcattatgcc cagtacatga ccttatggga ctttcctact tggcagtaca tctacgtatt      360
```

```
agtcatcgct attaccatgg tgatgcggtt ttggcagtac atcaatgggc gtggatagcg      420
gtttgactca cggggatttc caagtctcca ccccattgac gtcaatggga gtttgttttg      480
gcaccaaaat caacgggact ttccaaaatg tcgtaacaac tccgccccat tgacgcaaat      540
gggcggtagg cgtgtacggt gggaggtcta tataagc                                577

<210> SEQ ID NO 61
<211> LENGTH: 573
<212> TYPE: DNA
<213> ORGANISM: Artificial Sequence
<220> FEATURE:
<223> OTHER INFORMATION: Envelope- Beta globin intron- Enhance gene
      expression

<400> SEQUENCE: 61
gtgagtttgg ggacccttga ttgttctttc tttttcgcta ttgtaaaatt catgttatat       60 ggaggggggca aagttttcag ggtgttgttt agaatgggaa gatgtccctt gtatcaccat     120
ggaccctcat gataatttg tttctttcac tttctactct gttgacaacc attgtctcct      180
cttattttct tttcattttc tgtaactttt tcgttaaact ttagcttgca tttgtaacga     240
atttttaaat tcacttttgt ttatttgtca gattgtaagt actttctcta atcactttt      300 tttcaaggca atcagggtat attatattgt acttcagcac agttttagag aacaattgtt    360
ataattaaat gataaggtag aatatttctg catataaatt ctggctggcg tggaaatatt    420
cttattggta gaaacaacta caccctggtc atcatcctgc ctttctcttt atggttacaa    480
tgatatacac tgtttgagat gaggataaaa tactctgagt ccaaaccggg cccctctgct    540
aaccatgttc atgccttctt ctctttccta cag                                 573

<210> SEQ ID NO 62
<211> LENGTH: 1519
<212> TYPE: DNA
<213> ORGANISM: Artificial Sequence
<220> FEATURE:
<223> OTHER INFORMATION: Envelope- VSV-G- Glycoprotein envelope-cell
      entry

<400> SEQUENCE: 62
atgaagtgcc ttttgtactt agcctttttta ttcattgggg tgaattgcaa gttcaccata     60
gtttttccac acaaccaaaa aggaaactgg aaaaatgttc cttctaatta ccattattgc    120
ccgtcaagct cagatttaaa ttggcataat gacttaatag gcacagcctt acaagtcaaa    180
atgcccaaga gtcacaaggc tattcaagca gacggttgga tgtgtcatgc ttccaaatgg    240
gtcactactt gtgatttccg ctggtatgga ccgaagtata taacacattc catccgatcc    300
ttcactccat ctgtagaaca atgcaaggaa agcattgaac aaacgaaaca aggaacttgg    360
ctgaatccag gcttccctcc tcaaagttgt ggatatgcaa ctgtgacgga tgccgaagca    420
gtgattgtcc aggtgactcc tcaccatgtg ctggttgatg aatacacagg agaatgggtt    480
gattcacagt tcatcaacgg aaaatgcagc aattacatat gccccactgt ccataactct    540
acaacctggc attctgacta aaggtcaaa gggctatgtg attctaacct catttccatg     600
gacatcacct tcttctcaga ggacggagag ctatcatccc tggaaaagga gggcacaggg    660
ttcagaagta actactttgc ttatgaaact ggaggcaagg cctgcaaaat gcaatactgc    720
aagcattggg gagtcagact cccatcaggt gtctggttcg agatggctga taaggatctc    780
tttgctgcag ccagattccc tgaatgccca gaagggcaa gtatctctgc tccatctcag    840
```

| | |
|---|---:|
| acctcagtgg atgtaagtct aattcaggac gttgagagga tcttggatta ttccctctgc | 900 |
| caagaaacct ggagcaaaat cagagcgggt cttccaatct ctccagtgga tctcagctat | 960 |
| cttgctccta aaacccagg aaccggtcct gctttcacca taatcaatgg taccctaaaa | 1020 |
| tactttgaga ccagatacat cagagtcgat attgctgctc caatcctctc aagaatggtc | 1080 |
| ggaatgatca gtggaactac cacagaaagg gaactgtggg atgactgggc accatatgaa | 1140 |
| gacgtggaaa ttggacccaa tggagttctg aggaccagtt caggatataa gtttcctta | 1200 |
| tacatgattg acatggtat gttggactcc gatcttcatc ttagctcaaa ggctcaggtg | 1260 |
| ttcgaacatc ctcacattca agacgctgct tcgcaacttc ctgatgatga gagtttattt | 1320 |
| tttggtgata ctgggctatc caaaaatcca atcgagcttg tagaaggttg gttcagtagt | 1380 |
| tggaaaagct ctattgcctc ttttttcttt atcatagggt taatcattgg actattcttg | 1440 |
| gttctccgag ttggtatcca tctttgcatt aaattaaagc acaccaagaa aagacagatt | 1500 |
| tatacagaca tagagatga | 1519 |

<210> SEQ ID NO 63
<211> LENGTH: 450
<212> TYPE: DNA
<213> ORGANISM: Artificial Sequence
<220> FEATURE:
<223> OTHER INFORMATION: Envelope- Rabbit beta globin poly A- RNA stability

<400> SEQUENCE: 63

| | |
|---|---:|
| agatctttt ccctctgcca aaaattatgg ggacatcatg aagcccttg agcatctgac | 60 |
| ttctggctaa taaggaaat ttattttcat tgcaatagtg tgttggaatt ttttgtgtct | 120 |
| ctcactcgga aggacatatg ggagggcaaa tcatttaaaa catcagaatg agtatttggt | 180 |
| ttagagtttg gcaacatatg cccatatgct ggctgccatg aacaaaggtt ggctataaag | 240 |
| aggtcatcag tatatgaaac agccccctgc tgtccattcc ttattccata gaaaagcctt | 300 |
| gacttgaggt tagatttttt ttatattttg ttttgtgtta ttttttctt taacatccct | 360 |
| aaaattttcc ttcacatgttt tactagccag attttcctc ctctcctgac tactcccagt | 420 |
| catagctgtc cctcttctct tatggagatc | 450 |

<210> SEQ ID NO 64
<211> LENGTH: 1104
<212> TYPE: DNA
<213> ORGANISM: Artificial Sequence
<220> FEATURE:
<223> OTHER INFORMATION: Promoter- EF-1

<400> SEQUENCE: 64

| | |
|---|---:|
| ccggtgccta gagaaggtgg cgcggggtaa actgggaaag tgatgtcgtg tactggctcc | 60 |
| gccttttcc cgagggtggg ggagaaccgt atataagtgc agtagtcgcc gtgaacgttc | 120 |
| tttttcgcaa cgggtttgcc gccagaacac aggtaagtgc cgtgtgtggt tcccgcgggc | 180 |
| ctggcctctt tacgggttat ggcccttgcg tgccttgaat tacttccacg cccctggctg | 240 |
| cagtacgtga ttcttgatcc cgagcttcgg gttggaagtg ggtgggagag ttcgaggcct | 300 |
| tgcgcttaag gagcccccttc gcctcgtgct tgagttgagg cctggcctgg gcgctggggc | 360 |
| cgccgcgtgc gaatctggtg gcaccttcgc gcctgtctcg ctgctttcga taagtctcta | 420 |
| gccatttaaa atttttgatg acctgctgcg acgcttttt tctggcaaga tagtcttgta | 480 |
| aatgcgggcc aagatctgca cactggtatt tcggttttg gggccgcggg cggcgacggg | 540 |

```
gcccgtgcgt cccagcgcac atgttcggcg aggcggggcc tgcgagcgcg gccaccgaga    600
atcggacggg ggtagtctca agctggccgg cctgctctgg tgcctggcct cgcgccgccg    660
tgtatcgccc cgccctgggc ggcaaggctg gcccggtcgg caccagttgc gtgagcggaa    720
agatggccgc ttcccggccc tgctgcaggg agctcaaaat ggaggacgcg cgctcggga     780
gagcgggcgg gtgagtcacc cacacaaagg aaaagggcct ttccgtcctc agccgtcgct    840
tcatgtgact ccacggagta ccgggcgccg tccaggcacc tcgattagtt ctcgagcttt    900
tggagtacgt cgtctttagg ttgggggggag gggttttatg cgatggagtt tccccacact   960
gagtgggtgg agactgaagt taggccagct tggcacttga tgtaattctc cttggaattt    1020
gccctttttg agtttggatc ttggttcatt ctcaagcctc agacagtggt tcaaagtttt    1080
tttcttccat ttcaggtgtc gtga                                           1104

<210> SEQ ID NO 65
<211> LENGTH: 511
<212> TYPE: DNA
<213> ORGANISM: Artificial Sequence
<220> FEATURE:
<223> OTHER INFORMATION: Promoter- PGK

<400> SEQUENCE: 65
ggggttgggg ttgcgccttt tccaaggcag ccctgggttt gcgcagggac gcggctgctc     60
tgggcgtggt tccgggaaac gcagcggcgc cgaccctggg tctcgcacat tcttcacgtc    120
cgttcgcagc gtcacccgga tcttcgccgc tacccttgtg ggcccccggc gacgcttcc    180
tgctccgccc ctaagtcggg aaggttcctt gcggttcgcg gcgtgccgga cgtgacaaac    240
ggaagccgca cgtctcacta gtaccctcgc agacggacag cgccagggag caatggcagc    300
gcgccgaccg cgatgggctg tggccaatag cggctgctca gcaggcgcg ccgagagcag     360
cggccgggaa ggggcggtgc gggaggcggg gtgtggggcg gtagtgtggg ccctgttcct    420
gcccgcgcg tgttccgcat tctgcaagcc tccggagcgc acgtcggcag tcggctccct    480
cgttgaccga atcaccgacc tctctcccca g                                   511

<210> SEQ ID NO 66
<211> LENGTH: 1162
<212> TYPE: DNA
<213> ORGANISM: Artificial Sequence
<220> FEATURE:
<223> OTHER INFORMATION: Promoter- UbC

<400> SEQUENCE: 66
gcgccgggtt ttggcgcctc ccgcgggcgc ccccctcctc acggcgagcg ctgccacgtc     60
agacgaaggg cgcaggagcg ttcctgatcc ttccgcccgg acgctcagga cagcggcccg    120
ctgctcataa gactcggcct tagaacccca gtatcagcag aaggacattt taggacggga    180
cttgggtgac tctagggcac tggttttctt tccagagagc ggaacaggcg aggaaaagta    240
gtcccttctc ggcgattctg cggagggatc tccgtggggc ggtgaacgcc gatgattata    300
taaggacgcg ccgggtgtgg cacagctagt tccgtcgcag ccgggatttg gtcgcggtt    360
cttgtttgtg gatcgctgtg atcgtcactt ggtgagttgc gggctgctgg gctgccggg    420
gctttcgtgg ccgccgggcc gctcggtggg acggaagcgt gtggagagac cgccaagggc    480
tgtagtctgg gtccgcgagc aaggttgccc tgaactgggg gttgggggga gcgcacaaaa    540
tggcggctgt tccgagtct tgaatggaag acgcttgtaa ggcgggctgt gaggtcgttg      600
aaacaaggtg gggggcatgg tgggcggcaa gaacccaagg tcttgaggcc ttcgctaatg    660
```

```
cgggaaagct cttattcggg tgagatgggc tggggcacca tctgggacc ctgacgtgaa      720 gtttgtcact gactggagaa ctcgggtttg tcgtctggtt gcggggcgg cagttatgcg       780 gtgccgttgg gcagtgcacc cgtacctttg ggagcgcgcg cctcgtcgtg tcgtgacgtc       840
acccgttctg ttggcttata atgcaggtg gggccacctg ccggtaggtg tgcggtaggc        900
ttttctccgt cgcaggacgc agggttcggg cctagggtag gctctcctga atcgacaggc       960
gccggacctc tggtgagggg agggataagt gaggcgtcag tttctttggt cggttttatg      1020
tacctatctt cttaagtagc tgaagctccg gttttgaact atgcgctcgg ggttggcgag      1080
tgtgttttgt gaagttttt aggcacctt tgaaatgtaa tcatttgggt caatatgtaa       1140
ttttcagtgt tagactagta aa                                               1162

<210> SEQ ID NO 67
<211> LENGTH: 120
<212> TYPE: DNA
<213> ORGANISM: Artificial Sequence
<220> FEATURE:
<223> OTHER INFORMATION: Poly A- SV40

<400> SEQUENCE: 67
gtttattgca gcttataatg gttacaaata aagcaatagc atcacaaatt tcacaaataa       60
agcatttttt tcactgcatt ctagttgtgg tttgtccaaa ctcatcaatg tatcttatca      120

<210> SEQ ID NO 68
<211> LENGTH: 227
<212> TYPE: DNA
<213> ORGANISM: Artificial Sequence
<220> FEATURE:
<223> OTHER INFORMATION: Poly A- bGH

<400> SEQUENCE: 68
gactgtgcct tctagttgcc agccatctgt tgtttgcccc tcccccgtgc cttccttgac       60
cctggaaggt gccactccca ctgtcctttc ctaataaaat gaggaaattg catcgcattg      120
tctgagtagg tgtcattcta ttctgggggg tggggtgggg caggacagca agggggagga      180 tgggaagac aatagcaggc atgctgggga tgcggtgggc tctatgg                    227

<210> SEQ ID NO 69
<211> LENGTH: 1512
<212> TYPE: DNA
<213> ORGANISM: Artificial Sequence
<220> FEATURE:
<223> OTHER INFORMATION: HIV Gag- Bal

<400> SEQUENCE: 69
atgggtgcga gagcgtcagt attaagcggg ggagaattag ataggtggga aaaaattcgg       60
ttaaggccag ggggaaagaa aaaatataga ttaaaacata tagtatgggc aagcagggaa      120
ctagaaagat tcgcagtcaa tcctggcctg ttagaaacat cagaaggctg cagacaaata      180
ctgggacagc tacaaccatc ccttcagaca ggatcagaag aacttagatc attatataat      240
acagtagcaa ccctctattg tgtacatcaa aagatagagg taaaagacac caaggaagct      300
ttagacaaaa tagaggaaga gcaaaacaaa tgtaagaaaa aggcacagca agcagcagct      360
gacacaggaa acagcggtca ggtcagccaa aatttcccta tagtgcagaa cctccagggg      420
caaatggtac atcaggccat atcacctaga actttaaatg catgggtaaa agtaatagaa      480
gagaaagctt tcagcccaga agtaataccc atgttttcag cattatcaga aggagccacc      540
```

```
ccacaagatt taaacaccat gctaaacaca gtgggggggac atcaagcagc catgcaaatg      600
ttaaaagaac ccatcaatga ggaagctgca agatgggata gattgcatcc cgtgcaggca      660
gggcctgttg caccaggcca gataagagat ccaagggggaa gtgacatagc aggaactacc      720
agtacccttc aggaacaaat aggatggatg acaagtaatc cacctatccc agtaggagaa      780
atctataaaa gatggataat cctgggatta aataaaatag taaggatgta tagccctacc      840
agcattttgg acataagaca aggaccaaag gaacccttta gagactatgt agaccggttc      900
tataaaactc taagagccga gcaagcttca caggaggtaa aaaattggat gacagaaacc      960
ttgttggtcc aaaatgcgaa cccagattgt aagactattt taaaagcatt gggaccagca     1020
gctacactag aagaaatgat gacagcatgt cagggagtgg gaggacccag ccataaagca     1080
agaattttgg cagaagcaat gagccaagta acaaattcag ctaccataat gatgcagaaa     1140
ggcaatttta ggaaccaaag aaagattgtt aaatgtttca attgtggcaa agaagggcac     1200
atagccagaa actgcagggc ccctaggaaa aggggctgtt ggaaatgtgg aaaggaagga     1260
caccaaatga aagactgtac tgagagacag gctaattttt tagggaaaat ctggccttcc     1320
cacaaaggaa ggccagggaa tttccttcag agcagaccag agccaacagc cccaccagcc     1380
ccaccagaag agagcttcag gtttggggaa gagacaacaa ctccctctca gaagcaggag     1440
ctgatagaca aggaactgta tcctttagct tccctcagat cactctttgg caacgacccc     1500
tcgtcacaat aa                                                         1512

<210> SEQ ID NO 70
<211> LENGTH: 1872
<212> TYPE: DNA
<213> ORGANISM: Artificial Sequence
<220> FEATURE:
<223> OTHER INFORMATION: HIV Pol- Bal

<400> SEQUENCE: 70
atgaatttgc caggaagatg gaaaccaaaa atgataggggg gaattggagg ttttatcaaa       60
gtaagacagt atgatcagat actcatagaa atctgtggac ataaagctat aggtacagta      120
ttaataggac ctacacctgt caacataatt ggaagaaatc tgttgactca gattggttgc      180
actttaaatt ttcccattag tcctattgaa actgtaccag taaaattaaa accaggaatg      240
gatggcccaa aagttaaaca atggccactg acagaagaaa aaataaaagc attaatggaa      300
atctgtacag aaatggaaaa ggaagggaaa atttcaaaaa ttgggcctga aaatccatac      360
aatactccag tatttgccat aaagaaaaaa gacagtacta atggagaaaa attagtagat      420
ttcagagaac ttaataagaa aactcaagac ttctgggaag tacaattagg aatacacatc      480
ccgcaggggt taaaaaagaa aaaatcagta acagtactgg atgtgggtga tgcatatttt      540
tcagttccct tagataaaga attcaggaag tatactgcat ttaccatacc tagtataaac      600
aatgaaacac cagggatcag atatcagtac aatgtacttc cacagggatg gaaaggatca      660
ccagcaatat tccaaagtag catgacaaga atcttagagc cttttagaaa acaaaatcca      720
gaaatagtga tctatcaata catggatgat ttgtatgtag gatctgactt agaaataggg      780
cagcatagaa caaaaataga ggaactgaga caacatctgt tgaggtgggg atttaccaca      840
ccagacaaaa aacatcagaa agaacctcca ttcctttgga tgggttatga actccatcct      900
gataaatgga cagtacagcc tatagtgctg ccagaaaaag acagctggac tgtcaatgac      960
atacagaagt tagtgggaaa attgaattgg gcaagtcaga tttacccagg aattaaagta     1020
aagcaattat gtaggctcct taggggaacc aaggcattaa cagaagtaat accactaaca     1080
```

```
aaagaaacag agctagaact ggcagagaac agggaaattc taaaagaacc agtacatggg    1140
gtgtattatg acccatcaaa agacttaata gcagaaatac agaagcaggg gcaaggccaa    1200
tggacatatc aaatttatca agagccattt aaaaatctga aaacaggaaa atatgcaaga    1260
atgaggggtg cccacactaa tgatgtaaaa caattaacag aggcagtgca aaaaataacc    1320
acagaaagca tagtaatatg gggaaagact cctaaattta aactacccat acaaaaagaa    1380
acatgggaaa catggtggac agagtattgg caagccacct ggattcctga gtgggagttt    1440
gtcaataccc ctcccttagt gaaattatgg taccagttag agaaagaacc cataatagga    1500
gcagaaacat tctatgtaga tggagcagct aaccgggaga ctaaattagg aaaagcagga    1560
tatgttacta acagaggaag acaaaaagtt gtctccctaa ctgacacaac aaatcagaag    1620
actgagttac aagcaattca tctagcttta caagattcag gattagaagt aaacatagta    1680
acagactcac aatatgcatt aggaatcatt caagcacaac cagataaaag tgaatcagag    1740
ttagtcagtc aaataataga acagttaata aaaaaggaaa aggtctacct ggcatgggta    1800
ccagcgcaca aaggaattgg aggaaatgaa caagtagata aattagtcag tactggaatc    1860
aggaaagtac ta                                                       1872

<210> SEQ ID NO 71
<211> LENGTH: 867
<212> TYPE: DNA
<213> ORGANISM: Artificial Sequence
<220> FEATURE:
<223> OTHER INFORMATION: HIV Integrase- Bal

<400> SEQUENCE: 71
tttttagatg gaatagatat agcccaagaa gaacatgaga aatatcacag taattggaga      60
gcaatggcta gtgattttaa cctgccacct gtggtagcaa aagaaatagt agccagctgt     120
gataaatgtc agctaaaagg agaagccatg catggacaag tagactgtag tccaggaata     180
tggcaactag attgtacaca tttagaagga aaaattatcc tggtagcagt tcatgtagcc     240
agtggatata tagaagcaga agttattcca gcagagacag ggcaggaaac agcatacttt     300
ctcttaaaat tagcaggaag atggccagta aaaacaatac atacagacaa tggcagcaat     360
ttcactagta ctacagtcaa ggccgcctgt tggtgggcgg ggatcaagca ggaatttggc     420
attccctaca atccccaaag tcagggagta gtagaatcta taaataaaga attaaagaaa     480
attataggac aggtaagaga tcaggctgaa catcttaaaa cagcagtaca aatggcagta     540
ttcatccaca attttaaaag aaaaggggg attgggggt atagtgcagg ggaaagaata     600
gtagacataa tagcaacaga catacaaact aaagaattac aaaaacaaat tacaaaaatt     660
caaaattttc gggtttatta cagggacagc agagatccac tttggaaagg accagcaaag     720
cttctctgga aaggtgaagg ggcagtagta atacaagata atagtgacat aaaagtagta     780
ccaagaagaa aagcaaagat cattagggat tatggaaaac agatggcagg tgatgattgt     840
gtggcaagta gacaggatga ggattag                                        867

<210> SEQ ID NO 72
<211> LENGTH: 1695
<212> TYPE: DNA
<213> ORGANISM: Artificial Sequence
<220> FEATURE:
<223> OTHER INFORMATION: Envelope- RD114

<400> SEQUENCE: 72
```

| | |
|---|---|
| atgaaactcc caacaggaat ggtcatttta tgtagcctaa taatagttcg ggcagggttt | 60 |
| gacgaccccc gcaaggctat cgcattagta caaaaacaac atggtaaacc atgcgaatgc | 120 |
| agcggagggc aggtatccga ggccccaccg aactccatcc aacaggtaac ttgcccaggc | 180 |
| aagacggcct acttaatgac caaccaaaaa tggaaatgca gagtcactcc aaaaaatctc | 240 |
| acccctagcg ggggagaact ccagaactgc ccctgtaaca ctttccagga ctcgatgcac | 300 |
| agttcttgtt atactgaata ccggcaatgc agggcgaata taagacata ctacacggcc | 360 |
| accttgctta aaatacggtc tgggagcctc aacgaggtac agatattaca aaccccaat | 420 |
| cagctcctac agtccccttg tagggctct ataaatcagc ccgtttgctg gagtgccaca | 480 |
| gcccccatcc atatctccga tggtggagga cccctcgata ctaagagagt gtggacagtc | 540 |
| caaaaaaggc tagaacaaat tcataaggct atgcatcctg aacttcaata ccaccccta | 600 |
| gccctgccca aagtcagaga tgaccttagc cttgatgcac ggacttttga tatcctgaat | 660 |
| accactttta ggttactcca gatgtccaat tttagccttg cccaagattg ttggctctgt | 720 |
| ttaaaactag gtaccctac ccctcttgcg atacccactc cctctttaac ctactcccta | 780 |
| gcagactccc tagcgaatgc ctcctgtcag attatacctc ccctcttggt tcaaccgatg | 840 |
| cagttctcca actcgtcctg tttatcttcc cctttcatta acgatacgga acaaatagac | 900 |
| ttaggtgcag tcacctttac taactgcacc tctgtagcca atgtcagtag tcctttatgt | 960 |
| gccctaaacg ggtcagtctt cctctgtgga ataacatgg catacaccta tttaccccaa | 1020 |
| aactggacag gactttgcgt ccaagcctcc ctcctcccg acattgacat catcccgggg | 1080 |
| gatgagccag tccccattcc tgccattgat cattatatac atagacctaa acgagctgta | 1140 |
| cagttcatcc ctttactagc tggactggga atcaccgcag cattcaccac cggagctaca | 1200 |
| ggcctaggtg tctccgtcac ccagtataca aaattatccc atcagttaat atctgatgtc | 1260 |
| caagtcttat ccggtaccat acaagattta caagaccagg tagactcgtt agctgaagta | 1320 |
| gttctccaaa ataggagggg actggaccta ctaacggcag aacaaggagg aatttgttta | 1380 |
| gccttacaag aaaaatgctg tttttatgct aacaagtcag gaattgtgag aaacaaaata | 1440 |
| agaaccctac aagaagaatt acaaaaacgc agggaaagcc tggcatccaa ccctctctgg | 1500 |
| accgggctgc agggctttct tccgtacctc ctacctctcc tgggacccct actcaccctc | 1560 |
| ctactcatac taaccattgg gccatgcgtt ttcaatcgat tggtccaatt tgttaaagac | 1620 |
| aggatctcag tggtccaggc tctggttttg actcagcaat atcaccagct aaaacccata | 1680 |
| gagtacgagc catga | 1695 |

<210> SEQ ID NO 73
<211> LENGTH: 2013
<212> TYPE: DNA
<213> ORGANISM: Artificial Sequence
<220> FEATURE:
<223> OTHER INFORMATION: Envelope- GALV

<400> SEQUENCE: 73

| | |
|---|---|
| atgcttctca cctcaagccc gcaccacctt cggcaccaga tgagtcctgg gagctggaaa | 60 |
| agactgatca tcctcttaag ctgcgtattc ggagacggca aaacgagtct gcagaataag | 120 |
| aaccccccacc agcctgtgac cctcacctgg caggtactgt cccaaactgg ggacgttgtc | 180 |
| tgggacaaaa aggcagtcca gcccctttgg acttggtggc cctctcttac acctgatgta | 240 |
| tgtgccctgg cggccggtct tgagtcctgg gatatcccgg gatccgatgt atcgtcctct | 300 |
| aaaagagtta gacctcctga ttcagactat actgccgctt ataagcaaat cacctgggga | 360 |

```
gccatagggt gcagctaccc tcgggctagg accaggatgg caaattcccc cttctacgtg      420
tgtccccgag ctggccgaac ccattcagaa gctaggaggt gtgggggct agaatcccta       480 tactgtaaag aatggagttg tgagaccacg ggtaccgttt attggcaacc caagtcctca     540
tgggacctca taactgtaaa atgggaccaa aatgtgaaat gggagcaaaa atttcaaaag     600
tgtgaacaaa ccggctggtg taaccccctc aagatagact tcacagaaaa aggaaaactc     660
tccagagatt ggataacgga aaaaacctgg gaattaaggt tctatgtata tggcacccca     720
ggcatacagt tgactatccg cttagaggtc actaacatgc cggttgtggc agtgggccca     780
gaccctgtcc ttgcggaaca gggacctcct agcaagcccc tcactctccc tctctcccca     840
cggaaagcgc cgcccacccc tctacccccg gcggctagtg agcaaacccc tgcggtgcat     900
ggagaaactg ttaccctaaa ctctccgcct ccaccagtg gcgaccgact ctttggcctt      960 gtgcagggg ccttcctaac cttgaatgct accaacccag gggccactaa gtcttgctgg      1020
ctctgtttgg gcatgagccc ccttattat gaagggatag cctcttcagg agaggtcgct      1080
tatacctcca accatacccg atgccactgg ggggcccaag aaaagcttac cctcactgag     1140
gtctccggac tcgggtcatg catagggaag gtgcctctta cccatcaaca tctttgcaac     1200
cagaccttac ccatcaattc ctctaaaaac catcagtatc tgctcccctc aaaccatagc     1260
tggtgggcct gcagcactgg cctcaccccc tgcctctcca cctcagtttt taatcagtct     1320
aaagacttct gtgtccaggt ccagctgatc ccccgcatct attaccattc tgaagaaacc     1380
ttgttacaag cctatgacaa atcaccccc aggtttaaaa gagagcctgc ctcacttacc      1440
ctagctgtct tcctggggtt agggattgcg gcaggtatag gtactggctc aaccgcccta     1500
attaaagggc ccatagacct ccagcaaggc ctaaccagcc tccaaatcgc cattgacgct     1560
gacctccggg cccttcagga ctcaatcagc aagctagagg actcactgac ttccctatct     1620
gaggtagtac tccaaaatag gagaggcctt gacttactat tccttaaaga aggaggcctc     1680
tgcgcggccc taaaagaaga gtgctgtttt tatgtagacc actcaggtgc agtacgagac     1740
tccatgaaaa aacttaaaga aagactagat aaaagacagt tagagcgcca gaaaaaccaa     1800
aactggtatg aagggtggtt caataactcc ccttggttta ctaccctact atcaaccatc     1860
gctgggcccc tattgctcct ccttttgtta ctcactcttg ggccctgcat catcaataaa     1920
ttaatccaat tcatcaatga taggataagt gcagtcaaaa tttagtcct tagacagaaa     1980 tatcagaccc tagataacga ggaaaacctt taa                                  2013
```

<210> SEQ ID NO 74
<211> LENGTH: 1530
<212> TYPE: DNA
<213> ORGANISM: Artificial Sequence
<220> FEATURE:
<223> OTHER INFORMATION: Envelope- FUG

<400> SEQUENCE: 74

```
atggttccgc aggttctttt gtttgtactc cttctgggtt tttcgttgtg tttcgggaag      60
ttccccattt acacgatacc agacgaactt ggtccctgga gcctattga catacaccat     120 ctcagctgtc caaataacct ggttgtggag gatgaaggat gtaccaacct gtccgagttc    180
tcctacatgg aactcaaagt gggatacatc tcagccatca agtgaacgg gttcacttgc     240 acaggtgttg tgacagaggc agagacctac accaactttg ttggttatgt cacaaccaca    300
ttcaagagaa agcatttccg ccccaccca gacgcatgta gagccgcgta taactggaag     360
```
atggccggtg accccagata tgaagagtcc ctacacaatc cataccccga ctaccactgg 420
cttcgaactg taagaaccac caaagagtcc ctcattatca tatccccaag tgtgacagat 480
ttggacccat atgacaaatc ccttcactca agggtcttcc ctggcggaaa gtgctcagga 540
ataacggtgt cctctaccta ctgctcaact aaccatgatt acaccatttg gatgcccgag 600
aatccgagac caaggacacc ttgtgacatt tttaccaata gcagagggaa gagagcatcc 660
aacgggaaca agacttgcgg ctttgtggat gaaagaggcc tgtataagtc tctaaaagga 720
gcatgcaggc tcaagttatg tggagttctt ggacttagac ttatggatgg aacatgggtc 780
gcgatgcaaa catcagatga gaccaaatgg tgccctccag atcagttggt gaatttgcac 840
gactttcgct cagacgagat cgagcatctc gttgtggagg agttagttaa gaaaagagag 900
gaatgtctgg atgcattaga gtccatcatg accaccaagt cagtaagttt cagacgtctc 960
agtcacctga gaaaacttgt cccagggttt ggaaaagcat ataccatatt caacaaaacc 1020
ttgatggagg ctgatgctca ctacaagtca gtccggacct ggaatgagat catcccctca 1080
aaagggtgtt tgaaagttgg aggaaggtgc catcctcatg tgaacggggt gtttttcaat 1140
ggtataatat tagggcctga cgaccatgtc ctaatcccag agatgcaatc atccctcctc 1200
cagcaacata tggagttgtt ggaatcttca gttatccccc tgatgcaccc cctggcagac 1260
ccttctacag ttttcaaaga aggtgatgag gctgaggatt ttgttgaagt tcacctcccc 1320
gatgtgtaca aacagatctc aggggttgac ctgggtctcc cgaactgggg aaagtatgta 1380
ttgatgactg caggggccat gattggcctg gtgttgatat tttccctaat gacatggtgc 1440
agagttggta tccatctttg cattaaatta aagcacacca agaaaagaca gatttataca 1500
gacatagaga tgaaccgact tggaaagtaa 1530

<210> SEQ ID NO 75
<211> LENGTH: 1497
<212> TYPE: DNA
<213> ORGANISM: Artificial Sequence
<220> FEATURE:
<223> OTHER INFORMATION: Envelope- LCMV

<400> SEQUENCE: 75
atgggtcaga ttgtgacaat gtttgaggct ctgcctcaca tcatcgatga ggtgatcaac 60
attgtcatta ttgtgcttat cgtgatcacg ggtatcaagg ctgtctacaa ttttgccacc 120
tgtgggatat tcgcattgat cagtttccta cttctggctg gcaggtcctg tggcatgtac 180
ggtcttaagg gacccgacat ttacaaagga gtttaccaat ttaagtcagt ggagtttgat 240
atgtcacatc tgaacctgac catgcccaac gcatgttcag ccaacaactc ccaccattac 300
atcagtatgg ggacttctgg actagaattg accttcacca atgattccat catcagtcac 360
aacttttgca atctgacctc tgccttcaac aaaaagacct ttgaccacac actcatgagt 420
atagtttcga gcctacacct cagtatcaga gggaactcca actataaggc agtatcctgc 480
gacttcaaca atggcataac catccaatac aacttgacat tctcagatcg acaaagtgct 540
cagagccagt gtagaacctt cagaggtaga gtcctagata tgtttagaac tgccttcggg 600
gggaaataca tgaggagtgg ctggggctgg acaggctcag atggcaagac cacctggtgt 660
agccagacga gttaccaata cctgattata caaaatagaa cctgggaaaa ccactgcaca 720
tatgcaggtc cttttgggat gtccaggatt ctcctttccc aagagaagac taagttcttc 780
actaggagac tagcgggcac attcacctgg actttgtcag actcttcagg ggtggagaat 840
ccaggtggtt attgcctgac caaatggatg attcttgctg cagagcttaa gtgtttcggg 900

```
aacacagcag ttgcgaaatg caatgtaaat catgatgccg aattctgtga catgctgcga    960
ctaattgact acaacaaggc tgctttgagt aagttcaaag aggacgtaga atctgccttg   1020
cacttattca aaacaacagt gaattctttg atttcagatc aactactgat gaggaaccac   1080
ttgagagatc tgatgggggt gccatattgc aattactcaa agttttggta cctagaacat   1140
gcaaagaccg gcgaaactag tgtccccaag tgctggcttg tcaccaatgg ttcttactta   1200
aatgagaccc acttcagtga tcaaatcgaa caggaagccg ataacatgat tacagagatg   1260
ttgaggaagg attacataaa gaggcagggg agtacccccc tagcattgat ggaccttctg   1320
atgttttcca catctgcata tctagtcagc atcttcctgc accttgtcaa aataccaaca   1380
cacaggcaca taaaaggtgg ctcatgtcca aagccacacc gattaaccaa caaaggaatt   1440
tgtagttgtg gtgcatttaa ggtgcctggt gtaaaaaccg tctggaaaag acgctga      1497
```

<210> SEQ ID NO 76
<211> LENGTH: 1692
<212> TYPE: DNA
<213> ORGANISM: Artificial Sequence
<220> FEATURE:
<223> OTHER INFORMATION: Envelope- FPV

<400> SEQUENCE: 76

```
atgaacactc aaatcctggt tttcgccctt gtggcagtca tccccacaaa tgcagacaaa     60
atttgtcttg gacatcatgc tgtatcaaat ggcaccaaag taaacacact cactgagaga    120
ggagtagaag ttgtcaatgc aacggaaaca gtggagcgga caaacatccc caaaatttgc    180
tcaaaaggga aaagaaccac tgatcttggc caatgcggac tgttagggac cattaccgga    240
ccacctcaat gcgaccaatt tctagaattt tcagctgatc taataatcga gagacgagaa    300
ggaaatgatg tttgttaccc ggggaagttt gttaatgaag aggcattgcg acaaatcctc    360
agaggatcag gtgggattga caaagaaaca atgggattca catatagtgg aataaggacc    420
aacggaacaa ctagtgcatg tagaagatca gggtcttcat tctatgcaga aatggagtgg    480
ctcctgtcaa atacagacaa tgctgctttc ccacaaatga caaaatcata caaaaacaca    540
aggagagaat cagctctgat agtctgggga atccaccatt caggatcaac caccgaacag    600
accaaactat atgggagtgg aaataaactg ataacagtcg ggagttccaa atatcatcaa    660
tcttttgtgc cgagtccagg aacacgaccg cagataaatg gccagtccgg acggattgat    720
tttcattggt tgatcttgga tcccaatgat acagttactt ttagtttcaa tggggctttc    780
atagctccaa atcgtgccag cttcttgagg ggaaagtcca tggggatcca gagcgatgtg    840
caggttgatg ccaattgcga aggggaatgc taccacagtg gagggactat aacaagcaga    900
ttgccttttc aaaacatcaa tagcagagca gttggcaaat gcccaagata tgtaaaacag    960
gaaagtttat tattggcaac tgggatgaag aacgttcccg aaccttccaa aaaaaggaaa   1020
aaaagaggcc tgtttggcgc tatagcaggg tttattgaaa atggttggga aggtctggtc   1080
gacgggtggt acggtttcag gcatcagaat gcacaaggag aaggaactgc agcagactac   1140
aaaagcaccc aatcggcaat tgatcagata accggaaagt taaatagact cattgagaaa   1200
accaaccagc aatttgagct aatagataat gaattcactg aggtggaaaa gcagattggc   1260
aatttaatta actggaccaa agactccatc acagaagtat ggtcttacaa tgctgaactt   1320
cttgtggcaa tggaaaacca gcacactatt gatttggctg attcagagat gaacaagctg   1380
tatgagcgag tgaggaaaca attaagggaa aatgctgaag aggatggcac tggttgcttt   1440
```

| | |
|---|---|
| gaaattttc ataaatgtga cgatgattgt atggctagta taaggaacaa tacttatgat | 1500 |
| cacagcaaat acagagaaga agcgatgcaa aatagaatac aaattgaccc agtcaaattg | 1560 |
| agtagtggct acaaagatgt gatactttgg tttagcttcg gggcatcatg cttttttgctt | 1620 |
| cttgccattg caatgggcct tgttttcata tgtgtgaaga acggaaacat gcggtgcact | 1680 |
| atttgtatat aa | 1692 |

<210> SEQ ID NO 77
<211> LENGTH: 1266
<212> TYPE: DNA
<213> ORGANISM: Artificial Sequence
<220> FEATURE:
<223> OTHER INFORMATION: Envelope- RRV

<400> SEQUENCE: 77

| | |
|---|---|
| agtgtaacag agcactttaa tgtgtataag gctactagac catacctagc acattgcgcc | 60 |
| gattgcgggg acgggtactt ctgctatagc ccagttgcta tcgaggagat ccgagatgag | 120 |
| gcgtctgatg gcatgcttaa gatccaagtc tccgcccaaa taggtctgga caaggcaggc | 180 |
| acccacgccc acacgaagct ccgatatatg gctggtcatg atgttcagga atctaagaga | 240 |
| gattccttga gggtgtacac gtccgcagcg tgctccatac atgggacgat gggacacttc | 300 |
| atcgtcgcac actgtccacc aggcgactac ctcaaggttt cgttcgagga cgcagattcg | 360 |
| cacgtgaagg catgtaaggt ccaatacaag cacaatccat gccggtggg tagagagaag | 420 |
| ttcgtggtta gaccacactt tggcgtagag ctgccatgca cctcatacca gctgacaacg | 480 |
| gctcccaccg acgaggagat tgacatgcat acaccgccag atataccgga tcgcaccctg | 540 |
| ctatcacaga cggcgggcaa cgtcaaaata acagcaggcg gcaggactat caggtacaac | 600 |
| tgtacctgcg gccgtgacaa cgtaggcact accagtactg acaagaccat caacacatgc | 660 |
| aagattgacc aatgccatgc tgccgtcacc agccatgaca aatggcaatt tacctctcca | 720 |
| tttgttccca gggctgatca gacagctagg aaaggcaagg tacacgttcc gttccctctg | 780 |
| actaacgtca cctgccgagt gccgttggct cgagcgccgg atgccaccta tggtaagaag | 840 |
| gaggtgaccc tgagattaca cccagatcat ccgacgctct tctcctatag gagtttagga | 900 |
| gccgaaccgc acccgtacga ggaatgggtt gacaagttct ctgagcgcat catcccagtg | 960 |
| acggaagaag ggattgagta ccagtggggc aacaacccgc cggtctgcct gtgggcgcaa | 1020 |
| ctgacgaccg agggcaaacc ccatggctgg ccacatgaaa tcattcagta ctattatgga | 1080 |
| ctataccccg ccgccactat tgccgcagta tccggggcga gtctgatggc cctcctaact | 1140 |
| ctggcggcca catgctgcat gctggccacc gcgaggagaa agtgcctaac accgtacgcc | 1200 |
| ctgacgccag gagcggtggt accgttgaca ctggggctgc tttgctgcgc accgagggcg | 1260 |
| aatgca | 1266 |

<210> SEQ ID NO 78
<211> LENGTH: 1266
<212> TYPE: DNA
<213> ORGANISM: Artificial Sequence
<220> FEATURE:
<223> OTHER INFORMATION: Envelope- MLV 10A1

<400> SEQUENCE: 78

| | |
|---|---|
| agtgtaacag agcactttaa tgtgtataag gctactagac catacctagc acattgcgcc | 60 |
| gattgcgggg acgggtactt ctgctatagc ccagttgcta tcgaggagat ccgagatgag | 120 |
| gcgtctgatg gcatgcttaa gatccaagtc tccgcccaaa taggtctgga caaggcaggc | 180 |

```
acccacgccc acacgaagct ccgatatatg gctggtcatg atgttcagga atctaagaga      240
gattccttga gggtgtacac gtccgcagcg tgctccatac atgggacgat gggacacttc      300
atcgtcgcac actgtccacc aggcgactac ctcaaggttt cgttcgagga cgcagattcg      360
cacgtgaagg catgtaaggt ccaatacaag cacaatccat tgccggtggg tagagagaag      420
ttcgtggtta gaccacactt tggcgtagag ctgccatgca cctcatacca gctgacaacg      480
gctcccaccg acgaggagat tgacatgcat acaccgccag atataccgga tcgcaccctg      540
ctatcacaga cggcgggcaa cgtcaaaata acagcaggcg gcaggactat caggtacaac      600
tgtacctgcg gccgtgacaa cgtaggcact accagtactg acaagaccat caacacatgc      660
aagattgacc aatgccatgc tgccgtcacc agccatgaca aatggcaatt tacctctcca      720
tttgttccca gggctgatca gacagctagg aaaggcaagg tacacgttcc gttccctctg      780
actaacgtca cctgccgagt gccgttggct cgagcgccgg atgccaccta tggtaagaag      840
gaggtgaccc tgagattaca cccagatcat ccgacgctct tctcctatag gagtttagga      900
gccgaaccgc acccgtacga ggaatgggtt gacaagttct ctgagcgcat catcccagtg      960
acggaagaag ggattgagta ccagtggggc aacaacccgc cggtctgcct gtgggcgcaa     1020
ctgacgaccg agggcaaacc ccatggctgg ccacatgaaa tcattcagta ctattatgga     1080
ctataccccg ccgccactat tgccgcagta tccggggcga gtctgatggc cctcctaact     1140
ctggcggcca catgctgcat gctggccacc gcgaggagaa agtgcctaac accgtacgcc     1200
ctgacgccag gagcggtggt accgttgaca ctggggctgc tttgctgcgc accgagggcg     1260
aatgca                                                                1266

<210> SEQ ID NO 79
<211> LENGTH: 2030
<212> TYPE: DNA
<213> ORGANISM: Artificial Sequence
<220> FEATURE:
<223> OTHER INFORMATION: Envelope- Ebola

<400> SEQUENCE: 79
atgggtgtta caggaatatt gcagttacct cgtgatcgat tcaagaggac atcattcttt       60
ctttgggtaa ttatcctttt ccaaagaaca ttttccatcc cacttggagt catccacaat      120
agcacattac aggttagtga tgtcgacaaa ctggtttgcc gtgacaaact gtcatccaca      180
aatcaattga tcagttgg actgaatctc gaagggaatg gagtggcaac tgacgtgcca      240
tctgcaacta aaagatgggg cttcaggtcc ggtgtcccac caaaggtggt caattatgaa      300
gctggtgaat gggctgaaaa ctgctacaat cttgaaatca aaaaacctga cgggagtgag      360
tgtctaccag cagcgccaga cgggattcgg ggcttccccc ggtgccggta tgtgcacaaa      420
gtatcaggaa cgggaccgtg tgccggagac tttgccttcc acaaagaggg tgctttcttc      480
ctgtatgacc gacttgcttc cacagttatc taccgaggaa cgactttcgc tgaaggtgtc      540
gttgcatttc tgatactgcc ccaagctaag aaggacttct cagctcaca ccccttgaga      600 gagccggtca tgcaacggag gacccgtct agtggctact attctaccac aattagatat      660
caagctaccg gttttggaac caatgagaca gagtatttgt tcgaggttga caatttgacc      720
tacgtccaac ttgaatcaag attcacacca cagtttctgc tccagctgaa tgagacaata      780
tatacaagtg ggaaaaggag caataccacg ggaaaactaa tttggaaggt caaccccgaa      840
attgatacaa caatcgggga gtgggccttc tgggaaacta aaaaaacctc actagaaaaa      900
```

```
ttcgcagtga agagttgtct ttcacagctg tatcaaacag agccaaaaac atcagtggtc      960
agagtccggc gcgaacttct tccgacccag ggaccaacac aacaactgaa gaccacaaaa     1020
tcatggcttc agaaaattcc tctgcaatgg ttcaagtgca cagtcaagga agggaagctg     1080
cagtgtcgca tctgacaacc cttgccacaa tctccacgag tcctcaaccc cccacaacca     1140
aaccaggtcc ggacaacagc acccacaata cacccgtgta taaacttgac atctctgagg     1200
caactcaagt tgaacaacat caccgcagaa cagacaacga cagcacagcc tccgacactc     1260
cccccgccac gaccgcagcc ggaccctaa aagcagagaa caccaacacg agcaagggta     1320
ccgacctcct ggaccccgcc accacaacaa gtccccaaaa ccacagcgag accgctggca     1380
acaacaacac tcatcaccaa gataccggag aagagagtgc cagcagcggg aagctaggct     1440
taattaccaa tactattgct ggagtcgcag gactgatcac aggcgggagg agagctcgaa     1500
gagaagcaat tgtcaatgct caacccaaat gcaaccctaa tttacattac tggactactc     1560
aggatgaagg tgctgcaatc ggactggcct ggataccata tttcgggcca gcagccgagg     1620
gaatttacat agagggctg atgcacaatc aagatggttt aatctgtggg ttgagacagc     1680
tggccaacga gacgactcaa gctcttcaac tgttcctgag agccacaacc gagctacgca     1740 cctttcaat cctcaaccgt aaggcaattg atttcttgct gcagcgatgg ggcggcacat     1800
gccacatttt gggaccggac tgctgtatcg aaccacatga ttggaccaag aacataacag     1860
acaaaattga tcagattatt catgattttg ttgataaaac ccttccggac caggggggaca     1920 atgacaattg gtggacagga tggagacaat ggataccggc aggtattgga gttacaggcg     1980
ttataattgc agttatcgct ttattctgta tatgcaaatt tgtcttttag                2030

<210> SEQ ID NO 80
<211> LENGTH: 389
<212> TYPE: DNA
<213> ORGANISM: Artificial Sequence
<220> FEATURE:
<223> OTHER INFORMATION: Short WPRE sequence

<400> SEQUENCE: 80
aatcaacctc tggattacaa aatttgtgaa agattgactg atattcttaa ctatgttgct       60
ccttttacgc tgtgtggata tgctgcttta atgcctctgt atcatgctat tgcttcccgt      120
acggctttcg ttttctcctc cttgtataaa tcctggttgc tgtctctttta tgaggagttg      180 tggcccgttg tccgtcaacg tggcgtggtg tgctctgtgt ttgctgacgc aaccccact      240 ggctggggca ttgccaccac ctgtcaactc ctttctggga ctttcgcttt cccctccccg      300
atcgccacgg cagaactcat cgccgcctgc cttgcccgct gctggacagg gctaggttg      360 ctgggcactg ataattccgt ggtgttgtc                                         389

<210> SEQ ID NO 81
<211> LENGTH: 31
<212> TYPE: DNA
<213> ORGANISM: Artificial Sequence
<220> FEATURE:
<223> OTHER INFORMATION: Primer

<400> SEQUENCE: 81
taagcagaat tcatgaattt gccaggaaga t                                       31

<210> SEQ ID NO 82
<211> LENGTH: 36
<212> TYPE: DNA
<213> ORGANISM: Artificial Sequence
```

```
<220> FEATURE:
<223> OTHER INFORMATION: Primer

<400> SEQUENCE: 82
ccatacaatg aatggacact aggcggccgc acgaat                              36

<210> SEQ ID NO 83
<211> LENGTH: 2745
<212> TYPE: DNA
<213> ORGANISM: Artificial Sequence
<220> FEATURE:
<223> OTHER INFORMATION: Gag, Pol, Integrase fragment

<400> SEQUENCE: 83
gaattcatga atttgccagg aagatggaaa ccaaaaatga taggggggaat tggaggtttt    60 atcaaagtaa gacagtatga tcagatactc atagaaatct gcggacataa agctataggt   120
acagtattag taggacctac acctgtcaac ataattggaa gaaatctgtt gactcagatt   180
ggctgcactt taaattttcc cattagtcct attgagactg taccagtaaa attaaagcca   240
ggaatggatg gcccaaaagt taaacaatgg ccattgacag aagaaaaaat aaaagcatta   300
gtagaaattt gtacagaaat ggaaaaggaa ggaaaaattt caaaaattgg gcctgaaaat   360
ccatacaata ctccagtatt tgccataaag aaaaaagaca gtactaaatg gagaaaatta   420
gtagatttca gagaacttaa taagagaact caagatttct gggaagttca attaggaata   480
ccacatcctg cagggttaaa acagaaaaaa tcagtaacag tactggatgt gggcgatgca   540
tatttttcag ttcccttaga taaagacttc aggaagtata ctgcatttac catacctagt   600
ataaacaatg agacaccagg gattagatat cagtacaatg tgcttccaca gggatggaaa   660
ggatcaccag caatattcca gtgtagcatg acaaaaatct tagagccttt tagaaaacaa   720
aatccagaca tagtcatcta tcaatacatg gatgatttgt atgtaggatc tgacttagaa   780
atagggcagc atagaacaaa aatagaggaa ctgagacaac atctgttgag gtggggattt   840
accacaccag acaaaaaaca tcagaaagaa cctccattcc tttggatggg ttatgaactc   900
catcctgata atggacagt acagcctata gtgctgccag aaaaggacag ctggactgtc   960
aatgacatac agaaattagt gggaaaattg aattgggcaa gtcagattta tgcagggatt  1020
aaagtaaggc aattatgtaa actccttagg ggaaccaaag cactaacaga agtagtacca  1080
ctaacagaag aagcagagct agaactggca gaaaacaggg agattctaaa agaaccggta  1140
catggagtgt attatgaccc atcaaaagac ttaatagcag aaatacagaa gcaggggcaa  1200
ggccaatgga catatcaaat ttatcaagag ccatttaaaa atctgaaaac aggaaagtat  1260
gcaagaatga gggtgcccca cactaatgat gtgaaacaat taacagaggc agtacaaaaa  1320
atagccacag aaagcatagt aatatgggga aagactccta aatttaaatt acccatacaa  1380
aaggaaacat gggaagcatg gtggacagag tattggcaag ccacctggat tcctgagtgg  1440
gagtttgtca atacccctcc cttagtgaag ttatggtacc agttagagaa agaacccata  1500
ataggagcag aaactttcta tgtagatggg gcagccaata gggaaactaa attaggaaaa  1560
gcaggatatg taactgacag aggaagacaa aaagttgtcc ccctaacgga cacaacaaat  1620
cagaagactg agttacaagc aattcatcta gctttgcagg attcgggatt agaagtaaac  1680
atagtgacag actcacaata tgcattggga atcattcaag cacaaccaga taagagtgaa  1740
tcagagttag tcagtcaaat aatagagcag ttaataaaaa aggaaaaagt ctacctggca  1800
tgggtaccag cacacaaagg aattggagga aatgaacaag tagataaatt ggtcagtgct  1860
```

```
ggaatcagga aagtactatt tttagatgga atagataagg cccaagaaga acatgagaaa    1920
tatcacagta attggagagc aatggctagt gattttaacc taccacctgt agtagcaaaa    1980
gaaatagtag ccagctgtga taaatgtcag ctaaaagggg aagccatgca tggacaagta    2040
gactgtagcc caggaatatg gcagctagat tgtacacatt tagaaggaaa agttatcttg    2100
gtagcagttc atgtagccag tggatatata gaagcagaag taattccagc agagacaggg    2160
caagaaacag catacttcct cttaaaatta gcaggaagat ggccagtaaa aacagtacat    2220
acagacaatg gcagcaattt caccagtact acagttaagg ccgcctgttg gtgggcgggg    2280
atcaagcagg aatttggcat tccctacaat ccccaaagtc aaggagtaat agaatctatg    2340
aataaagaat taagaaaat tataggacag gtaagagatc aggctgaaca tcttaagaca    2400
gcagtacaaa tggcagtatt catccacaat tttaaaagaa aagggggat tgggggtac    2460 agtgcagggg aaagaatagt agacataata gcaacagaca tacaaactaa agaattacaa    2520
aaacaaatta caaaaattca aaattttcgg gtttattaca gggacagcag agatccagtt    2580
tggaaaggac cagcaaagct cctctggaaa ggtgaagggg cagtagtaat acaagataat    2640
agtgacataa aagtagtgcc aagaagaaaa gcaaagatca tcagggatta tggaaaacag    2700
atggcaggtg atgattgtgt ggcaagtaga caggatgagg attaa                    2745
```

<210> SEQ ID NO 84
<211> LENGTH: 1586
<212> TYPE: DNA
<213> ORGANISM: Artificial Sequence
<220> FEATURE:
<223> OTHER INFORMATION: DNA Fragment containing Rev, RRE and rabbit
      beta globin poly A

<400> SEQUENCE: 84

```
tctagaatgg caggaagaag cggagacagc gacgaagagc tcatcagaac agtcagactc      60
atcaagcttc tctatcaaag caacccacct cccaatcccg aggggacccg acaggcccga     120
aggaatagaa gaagaaggtg gagagagaga cagagacaga tccattcgat tagtgaacgg     180
atccttggca cttatctggg acgatctgcg gagcctgtgc ctcttcagct accaccgctt     240
gagagactta ctcttgattg taacgaggat tgtggaactt ctgggacgca ggggggtggga    300 agcccctcaa tattggtgga atctcctaca atattggagt caggagctaa agaatagagg    360
agctttgttc cttgggttct tgggagcagc aggaagcact atgggcgcag cgtcaatgac    420
gctgacggta caggccagac aattattgtc tggtatagtg cagcagcaga caatttgct    480 gagggctatt gaggcgcaac agcatctgtt gcaactcaca gtctggggca tcaagcagct    540
ccaggcaaga atcctggctg tggaaagata cctaaaggat caacagctcc tagatctttt    600
tccctctgcc aaaaattatg gggacatcat gaagccctt gagcatctga cttctggcta    660
ataaaggaaa tttatttca ttgcaatagt gtgttggaat ttttgtgtc tctcactcgg    720 aaggacatat gggagggcaa atcatttaaa acatcagaat gagtatttgg tttagagttt    780
ggcaacatat gccatatgct ggctgccatg aacaaaggtg gctataaaga ggtcatcagt    840
atatgaaaca gccccctgct gtccattcct tattccatag aaaagccttg acttgaggtt    900
agattttttt tatattttgt tttgtgttat ttttttcttt aacatcccta aaattttcct    960
tacatgtttt actagccaga ttttttcctcc tctcctgact actcccagtc atagctgtcc   1020
ctcttctctt atgaagatcc ctcgacctgc agcccaagct tggcgtaatc atggtcatag   1080
ctgtttcctg tgtgaaattg ttatccgctc acaattccac acaacatacg agccggaagc   1140
```

```
ataaagtgta aagcctgggg tgcctaatga gtgagctaac tcacattaat tgcgttgcgc    1200
tcactgcccg ctttccagtc gggaaacctg tcgtgccagc ggatccgcat ctcaattagt    1260
cagcaaccat agtcccgccc ctaactccgc ccatcccgcc cctaactccg cccagttccg    1320
cccattctcc gccccatggc tgactaattt tttttattta tgcagaggcc gaggccgcct    1380
cggcctctga gctattccag aagtagtgag gaggcttttt tggaggccta ggcttttgca    1440
aaaagctaac ttgtttattg cagcttataa tggttacaaa taaagcaata gcatcacaaa    1500
tttcacaaat aaagcatttt tttcactgca ttctagttgt ggtttgtcca aactcatcaa    1560
tgtatcttat cagcggccgc cccggg                                        1586
```

<210> SEQ ID NO 85
<211> LENGTH: 1614
<212> TYPE: DNA
<213> ORGANISM: Artificial Sequence
<220> FEATURE:
<223> OTHER INFORMATION: DNA fragment containing the CAG
      enhancer/promoter/intron sequence

<400> SEQUENCE: 85

```
acgcgttagt tattaatagt aatcaattac ggggtcatta gttcatagcc catatatgga      60
gttccgcgtt acataactta cggtaaatgg cccgcctggc tgaccgccca acgaccccg     120 cccattgacg tcaataatga cgtatgttcc catagtaacg ccaatagggg ctttccattg    180
acgtcaatgg gtggactatt tacggtaaac tgcccacttg gcagtacatc aagtgtatca    240
tatgccaagt acgcccccta ttgacgtcaa tgacggtaaa tggcccgcct ggcattatgc    300
ccagtacatg accttatggg actttcctac ttggcagtac atctacgtat tagtcatcgc    360
tattaccatg gtcgaggtg agccccacgt tctgcttcac tctccccatc tcccccccct    420
cccacccccc aattttgtat ttatttattt tttaattatt ttgtgcagcg atgggggcgg    480 ggggggggg ggcgcgcgcc aggcggggcg gggcggggcg aggggcgggg cgggcgagg    540 cggagaggtg cggcggcagc caatcagagc ggcgcgctcc gaaagtttcc ttttatggcg    600
aggcggcggc ggcggcggcc ctataaaaag cgaagcgcgc ggcgggcggg agtcgctgcg    660
ttgccttcgc cccgtgcccc gctccgcgcc gcctcgcgcc gcccgccccg gctctgactg    720
accgcgttac tcccacaggt gagcgggcgg gacggccctt ctcctccggg ctgtaattag    780
cgcttggttt aatgacggct cgtttctttt ctgtggctgc gtgaaagcct taaagggctc    840
cgggagggcc ctttgtgcgg ggggagcgg ctcgggggt gcgtgcgtgt gtgtgtgcgt    900
ggggagcgcc gcgtgcggcc cgcgctgccc ggcggctgtg agcgctgcgg gcgcggcgcg    960
gggctttgtg cgctccgcgt gtgcgcgagg ggagcgcggc cggggcggt gccccgcggt    1020 gcggggggc tgcgagggga acaaaggctg cgtgcgggt gtgtgcgtgg ggggtgagc    1080 agggggtgtg ggcgcggcgg tcgggctgta acccccccct gcaccccct ccccgagttg    1140 ctgagcacgg cccggcttcg ggtgcgggc tccgtgcggg gcgtggcgcg ggctcgccg    1200 tgccgggcgg gggtggcgg caggtggggg tgccgggcg ggcggggccg cctcgggccg    1260
gggagggctc gggggagggg cgcggcggcc ccggagcgcc ggcggctgtc gaggcgcggc    1320
gagccgcagc cattgccttt tatggtaatc gtgcgagagg gcgcagggac ttcctttgtc    1380
ccaaatctgg cggagccgaa atctgggagg cgccgccgca ccccctctag cgggcgcggg    1440
cgaagcggtg cggcgccggc aggaaggaaa tgggcgggga gggccttcgt gcgtcgccgc    1500
gccgccgtcc ccttctccat ctccagcctc ggggctgccg caggggacg gctgccttcg    1560
``` gggggacgg ggcagggcgg ggttcggctt ctggcgtgtg accggcggga attc    1614

<210> SEQ ID NO 86
<211> LENGTH: 1531
<212> TYPE: DNA
<213> ORGANISM: Artificial Sequence
<220> FEATURE:
<223> OTHER INFORMATION: DNA fragment containing VSV-G

<400> SEQUENCE: 86
gaattcatga agtgcctttt gtacttagcc ttttttattca ttggggtgaa ttgcaagttc    60
accatagttt ttccacacaa ccaaaaagga aactggaaaa atgttccttc taattaccat    120
tattgcccgt caagctcaga tttaaattgg cataatgact taataggcac agccttacaa    180
gtcaaaatgc ccaagagtca caaggctatt caagcagacg gttggatgtg tcatgcttcc    240
aaatgggtca ctacttgtga tttccgctgg tatggaccga agtatataac acattccatc    300
cgatccttca ctccatctgt agaacaatgc aaggaaagca ttgaacaaac gaaacaagga    360
acttggctga atccaggctt ccctcctcaa agttgtggaa atgcaactgt gacggatgcc    420
gaagcagtga ttgtccaggt gactcctcac catgtgctgg ttgatgaata cacaggagaa    480
tgggttgatt cacagttcat caacggaaaa tgcagcaatt acatatgccc cactgtccat    540
aactctacaa cctggcattc tgactataag gtcaaagggc tatgtgattc taacctcatt    600
tccatggaca tcaccttctt ctcagaggac ggagagctat catccctggg aaaggagggc    660
acagggttca gaagtaacta ctttgcttat gaaactggag gcaaggcctg caaaatgcaa    720
tactgcaagc attggggagt cagactccca tcaggtgtct ggttcgagat ggctgataag    780
gatctctttg ctgcagccag attccctgaa tgcccagaag ggtcaagtat ctctgctcca    840
tctcagacct cagtggatgt aagtctaatt caggacgttg agaggatctt ggattattcc    900
ctctgccaag aaacctggag caaaatcaga gcgggtcttc aatctctcc agtggatctc    960
agctatcttg ctcctaaaaa cccaggaacc ggtcctgctt tcaccataat caatggtacc    1020
ctaaaatact ttgagaccag atacatcaga gtcgatattg ctgctccaat cctctcaaga    1080
atggtcggaa tgatcagtgg aactaccaca gaaagggaac tgtgggatga ctgggcacca    1140
tatgaagacg tggaaattgg acccaatgga gttctgagga ccagttcagg atataagttt    1200
cctttataca tgattggaca tggtatgttg gactccgatc ttcatcttag ctcaaaggct    1260
caggtgttcg aacatcctca cattcaagac gctgcttcgc aacttcctga tgatgagagt    1320
ttatttttg gtgatactgg gctatccaaa aatccaatcg agcttgtaga aggttggttc    1380
agtagttgga aaagctctat tgcctctttt ttctttatca tagggttaat cattggacta    1440
ttcttggttc tccgagttgg tatccatctt tgcattaaat taaagcacac caagaaaaga    1500
cagatttata cagacataga gatgagaatt c    1531

<210> SEQ ID NO 87
<211> LENGTH: 1227
<212> TYPE: DNA
<213> ORGANISM: Artificial Sequence
<220> FEATURE:
<223> OTHER INFORMATION: Helper plasmid containing RRE and rabbit beta
      globin poly A

<400> SEQUENCE: 87
tctagaagga gctttgttcc ttgggttctt gggagcagca ggaagcacta tgggcgcagc    60
gtcaatgacg ctgacggtac aggccagaca attattgtct ggtatagtgc agcagcagaa    120

-continued

| | |
|---|---|
| caatttgctg agggctattg aggcgcaaca gcatctgttg caactcacag tctggggcat | 180 |
| caagcagctc caggcaagaa tcctggctgt ggaaagatac ctaaaggatc aacagctcct | 240 |
| agatctttt ccctctgcca aaaattatgg ggacatcatg aagccccttg agcatctgac | 300 |
| ttctggctaa taaaggaaat ttattttcat tgcaatagtg tgttggaatt ttttgtgtct | 360 |
| ctcactcgga aggacatatg ggagggcaaa tcatttaaaa catcagaatg agtatttggt | 420 |
| ttagagtttg gcaacatatg ccatatgctg gctgccatga acaaaggtgg ctataaagag | 480 |
| gtcatcagta tatgaaacag cccctgctg tccattcctt attccataga aaagccttga | 540 |
| cttgaggtta gatttttttt atattttgtt ttgtgttatt tttttcttta acatccctaa | 600 |
| aattttcctt acatgtttta ctagccagat ttttcctcct ctcctgacta ctcccagtca | 660 |
| tagctgtccc tcttctctta tgaagatccc tcgacctgca gcccaagctt ggcgtaatca | 720 |
| tggtcatagc tgtttcctgt gtgaaattgt tatccgctca caattccaca acatacga | 780 |
| gccggaagca taaagtgtaa agcctggggt gcctaatgag tgagctaact cacattaatt | 840 |
| gcgttgcgct cactgcccgc tttccagtcg ggaaacctgt cgtgccagcg gatccgcatc | 900 |
| tcaattagtc agcaaccata gtcccgcccc taactccgcc catcccgccc ctaactccgc | 960 |
| ccagttccgc ccattctccg ccccatggct gactaatttt ttttatttat gcagaggccg | 1020 |
| aggccgcctc ggcctctgag ctattccaga agtagtgagg aggcttttt ggaggcctag | 1080 |
| gcttttgcaa aaagctaact tgtttattgc agcttataat ggttacaaat aaagcaatag | 1140 |
| catcacaaat ttcacaaata aagcattttt ttcactgcat tctagttgtg gtttgtccaa | 1200 |
| actcatcaat gtatcttatc acccggg | 1227 |

<210> SEQ ID NO 88
<211> LENGTH: 884
<212> TYPE: DNA
<213> ORGANISM: Artificial Sequence
<220> FEATURE:
<223> OTHER INFORMATION: RSV promoter and HIV Rev

<400> SEQUENCE: 88

| | |
|---|---|
| caattgcgat gtacgggcca gatatacgcg tatctgaggg gactagggtg tgtttaggcg | 60 |
| aaaagcgggg cttcggttgt acgcggttag gagtcccctc aggatatagt agtttcgctt | 120 |
| ttgcataggg aggggggaaat gtagtcttat gcaatacact tgtagtcttg caacatggta | 180 |
| acgatgagtt agcaacatgc cttacaagga gagaaaaagc accgtgcatg ccgattggtg | 240 |
| gaagtaaggt ggtacgatcg tgccttatta ggaaggcaac agacaggtct gacatggatt | 300 |
| ggacgaacca ctgaattccg cattgcagag ataattgtat ttaagtgcct agctcgatac | 360 |
| aataaacgcc atttgaccat tcaccacatt ggtgtgcacc tccaagctcg agctcgttta | 420 |
| gtgaaccgtc agatcgcctg gagacgccat ccacgctgtt ttgacctcca tagaagacac | 480 |
| cgggaccgat ccagcctccc ctcgaagcta gcgattaggc atctcctatg gcaggaagaa | 540 |
| gcggagacag cgacgaagaa ctcctcaagg cagtcagact catcaagttt ctctatcaaa | 600 |
| gcaacccacc tcccaatccc gaggggaccc gacaggcccg aaggaataga agaagaaggt | 660 |
| ggagagagag acagagacag atccattcga ttagtgaacg gatccttagc acttatctgg | 720 |
| gacgatctgc ggagcctgtg cctcttcagc taccaccgct tgagagactt actcttgatt | 780 |
| gtaacgagga ttgtggaact tctgggacgc aggggtggg aagccctcaa atattggtgg | 840 |
| aatctcctac aatattggag tcaggagcta agaatagtc taga | 884 |

```
<210> SEQ ID NO 89
<211> LENGTH: 19
<212> TYPE: DNA
<213> ORGANISM: Artificial Sequence
<220> FEATURE:
<223> OTHER INFORMATION: Target sequence

<400> SEQUENCE: 89
atggcaggaa gaagcggag                                                    19

<210> SEQ ID NO 90
<211> LENGTH: 52
<212> TYPE: DNA
<213> ORGANISM: Artificial Sequence
<220> FEATURE:
<223> OTHER INFORMATION: shRNA sequence

<400> SEQUENCE: 90
atggcaggaa gaagcggagt tcaagagact ccgcttcttc ctgccatttt tt              52

<210> SEQ ID NO 91
<211> LENGTH: 279
<212> TYPE: DNA
<213> ORGANISM: Artificial Sequence
<220> FEATURE:
<223> OTHER INFORMATION: H1 promoter and shRT sequence

<400> SEQUENCE: 91
gaacgctgac gtcatcaacc cgctccaagg aatcgcgggc ccagtgtcac taggcgggaa      60
cacccagcgc gcgtgcgccc tggcaggaag atggctgtga gggacagggg agtggcgccc     120
tgcaatattt gcatgtcgct atgtgttctg ggaaatcacc ataaacgtga aatgtctttg     180
gatttgggaa tcttataagt tctgtatgag accacttgga tccgcggaga cagcgacgaa     240
gagcttcaag agagctcttc gtcgctgtct ccgcttttt                            279

<210> SEQ ID NO 92
<211> LENGTH: 275
<212> TYPE: DNA
<213> ORGANISM: Artificial Sequence
<220> FEATURE:
<223> OTHER INFORMATION: H1 CCR5 sequence

<400> SEQUENCE: 92
gaacgctgac gtcatcaacc cgctccaagg aatcgcgggc ccagtgtcac taggcgggaa      60
cacccagcgc gcgtgcgccc tggcaggaag atggctgtga gggacagggg agtggcgccc     120
tgcaatattt gcatgtcgct atgtgttctg ggaaatcacc ataaacgtga aatgtctttg     180
gatttgggaa tcttataagt tctgtatgag accacttgga tccgtgtcaa gtccaatcta     240
tgttcaagag acatagattg gacttgacac ttttt                                275

<210> SEQ ID NO 93
<211> LENGTH: 20
<212> TYPE: DNA
<213> ORGANISM: Artificial Sequence
<220> FEATURE:
<223> OTHER INFORMATION: Primer

<400> SEQUENCE: 93
aggaattgat ggcgagaagg                                                  20

<210> SEQ ID NO 94
<211> LENGTH: 24
<212> TYPE: DNA
```

```
<213> ORGANISM: Artificial Sequence
<220> FEATURE:
<223> OTHER INFORMATION: Primer

<400> SEQUENCE: 94
ccccaaagaa ggtcaaggta atca                                               24

<210> SEQ ID NO 95
<211> LENGTH: 18
<212> TYPE: DNA
<213> ORGANISM: Artificial Sequence
<220> FEATURE:
<223> OTHER INFORMATION: Primer

<400> SEQUENCE: 95
agcgcggcta cagcttca                                                      18

<210> SEQ ID NO 96
<211> LENGTH: 20
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (20)..(20)
<223> OTHER INFORMATION: n = p

<400> SEQUENCE: 96
ggcgacgtag cacagcttcn                                                    20

<210> SEQ ID NO 97
<211> LENGTH: 20
<212> TYPE: DNA
<213> ORGANISM: Artificial Sequence
<220> FEATURE:
<223> OTHER INFORMATION: AGT103 CCR5 miR30

<400> SEQUENCE: 97
tgtaaactga gcttgctcta                                                    20

<210> SEQ ID NO 98
<211> LENGTH: 20
<212> TYPE: DNA
<213> ORGANISM: Artificial Sequence
<220> FEATURE:
<223> OTHER INFORMATION: AGT103-R5-1

<400> SEQUENCE: 98
tgtaaactga gcttgctcgc                                                    20

<210> SEQ ID NO 99
<211> LENGTH: 19
<212> TYPE: DNA
<213> ORGANISM: Artificial Sequence
<220> FEATURE:
<223> OTHER INFORMATION: AGT103-R5-2

<400> SEQUENCE: 99
catagattgg acttgacac                                                     19

<210> SEQ ID NO 100
<211> LENGTH: 642
<212> TYPE: DNA
<213> ORGANISM: Artificial Sequence
<220> FEATURE:
<223> OTHER INFORMATION: CAG promoter
```

<400> SEQUENCE: 100

```
tagttattaa tagtaatcaa ttacggggtc attagttcat agcccatata tggagttccg      60
cgttacataa cttacggtaa atggcccgcc tggctgaccg cccaacgacc cccgcccatt     120
gacgtcaata atgacgtatg ttcccatagt aacgccaata gggactttcc attgacgtca     180
atgggtggac tatttacggt aaactgccca cttggcagta catcaagtgt atcatatgcc     240
aagtacgccc cctattgacg tcaatgacgg taaatggccc gcctggcatt atgcccagta     300
catgacctta tgggactttc ctacttggca gtacatctac gtattagtca tcgctattac     360
catgggtcga ggtgagcccc acgttctgct tcactctccc catctccccc ccctccccac     420
ccccaatttt gtatttattt attttttaat tattttgtgc agcgatgggg gcggggggg      480
gggggcgcg cgccaggcgg ggcggggcgg ggcgagggc ggggcgggc gaggcggaga        540
ggtgcggcgg cagccaatca gagcggcgcg ctccgaaagt ttccttttat ggcgaggcgg     600
cggcggcggc ggccctataa aaagcgaagc gcgcggcggg cg                        642
```

<210> SEQ ID NO 101
<211> LENGTH: 217
<212> TYPE: DNA
<213> ORGANISM: Artificial Sequence
<220> FEATURE:
<223> OTHER INFORMATION: H1 element

<400> SEQUENCE: 101

```
gaacgctgac gtcatcaacc cgctccaagg aatcgcgggc ccagtgtcac taggcgggaa      60
cacccagcgc gcgtgcgccc tggcaggaag atggctgtga gggacagggg agtggcgccc    120
tgcaatattt gcatgtcgct atgtgttctg ggaaatcacc ataaacgtga aatgtctttg    180
gatttgggaa tcttataagt tctgtatgag accactt                              217
```

<210> SEQ ID NO 102
<211> LENGTH: 250
<212> TYPE: DNA
<213> ORGANISM: Artificial Sequence
<220> FEATURE:
<223> OTHER INFORMATION: 3' LTR

<400> SEQUENCE: 102

```
tggaagggct aattcactcc caacgaagat aagatctgct ttttgcttgt actgggtctc      60
tctggttaga ccagatctga gcctgggagc tctctggcta actagggaac ccactgctta    120
agcctcaata aagcttgcct tgagtgcttc aagtagtgtg tgcccgtctg ttgtgtgact    180
ctggtaacta gagatccctc agacccttt agtcagtgtg gaaaatctct agcagtagta     240
gttcatgtca                                                             250
```

<210> SEQ ID NO 103
<211> LENGTH: 243
<212> TYPE: DNA
<213> ORGANISM: Artificial Sequence
<220> FEATURE:
<223> OTHER INFORMATION: 7SK promoter

<400> SEQUENCE: 103

```
ctgcagtatt tagcatgccc cacccatctg caaggcattc tggatagtgt caaaacagcc      60
ggaaatcaag tccgtttatc tcaaacttta gcattttggg aataaatgat atttgctatg    120
ctggttaaat tagattttag ttaaatttcc tgctgaagct ctagtacgat aagcaacttg    180
```

```
acctaagtgt aaagttgaga tttccttcag gtttatatag cttgtgcgcc gcctggctac    240
ctc                                                                  243

<210> SEQ ID NO 104
<211> LENGTH: 132
<212> TYPE: DNA
<213> ORGANISM: Artificial Sequence
<220> FEATURE:
<223> OTHER INFORMATION: miR155 Tat

<400> SEQUENCE: 104
ctggaggctt gctgaaggct gtatgctgtc cgcttcttcc tgccataggg ttttggccac     60
tgactgaccc tatggggaag aagcggacag gacacaaggc ctgttactag cactcacatg    120
gaacaaatgg cc                                                        132

<210> SEQ ID NO 105
<211> LENGTH: 3992
<212> TYPE: DNA
<213> ORGANISM: Artificial Sequence
<220> FEATURE:
<223> OTHER INFORMATION: pRSV Rev

<400> SEQUENCE: 105
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gaattcgatg    240
tacgggccag atatacgcgt atctgagggg actaggtgt gtttaggcga aaagcggggc     300
ttcggttgta cgcggttagg agtcccctca ggatatagta gtttcgcttt tgcataggga    360
gggggaaatg tagtcttatg caatacactt gtagtcttgc aacatggtaa cgatgagtta    420
gcaacatgcc ttacaaggag agaaaaagca ccgtgcatgc cgattggtgg aagtaaggtg    480
gtacgatcgt gccttattag gaaggcaaca gacaggtctg acatggattg gacgaaccac    540
tgaattccgc attgcagaga taattgtatt taagtgccta gctcgataca ataaacgcca    600
tttgaccatt caccacattg gtgtgcacct ccaagctcga gctcgtttag tgaaccgtca    660
gatcgcctgg agacgccatc cacgctgttt tgacctccat agaagacacc gggaccgatc    720
cagcctcccc tcgaagctag tcgattaggc atctcctatg gcaggaagaa gcggagacag    780
cgacgaagac ctcctcaagg cagtcagact catcaagttt ctctatcaaa gcaacccacc    840
tcccaatccc gaggggaccc gacaggcccg aaggaataga agaagaaggt ggagagagag    900
acagagacag atccattcga ttagtgaacg gatccttagc acttatctgg gacgatctgc    960
ggagcctgtg cctcttcagc taccaccgct tgagagactt actcttgatt gtaacgagga   1020
ttgtggaact tctgggacgc aggggtggg aagcccctcaa atattggtgg aatctcctac    1080
aatattggag tcaggagcta aagaatagtg ctgttagctt gctcaatgcc acagctatag    1140
cagtagctga ggggacagat agggttatag aagtagtaca agaagcttgg cactggccgt    1200
cgttttacat gatctgagcc tgggagatct ctggctaact agggaaccca ctgcttaagc    1260
ctcaataaag cttgccttga gtgcttcaag tagtgtgtgc ccgtctgttg tgtgactctg    1320
gtaactagag atcacaaagc aaccatagta cgcgccctgt agcggcgcat taagcgcggc    1380
gggtgtggtg gttacgcgca gcgtgaccgc tacacttgcc agcgccctag cgcccgctcc    1440
tttcgctttc ttcccttcct ttctcgccac gttcgccggc tttccccgtc aagctctaaa   1500
```

-continued

```
tcggggctc cctttagggt tccgatttag tgctttacgg cacctcgacc ccaaaaaact   1560
tgatttgggt gatggttcac gtagtgggcc atcgccctga tagacggttt ttcgcccttt   1620
gacgttggag tccacgttct ttaatagtgg actcttgttc caaactggaa caacactcaa   1680
ccctatctcg ggctattctt ttgatttata agggattttg ccgatttcgg cctattggtt   1740
aaaaaatgag ctgatttaac aaaaatttaa cgcgaatttt aacaaaatat taacgtttac   1800
aattttatgg tgcactctca gtacaatctg ctctgatgcc gcatagttaa gccagccccg   1860
acacccgcca cacccgctg acgcgccctg acgggcttgt ctgctcccgg catccgctta   1920
cagacaagct gtgaccgtct ccgggagctg catgtgtcag aggttttcac cgtcatcacc   1980
gaaacgcgcg agacgaaagg gcctcgtgat acgcctattt ttataggtta atgtcatgat   2040
aataatggtt tcttagacgt caggtggcac ttttcgggga atgtgcgcg aaccccctat   2100 ttgtttattt ttctaaatac attcaaatat gtatccgctc atgagacaat aaccctgata   2160
aatgcttcaa taatattgaa aaggaagag tatgagtatt caacatttcc gtgtcgccct   2220
tattcccttt tttgcggcat tttgccttcc tgttttgct cacccagaaa cgctggtgaa   2280
agtaaaagat gctgaagatc agttgggtgc acgagtgggt tacatcgaac tggatctcaa   2340
cagcggtaag atccttgaga gttttcgccc cgaagaacgt tttccaatga tgagcacttt   2400
taaagttctg ctatgtggcg cggtattatc ccgtattgac gccgggcaag agcaactcgg   2460
tcgccgcata cactattctc agaatgactt ggttgagtac tcaccagtca cagaaaagca   2520
tcttacggat ggcatgacag taagagaatt atgcagtgct gccataacca tgagtgataa   2580
cactgcggcc aacttacttc tgacaacgat cggaggaccg aaggagctaa ccgcttttt   2640 gcacaacatg ggggatcatg taactcgcct tgatcgttgg gaaccggagc tgaatgaagc   2700
cataccaaac gacgagcgtg acaccacgat gcctgtagca atggcaacaa cgttgcgcaa   2760
actattaact ggcgaactac ttactctagc ttcccggcaa caattaatag actggatgga   2820
ggcggataaa gttgcaggac cacttctgcg ctcggccctt ccggctggct ggtttattgc   2880
tgataaatct ggagccggtg agcgtgggtc tcgcggtatc attgcagcac tggggccaga   2940
tggtaagccc tcccgtatcg tagttatcta cacgacgggg agtcaggcaa ctatggatga   3000
acgaaataga cagatcgctg agataggtgc ctcactgatt aagcattggt aactgtcaga   3060
ccaagtttac tcatatatac tttagattga tttaaaactt catttttaat ttaaaaggat   3120
ctaggtgaag atccttttg ataatctcat gaccaaaatc ccttaacgtg agttttcgtt   3180
ccactgagcg tcagaccccg tagaaaagat caaaggatct tcttgagatc cttttttct   3240 gcgcgtaatc tgctgcttgc aaacaaaaaa accaccgcta ccagcggtgg tttgtttgcc   3300
ggatcaagag ctaccaactc tttttccgaa ggtaactggc ttcagcagag cgcagatacc   3360
aaatactgtc cttctagtgt agccgtagtt aggccaccac ttcaagaact ctgtagcacc   3420
gcctacatac ctcgctctgc taatcctgtt accagtggct gctgccagtg gcgataagtc   3480
gtgtcttacc gggttggact caagacgata gttaccggat aaggcgcagc ggtcgggctg   3540
aacggggggt tcgtgcacac agcccagctt ggagcgaacg acctacaccg aactgagata   3600
cctacagcgt gagctatgag aaagcgccac gcttcccgaa gggagaaagg cggacaggta   3660
tccggtaagc ggcagggtcg gaacaggaga gcgcacgagg gagcttccag ggggaaacgc   3720
ctggtatctt tatagtcctg tcgggtttcg ccacctctga cttgagcgtc gatttttgtg   3780
atgctcgtca gggggcgga gcctatggaa aaacgccagc aacgcggcct ttttacggtt   3840
``` cctggcctttt tgctggcctt ttgctcacat gttctttcct gcgttatccc ctgattctgt    3900
ggataaccgt attaccgcct ttgagtgagc tgataccgct cgccgcagcc gaacgaccga    3960
gcgcagcgag tcagtgagcg aggaagcgga ag    3992

<210> SEQ ID NO 106
<211> LENGTH: 6363
<212> TYPE: DNA
<213> ORGANISM: Artificial Sequence
<220> FEATURE:
<223> OTHER INFORMATION: pCMV-VSV-G

<400> SEQUENCE: 106
gagcttggcc cattgcatac gttgtatcca tatcataata tgtacattta tattggctca      60
tgtccaacat taccgccatg ttgacattga ttattgacta gttattaata gtaatcaatt     120
acggggtcat tagttcatag cccatatatg gagttccgcg ttacataact tacggtaaat     180
ggcccgcctg gctgaccgcc caacgacccc cgcccattga cgtcaataat gacgtatgtt     240
cccatagtaa cgccaatagg gactttccat tgacgtcaat gggtggagta tttacggtaa     300
actgcccact tggcagtaca tcaagtgtat catatgccaa gtacgccccc tattgacgtc     360
aatgacggta aatggcccgc ctggcattat gcccagtaca tgaccttatg gactttcct     420 acttggcagt acatctacgt attagtcatc gctattacca tggtgatgcg gttttggcag     480
tacatcaatg ggcgtggata gcggtttgac tcacggggat ttccaagtct ccaccccatt     540
gacgtcaatg ggagtttgtt ttggcaccaa aatcaacggg actttccaaa atgtcgtaac     600
aactccgccc cattgacgca aatgggcggt aggcgtgtac ggtgggaggt ctatataagc     660
agagctcgtt tagtgaaccg tcagatcgcc tggagacgcc atccacgctg ttttgacctc     720
catagaagac accgggaccg atccagcctc cggtcgaccg atcctgagaa cttcagggtg     780
agtttgggga cccttgattg ttctttcttt ttcgctattg taaaattcat gttatatgga     840
gggggcaaag ttttcagggt gttgtttaga atgggaagat gtcccttgta tcaccatgga     900
ccctcatgat aattttgttt ctttcacttt ctactctgtt gacaaccatt gtctcctctt     960
attttctttt cattttctgt aacttttcg ttaaacttta gcttgcattt gtaacgaatt    1020
tttaaattca cttttgttta tttgtcagat tgtaagtact ttctctaatc acttttttt    1080 caaggcaatc agggtatatt atattgtact tcagcacagt tttagagaac aattgttata    1140
attaaatgat aaggtagaat atttctgcat ataaattctg gctggcgtgg aaatattctt    1200
attggtagaa acaactacac cctggtcatc atcctgcctt tctctttatg gttacaatga    1260
tatacactgt ttgagatgag gataaaatac tctgagtcca aaccgggccc ctctgctaac    1320
catgttcatg ccttcttctc tttcctacag ctcctgggca acgtgctggt tgttgtgctg    1380
tctcatcatt ttggcaaaga attcctcgac ggatccgcca tgaagtgcct tttgtactta    1440
gcctttttat tcattgggt gaattgcaag ttcaccatag ttttccaca caaccaaaaa    1500 ggaaactgga aaaatgttcc ttctaattac cattattgcc cgtcaagctc agatttaaat    1560
tggcataatg acttaatagg cacagcctta caagtcaaaa tgcccaagag tcacaaggct    1620
attcaagcag acggttggat gtgtcatgct tccaaatggg tcactacttg tgatttccgc    1680
tggtatggac cgaagtatat aacacattcc atccgatcct tcactccatc tgtagaacaa    1740
tgcaaggaaa gcattgaaca aacgaaacaa ggaacttggc tgaatccagg cttccctcct    1800
caaagttgtg gatatgcaac tgtgacggat gccgaagcag tgattgtcca ggtgactcct    1860
caccatgtgc tggttgatga atacacagga gaatggggttg attcacagtt catcaacgga    1920

```
aaatgcagca attacatatg ccccactgtc cataactcta caacctggca ttctgactat   1980
aaggtcaaag ggctatgtga ttctaacctc atttccatgg acatcacctt cttctcagag   2040
gacggagagc tatcatccct gggaaggag ggcacagggt tcagaagtaa ctactttgct    2100
tatgaaactg gaggcaaggc ctgcaaaatg caatactgca agcattgggg agtcagactc   2160
ccatcaggtg tctggttcga gatggctgat aaggatctct tgctgcagc cagattccct    2220 gaatgcccag aagggtcaag tatctctgct ccatctcaga cctcagtgga tgtaagtcta   2280
attcaggacg ttgagaggat cttggattat tccctctgcc aagaaacctg agcaaaatc    2340 agagcgggtc ttccaatctc tccagtggat ctcagctatc ttgctcctaa aacccagga    2400 accggtcctg ctttcaccat aatcaatggt accctaaaat actttgagac cagatacatc   2460
agagtcgata ttgctgctcc aatcctctca agaatggtcg aatgatcag tggaactacc    2520 acagaaaggg aactgtggga tgactgggca ccatatgaag acgtggaaat tggacccaat   2580
ggagttctga ggaccagttc aggatataag tttcctttat acatgattgg acatggtatg   2640
ttggactccg atcttcatct tagctcaaag gctcaggtgt tcgaacatcc tcacattcaa   2700
gacgctgctt cgcaacttcc tgatgatgag agtttatttt ttggtgatac tgggctatcc   2760
aaaaatccaa tcgagcttgt agaaggttgg ttcagtagtt ggaaaagctc tattgcctct   2820
ttttctttta tcatagggtt aatcattgga ctattcttgg ttctccgagt tggtatccat   2880
ctttgcatta aattaaagca caccaagaaa agacagattt atacagacat agagatgaac   2940
cgacttggaa agtgataagg atccgtcgag gaattcactc ctcaggtgca ggctgcctat   3000
cagaaggtgg tggctggtgt ggccaatgcc ctggctcaca ataccactg agatcttttt    3060 ccctctgcca aaaattatgg ggacatcatg aagcccttg agcatctgac ttctggctaa    3120
taaaggaaat ttattttcat tgcaatagtg tgttggaatt ttttgtgtct ctcactcgga   3180
aggacatatg ggagggcaaa tcatttaaaa catcagaatg agtatttggt ttagagtttg   3240
gcaacatatg cccatatgct ggctgccatg aacaaaggtt ggctataaag aggtcatcag   3300
tatatgaaac agcccctgc tgtccattcc ttattccata gaaaagcctt gacttgaggt    3360 tagattttt ttatatttg ttttgtgtta ttttttttctt taacatccct aaaatttttcc   3420 ttacatgttt tactagccag attttttcctc ctctcctgac tactcccagt catagctgtc   3480
cctcttctct tatggagatc cctcgacgga tcggccgcaa ttcgtaatca tgtcatagct   3540
gtttcctgtg tgaaattgtt atccgctcac aattccacac aacatacgag ccggaagcat   3600
aaagtgtaaa gcctggggtg cctaatgagt gagctaactc acattaattg cgttgcgctc   3660
actgcccgct ttccagtcgg gaaacctgtc gtgccagctg cattaatgaa tcggccaacg   3720 cgcgggaga ggcggtttgc gtattgggcg ctcttccgct tcctcgctca ctgactcgct    3780
gcgctcggtc gttcggctgc ggcgagcggt atcagctcac tcaaaggcgg taatacggtt   3840
atccacagaa tcaggggata acgcaggaaa gaacatgtga gcaaaaggcc agcaaaaggc   3900
caggaaccgt aaaaaggccg cgttgctggc gtttttccat aggctccgcc ccctgacga    3960 gcatcacaaa aatcgacgct caagtcagag gtggcgaaac ccgacaggac tataaagata   4020
ccaggcgttt cccctggaa gctccctcgt gcgctctcct gttccgaccc tgccgcttac    4080
cggatacctg tccgcctttc tcccttcggg aagcgtggcg ctttctcata gctcacgctg   4140
taggtatctc agttcggtgt aggtcgttcg ctccaagctg ggctgtgtgc acgaaccccc   4200
cgttcagccc gaccgctgcg ccttatccgg taactatcgt cttgagtcca acccggtaag   4260
```

```
acacgactta tcgccactgg cagcagccac tggtaacagg attagcagag cgaggtatgt    4320
aggcggtgct acagagttct tgaagtggtg gcctaactac ggctacacta agaacagt      4380 atttggtatc tgcgctctgc tgaagccagt taccttcgga aaaagagttg gtagctcttg   4440
atccggcaaa caaccaccg ctggtagcgg tggttttttt gtttgcaagc agcagattac    4500
gcgcagaaaa aaggatctc aagaagatcc tttgatcttt tctacggggt ctgacgctca    4560
gtggaacgaa aactcacgtt aagggatttt ggtcatgaga ttatcaaaaa ggatcttcac   4620
ctagatcctt ttaaattaaa aatgaagttt taaatcaatc taaagtatat atgagtaaac   4680
ttggtctgac agttaccaat gcttaatcag tgaggcacct atctcagcga tctgtctatt   4740
tcgttcatcc atagttgcct gactccccgt cgtgtagata actacgatac gggagggctt   4800
accatctggc cccagtgctg caatgatacc gcgagaccca cgctcaccgg ctccagattt   4860
atcagcaata accagccag ccggaagggc cgagcgcaga agtggtcctg caactttatc    4920
cgcctccatc cagtctatta attgttgccg gaagctaga gtaagtagtt cgccagttaa    4980 tagtttcgc aacgttgttg ccattgctac aggcatcgtg gtgtcacgct cgtcgtttgg    5040
tatggcttca ttcagctccg gttcccaacg atcaaggcga gttacatgat cccccatgtt   5100
gtgcaaaaaa gcggttagct ccttcggtcc tccgatcgtt gtcagaagta agttggccgc   5160
agtgttatca ctcatggtta tggcagcact gcataattct cttactgtca tgccatccgt   5220
aagatgcttt tctgtgactg gtgagtactc aaccaagtca ttctgagaat agtgtatgcg   5280
gcgaccgagt tgctcttgcc cggcgtcaat acgggataat accgcgccac atagcagaac   5340
tttaaaagtg ctcatcattg gaaaacgttc ttcggggcga aaactctcaa ggatcttacc   5400
gctgttgaga tccagttcga tgtaacccac tcgtgcaccc aactgatctt cagcatcttt   5460
tactttcacc agcgtttctg ggtgagcaaa aacaggaagg caaaatgccg caaaaaaggg   5520
aataagggcg acacggaaat gttgaatact catactcttc ctttttcaat attattgaag   5580
catttatcag ggttattgtc tcatgagcgg atacatattt gaatgtattt agaaaaataa   5640
acaaataggg gttccgcgca catttccccg aaaagtgcca cctaaattgt aagcgttaat   5700
attttgttaa aattcgcgtt aaattttgt taaatcagct cattttttaa ccaataggcc    5760
gaaatcggca aaatccctta taaatcaaaa gaatagaccg agatagggtt gagtgttgtt   5820
ccagtttgga acaagagtcc actattaaag aacgtggact ccaacgtcaa agggcgaaaa   5880
accgtctatc agggcgatgg cccactacgt gaaccatcac cctaatcaag ttttttgggg   5940
tcgaggtgcc gtaaagcact aaatcggaac cctaaaggga gccccgatt tagagcttga    6000 cggggaaagc cggcgaacgt ggcgagaaag gaagggaaga agcgaaagg agcgggcgct    6060 agggcgctgg caagtgtagc ggtcacgctg cgcgtaacca ccacccgc cgcgcttaat     6120 gcgccgctac agggcgcgtc ccattcgcca ttcaggctgc gcaactgttg ggaagggcga   6180
tcggtgcggg cctcttcgct attacgccag ctggcgaaag ggggatgtgc tgcaaggcga   6240
ttaagttggg taacgccagg gttttcccag tcacgacgtt gtaaaacgac ggccagtgag   6300
cgcgcgtaat acgactcact atagggcgaa ttggagctcc accgcggtgg cggccgctct   6360
aga                                                                6363
```

<210> SEQ ID NO 107
<211> LENGTH: 9496
<212> TYPE: DNA
<213> ORGANISM: Artificial Sequence
<220> FEATURE:
<223> OTHER INFORMATION: PSPAX2 delta Rev

<400> SEQUENCE: 107

```
gtcgacattg attattgact agttattaat agtaatcaat tacggggtca ttagttcata      60
gcccatatat ggagttccgc gttacataac ttacggtaaa tggcccgcct ggctgaccgc     120
ccaacgaccc ccgcccattg acgtcaataa tgacgtatgt tcccatagta acgccaatag     180
ggactttcca ttgacgtcaa tgggtggact atttacggta aactgcccac ttggcagtac     240
atcaagtgta tcatatgcca gtacgcccc ctattgacgt caatgacggt aaatggcccg     300
cctggcatta tgcccagtac atgaccttat gggactttcc tacttggcag tacatctacg     360
tattagtcat cgctattacc atgggtcgag gtgagcccca cgttctgctt cactctcccc     420
atctccccc cctccccacc cccaattttg tatttattta tttttaatt attttgtgca       480
gcgatggggg cggggggggg ggggcgcgc gccaggcggg gcgggcggg gcgaggggcg        540
gggcggggcg aggcggagag gtgcggcggc agccaatcag agcggcgcgc tccgaaagtt     600
tccttttatg gcgaggcggc ggcggcgcg gccctataaa agcgaagcg cgcggcgggc       660
gggagtcgct gcgttgcctt cgccccgtgc cccgctccgc gccgctcgc gccgcccgcc      720
ccggctctga ctgaccgcgt tactcccaca ggtgagcggg cggacgcc cttctcctcc       780
gggctgtaat tagcgcttgg tttaatgacg gctcgtttct tttctgtggc tgcgtgaaag     840
ccttaaaggg ctccgggagg gcccttttgtg cgggggggag cggctcgggg ggtgcgtgcg    900
tgtgtgtgtg cgtggggagc gccgcgtgcg gcccgcgctg cccggcggct gtgagcgctg     960
cgggcgcggc gcgggctttt gtgcgctccg cgtgtgcgcg aggggagcgc ggccggggc     1020
ggtgccccgc ggtgcggggg ggctgcgagg ggaacaaagg ctgcgtgcgg ggtgtgtgcg    1080
tgggggggtg agcaggggt gtgggcgcgg cggtcgggct gtaacccccc cctgcacccc     1140
cctccccgag ttgctgagca cggcccggct tcggtgcgg ggctccgtgc ggggcgtggc    1200
gcggggctcg ccgtgccggg cggggggtgg cggcaggtgg gggtgccggg cggggcgggg    1260
ccgcctcggg ccggggaggg ctcgggggag gggcgcggcg gccccggagc gccggcggct    1320
gtcgaggcgc ggcgagccgc agccattgcc ttttatggta atcgtgcgag agggcgcagg    1380
gacttccttt gtcccaaatc tggcggagcc gaaatctggg aggcgccgcc gcaccccctc    1440
tagcgggcgc gggcgaagcg gtgcggcgcc ggcaggaagg aaatgggcgg ggagggcctt    1500
cgtgcgtcgc cgcgccgccg tccccttctc catctccagc ctcggggctg ccgcagggg    1560
acggctgcct tcgggggga cggggcaggg cggggttcgg cttctggcgt gtgaccggcg    1620
gctctagagc ctctgctaac catgttcatg ccttcttctt tttcctacag ctcctgggca    1680
acgtgctggt tattgtgctg tctcatcatt ttggcaaaga attcgggccg gccgcgttga    1740
cgcgcacggc aagaggcgag gggcggcgac tggtgagaga tgggtgcgag agcgtcagta    1800
ttaagcgggg gagaattaga tcgatgggaa aaaattcggt taaggccagg gggaaagaaa    1860
aaatataaat taaaacatat agtatgggca agcagggagc tagaacgatt cgcagttaat    1920
cctggcctgt tagaaacatc agaaggctgt agacaaatac tgggacagct acaaccatcc    1980
cttcagacag gatcagaaga acttagatca ttatataata cagtagcaac cctctattgt    2040
gtgcatcaaa ggatagagat aaaagacacc aaggaagctt tagacaagat agaggaagag    2100
caaaacaaaa gtaagaaaaa agcacagcaa gcagcagctg acacaggaca cagcaatcag    2160
gtcagccaaa attaccctat agtgcagaac atccagggc aaatggtaca tcaggccata    2220
tcacctagaa ctttaaatgc atgggtaaaa gtagtagaag agaaggcttt cagcccagaa    2280
```

```
gtgatacccca tgttttcagc attatcagaa ggagccaccc cacaagatttt aaacaccatg   2340 ctaaacacag tgggggggaca tcaagcagcc atgcaaatgt aaaagagac catcaatgag    2400 gaagctgcag aatgggatag agtgcatcca gtgcatgcag ggcctattgc accaggccag    2460
atgagagaac caaggggaag tgacatagca ggaactacta gtacccttca ggaacaaata    2520
ggatggatga cacataatcc acctatccca gtaggagaaa tctataaaag atggataatc    2580
ctgggattaa ataaaatagt aagaatgtat agccctacca gcattctgga cataagacaa    2640
ggaccaaagg aacccttttag agactatgta gaccgattct ataaaactct aagagccgag   2700
caagcttcac aagaggtaaa aaattggatg acagaaacct tgttggtcca aaatgcgaac    2760
ccagattgta agactatttt aaaagcattg ggaccaggag cgacactaga agaaatgatg    2820
acagcatgtc agggagtggg gggacccggc cataaagcaa gagttttggc tgaagcaatg    2880
agccaagtaa caaatccagc taccataatg atacagaaag gcaattttag gaaccaaaga    2940
aagactgtta agtgtttcaa ttgtggcaaa gaagggcaca tagccaaaaa ttgcagggcc    3000
cctaggaaaa agggctgttg gaaatgtgga aaggaaggac accaaatgaa agattgtact    3060
gagagacagg ctaattttttt agggaagatc tggccttccc acaagggaag gccagggaat   3120
tttcttcaga gcagaccaga gccaacagcc ccaccagaag agagcttcag gtttggggaa    3180
gagacaacaa ctccctctca gaagcaggag ccgatagaca aggaactgta tcctttagct    3240
tccctcagat cactctttgg cagcgacccc tcgtcacaat aaagataggg gggcaattaa    3300
aggaagctct attagataca ggagcagatg atacagtatt agaagaaatg aatttgccag    3360
gaagatggaa accaaaaatg atagggggaa ttggaggttt tatcaaagta ggacagtatg    3420
atcagatact catagaaatc tgcggacata agctataggt acagtatta gtaggaccta    3480 cacctgtcaa cataattgga agaaatctgt tgactcagat tggctgcact ttaaattttc    3540
ccattagtcc tattgagact gtaccagtaa aattaaagcc aggaatggat ggcccaaaag    3600
ttaaacaatg gccattgaca gaagaaaaaa taaaagcatt agtagaaatt tgtacagaaa    3660
tggaaaagga aggaaaaatt tcaaaaattg ggcctgaaaa tccatacaat actccagtat    3720
ttgccataaa gaaaaagac agtactaaat ggagaaaatt agtagatttc agagaactta    3780
ataagagaac tcaagatttc tgggaagttc aattaggaat accacatcct gcagggttaa    3840
aacagaaaaa atcagtaaca gtactggatg tgggcgatgc atatttttca gttcccttag    3900
ataaagactt caggaagtat actgcattta ccatacctag tataaacaat gagacaccag    3960
ggattagata tcagtacaat gtgcttccac agggatggaa aggatcacca gcaatattcc    4020
agtgtagcat gacaaaaatc ttagagcctt ttagaaaaca aaatccagac atagtcatct    4080
atcaatacat ggatgatttg tatgtaggat ctgacttaga aatagggcag catagaacaa    4140
aaatagagga actgagacaa catctgttga ggtgggatt taccacacca gacaaaaaac    4200
atcagaaaga acctccattc ctttggatgg gttatgaact ccatcctgat aaatggacag    4260
tacagcctat agtgctgcca gaaaaggaca gctggactgt caatgacata cagaaattag    4320
tgggaaaatt gaattgggca agtcagattt atgcagggat taaagtaagg caattatgta    4380
aacttcttag gggaaccaaa gcactaacag aagtagtacc actaacgaaa gaagcagagc    4440
tagaactggc agaaaacagg gagattctaa aagaaccggt acatggagtg tattatgacc    4500
catcaaaaga cttaatagca gaaatacaga agcaggggca aggccaatgg acatatcaaa    4560
tttatcaaga gccatttaaa aatctgaaaa caggaaaata tgcaagaatg aagggtgccc    4620
acactaatga tgtgaaacaa ttaacagagg cagtacaaaa aatagccaca gaaagcatag    4680
```

```
taatatgggg aaagactcct aaatttaaat tacccataca aaaggaaaca tgggaagcat   4740
ggtggacaga gtattggcaa gccacctgga ttcctgagtg ggagtttgtc aatacccctc   4800
ccttagtgaa gttatggtac cagttagaga agaacccat aataggagca gaaactttct    4860
atgtagatgg ggcagccaat agggaaacta aattaggaaa agcaggatat gtaactgaca   4920
gaggaagaca aaaagttgtc cccctaacgg acacaacaaa tcagaagact gagttacaag   4980
caattcatct agctttgcag gattcgggat tagaagtaaa catagtgaca gactcacaat   5040
atgcattggg aatcattcaa gcacaaccag ataagagtga atcagagtta gtcagtcaaa   5100
taatagagca gttaataaaa aaggaaaaag tctacctggc atgggtacca gcacacaaag   5160
gaattggagg aaatgaacaa gtagatgggt tggtcagtgc tggaatcagg aaagtactat   5220
ttttagatgg aatagataag gcccaagaag aacatgagaa atatcacagt aattggagag   5280
caatggctag tgattttaac ctaccacctg tagtagcaaa agaaatagta gccagctgtg   5340
ataaatgtca gctaaaaggg gaagccatgc atggacaagt agactgtagc ccaggaatat   5400
ggcagctaga ttgtacacat ttagaaggaa aagttatctt ggtagcagtt catgtagcca   5460
gtggatatat agaagcagaa gtaattccag cagagacagg gcaagaaaca gcatacttcc   5520
tcttaaaatt agcaggaaga tggccagtaa aaacagtaca tacagacaat ggcagcaatt   5580
tcaccagtac tacagttaag gccgcctgtt ggtgggcggg gatcaagcag gaatttggca   5640
ttccctacaa tccccaaagt caaggagtaa tagaatctat gaataaagaa ttaaagaaaa   5700
ttataggaca ggtaagagat caggctgaac atcttaagac agcagtacaa atggcagtat   5760
tcatccacaa ttttaaaaga aaggggggga ttggggggta cagtgcaggg gaaagaatag   5820
tagacataat agcaacagac atacaaacta agaattacaa aaacaaatt acaaaaattc     5880 aaaattttcg ggtttattac agggacagca gagatccagt ttggaaagga ccagcaaagc   5940
tcctctggaa aggtgaaggg gcagtagtaa tacaagataa tagtgacata aaagtagtgc   6000
caagaagaaa agcaaagatc atcagggatt atggaaaaca gatggcaggt gatgattgtg   6060
tggcaagtag acaggatgag gattaacaca tggaattctg caacaactgc tgtttatcca   6120
tttcagaatt ggaggagctt tgttccttgg gttcttggga gcagcaggaa gcactatggg   6180
cgcagcgtca atgacgctga cggtacaggc cagacaatta ttgtctggta tagtgcagca   6240
gcagaacaat ttgctgaggg ctattgaggc gcaacagcat ctgttgcaac tcacagtctg   6300
gggcatcaag cagctccagg caagaatcct ggctgtggaa agatacctaa aggatcaaca   6360
gctcctgggg atttggggtt gctctggaaa actcatttgc accactgctg tgccttggaa   6420
tgctagttgg agtaataaat ctctggaaca gatttggaat cacacgacct ggatggagtg   6480
ggacagagaa attaacaatt acacaagctt gctagcagat cttttccct ctgccaaaaa    6540 ttatggggac atcatgaagc cccttgagca tctgacttct ggctaataaa ggaaatttat   6600
tttcattgca atagtgtgtt ggaatttttt gtgtctctca ctcggaagga catatgggag   6660
ggcaaatcat ttaaacatc agaatgagta tttggtttag agtttggcaa catatgccat    6720
atgctggctg ccatgaacaa aggtggctat aaagaggtca tcagtatatg aaacagcccc   6780
ctgctgtcca ttccttattc catagaaaag ccttgacttg aggttagatt ttttttatat    6840
tttgttttgt gttattttt tctttaacat ccctaaaatt ttccttacat gttttactag     6900
ccagattttt cctcctctcc tgactactcc cagtcatagc tgtccctctt ctcttatgaa   6960
gatccctcga cctgcagccc aagcttggcg taatcatggt catagctgtt tcctgtgtga   7020
```

```
aattgttatc cgctcacaat tccacacaac atacgagccg gaagcataaa gtgtaaagcc    7080
tggggtgcct aatgagtgag ctaactcaca ttaattgcgt tgcgctcact gcccgctttc    7140
cagtcgggaa acctgtcgtg ccagcggatc cgcatctcaa ttagtcagca accatagtcc    7200
cgcccctaac tccgcccatc ccgcccctaa ctccgcccag ttccgcccat tctccgcccc    7260
atggctgact aattttttt atttatgcag aggccgaggc cgcctcggcc tctgagctat    7320
tccagaagta gtgaggaggc ttttttggag gcctaggctt ttgcaaaaag ctaacttgtt    7380
tattgcagct tataatggtt acaaataaag caatagcatc acaaatttca caaataaagc    7440
atttttttca ctgcattcta gttgtggttt gtccaaactc atcaatgtat cttatcatgt    7500
ctggatccgc tgcattaatg aatcggccaa cgcgcgggga gaggcggttt gcgtattggg    7560
cgctcttccg cttcctcgct cactgactcg ctgcgctcgg tcgttcggct gcggcgagcg    7620
gtatcagctc actcaaaggc ggtaatacgg ttatccacag aatcagggga taacgcagga    7680
aagaacatgt gagcaaaagg ccagcaaaag gccaggaacc gtaaaaaggc cgcgttgctg    7740
gcgttttcc ataggctccg ccccctgac gagcatcaca aaaatcgacg ctcaagtcag    7800
aggtggcgaa acccgacagg actataaaga taccaggcgt ttccccctgg aagctccctc    7860
gtgcgctctc ctgttccgac cctgccgctt accggatacc tgtccgcctt tctcccttcg    7920
ggaagcgtgg cgctttctca atgctcacgc tgtaggtatc tcagttcggt gtaggtcgtt    7980
cgctccaagc tgggctgtgt gcacgaaccc cccgttcagc ccgaccgctg cgccttatcc    8040
ggtaactatc gtcttgagtc caacccggta agacacgact tatcgccact ggcagcagcc    8100
actggtaaca ggattagcag agcgaggtat gtaggcggtg ctacagagtt cttgaagtgg    8160
tggcctaact acggctacac tagaaggaca gtatttggta tctgcgctct gctgaagcca    8220
gttaccttcg gaaaaagagt tggtagctct tgatccggca acaaaccac cgctggtagc    8280
ggtggttttt ttgtttgcaa gcagcagatt acgcgcagaa aaaaggatc tcaagaagat    8340
cctttgatct tttctacggg gtctgacgct cagtggaacg aaaactcacg ttaagggatt    8400
ttggtcatga gattatcaaa aaggatcttc acctagatcc ttttaaatta aaaatgaagt    8460
tttaaatcaa tctaaagtat atatgagtaa acttggtctg acagttacca atgcttaatc    8520
agtgaggcac ctatctcagc gatctgtcta tttcgttcat ccatagttgc ctgactcccc    8580
gtcgtgtaga taactacgat acgggagggc ttaccatctg gccccagtgc tgcaatgata    8640
ccgcgagacc cacgctcacc ggctccagat ttatcagcaa taaaccagcc agccggaagg    8700
gccgagcgca gaagtggtcc tgcaacttta tccgcctcca tccagtctat taattgttgc    8760
cgggaagcta gagtaagtag ttcgccagtt aatagtttgc gcaacgttgt tgccattgct    8820
acaggcatcg tggtgtcacg ctcgtcgttt ggtatggctt cattcagctc cggttcccaa    8880
cgatcaaggc gagttacatg atcccccatg ttgtgcaaaa aagcggttag ctccttcggt    8940
cctccgatcg ttgtcagaag taagttggcc gcagtgttat cactcatggt tatggcagca    9000
ctgcataatt ctcttactgt catgccatcc gtaagatgct tttctgtgac tggtgagtac    9060
tcaaccaagt cattctgaga atagtgtatg cggcgaccga gttgctcttg cccggcgtca    9120
atacgggata taccgcgcc acatagcaga actttaaaag tgctcatcat tggaaaacgt    9180
tcttcgggc gaaaactctc aaggatctta ccgctgttga gatccagttc gatgtaaccc    9240
actcgtgcac ccaactgatc ttcagcatct tttactttca ccagcgtttc tgggtgagca    9300
aaaacaggaa ggcaaaatgc cgcaaaaaag ggaataaggg cgacacgaa atgttgaata    9360
ctcatactct tccttttttca atattattga agcatttatc agggttattg tctcatgagc    9420
```

```
ggatacatat ttgaatgtat ttagaaaaat aaacaaatag gggttccgcg cacatttccc    9480
cgaaaagtgc cacctg                                                    9496

<210> SEQ ID NO 108
<211> LENGTH: 1110
<212> TYPE: DNA
<213> ORGANISM: Artificial Sequence
<220> FEATURE:
<223> OTHER INFORMATION: Elongation Factor-1 alpha (EF1-alpha) promoter
      with 3-prime restriction recognition site

<400> SEQUENCE: 108
ccggtgccta gagaaggtgg cgcggggtaa actgggaaag tgatgtcgtg tactggctcc      60 gccttttttcc cgagggtggg ggagaaccgt atataagtgc agtagtcgcc gtgaacgttc    120
tttttcgcaa cgggtttgcc gccagaacac aggtaagtgc cgtgtgtggt tcccgcgggc    180
ctggcctctt tacgggttat ggcccttgcg tgccttgaat tacttccacg cccctggctg    240
cagtacgtga ttcttgatcc cgagcttcgg gttggaagtg ggtgggagag ttcgaggcct    300
tgcgcttaag gagccccttc gcctcgtgct tgagttgagg cctggcctgg gcgctggggc    360
cgccgcgtgc gaatctggtg gcaccttcgc gcctgtctcg ctgctttcga taagtctcta    420
gccatttaaa attttgatg acctgctgcg acgctttttt tctggcaaga tagtcttgta    480
aatgcgggcc aagatctgca cactggtatt tcggtttttg gggccgcggg cggcgacggg    540
gcccgtgcgt cccagcgcac atgttcggcg aggcggggcc tgcgagcgcg gccaccgaga    600
atcggacggg ggtagtctca agctggccgg cctgctctgg tgcctggcct cgcgccgccg    660
tgtatcgccc cgccctgggc ggcaaggctg gcccggtcgg caccagttgc gtgagcggaa    720
agatggccgc ttcccggccc tgctgcaggg agctcaaaat ggaggacgcg gcgctcggga    780
gagcgggcgg gtgagtcacc cacacaaagg aaaagggcct ttccgtcctc agccgtcgct    840
tcatgtgact ccacggagta ccgggcgccg tccaggcacc tcgattagtt ctcgagcttt    900
tggagtacgt cgtctttagg ttggggggag gggttttatg cgatggagtt tccccacact    960
gagtgggtgg agactgaagt taggccagct tggcacttga tgtaattctc cttggaattt   1020 gcccttttttg agtttggatc ttggttcatt ctcaagcctc agacagtggt tcaaagtttt   1080
tttcttccat ttcaggtgtc gtgatgtaca                                    1110

<210> SEQ ID NO 109
<211> LENGTH: 122
<212> TYPE: DNA
<213> ORGANISM: Artificial Sequence
<220> FEATURE:
<223> OTHER INFORMATION: miR21 Vif coding sequence with 5-prime
      restriction recognition site

<400> SEQUENCE: 109
cccgggcatc tccatggctg taccaccttg tcggggatg tgtacttctg aacttgtgtt       60
gaatctcatg gagttcagaa gaacacatcc gcactgacat tttggtatct ttcatctgac    120
ca                                                                   122

<210> SEQ ID NO 110
<211> LENGTH: 119
<212> TYPE: DNA
<213> ORGANISM: Artificial Sequence
<220> FEATURE:
<223> OTHER INFORMATION: miR185 Tat coding sequence with 5-prime
      restriction recognition sites
```

```
<400> SEQUENCE: 110
gctagcgggc ctggctcgag caggggggcga gggattccgc ttcttcctgc catagcgtgg      60
tcccctcccc tatggcaggc agaagcggca ccttccctcc caatgaccgc gtcttcgtc      119
```